(12) United States Patent
Yen et al.

(10) Patent No.: US 11,575,090 B2
(45) Date of Patent: Feb. 7, 2023

(54) ORGANIC COMPOUND AND ORGANIC ELECTROLUMINESCENCE DEVICE USING THE SAME

(71) Applicants: Feng-Wen Yen, Taipei (TW); Li-Chieh Chuang, Nantou (TW)

(72) Inventors: Feng-Wen Yen, Taipei (TW); Li-Chieh Chuang, Nantou (TW)

(73) Assignee: LUMINESCENCE TECHNOLOGY CORP., Hsin-Chu (TW)

( * ) Notice: Subject to any disclaimer, the term of this patent is extended or adjusted under 35 U.S.C. 154(b) by 351 days.

(21) Appl. No.: 16/798,435

(22) Filed: Feb. 24, 2020

(65) Prior Publication Data
US 2022/0131089 A1    Apr. 28, 2022

(51) Int. Cl.
H01L 51/00        (2006.01)
C07D 409/04   (2006.01)
C09K 11/06     (2006.01)
C07D 307/91   (2006.01)
C07D 333/76   (2006.01)
C07D 405/04   (2006.01)
H01L 51/50     (2006.01)

(52) U.S. Cl.
CPC ........ *H01L 51/0073* (2013.01); *C07D 307/91* (2013.01); *C07D 333/76* (2013.01); *C07D 405/04* (2013.01); *C07D 409/04* (2013.01); *C09K 11/06* (2013.01); *H01L 51/0052* (2013.01); *H01L 51/0054* (2013.01); *H01L 51/0055* (2013.01); *H01L 51/0072* (2013.01); *H01L 51/0074* (2013.01); *C09K 2211/1018* (2013.01); *H01L 51/5012* (2013.01); *H01L 51/5072* (2013.01); *H01L 51/5096* (2013.01)

(58) Field of Classification Search
None
See application file for complete search history.

(56) References Cited

U.S. PATENT DOCUMENTS

2014/0231754 A1* 8/2014 Yen ............... H01L 51/0056 585/27
2015/0144898 A1* 5/2015 Dai ........................ C09K 11/06 257/40

* cited by examiner

*Primary Examiner* — Jay Yang

(57) ABSTRACT

An organic compound of formula (1)

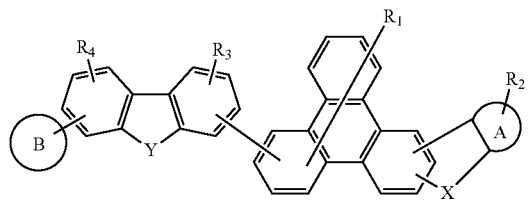

useful as a material of an organic electroluminescence device is disclosed. The same definition as described in the present invention.

13 Claims, 1 Drawing Sheet

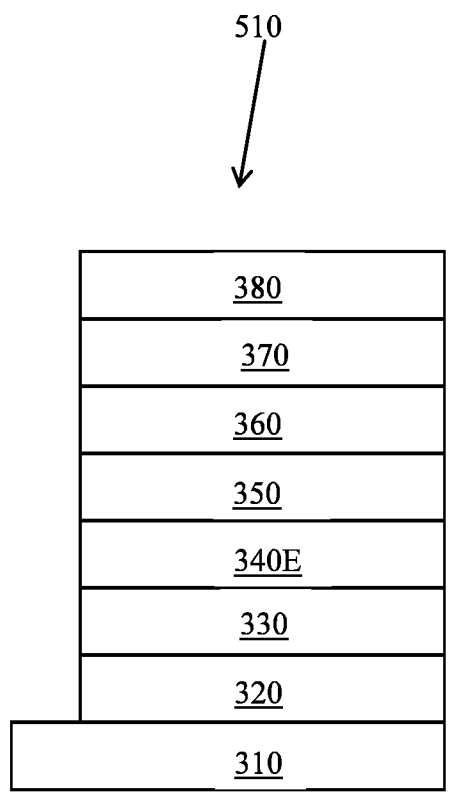

ORGANIC COMPOUND AND ORGANIC ELECTROLUMINESCENCE DEVICE USING THE SAME

FIELD

The present invention relates generally to a compound, and, more specifically, to an organic electroluminescence (herein after referred to as organic EL) device using the compound.

BACKGROUND

Organic electroluminescence (organic EL) devices, i.e., organic light-emitting diodes (OLEDs) that make use of organic compounds, are becoming increasingly desirable than before. The devices make use of thin organic films that emit light when voltage is applied across the device. They are becoming an interesting technology for use in applications such as flat panel displays, illumination, or backlighting.

One of the organic compounds, denoted H1 hereinafter, has the following structure:

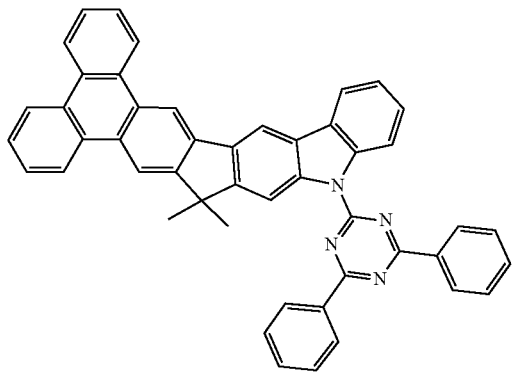

H1

As used herein, "top" means furthest away from the substrate, while "bottom" means closest to the substrate. Where a second layer is described as formed on or onto a first layer, the second layer is formed further away from substrate. There may be other layers between the second layer and the first layer, unless it is specified that the second layer is "in contact with" the first layer. For example, a cathode may be described as formed onto an anode, even though there are various organic layers in between.

SUMMARY

An organic compound has the following formula (1):

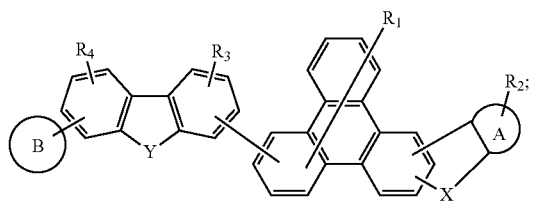

formula (1)

wherein X is selected from the group consisting of O, S, Se, $NR_5$ and $SiR_6R_7$;

wherein Y is selected from the group consisting of O and S;

wherein ring A represents an aromatic group;

wherein ring B represents a polycyclic aromatic group or a polycyclic hetero aromatic group;

wherein ring B is optionally substituted by aryl;

wherein $R_1$, $R_2$, $R_3$, and $R_4$ independently represent mono to a maximum possible number of substitutions, or no substitution;

wherein each of $R_1$ to $R_4$ substituents is selected from the group consisting of alkyl, aryl, aralkyl, heteroaryl, and combinations thereof; and wherein each of $R_5$ to $R_7$ represents no substitution or a substituent selected from the group consisting of alkyl, aryl, aralkyl, heteroaryl, and combinations thereof.

An organic EL device is also provided. The organic EL device may comprise an anode, a cathode and one or more organic layers formed between the anode and the cathode. At least one of the organic layers comprises the organic compound of formula (1).

BRIEF DESCRIPTION OF THE DRAWINGS

The FIG. 1s a schematic view showing an organic EL device according to an embodiment of the present invention.

DETAILED DESCRIPTION

Plural embodiments of the present disclosure are disclosed through drawings. For the purpose of clear illustration, many practical details will be illustrated along with the description below. It should be understood that, however, these practical details should not limit the present disclosure. In other words, in embodiments of the present disclosure, these practical details are not necessary. In addition, for the purpose of simplifying the drawings, some conventional structures and components are simply and schematically depicted in the FIGURES.

It is to be understood that although particular phrases used herein, such as "first", "second", "third", and so on, are used to describe different components, members, regions, layers, and/or sections, these components, members, regions, layers, and/or sections should not be limited by these terms. These phrases are used to distinguish one component, member, region, layer, or section from another component, member, region, layer, or section. In this way, a first component, member, region, layer, and/or section to be described below may be referred to as a second component, member, region, layer, and/or section, without departing from the spirit and scope of the present disclosure.

Spatially relative phrases, such as "onto", "on", "under", "below", "underlying", "beneath", "above", and so on used herein, are used for facilitating description of a relation between one component or feature and another component or feature depicted in the drawings. Therefore, it can be understood that, in addition to directions depicted in the drawings, the spatially relative terms mean to include all different orientations during usage or operations of the device. For example, it is assumed that a device in a FIGURE is reversed upside down, a component described as being "under", "below", or "beneath" another component or feature is oriented "onto" or "on" the other component or feature. Therefore, these exemplary terms "under" and "below" may include orientations above and below. The device may be otherwise oriented (e.g., turned by 90 degrees, or other orientations), and the spatially relative terms used herein should be explained accordingly.

Accordingly, it may be understood that when a component or a layer is referred to as being "onto", "on", "connected to", or "coupled to" another component or another layer, it may be immediately on the other component or layer, or connected to or coupled to the other component or layer, or there may be one or more intermediate components or intermediate layers. Further, it can be understood that when a component or a layer is referred to as being "between" two components or two layers, it may be the only component or layer between the two components or layers, or there may be one or more intermediate components or intermediate layers.

Terminologies used herein are only for the purpose of describing particular embodiments, but not limiting the present disclosure. The singular form of "a" and "the" used herein may also include the plural form, unless otherwise indicated in the context. Accordingly, it can be understood that when there terms "include" or "comprise" are used in the specification, it clearly illustrates the existence of a specified feature, bulk, step, operation, component, and/or member, while not excluding the existence or addition of one or more features, bulks, steps, operations, components, members and/or groups thereof. "And/or" used herein includes any and all combinations of one or more related terms that are listed. When a leading word, such as "at least one of", is added ahead of a component list, it is to describe the entire component list, but not individual components among the list.

The terms "substituted" and "substitution" refer to a substituent bonded to the relevant position, e.g., a carbon or nitrogen. When $R_1$ represents no substitution, $R_1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum possible number of substitutions in a ring structure will depend on the total number of available valencies in the ring atoms. A polycyclic aromatic hydrocarbyl may have two or more rings possible for being substituted. In this case, a long straight line may be drawn to pass through each of the rings in a formula. The following may be an example:

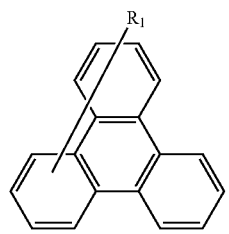

Although the single straight line of the example does not pass through all substitutable rings, $R_1$ may be substituted to all substitutable rings including the bottom right benzene. Occasionally, the straight line may be drawn to pass through the center benzene of the formula, to represents that $R_1$ may be substituted to all substitutable rings including the bottom right benzene. The following may be an example:

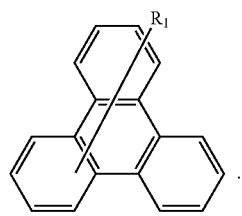

Generally, an organic EL device comprises at least one organic layer disposed between and electrically connected to an anode and a cathode. When an external voltage is applied across the organic EL device, electrons and holes are injected from the cathode and the anode, respectively. Electrons will be injected from a cathode into a LUMO (lowest unoccupied molecular orbital) and holes will be injected from an anode into a HOMO (highest occupied molecular orbital). Subsequently, the electrons recombine with holes in the light emitting layer to form excitons and then emit light. When luminescent molecules absorb energy to achieve an excited state, the exciton may either be in a singlet state or a triplet state, depending on how the spins of the electrons and holes have been combined.

The term "hydrogen" refers to a —H radical.

The terms "halogen" and "halide" are used interchangeably and refer to fluorine, chlorine, bromine, or iodine.

The term "trifluoromethyl" refers to a —$CF_3$ radical.

The term "cyano" refers to a —C≡N radical.

The term "silyl" refers to a —$Si(R_s)_3$ radical, wherein each $R_s$ can be same or different. $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combinations thereof. Preferred $R_s$ is selected from the group consisting of alkyl, cycloalkyl, aryl, heteroaryl, and combinations thereof.

As used herein, if the term "a first integer to a second integer" is used to express a plurality of solutions, it may cover the first integer, the second integer, and each integer between the first and the second integers. That is to say, when the term "a first integer to a second integer" expresses a plurality of solutions, all of its integers are parallel technical solutions. In this case, the term "a first integer to a second integer" is not used to express a numerical range. For example, 1 to 4 covers 1, 2, 3, 4 and does not include 1.5. For another example, 0 to 3 cover 0, 1, 2, and 3, wherein 0, 1, 2, and 3 are technical solutions in parallel. For another example, 1 to 5 covers 1, 2, 3, 4, and 5, among which 1, 2, 3, 4, and 5 are parallel technical solutions. These solutions may be, for example, the number of substituents or the number of carbon atoms. It is noted that "a maximum possible number of substitutions" is also a kind of integer.

As used herein, "combinations thereof" indicates that one or more members of the applicable list are combined to form a known or chemically stable arrangement that one of ordinary skill in the art can envision from the applicable list. For example, a monocyclic aromatic group and a polycyclic aromatic group may be bonded (a first kind of combination) together by a single bond. A monocyclic aromatic groups and a polycyclic aromatic group can also be fused (a second kind of combination) to to have two carbons common to two adjoining rings (the rings are "fused"). A biphenyl group can be combined (bonded) with a triazinyl group to form a biphenyltriazinyl group.

The term "aryl" or "aromatic group" as used herein are interchangeable with each other and contemplates monocyclic aromatic groups (or hydrocarbyls), polycyclic aromatic groups (or hydrocarbyls), fused ring hydrocarbon units, and combinations thereof. The polycyclic aromatic group may have two, three, four, five, or more rings in which two carbons are common to two adjoining rings (meaning that the two adjacent rings are "fused"). A polycyclic aromatic group can be named a bicyclic aromatic group if it has two rings; if it has three rings, it can be named a tricyclic aromatic group, and so on. In a polycyclic aromatic group, at least one of the polycyclic rings is an aromatic group, e.g., the other rings can be cycloalkyls, cycloalkenyls, aryl, heterocycles, and/or heteroaryls.

Suitable aromatic groups include but not limited to phenyl, biphenyl, terphenyl, m-terphenyl, p-terphenyl, o-terphenyl, pyrene (fluorene), benzofluorene, naphthalene, benzo[c]perylene, anthracene, triphenylene, pyrene, phenanthrene, phenalene, chrysene, 9,9'-Spirobi[9H-fluorene], perylene, 1,2,3,4-dibenzoanthracene, fluoranthene, benzoanthracene, benzo[c]phenanthrene, triphenylene, tetraphenylene, phenalene, fluorene, azulene, butadiene, fluorene (naphthalene hexane), pinene, tricycline, benzo[a]anthracene, benzo[c]phenanthrene, fluoranthene (benzofluorene), tetracene, benzofluorene, benzo[a]pyrene, benzo[e]pyrene, olympicene (6H-benzo[cd]pyrene), benzofluoranthene, benzo[a]fluoranthene, benzo[b]fluoranthene, benzo[j]fluoranthene, benzo[k]fluoranthene, dibenzoanthracene, dibenzo[a, h]anthracene, dibenzo[a, j]anthracene, pentacene, benzo[j]fluoranthene, picene, corannulene, bicalene, benzo[ghi]perylene, ovalene, anthanthrene, hexacene, Heptacene, coronene, deltaene, dibenzo[de, mn]tetrabenzene (zethrene).

Among the suitable aromatic groups, preferred include phenyl, biphenyl, terphenyl, m-terphenyl, p-terphenyl, o-terphenyl, pyrene (fluorene), benzofluorene, naphthalene, benzo[c]pyrene, anthracene, triphenylene, pyrene, phenanthrene, phenalene, chrysene, 9,9'-Spirobi[9H-fluorene], perylene, 1,2,3,4-dibenzoanthracene.

In terms of the number of carbon atoms, preferred aromatic groups are those containing 30 or fewer carbon atoms, preferably 6 to 30 carbon atoms, more preferably 6 to 20 carbon atoms, and most preferably 6, 10 or 12 carbon atoms.

In addition, the above-mentioned "aryl" or "aromatic group" may be optionally substituted, for example, by methyl, ethyl, butyl, isobutyl, octyloxy group, biphenyl, naphthalenyl, hexyl, or pyridyl. As another example, the two hydrogen atoms commonly bonded on the same carbon atom of benzofluorene may be further substituted with two methyl groups, which product may be named dimethyl-benzofluorene. Suitable substituted aromatic groups comprise 9,10-diphenylanthracene, biphenylanthracene, phenylanthracene, phenylnaphthalene, 9,9-dimethylfluorene, 1-methylnaphthalene, and sapotalin. Among the suitable substituted aromatic groups, preferred comprise 9,10-diphenylanthracene, biphenylanthracene, phenylanthracene, phenylnaphthalene, and 9,9-dimethylfluorene.

As used herein, the terms "heteroaryl" or "heteroaromatic group" are interchangeable with each other. "Heteroaryl" or "heteroaromatic group" may be selected from the group consisting of a monocyclic heteroaromatic group containing one, two, three, four, five or more heteroatoms, a polycyclic heteroaromatic group having two or more rings, and combinations thereof.

Heteroatoms include, but are not limited to, 0, S, Se, N, Si, P, and B. In many cases, O, S, N, or Si is the preferred heteroatom. The "monocyclic heteroaromatic group" is preferably a single ring having 5 or 6 ring atoms, and the ring may have one to six heteroatoms. A "polycyclic heteroaromatic group" may have two, three, four, five, six or more rings, where two carbons are common to two adjoining rings (meaning that the rings are "fused"). A polycyclic heteroaromatic group can be named a bicyclic heteroaromatic group if it has two rings; if it has three rings, it can be named a tricyclic heteroaromatic group, and so on. In a polycyclic heteroaromatic group, at least one of the rings is a heteroaryl, e.g., the other rings can be cycloalkyls, cycloalkenyls, aryl, heterocycles, and/or heteroaryls.

In terms of the number of carbon atoms, the polycyclic heteroaromatic groups can have from one to six heteroatoms per ring of the polycyclic heteroaromatic groups. Preferred heteroaryl groups are those containing 30 or fewer carbon atoms, preferably 3 to 30 carbon atoms, more preferably 3 to 20 carbon atoms, and most preferably 3 to 12 carbon atoms.

Suitable heteroaromatic groups) may include aza-aromatic groups, dibenzofuran, carbazole, biscarbazole, dibenzothiophene, pyridine, pyrimidine, triazine, pyrazine, Dibenzopyrazine, acridine, phenothiazine, phenoxazine, phenanthroline, phenanthroline, dihydrophenazine, benzonaphthofuran, benzimidazole, tribenzobenzofuran, pyrenobenzofuran, quinazoline, quinoxaline, benzoquinazoline, pyridine, pyrimidine, triazine, diazine, 1,3,5-triazine, dibenzoselenophene, furan, thiophene, benzofuran, benzothiophene, benzoselenophene, indolocarbazole, pyridylindole, pyrrolobispyrazole, imidazole, isoquinoline, quinolone, triazole, oxazole, thiazole, oxadiazole, oxatriazole, dioxazole, thiadiazole, pyridazine, oxazine, oxathiazine, oxadiazine, indole, benzimidazole, indazole, indoxazine, benzoxazole, benzoisoxazole, benzothiazole, Quinoline, isoquinoline, oxoline, naphthyridine, phthalazine, pyridine, xanthene, phenazine, benzofuropyridine, furobipyridine, benzothienopyridine, thienobispyridine, benzoselenolopyridine, and selenolobispyridine.

Among the suitable heteroaromatic groups, preferred include an azaaromatic group, dibenzofuran, carbazole, biscarbazole, dibenzothiophene, pyridine, pyrimidine, triazine, pyrazine, phenazine, acridine, phenothiazine, phenoxazine, phenanthroline, phenanthroline, dihydrophenazine, benzonaphthofuran, benzimidazole, tribenzobenzofuran, pyrenobenzofuran, imidazole, quinolone, or isoquinoline, quinazoline, quinoxaline, benzoquinazoline, dibenzoselenophene, indolocarbazole, benzimidazole, 1,2-azaborane, 1,3-azaborane, 1,4-azaborane, borazine, and other nitrogen analogs of the aza-derivatives described above.

Among the listed heteroaromatic groups, the "aza" designation in the fragments i.e., aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

In addition, the "heteroaryl" or "heteroaromatic group" may be optionally substituted. For example, carbazole can be further substituted with two isobutyl groups, which is named diisobutylcarbazole. Suitable substituted heteroaryls may include dimethyldibenzofuran, phenylcarbazole, diisobutylcarbazole, dimethylcarbazole, phenylpyridine, diphenyltriazine, diphenyl Pyrimidine, diphenylpyridine, naphthylcarbazole, triphenyltriazine, triphenylpyrimidine, triphenylpyridine, di-m-terphenyltriazine, di-m-terphenylpyrimidine, di-m-terphenylpyridine, phenylbiphenylpyrimidine, methylacridine, dimethylacridine, phenyldibenzopyrazine, phenylphenanthroline, 2-methylbenzimidazole, 2-ethylbenzimidazole.

The term "alkyl" refers to and includes both straight and branched chain alkyl radicals. Preferred alkyl groups are those containing 30 or fewer carbon atoms, preferably 1 to 20 carbon atoms, more preferably 1 to 15 carbon atoms, and most preferably 1 to 12 carbon atoms. Suitable alkyl groups include methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group is optionally substituted.

The terms "aralkyl" or "arylalkyl" are used interchangeably and refer to an alkyl group that is substituted with an aryl group. Preferred aralkyl groups are those containing 30 or fewer carbon atoms, preferably 6 to 30 carbon atoms. Additionally, the aralkyl group is optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The terms alkyl, aralkyl, heteroaryl, aryl, cycloalkyl, heteroalkyl, heterocycloalkyl, alkenyl, cycloalkenyl, heteroalkenyl, alkynyl, alkoxy, and heterocyclic group, as used herein, are independently unsubstituted, or independently substituted, with one or more general substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

In many instances, the general substituents are selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some instances, the preferred general substituents are selected from the group consisting of hydrogen, halogen, trifluoromethyl, cyano, nitro, silyl, and combinations thereof.

In yet other instances, the more preferred general substituents are selected from the group consisting of hydrogen, alkyl, aralkyl, heteroaryl and combinations thereof.

It is to be understood that when a molecular fragment is described as being a substituent or otherwise attached to another moiety, its name may be written as if it were a fragment (phenyl, phenylene, naphthyl, dibenzofuryl, hydrocarbyl, aromatic linker, arylene) or as if it were the whole molecule (e.g., benzene, naphthalene, dibenzofuran, hydrocarbon, aromatic compound, aromatic hydrocarbon). As used herein, these different ways of designating a substituent or attached fragment are considered to be equivalent.

The terms "$R_1$", "$R_2$", "$R_3$", "$R_4$", "$R_5$", "$R_6$" and "$R_7$" may independently be hydrogen or a substituent selected from the group consisting of deuterium, halogen, alkyl, cycloalkyl, heteroalkyl, heterocycloalkyl, aralkyl, alkoxy, aryloxy, amino, silyl, alkenyl, cycloalkenyl, heteroalkenyl, alkynyl, aryl, heteroaryl, and combination thereof. $R_1$ to $R_7$ may preferably be hydrogen or a substituent selected from the group consisting of hydrogen, alkyl, aryl, aralkyl, heteroaryl, and combination thereof.

Material and/or Film Definitions:

As used herein, abbreviations refer to materials and/or films as follows:
LiQ: 8-hydroxyquinolato-lithium
HAT-CN: Dipyrazino[2,3-f:2,3-]quinoxaline-2,3,6,7,10,11-hexacarbonitrile
EIL: electron injecting layer
ETL: electron transport layer
ETM: electron transport material
EML: emissive layer
EBL: electron blocking layer
HTL: hole transporting layer
HIL: hole injection layer
ITO: indium tin oxide
EL: electroluminescence An organic compound is described to have the following formula (1):

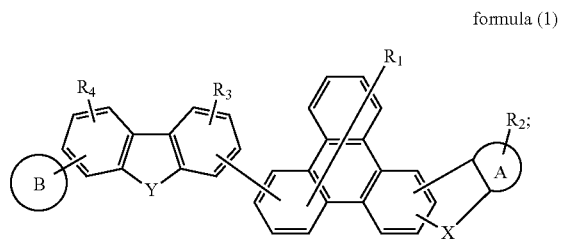

formula (1)

wherein X is selected from the group consisting of O, S, Se, $NR_5$ and $SiR_6R_7$;

wherein Y is selected from the group consisting of O and S;

wherein ring A represents an aromatic group;

wherein ring B represents a polycyclic aromatic group or a polycyclic heteroaromatic group;

wherein ring B is optionally substituted by aryl;

wherein $R_1$, $R_2$, $R_3$, and $R_4$ independently represent mono to a maximum possible number of substitutions, or no substitution;

wherein each of $R_1$ to $R_4$ substituents is selected from the group consisting of alkyl, aryl, aralkyl, heteroaryl, and combinations thereof; and wherein each of $R_5$ to $R_7$ represents no substitution or a substituent selected from the group consisting of alkyl, aryl, aralkyl, heteroaryl, and combinations thereof.

In some embodiments, an organic compound is described to have the following formula (1):

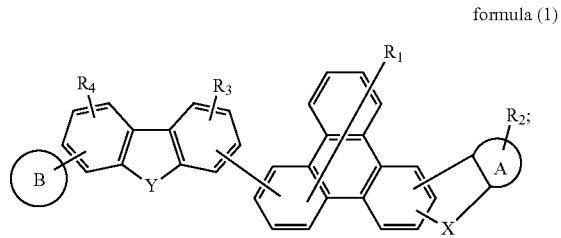

formula (1)

wherein X represents a divalent bridge selected from the group consisting of O, S, Se, $NR_5$ and $SiR_6R_7$;

wherein Y represents a divalent bridge selected from the group consisting of O and S;

wherein ring A represents a monocyclic aromatic group or a polycyclic aromatic group having two or three fused rings;

wherein ring B represents a polycyclic aromatic group or a polycyclic hetero aromatic group having at most five fused rings;

wherein $R_1$, $R_2$, $R_3$, and $R_4$ independently represent mono to a maximum possible number of substitutions, or no substitution;

wherein each of $R_1$ to $R_4$ substituents is selected from the group consisting of alkyl, aryl, aralkyl, heteroaryl, and combinations thereof; and wherein each of $R_5$ to $R_7$ represents no substitution or a substituent selected from the group consisting of alkyl, aryl, aralkyl, heteroaryl, and combinations thereof.

In some embodiments, an organic compound is described to have the following formula (26):

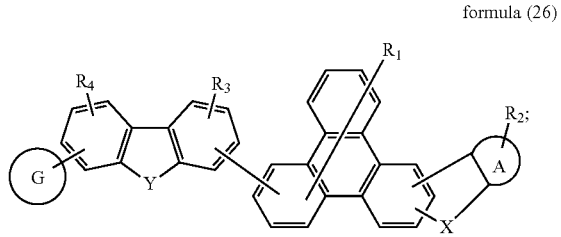

formula (26)

wherein ring G is selected from the group consisting of naphthyl, anthryl, phenanthryl, 9,9-dimethylfluorenyl, pyrenyl, chrysenyl, fluoranthenyl, dimethyl benzofluorenyl, triphenylenyl, perylenyl, and combinations thereof;

wherein ring A is selected from the group consisting of phenyl, naphthyl, anthryl, phenalenyl, and combinations thereof;

wherein X is selected from the group consisting of O, S, Se, $NR_5$ and $SiR_6R_7$;

wherein Y is selected from the group consisting of O and S;

wherein $R_5$ represents no substitution or a substituent selected from the group consisting of pyridinyl, dimethylphenyl, ethyl, hexylphenyl, dibenzothienyl, phenyl, triphenylenyl, anthryl, terphenyl, diphenyltriazinyl, naphthyl, biphenyl, and combinations thereof;

wherein $R_1$, $R_2$, $R_3$, and $R_4$ independently represent mono to a maximum possible number of substitutions, or no substitution;

wherein each of $R_1$ substituents is selected from the group consisting of methyl, hexyl, hexyl, phenyl, pyridinyl, and combinations thereof;

wherein each of $R_2$ substituents is selected from the group consisting of phenyl, pyridinyl, hexylphenyl, triphenylenyl, and combinations thereof;

wherein each of $R_3$ substituents is selected from the group consisting of phenyl, pyridinyl, naphthyl, and combinations thereof;

wherein each of $R_4$ substituents is selected from the group consisting of hexylphenyl, pyridinyl, naphthyl, and combinations thereof; and wherein each of $R_6$ to $R_7$ represents no substitution or a substituent selected from the group consisting of hexyl, hexylphenyl, and combinations thereof.

In some embodiments, an organic compound is described to have the following formula (27):

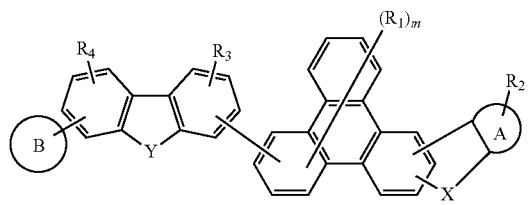

formula (27)

wherein X represents a divalent bridge selected from the group consisting of O, S, Se, $NR_5$ and $SiR_6R_7$; Y is O or S; m represents an integer of 0 to 7; ring A represents a substituted or unsubstituted fused ring hydrocarbons unit with one to three rings; ring B represents a fused ring hydrocarbon unit with two to five rings; $R_1$ to $R_7$ are independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

The organic compound of formula (1) may also have one of the following formula(2) to formula(25):

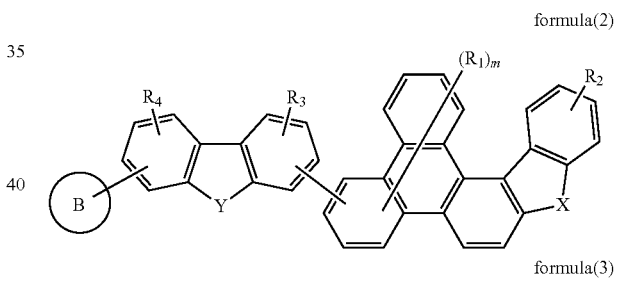

formula(2)

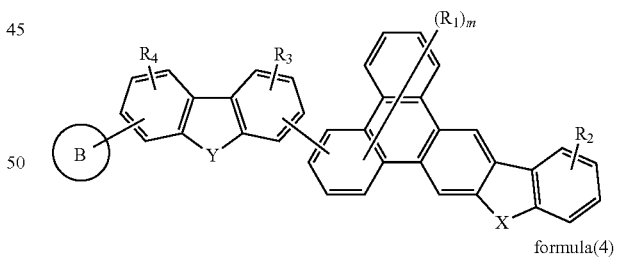

formula(3)

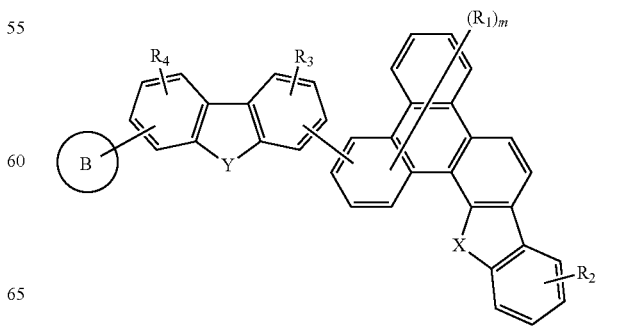

formula(4)

-continued
formula(5)
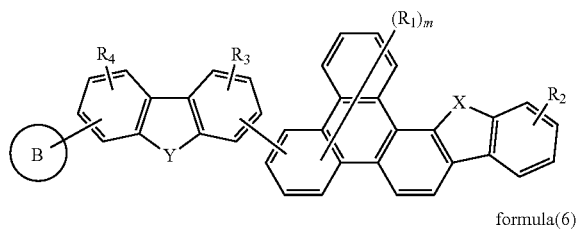
formula(6)
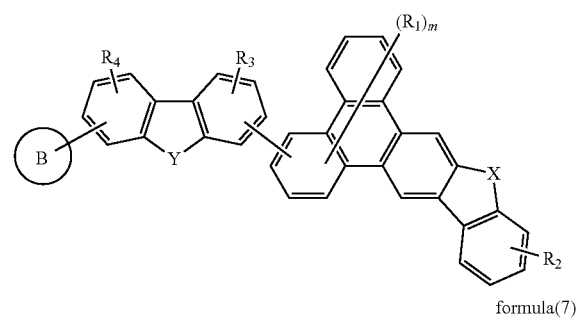
formula(7)
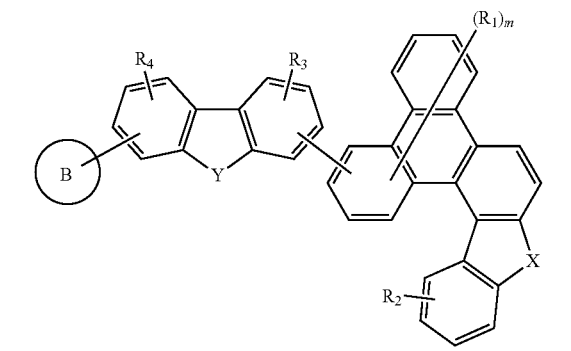
formula(8)
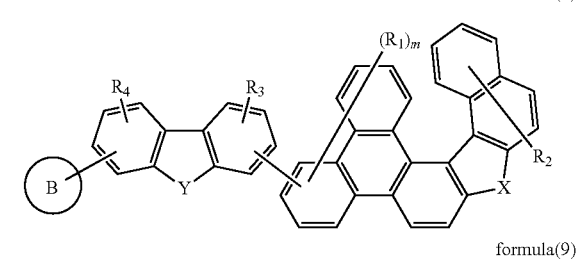
formula(9)
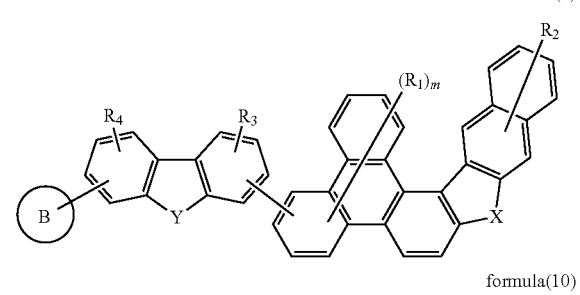
formula(10)
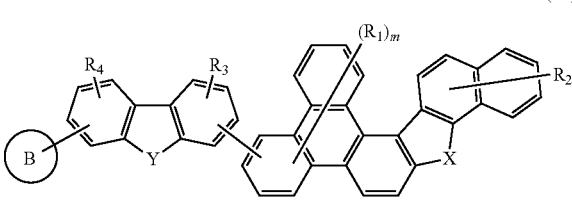
formula(11)
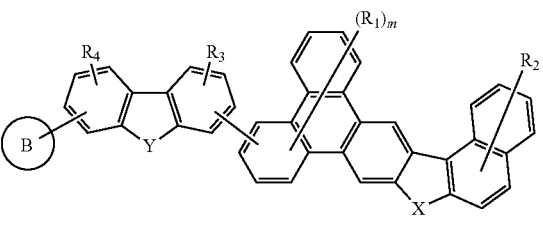
formula(12)
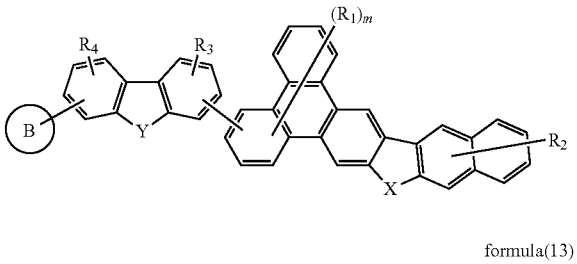
formula(13)
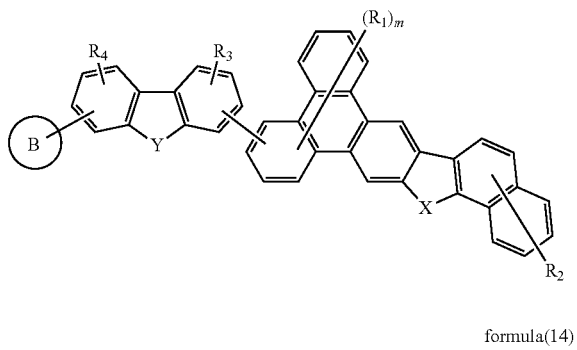
formula(14)
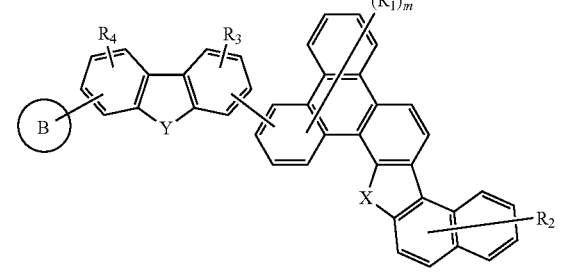
formula(15)

formula(16)
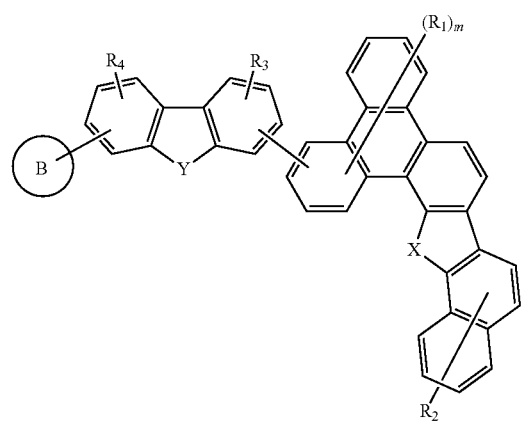
formula(17)
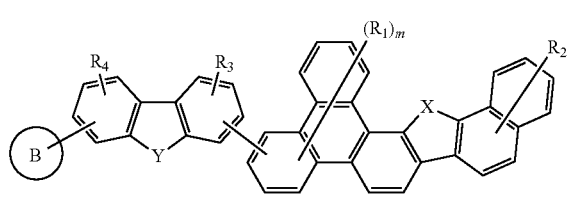
formula(18)
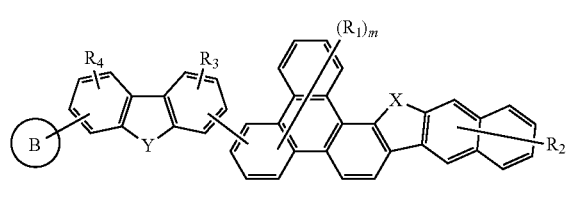
formula(19)
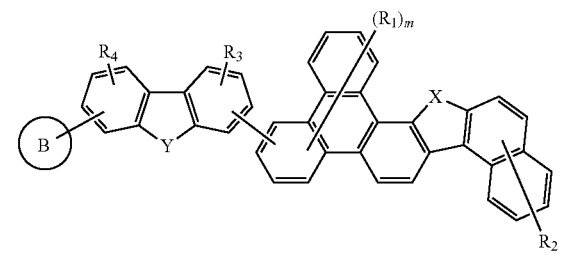
formula(20)
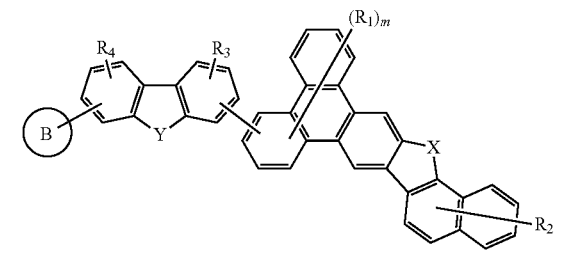
formula(21)
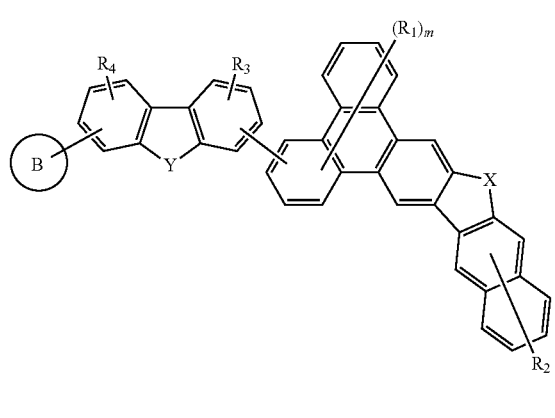
formula(22)
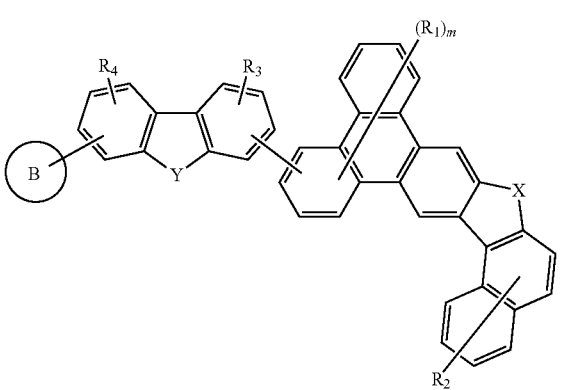
formula(23)
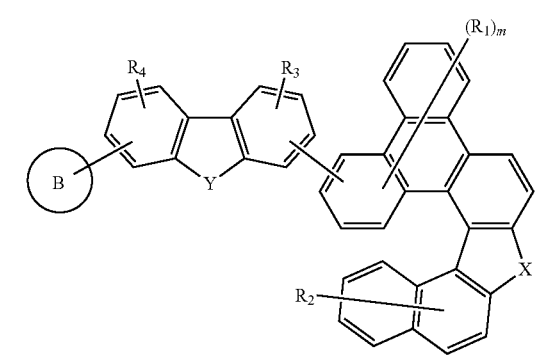
formula(24)
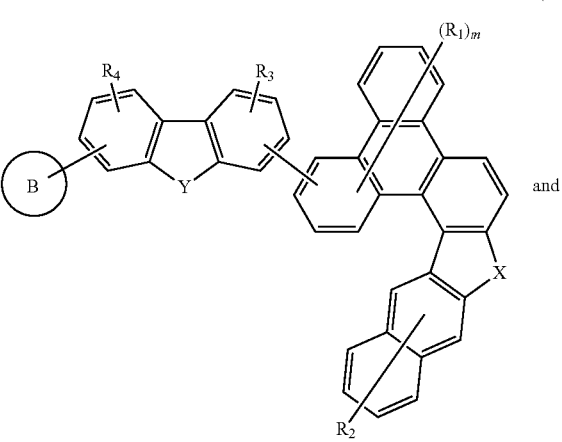
and formula(25)

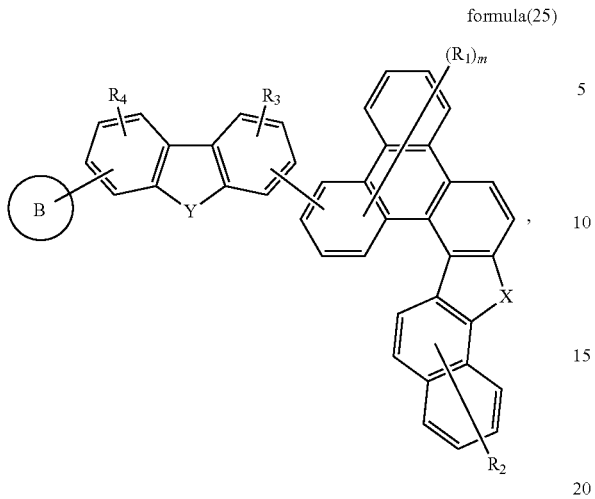

wherein m represents an integer of 0 to 7.

In an organic compound of formula (1), each of $R_1$ to $R_7$ may be optionally substituted by a halogen, an alkyl group, an aryl group, or a heteroaryl group.

In an organic compound of formula (1), ring B may be selected from the group consisting of a substituted or unsubstituted naphthyl group, an substituted or unsubstituted anthracenyl group, a substituted or unsubstituted phenanthrenyl group, a substituted or unsubstituted fluorene group, a substituted or unsubstituted pyrenyl group, a substituted or unsubstituted chrysenyl group, a substituted or unsubstituted fluoranthenyl group, a substituted or unsubstituted benzofluorene group, a substituted or unsubstituted triphenylene group and a substituted or unsubstituted perylenyl group, and combinations thereof. Preferably, ring B represents one of the following substituents:

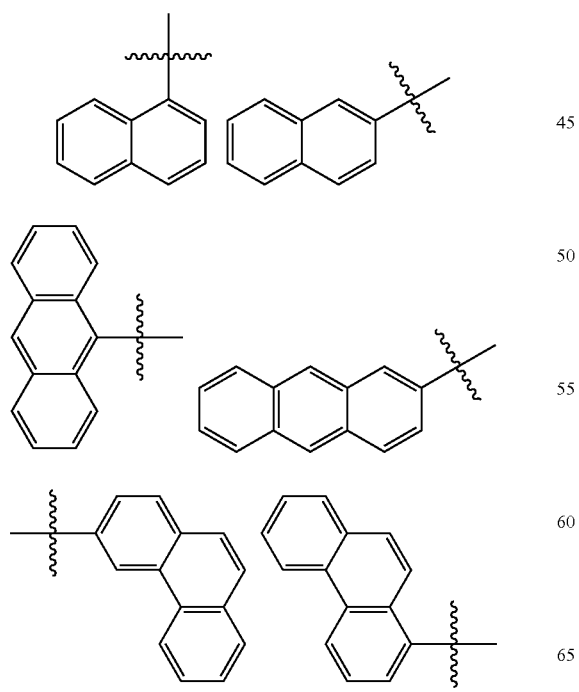

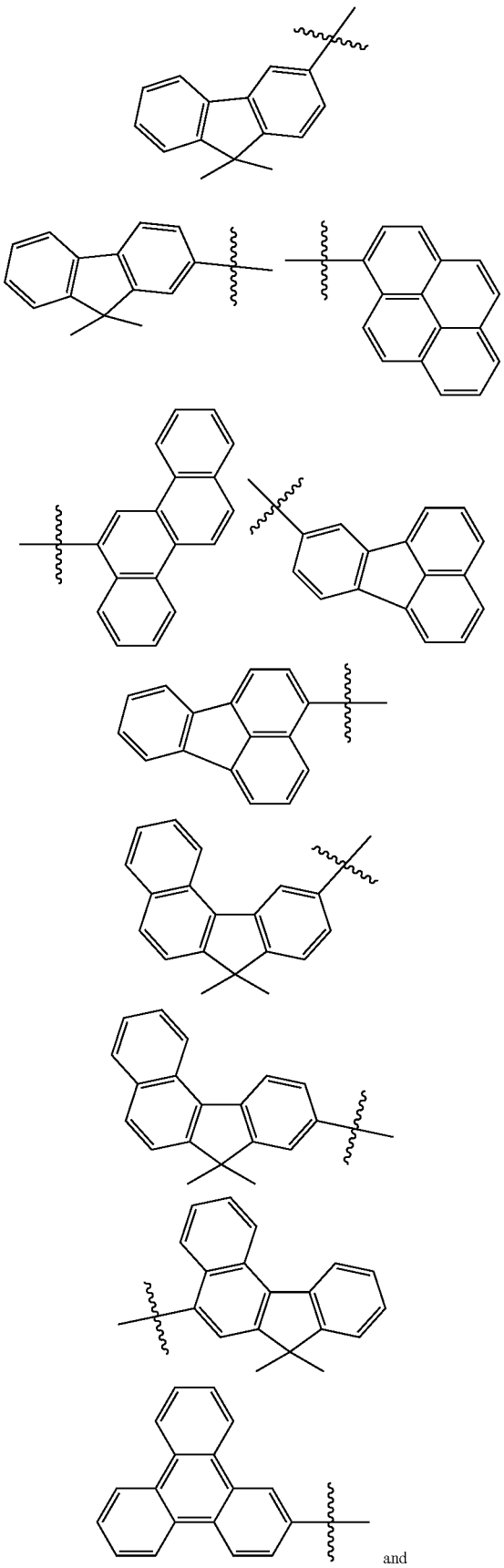

and

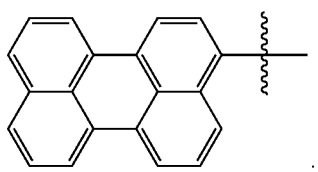
The organic compound of formula (1) may also be represented by one of the following formulas:
Compound 1
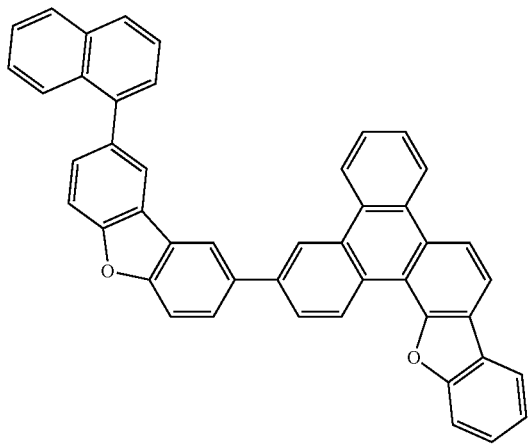
Compound 2
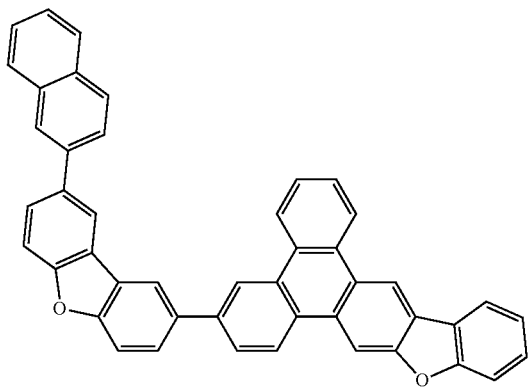
Compound 3
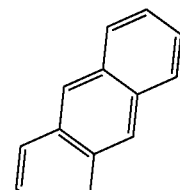
Compound 4
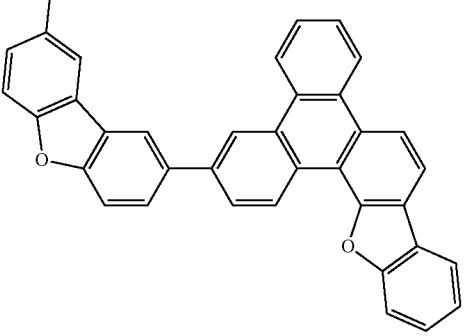
Compound 5
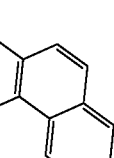
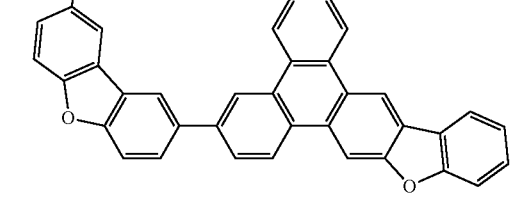
Compound 6
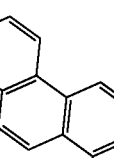
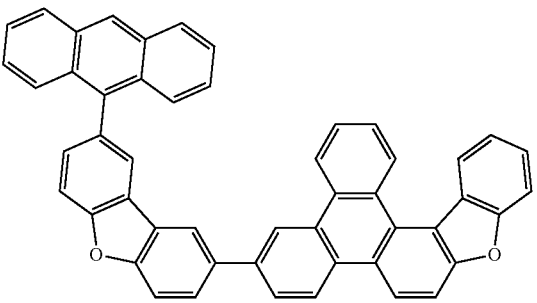
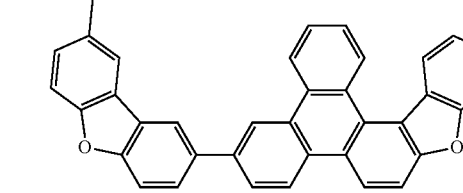

Compound 7
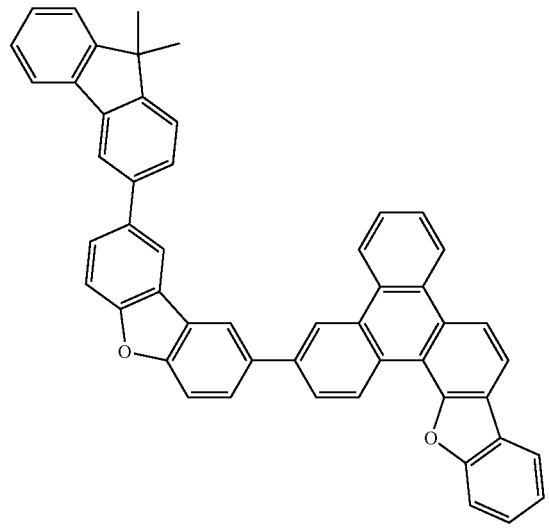
Compound 8
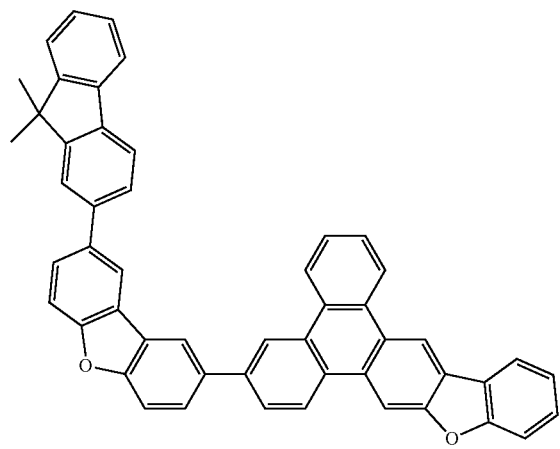
Compound 9
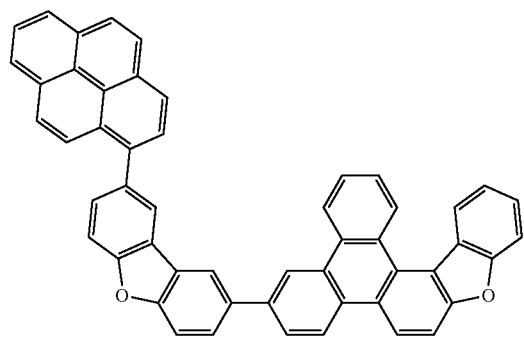
Compound 10
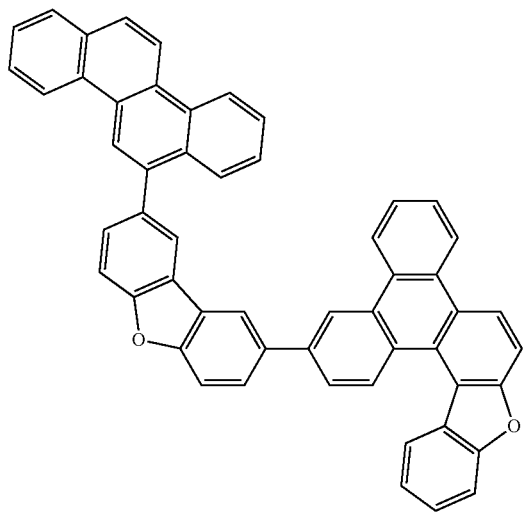
Compound 11
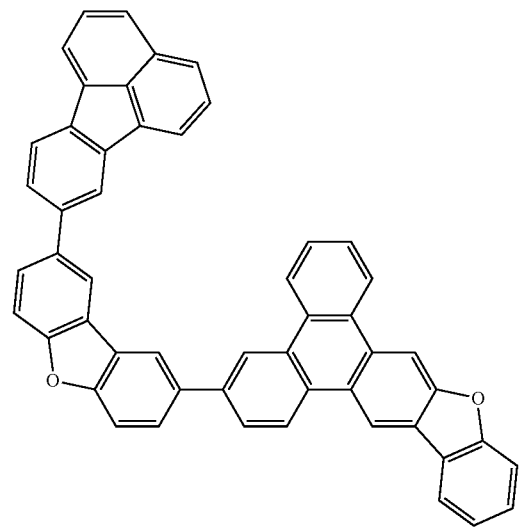
Compound 12
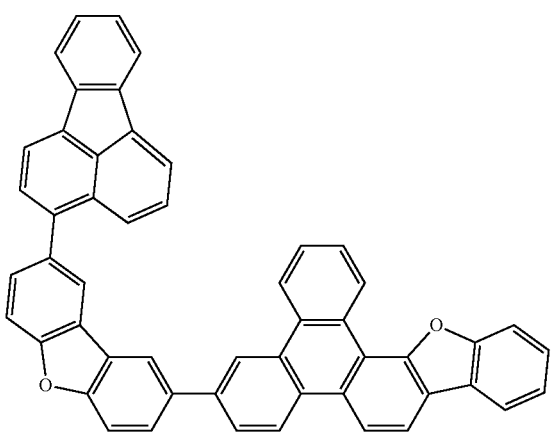

Compound 13
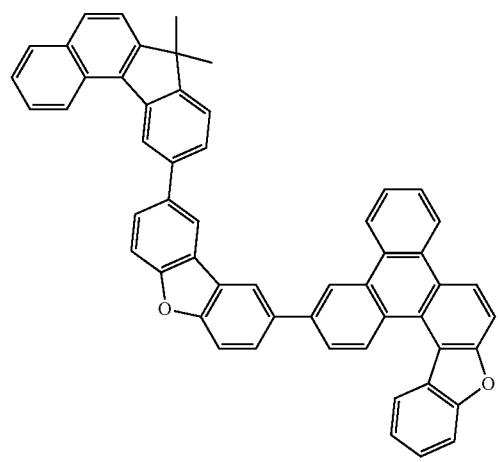
Compound 14
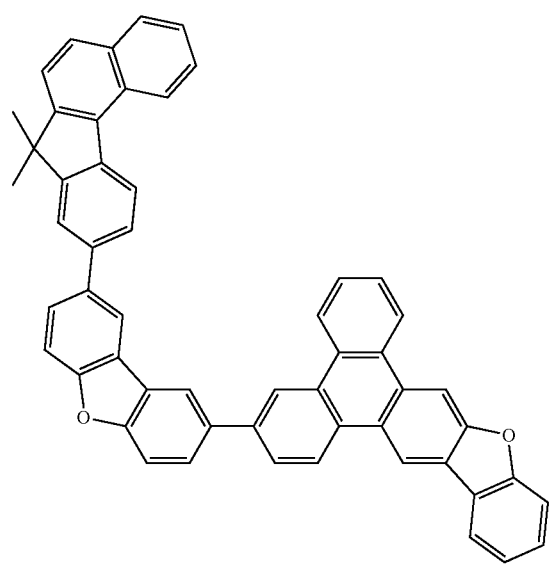
Compound 15
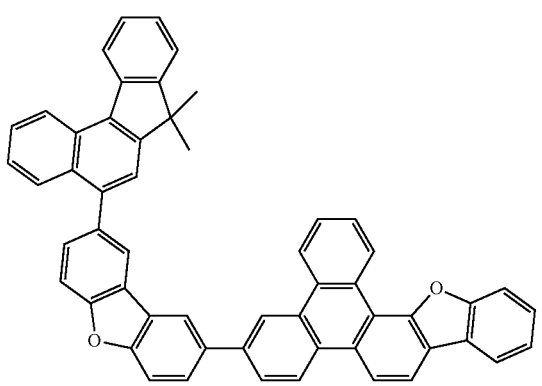
Compound 16
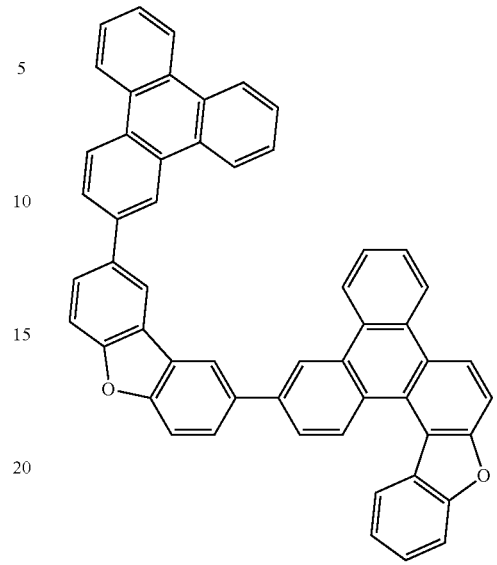
Compound 17
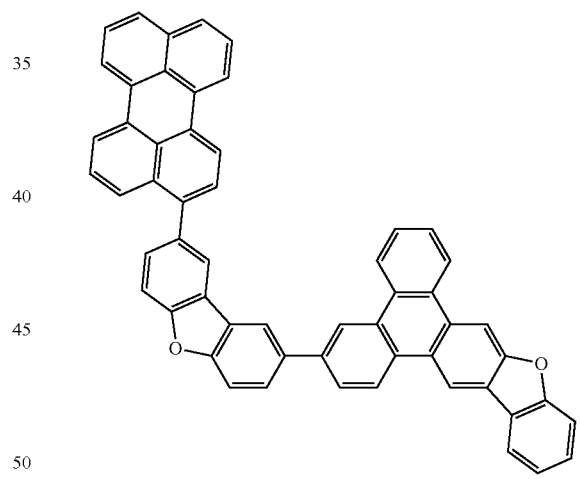
Compound 18
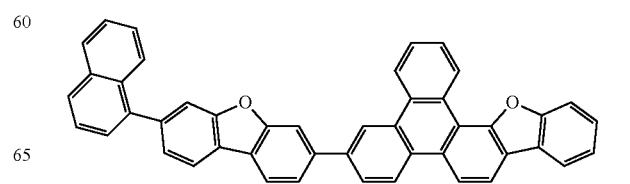

Compound 19
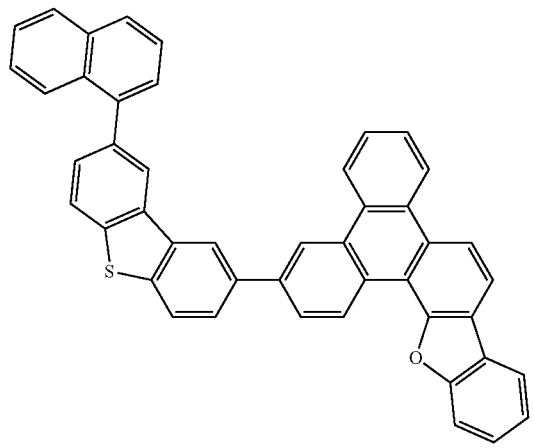
Compound 20
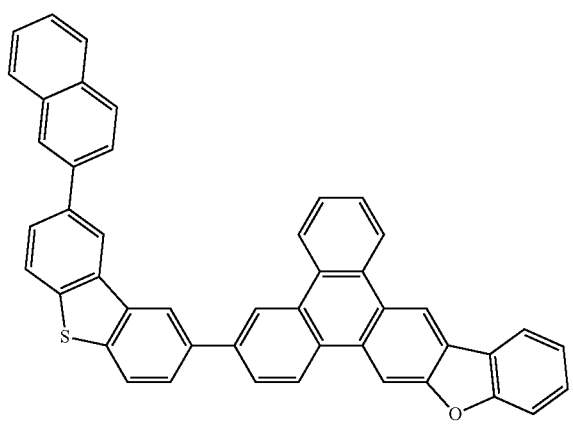
Compound 21
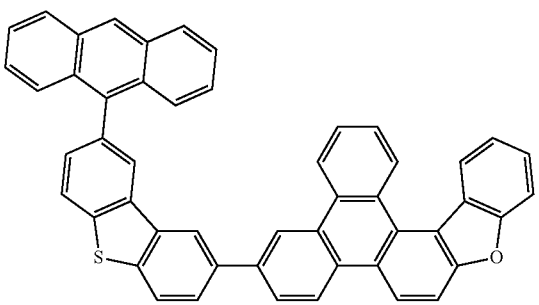
Compound 22
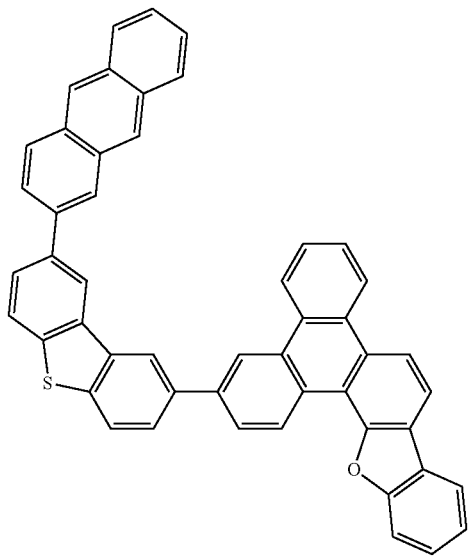
Compound 23
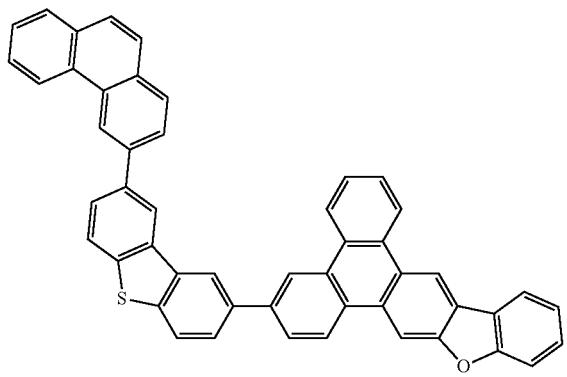
Compound 24
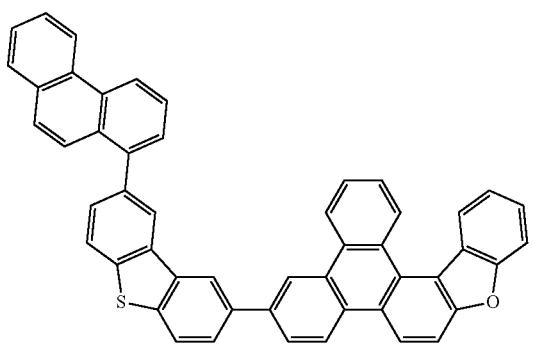

Compound 25
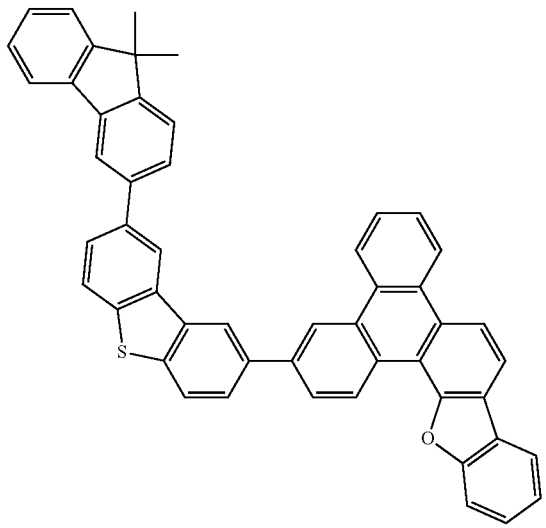
Compound 28
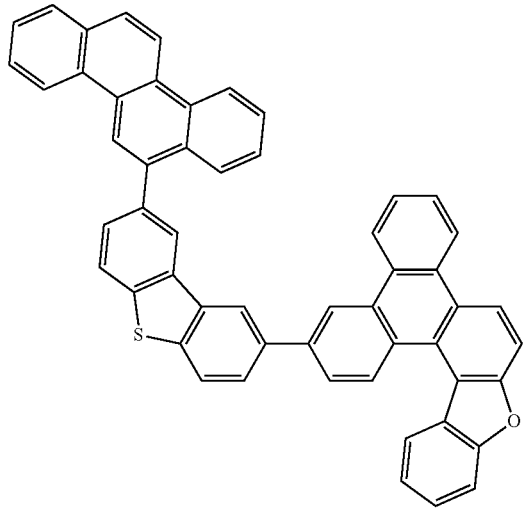
Compound 26
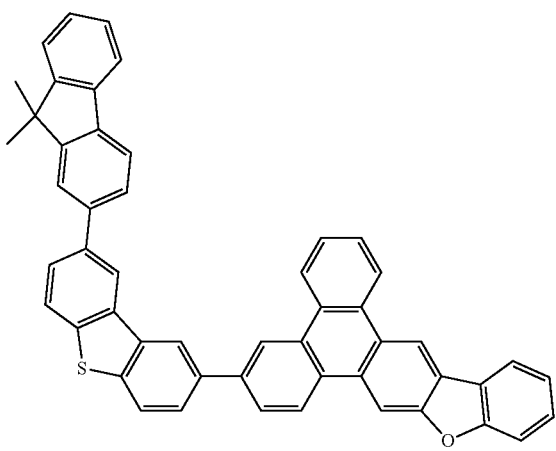
Compound 29
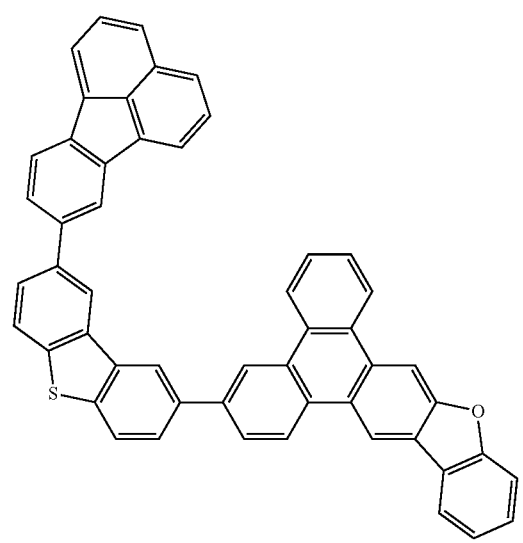
Compound 27
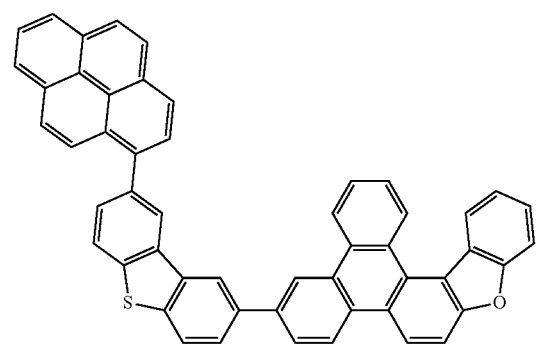
Compound 30
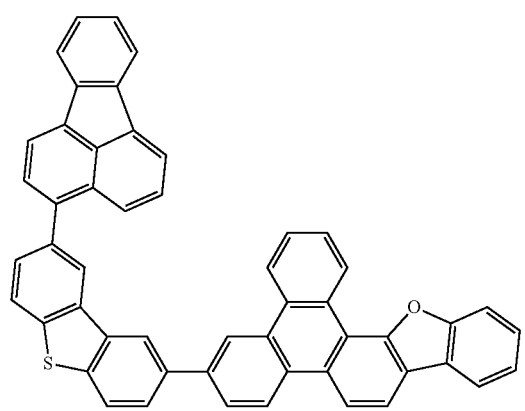

-continued
Compound 31
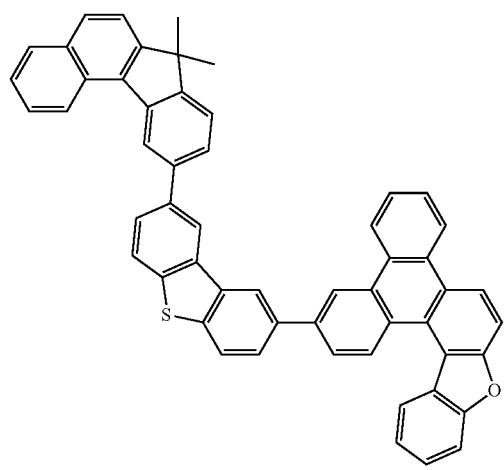
Compound 32
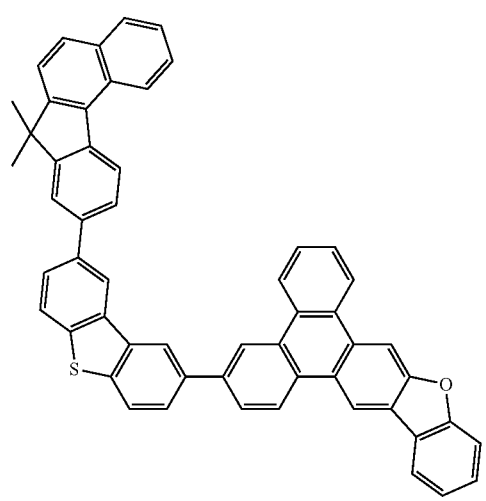
Compound 33
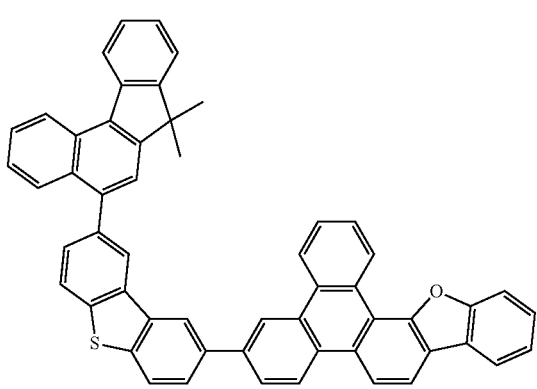
-continued
Compound 34
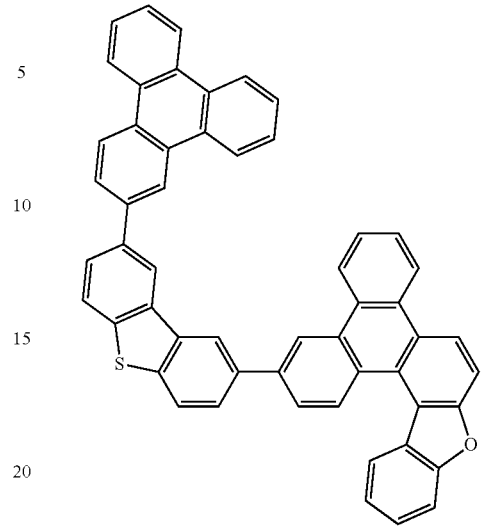
Compound 35
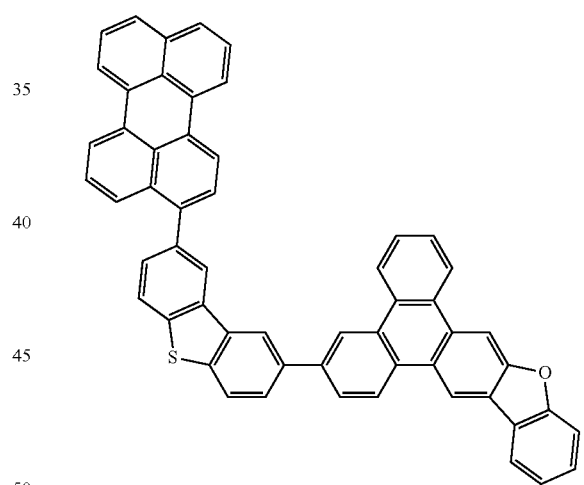
Compound 36
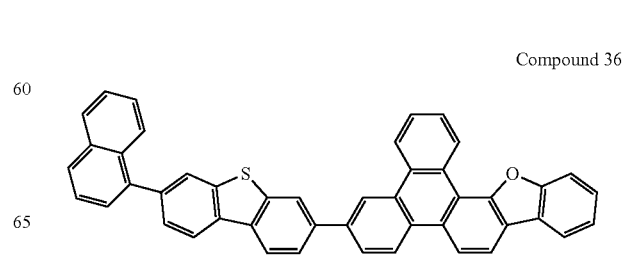

Compound 37
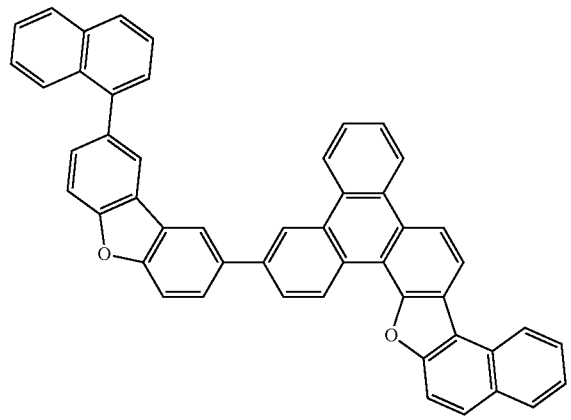
Compound 38
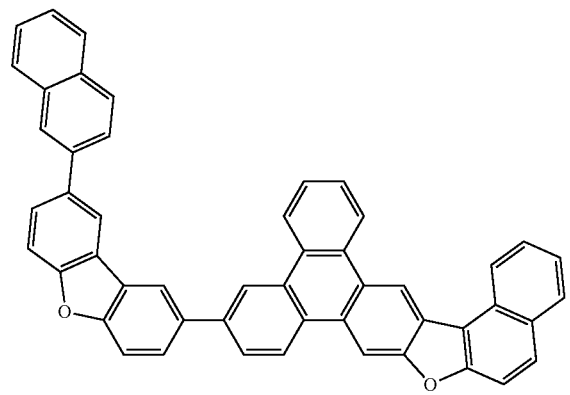
Compound 39
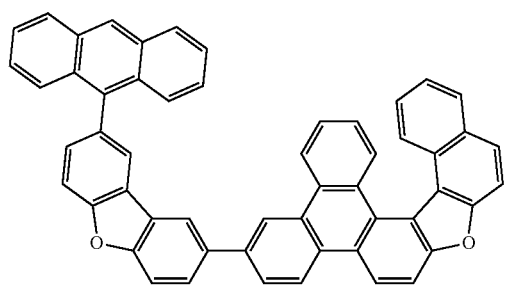
Compound 40
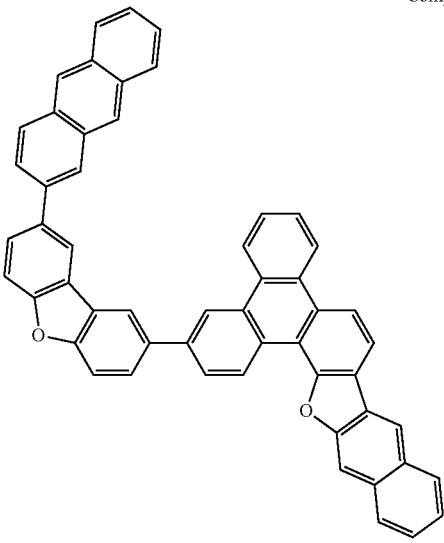
Compound 41
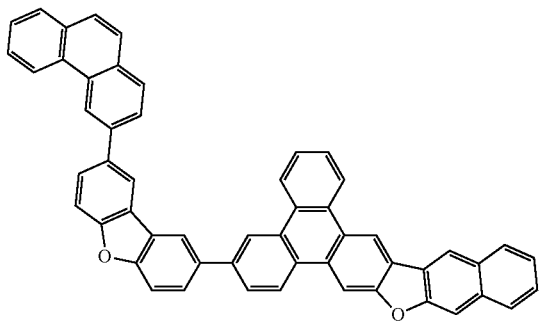
Compound 42
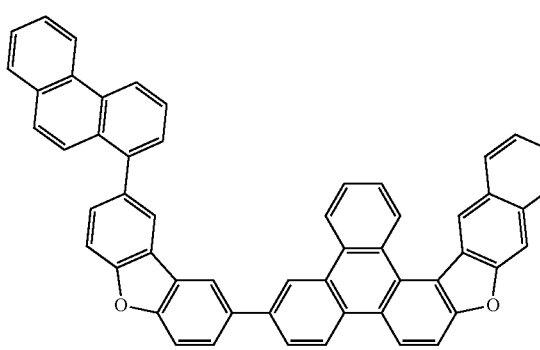

Compound 43
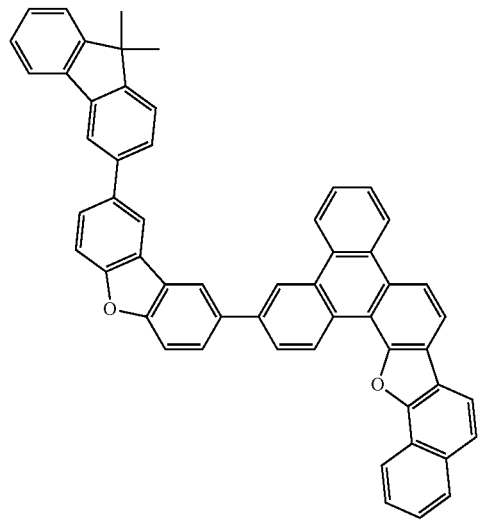
Compound 44
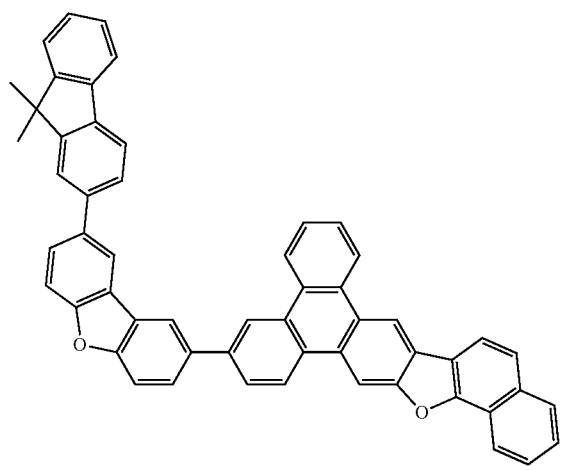
Compound 45
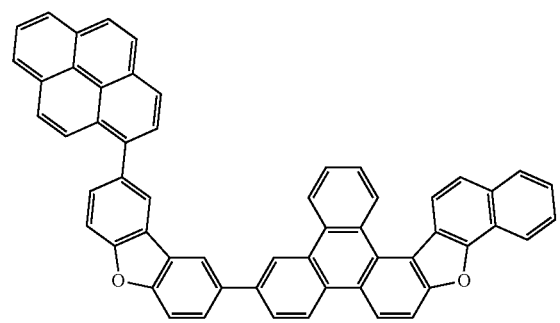
Compound 46
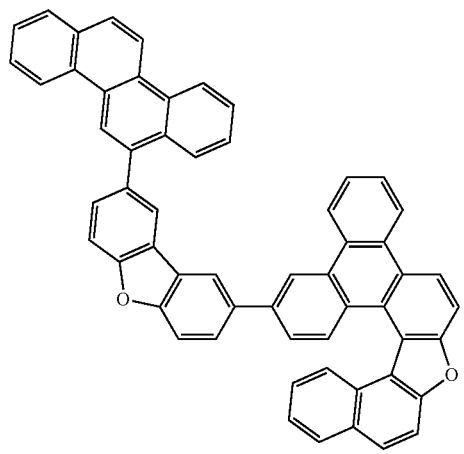
Compound 47
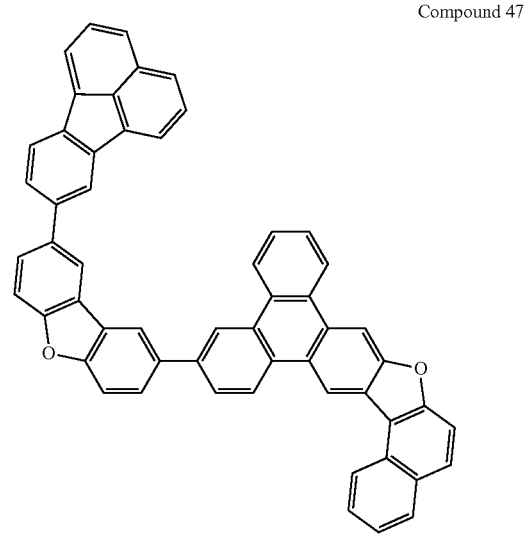
Compound 48
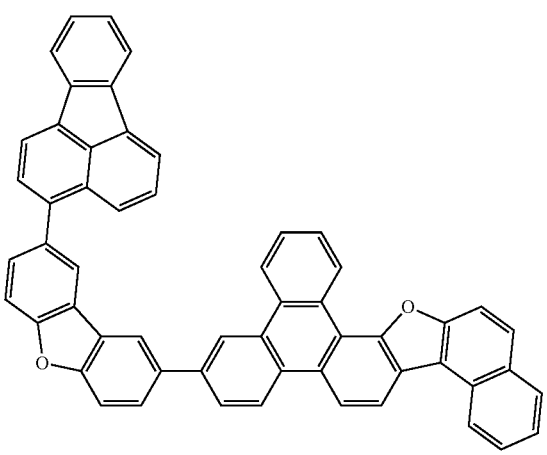

-continued
Compound 49
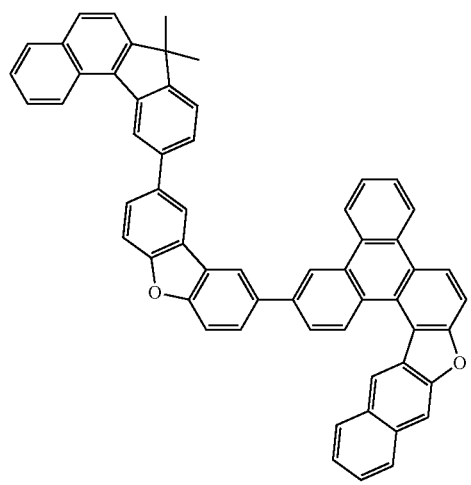
Compound 50
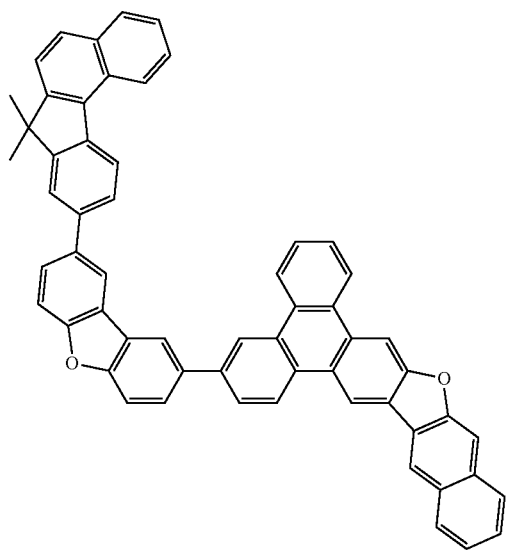
Compound 51
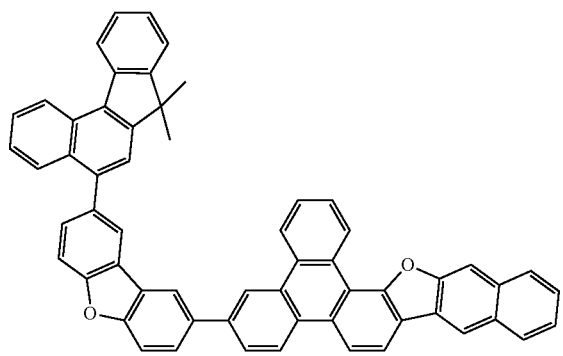
Compound 52
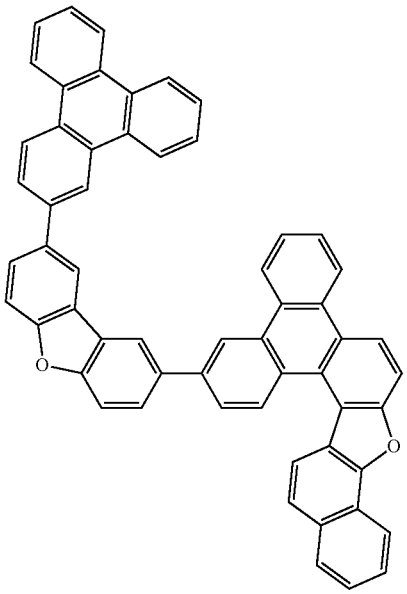
Compound 53
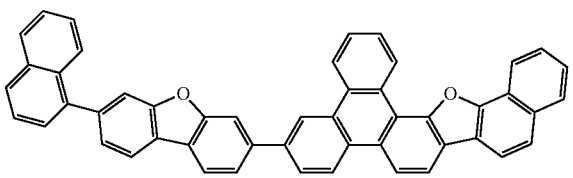
Compound 54

-continued
Compound 55
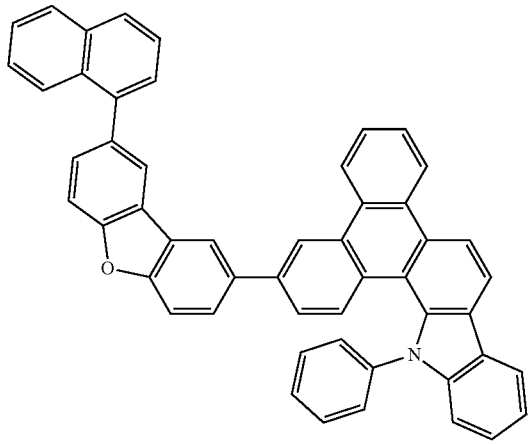
Compound 56
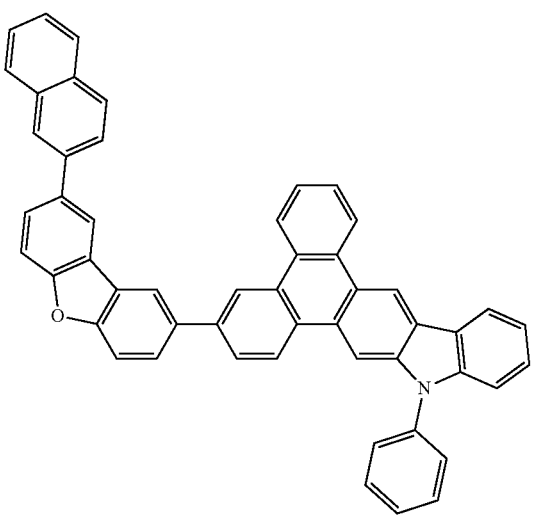
Compound 57
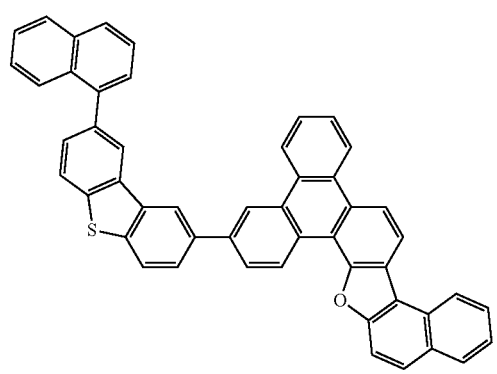
-continued
Compound 58
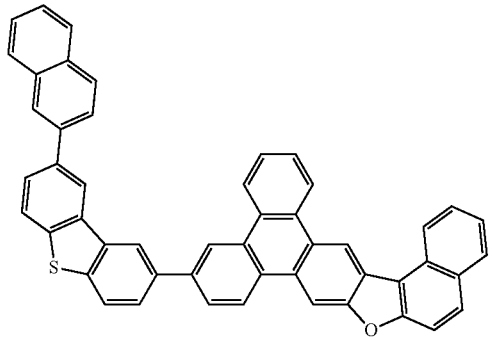
Compound 59
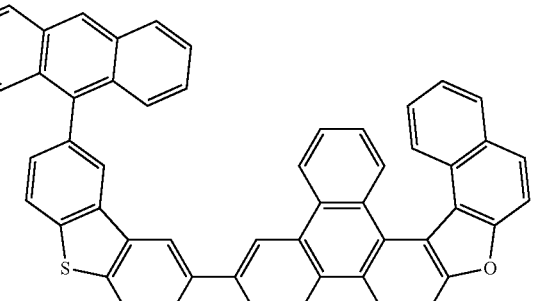
Compound 60
Compound 61
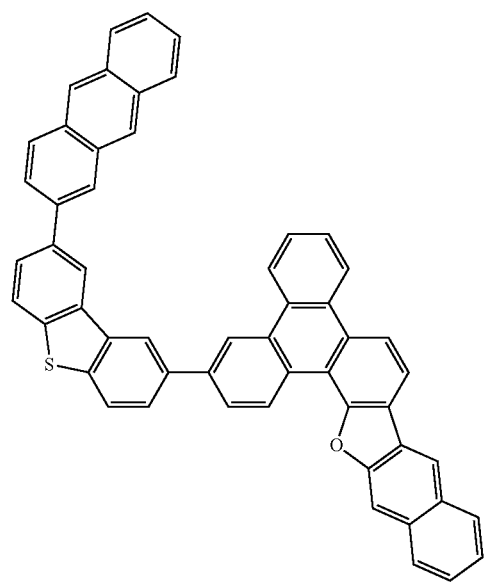

Compound 62
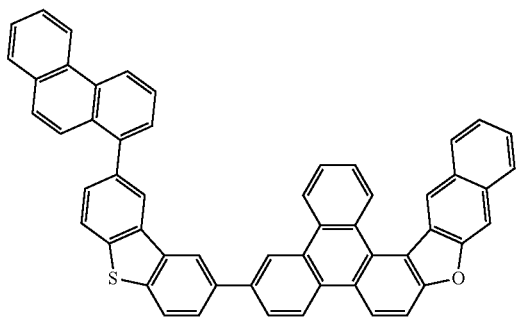
Compound 65
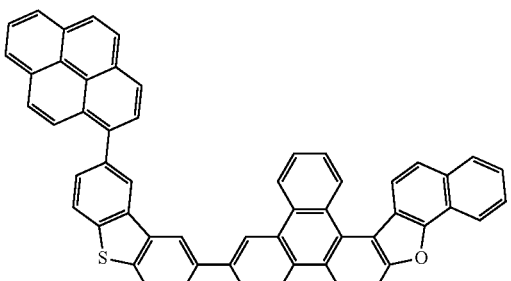
Compound 63
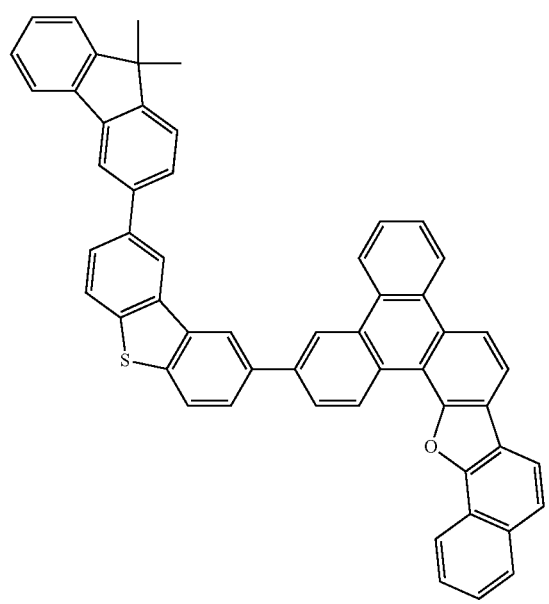
Compound 66
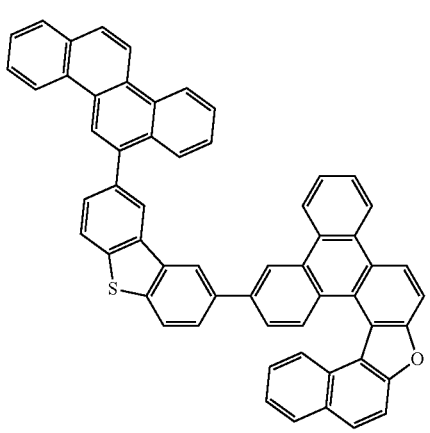
Compound 64
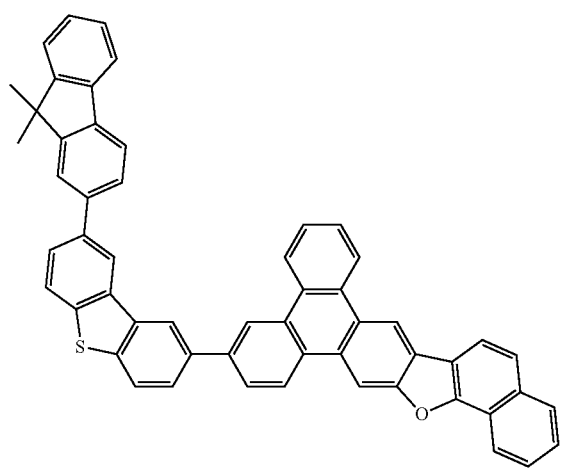
Compound 67
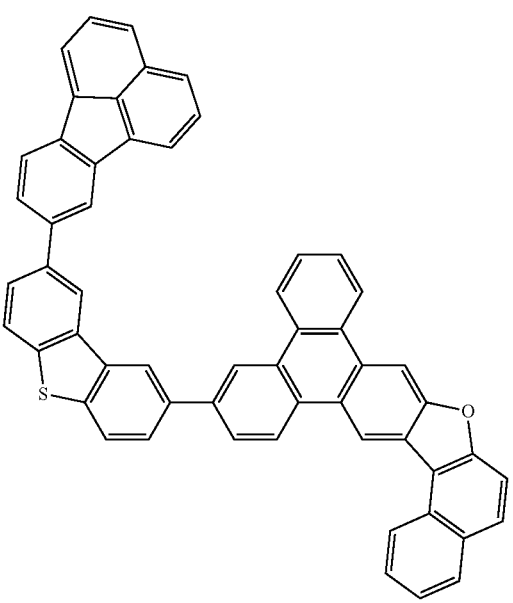

Compound 68
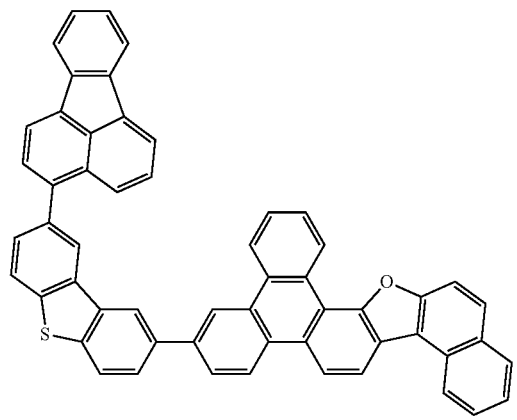
Compound 71
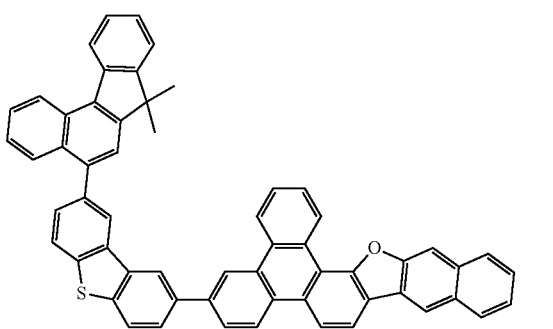
Compound 69
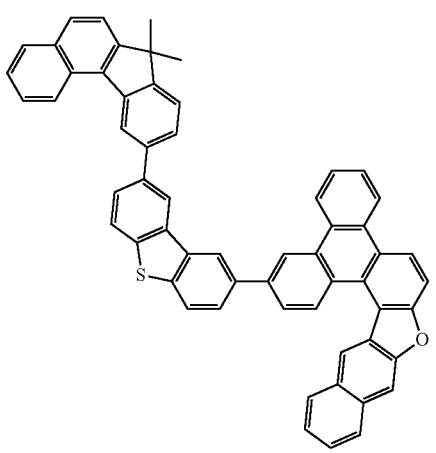
Compound 72
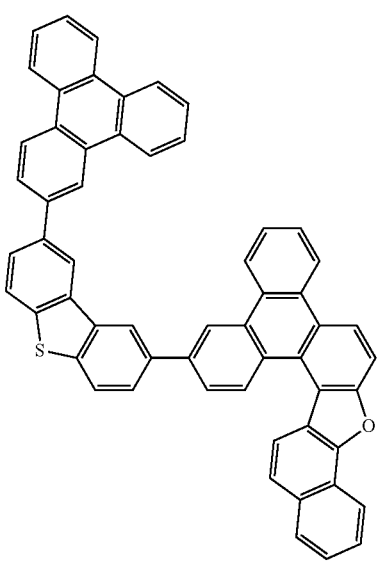
Compound 70
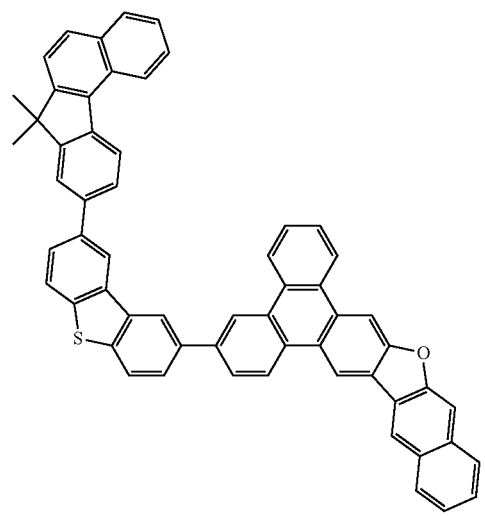
Compound 73
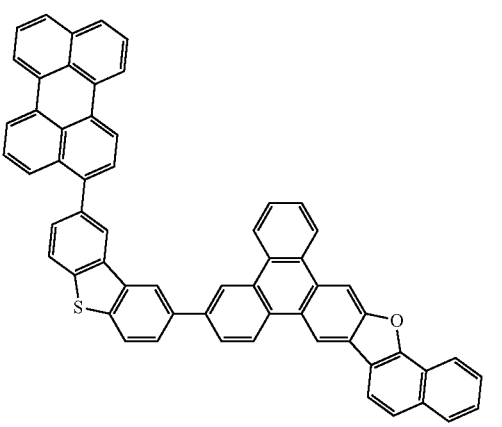
Compound 74
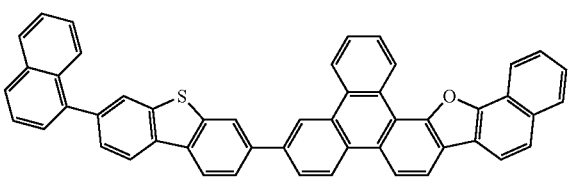

Compound 75
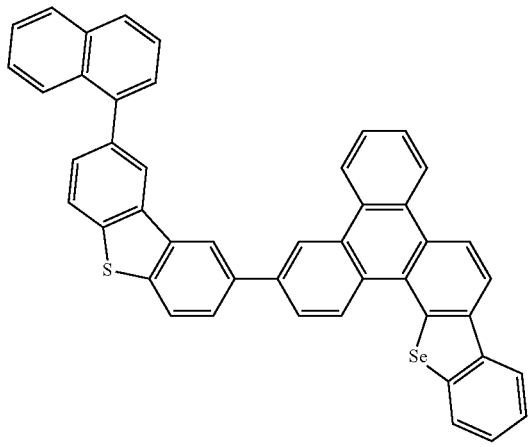
Compound 78
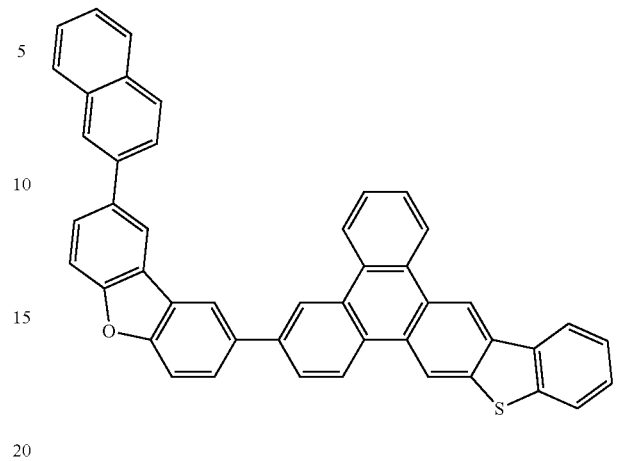
Compound 76
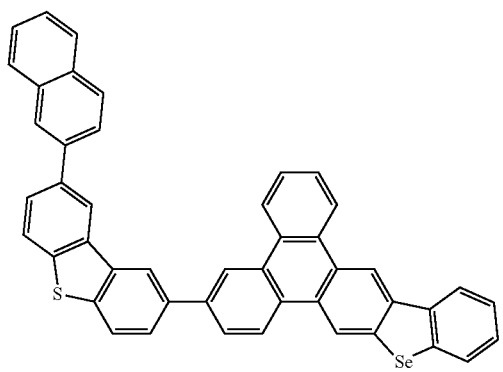
Compound 79
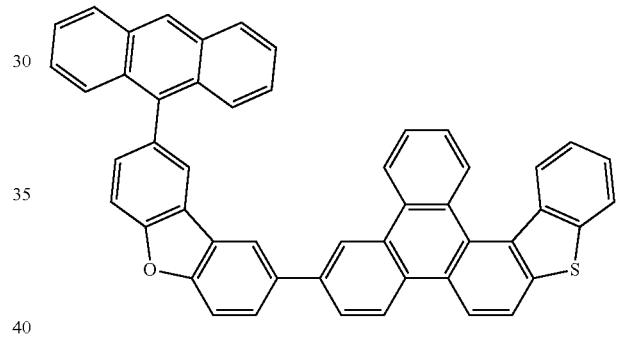
Compound 77
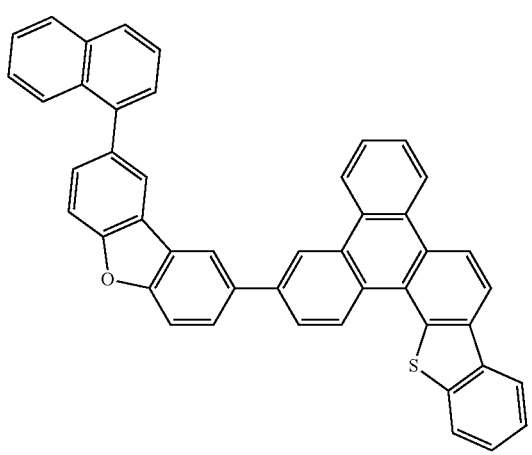
Compound 80
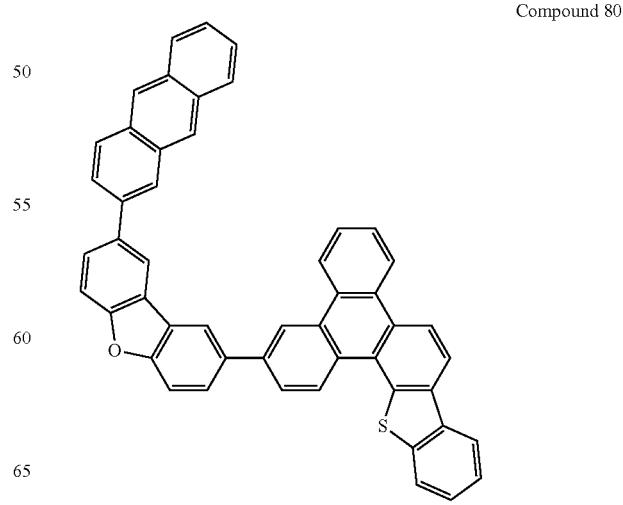

Compound 81
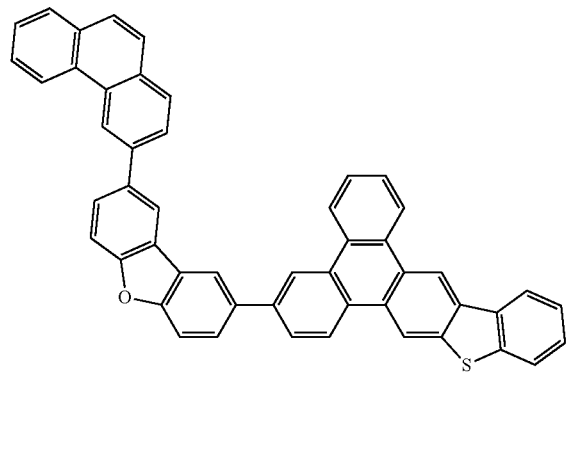
Compound 84
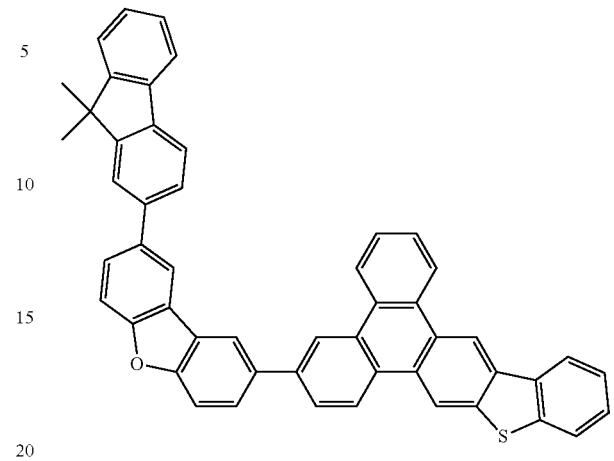
Compound 82
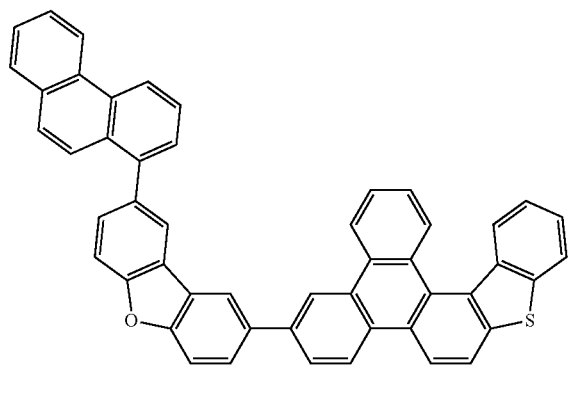
Compound 85
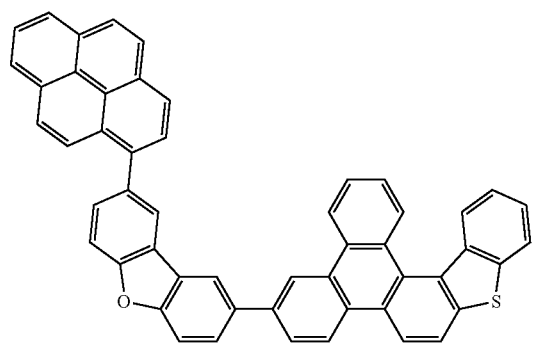
Compound 83
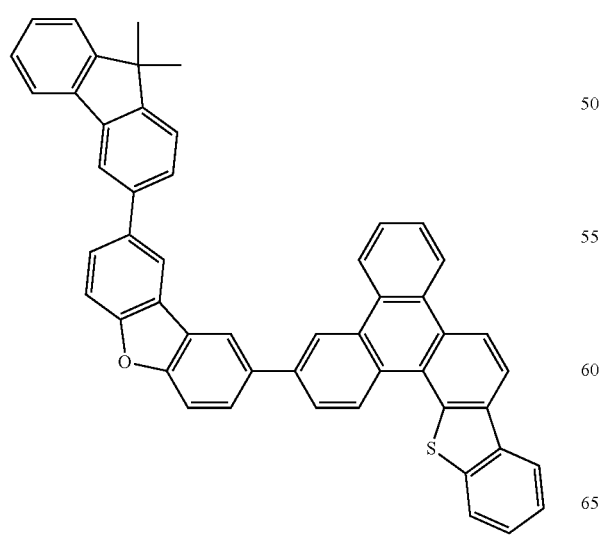
Compound 86
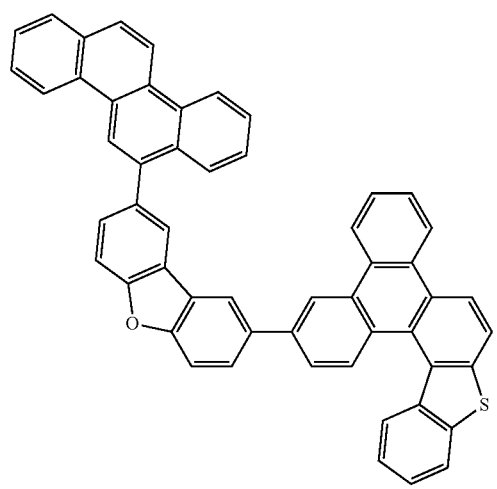

Compound 87
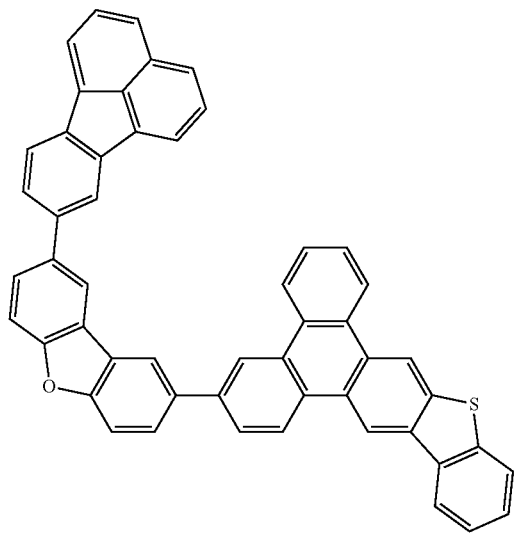
Compound 90
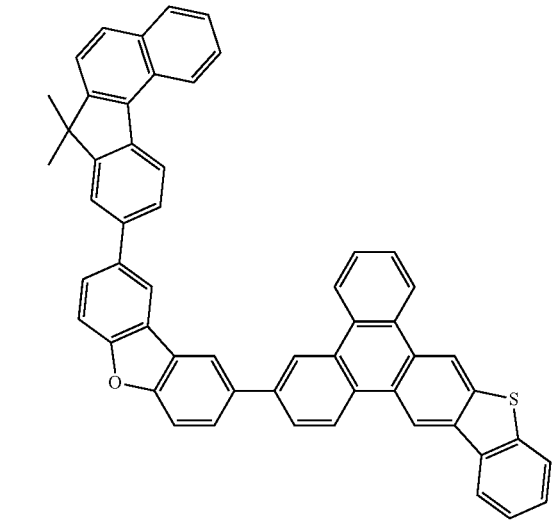
Compound 88
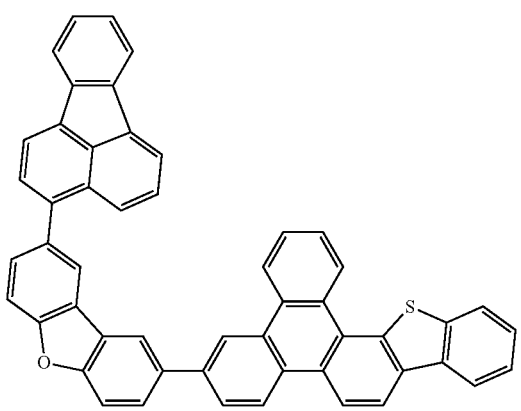
Compound 91
Compound 89
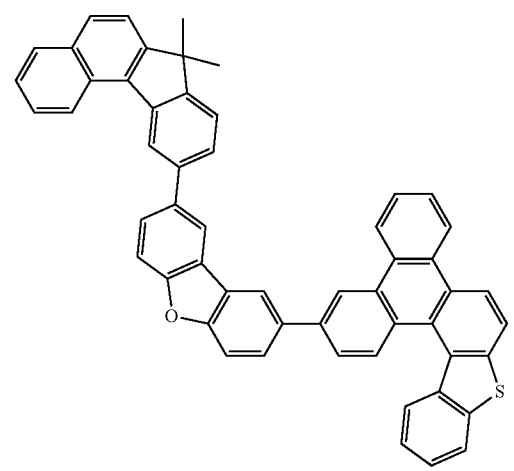
Compound 92
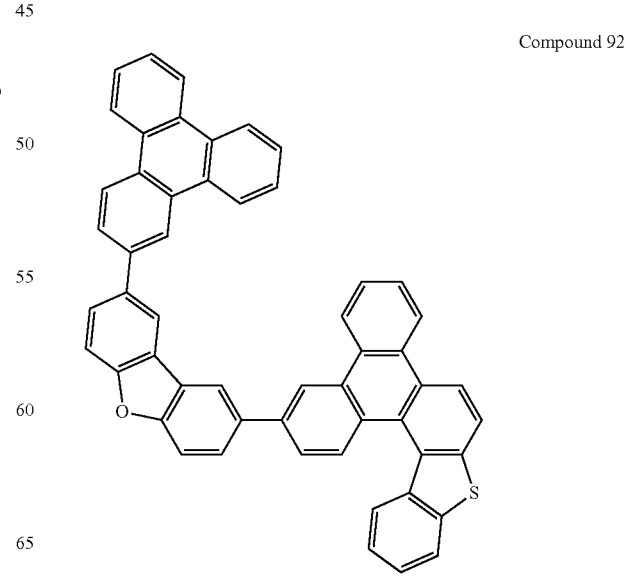

Compound 93
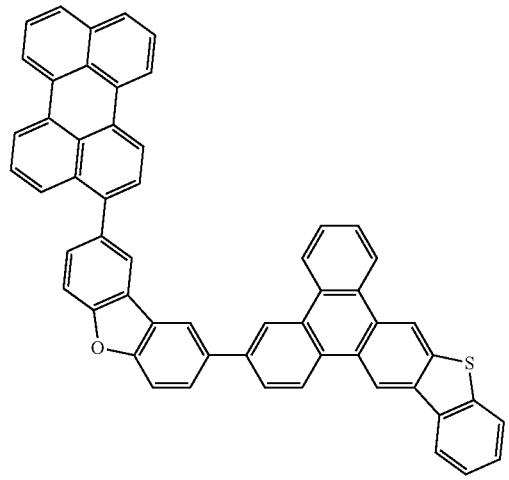
Compound 94
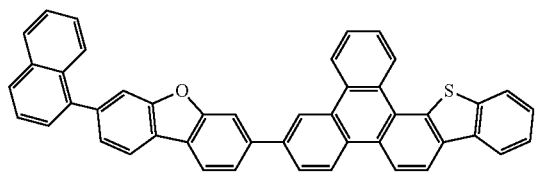
Compound 95
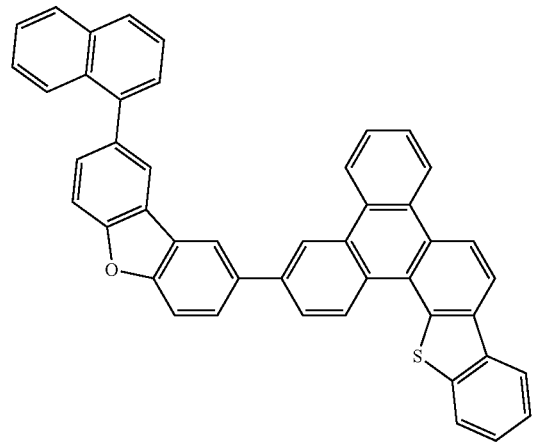
Compound 96
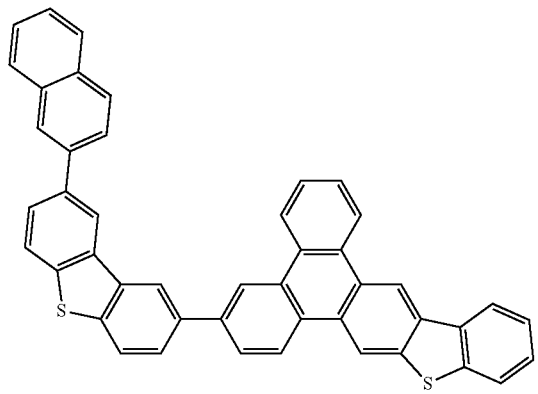
Compound 97
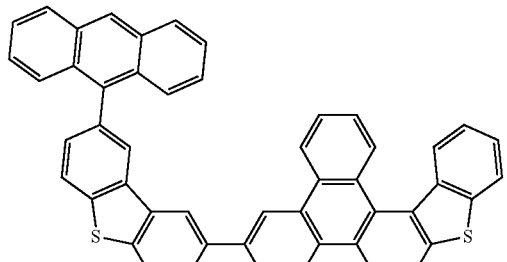
Compound 98
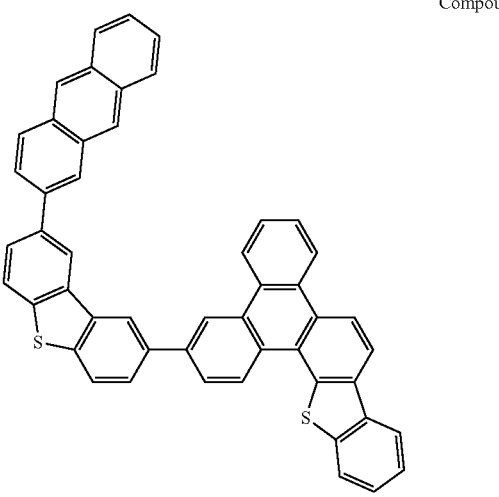
Compound 99
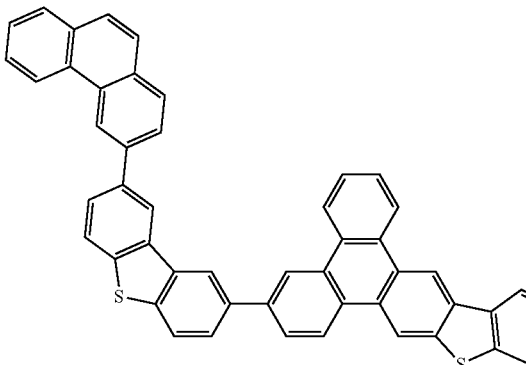
Compound 100
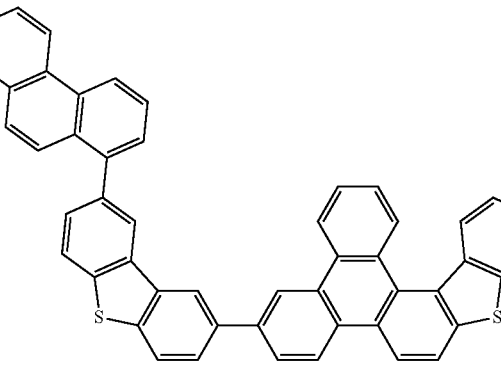

Compound 101
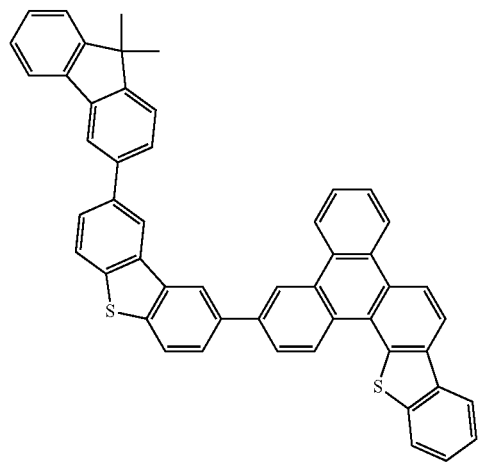
Compound 104
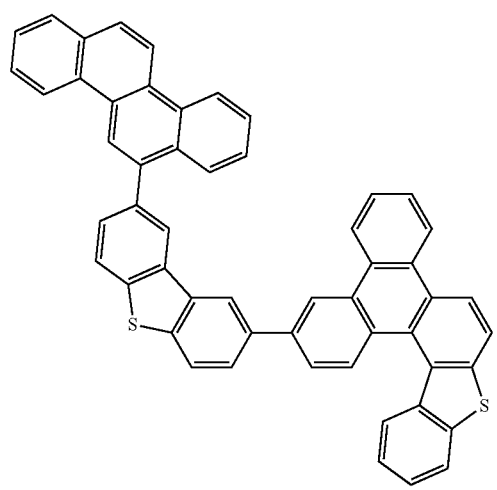
Compound 102
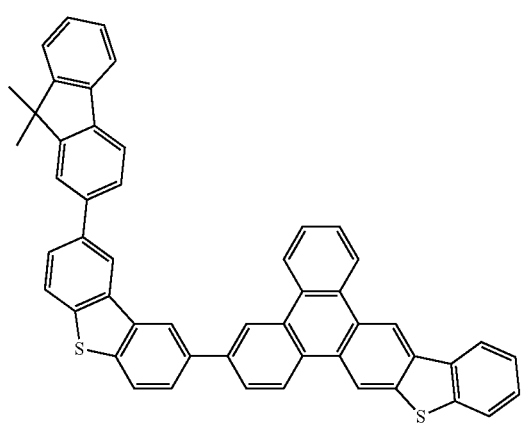
Compound 105
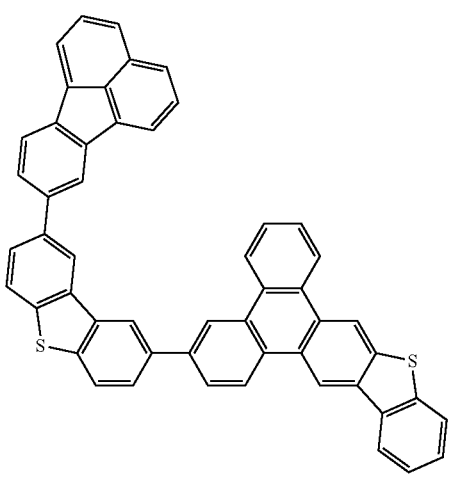
Compound 103
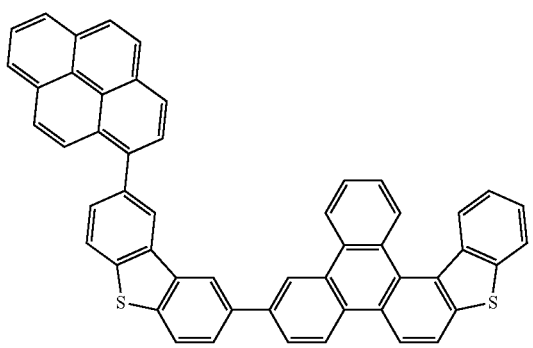
Compound 106
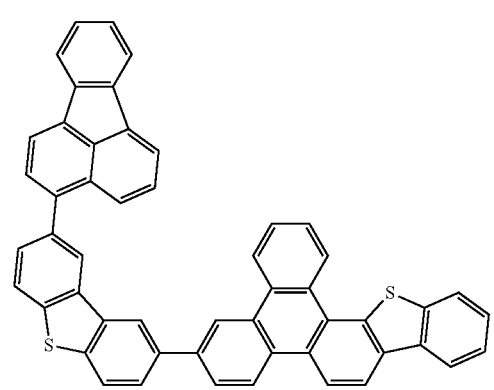

Compound 107
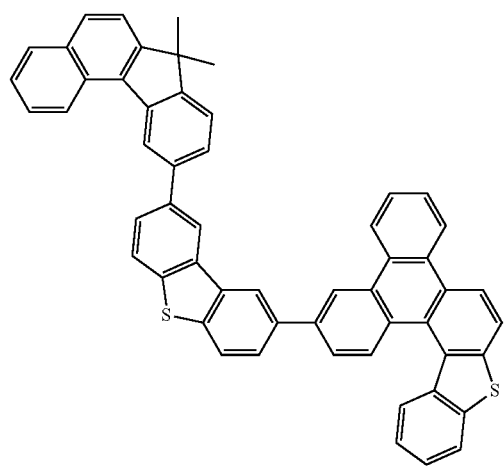
Compound 108
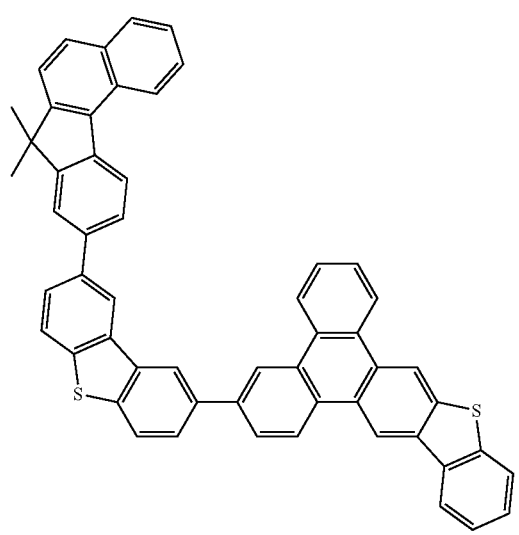
Compound 109
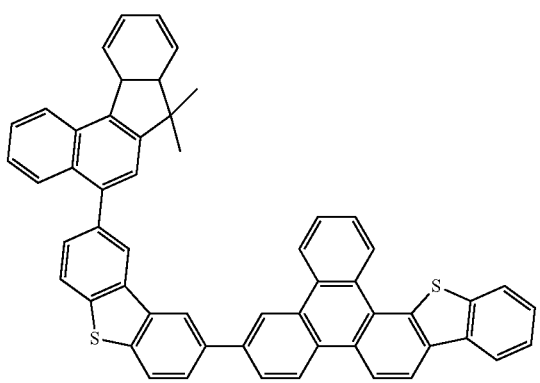
Compound 110
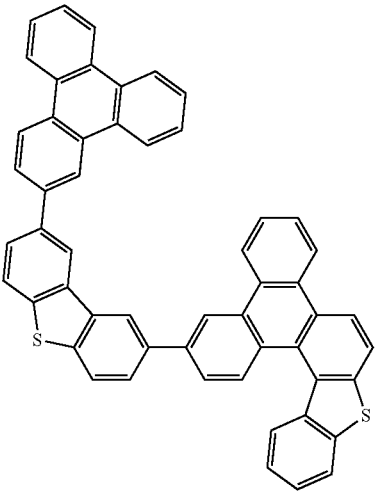
Compound 111
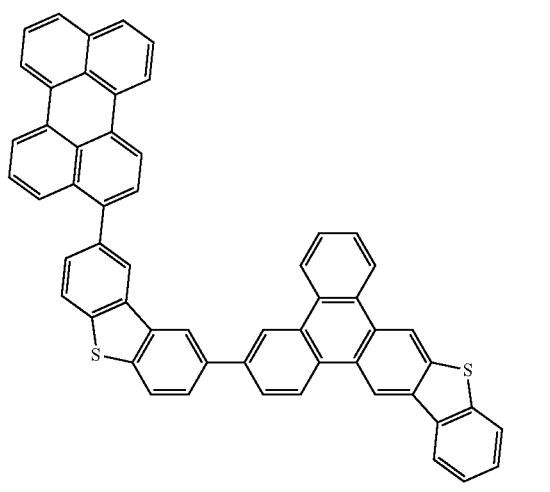
Compound 112
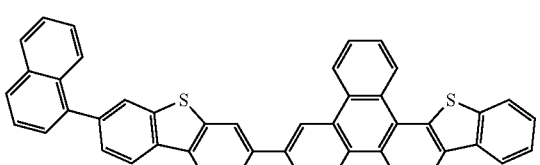
Compound 113
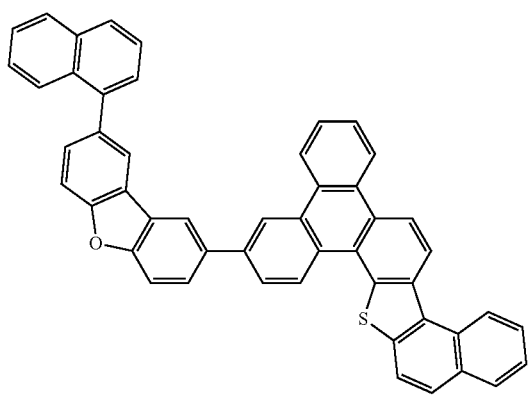

Compound 114
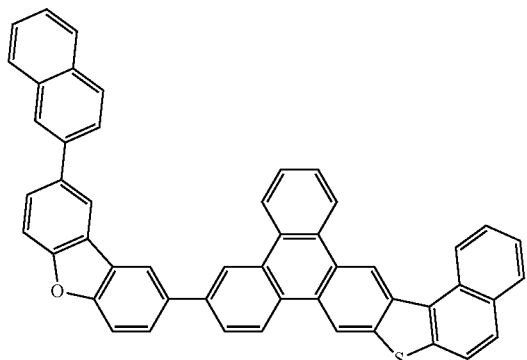
Compound 118
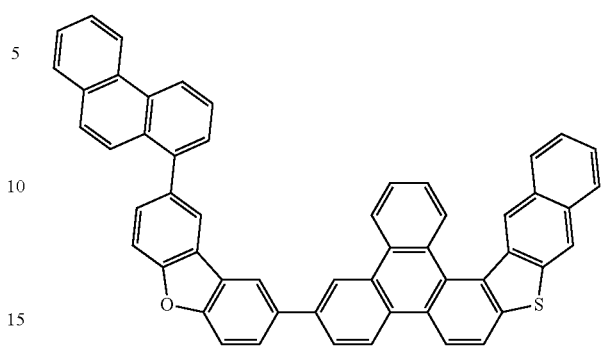
Compound 115
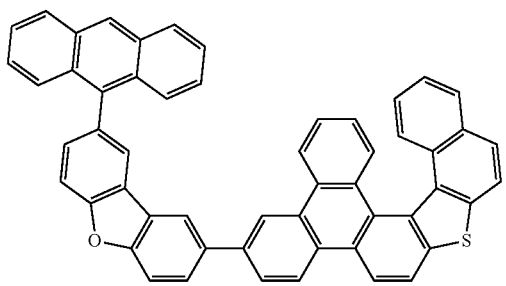
Compound 119
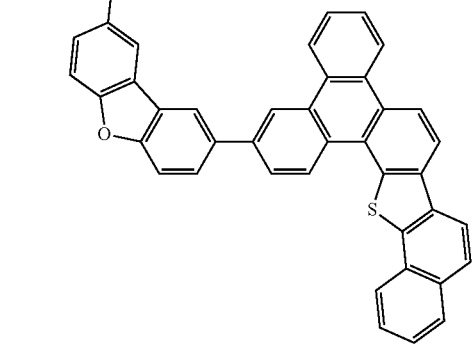
Compound 116
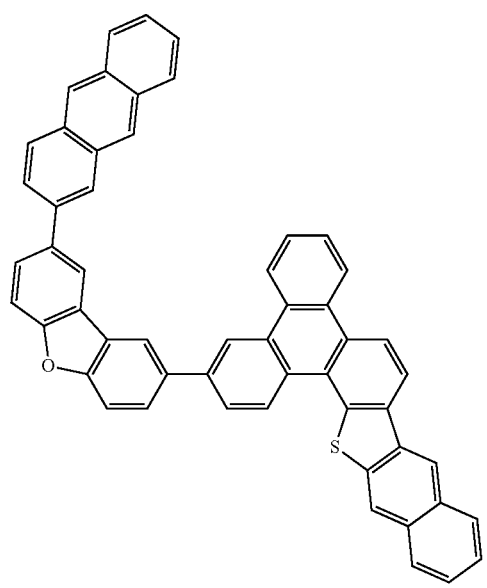
Compound 117
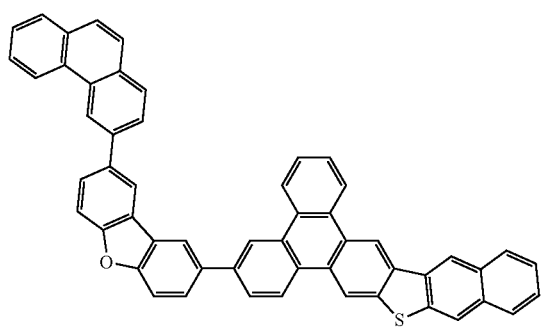
Compound 120
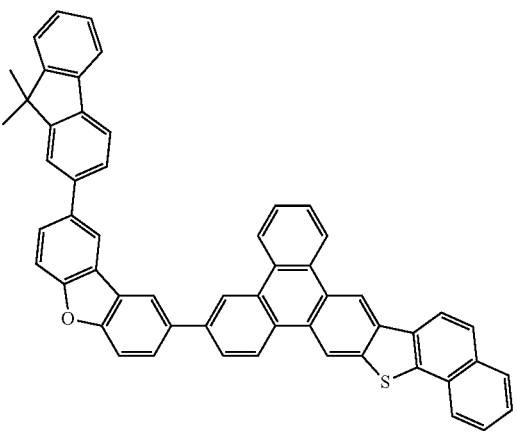

Compound 121
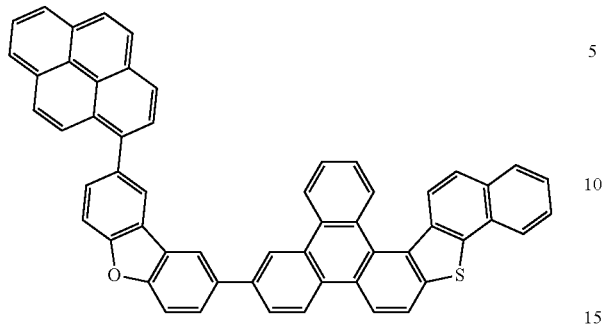
Compound 122
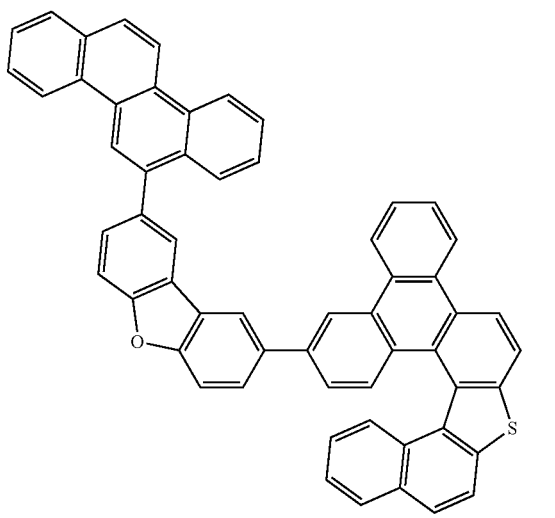
Compound 123
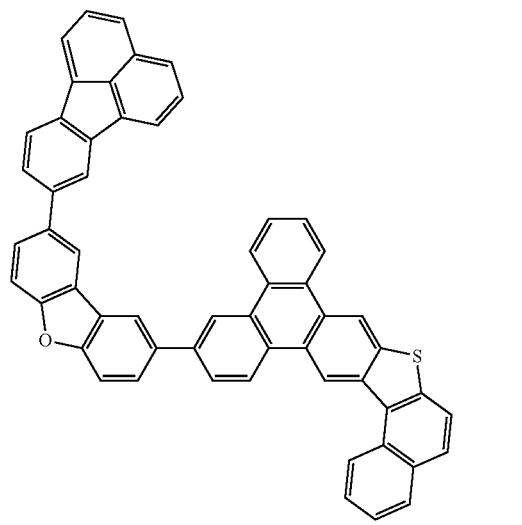
Compound 124
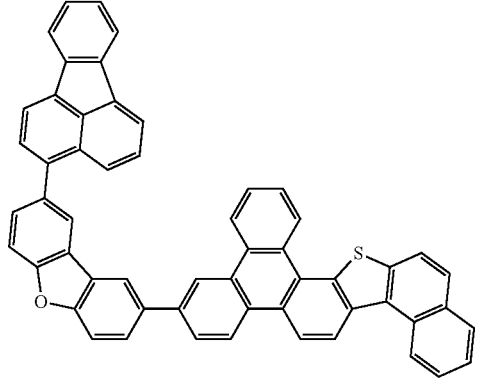
Compound 125
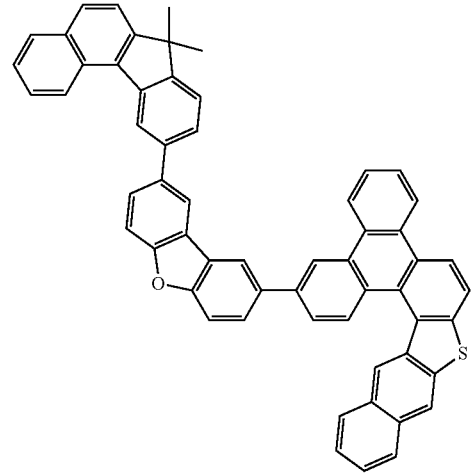
Compound 126
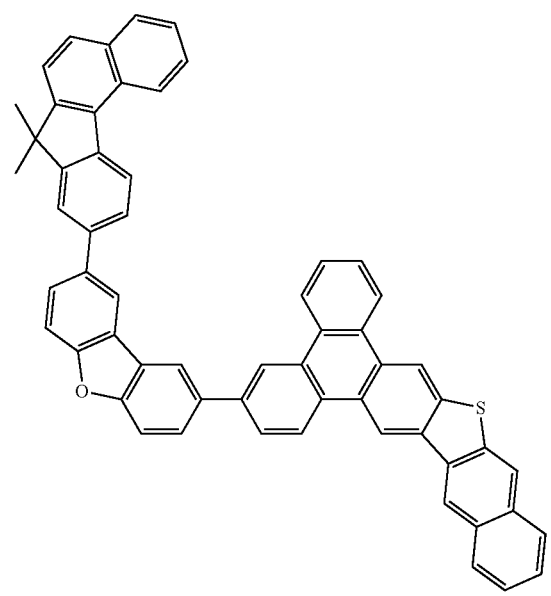

Compound 127
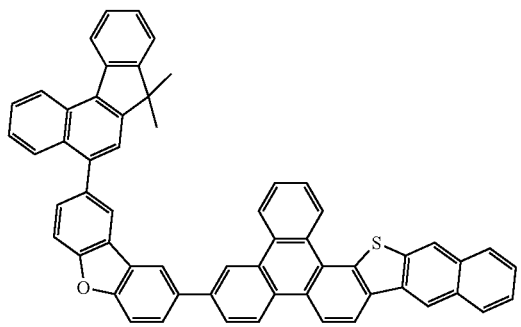
Compound 128
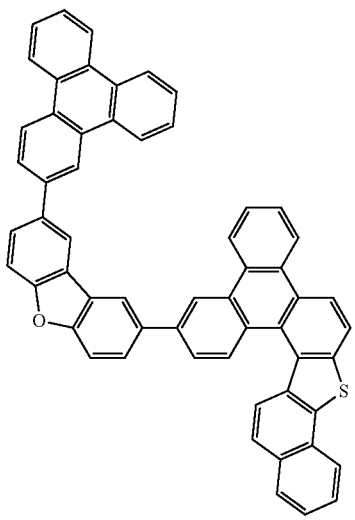
Compound 129
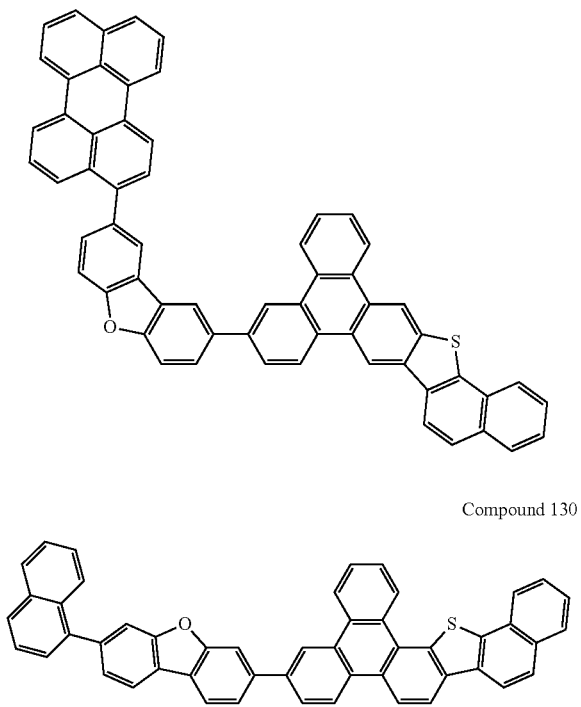
Compound 130
Compound 131
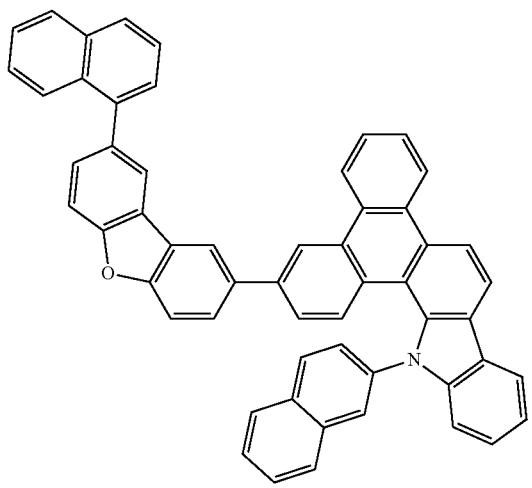
Compound 132
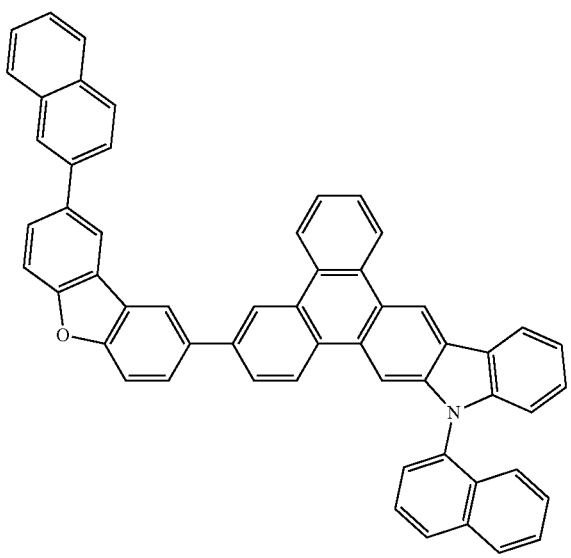
Compound 133
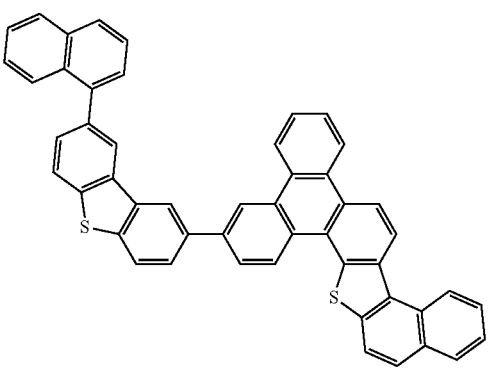

Compound 134
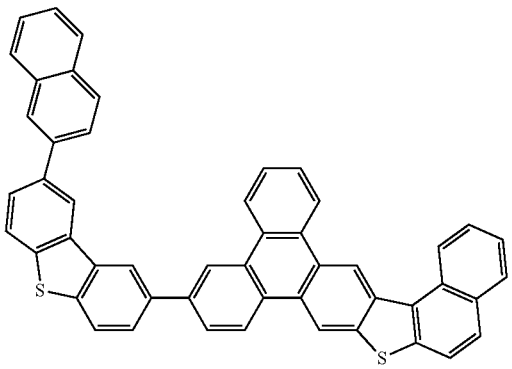
Compound 137
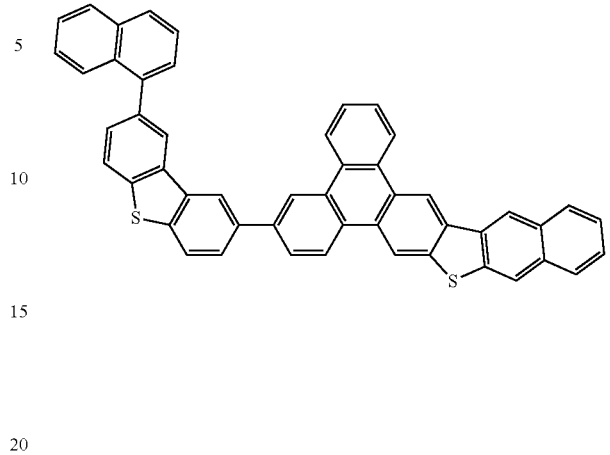
Compound 135
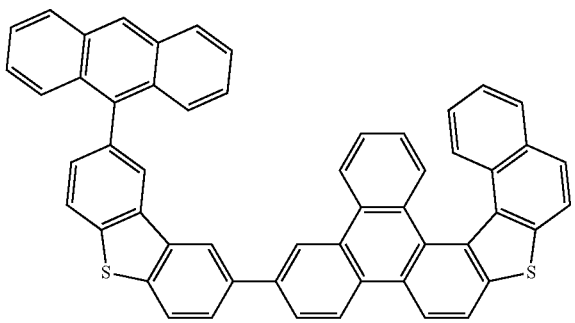
Compound 138
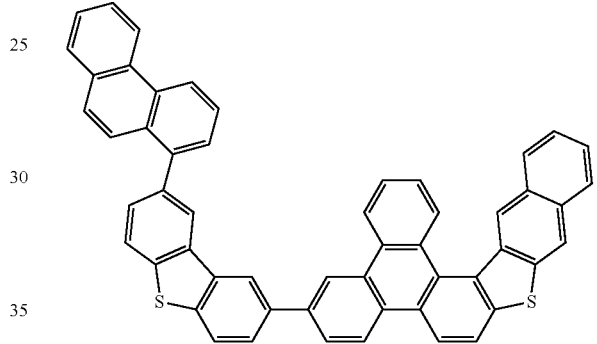
Compound 136
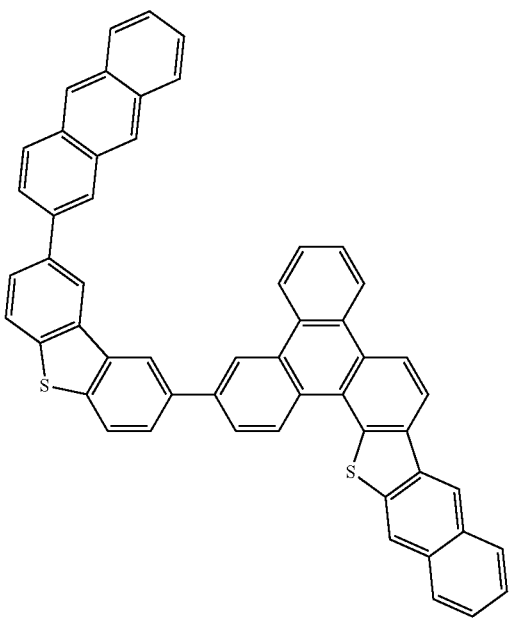
Compound 139
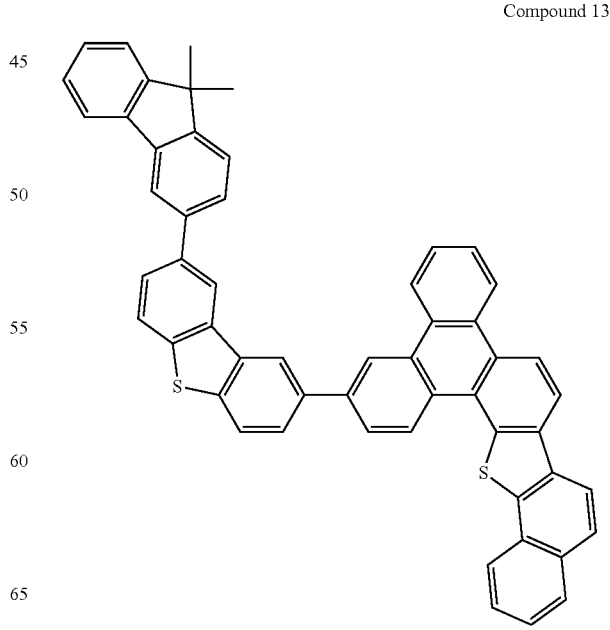

-continued
Compound 140
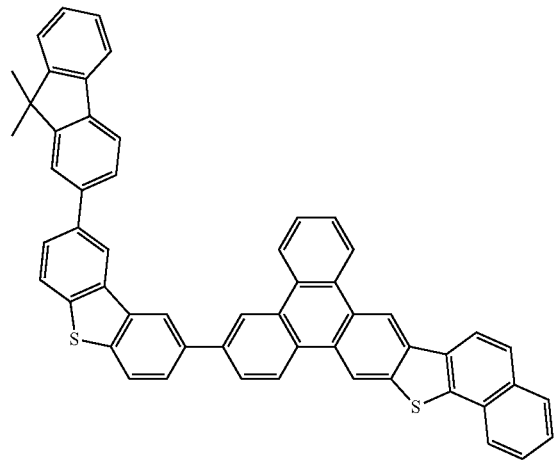
Compound 141
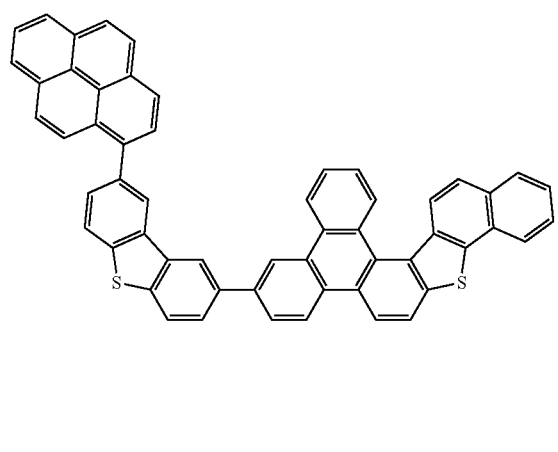
Compound 142
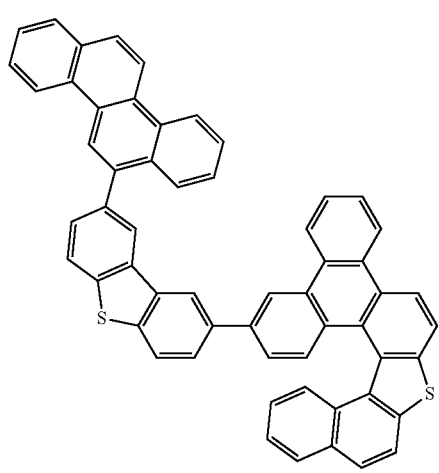
-continued
Compound 143
Compound 144
Compound 145
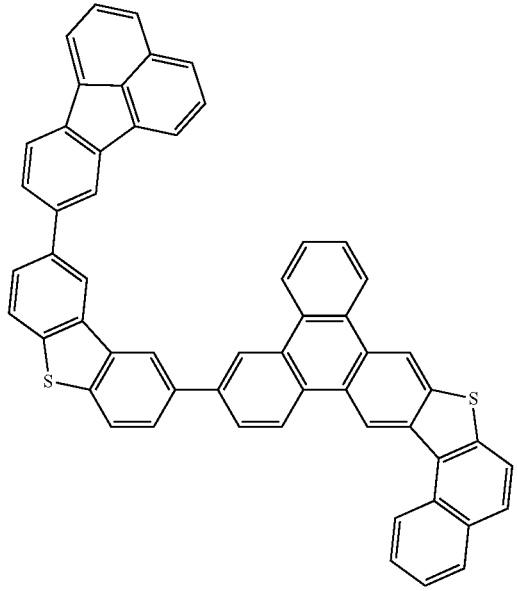

Compound 146
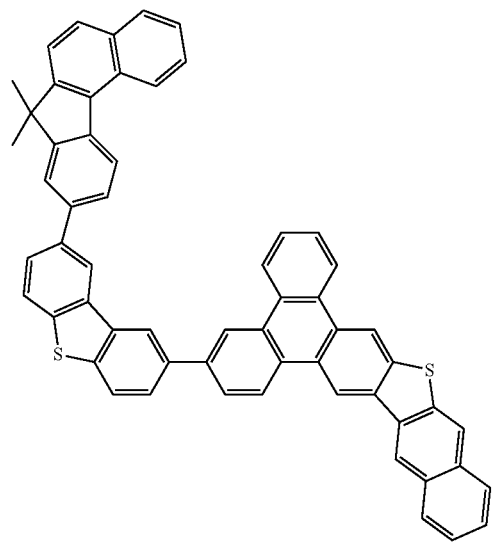
Compound 149
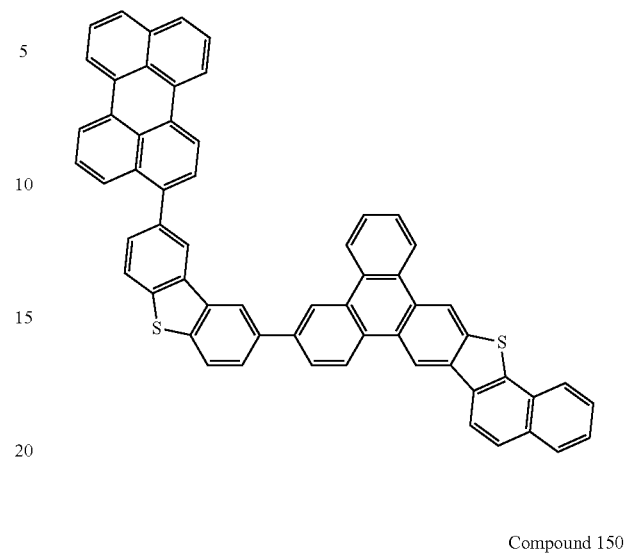
Compound 147
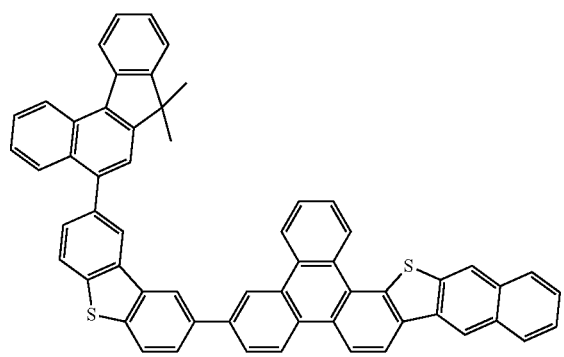
Compound 150
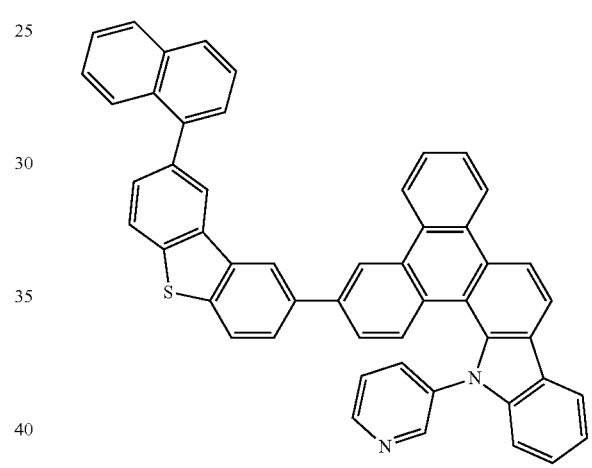
Compound 148
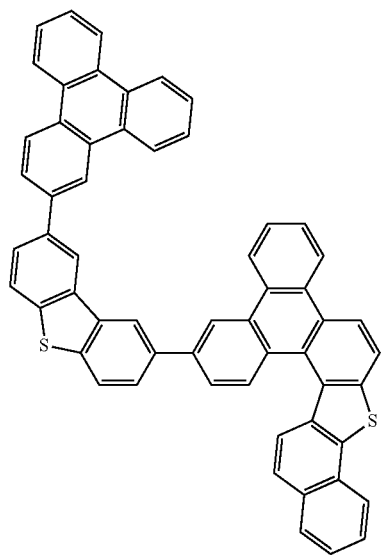
Compound 151
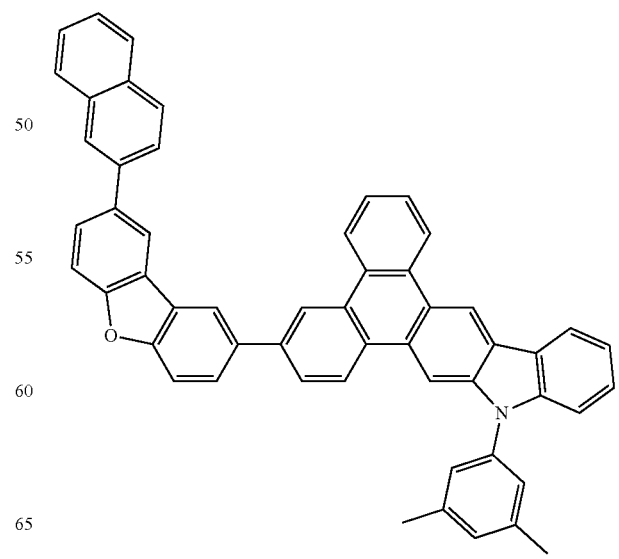

Compound 152
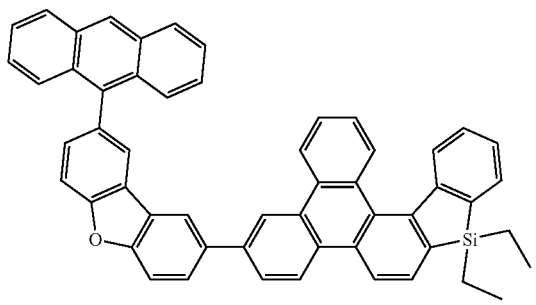
Compound 155
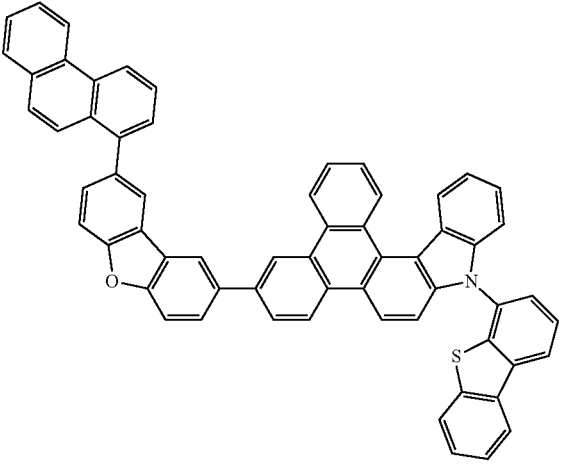
Compound 153
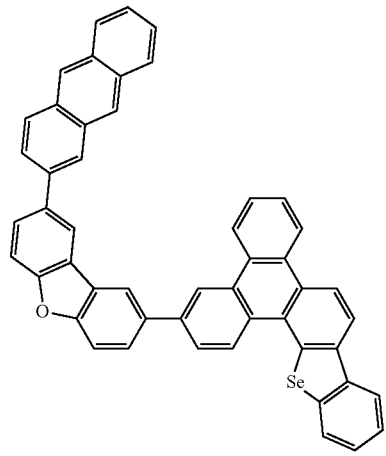
Compound 156
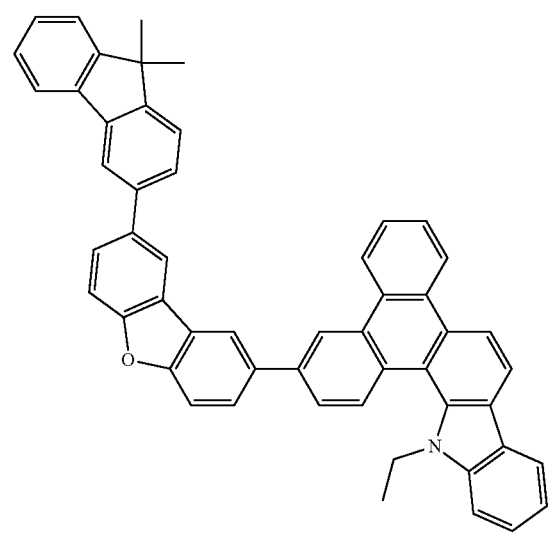
Compound 154
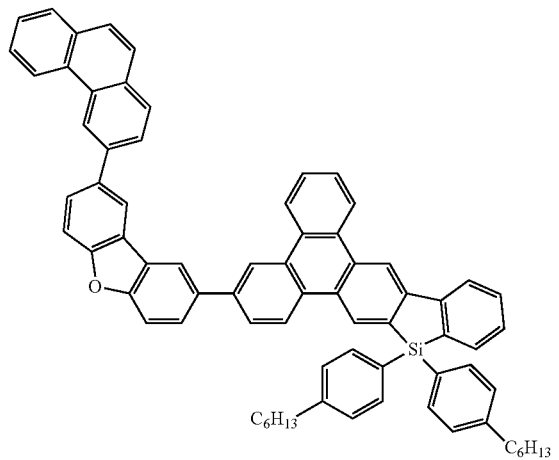
Compound 157
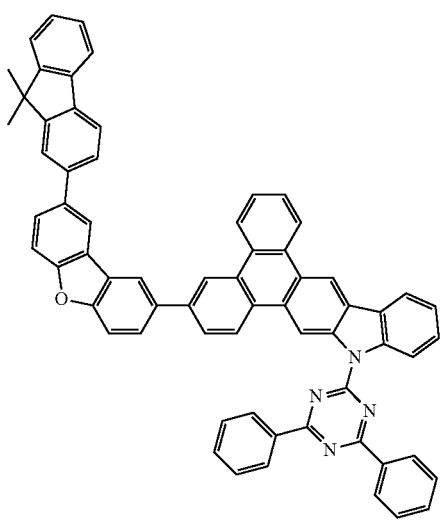

Compound 158
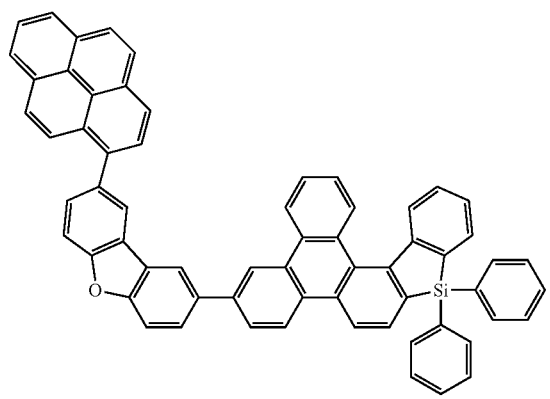
Compound 159
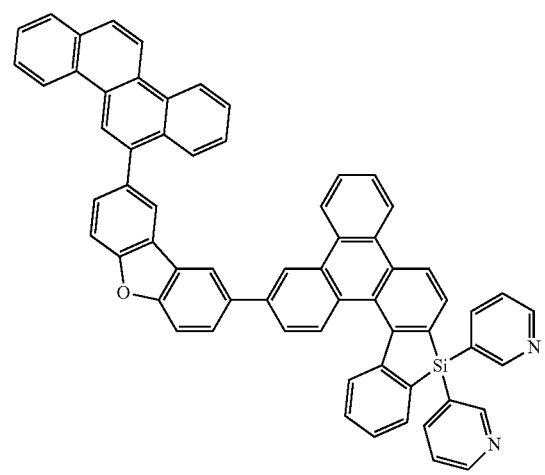
Compound 160
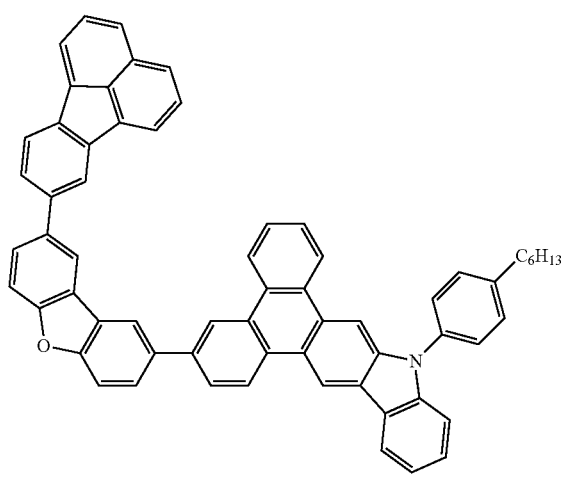
Compound 161
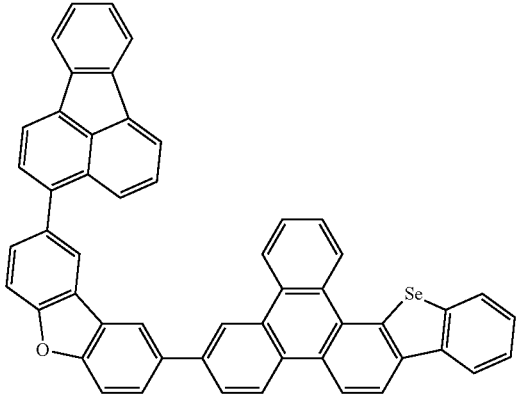
Compound 162
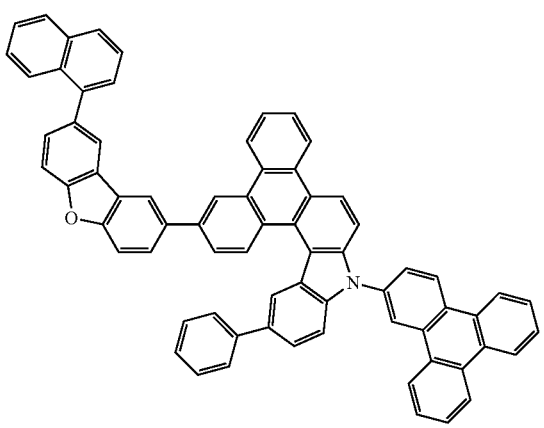
Compound 163
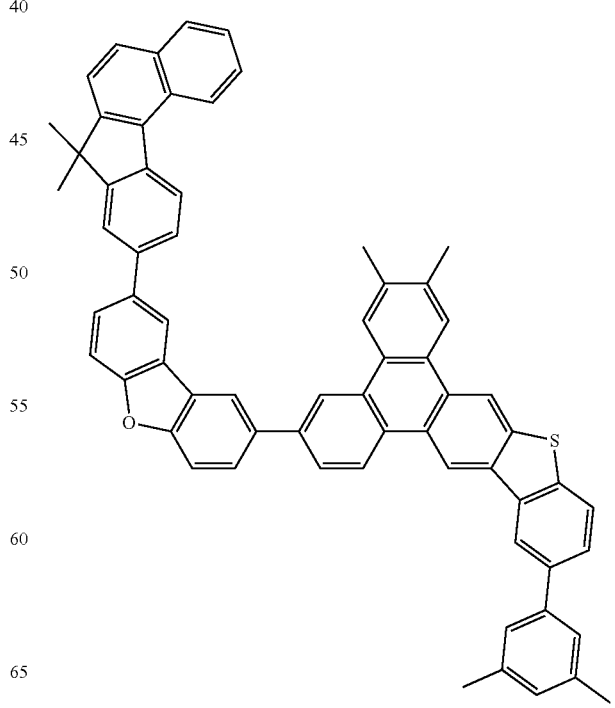

Compound 164
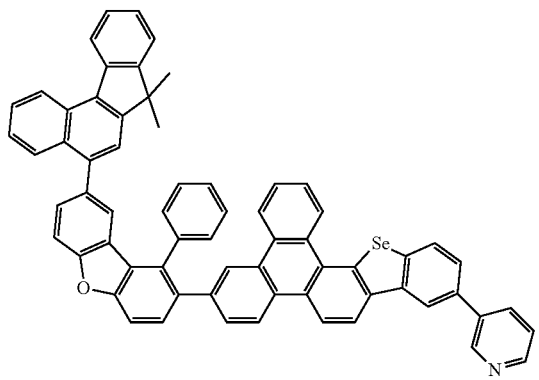
Compound 167
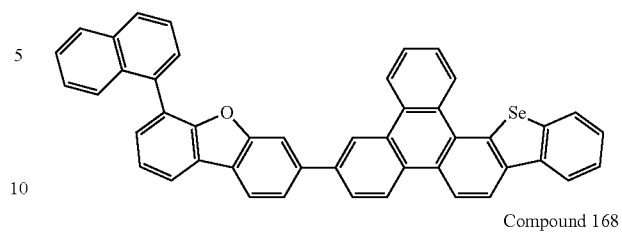
Compound 168
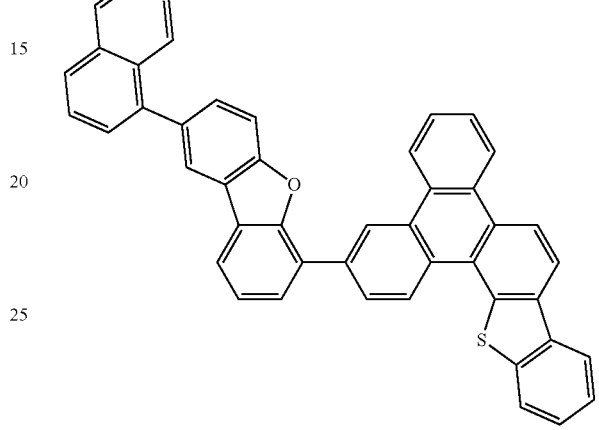
Compound 165
Compound 169
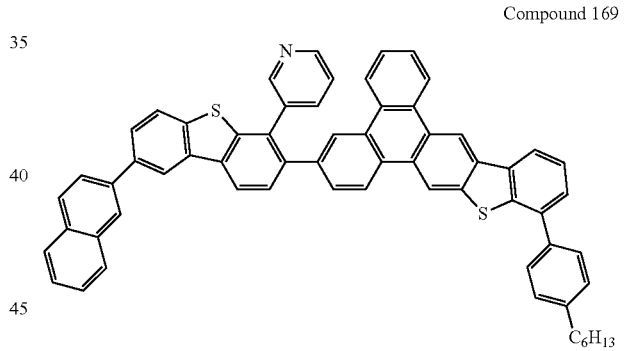
Compound 166
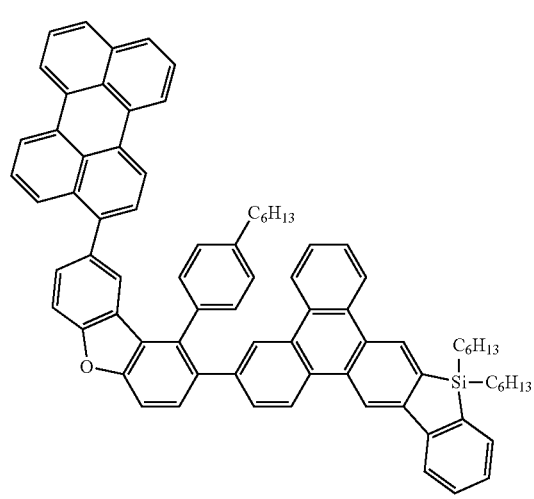
Compound 170
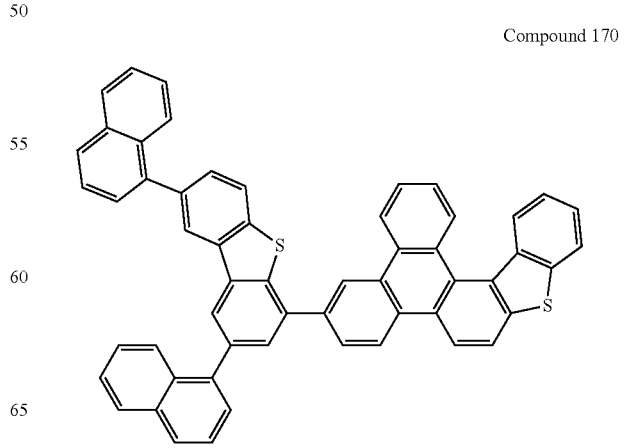

Compound 171
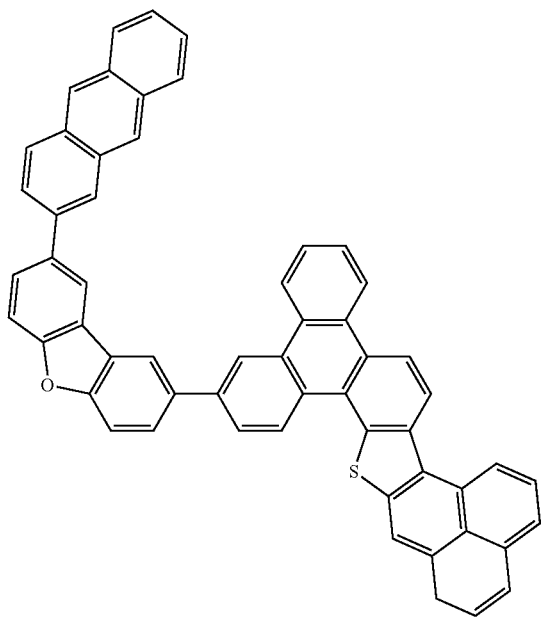
Compound 172
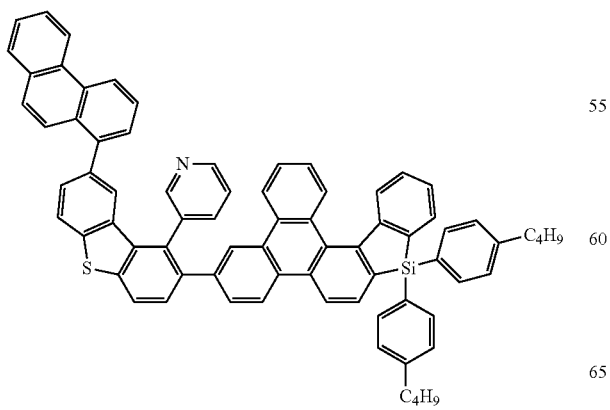
Compound 173
Compound 174
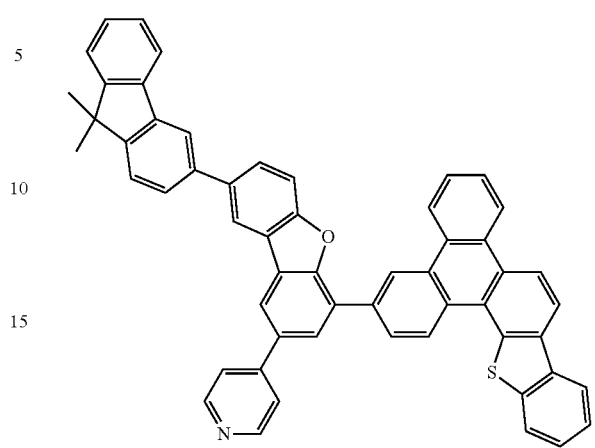
Compound 175
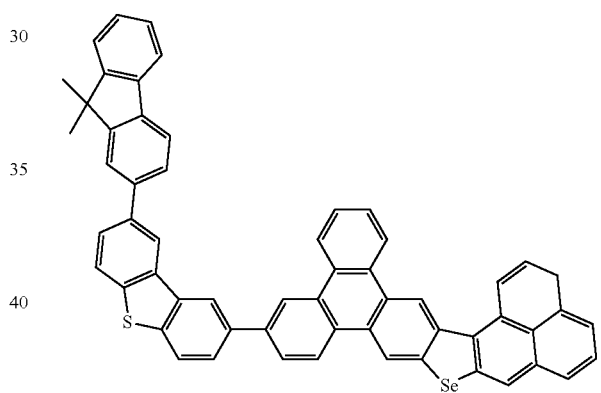
Compound 176
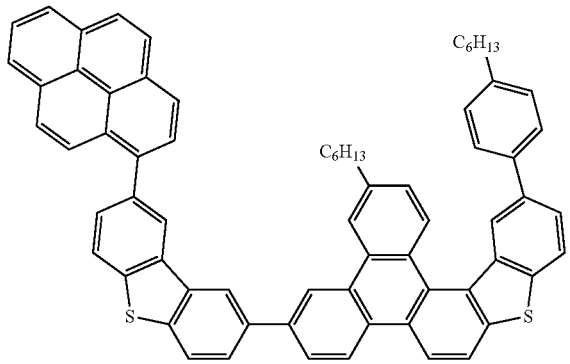

Compound 177
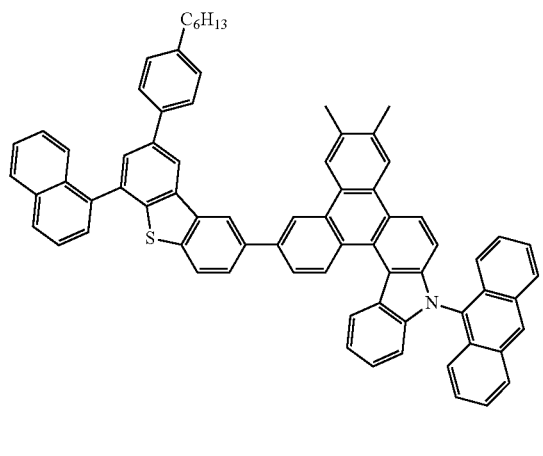
Compound 178
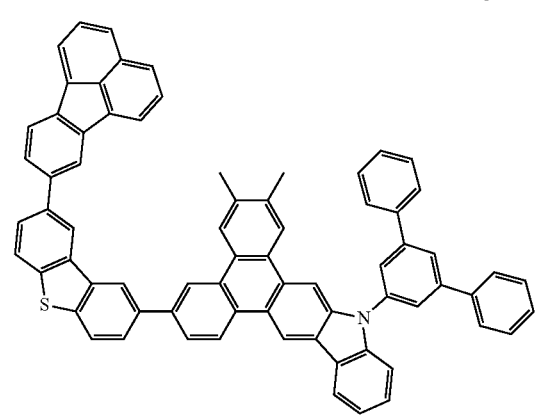
Compound 179
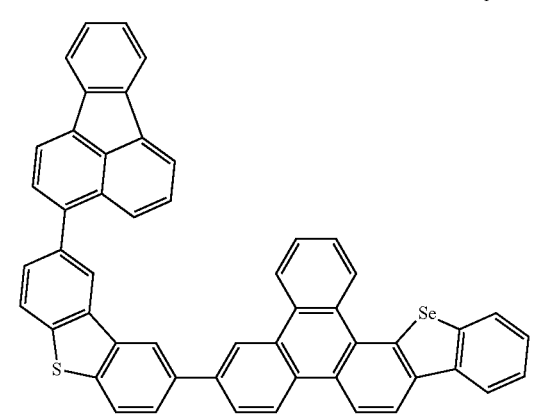
Compound 180
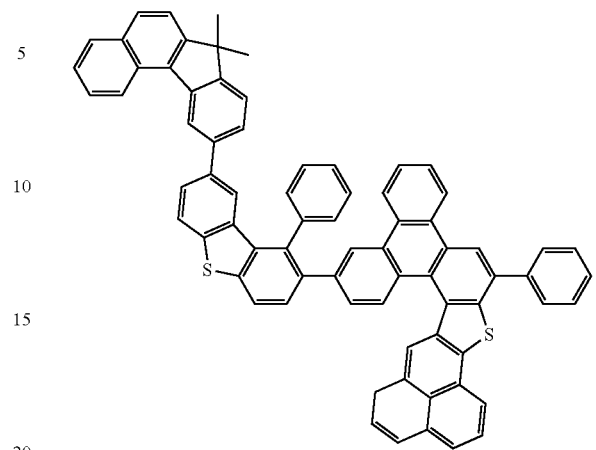
Compound 181
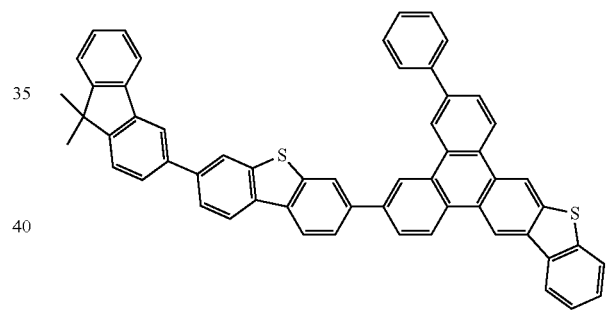
Compound 182
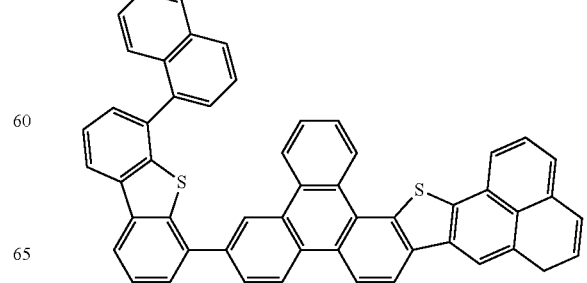

Compound 183
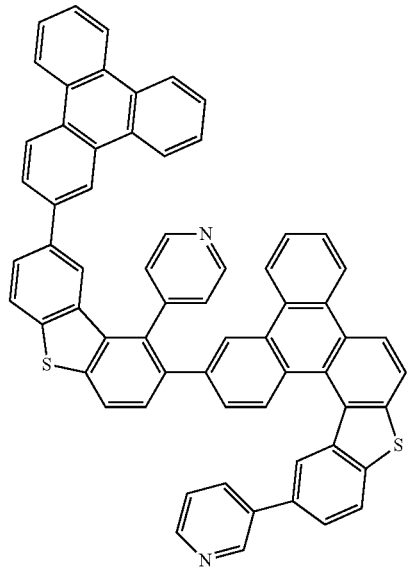
Compound 184
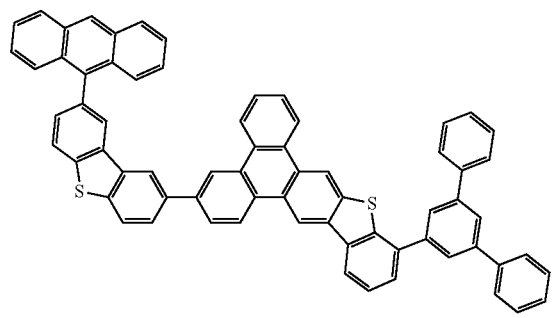
Compound 185
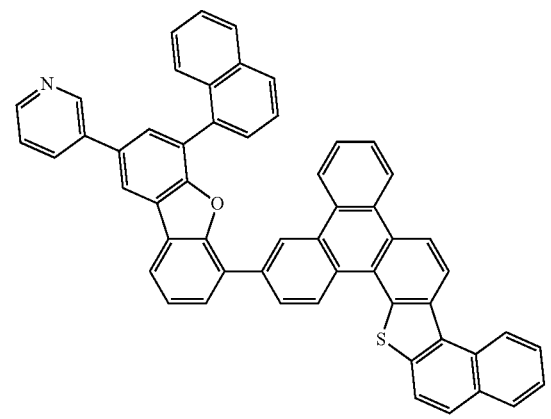
Compound 186
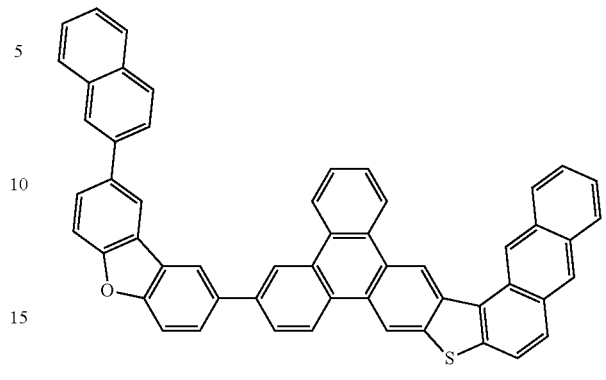
Compound 187
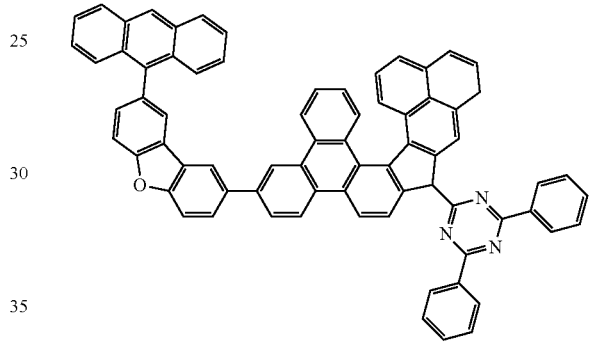
Compound 188
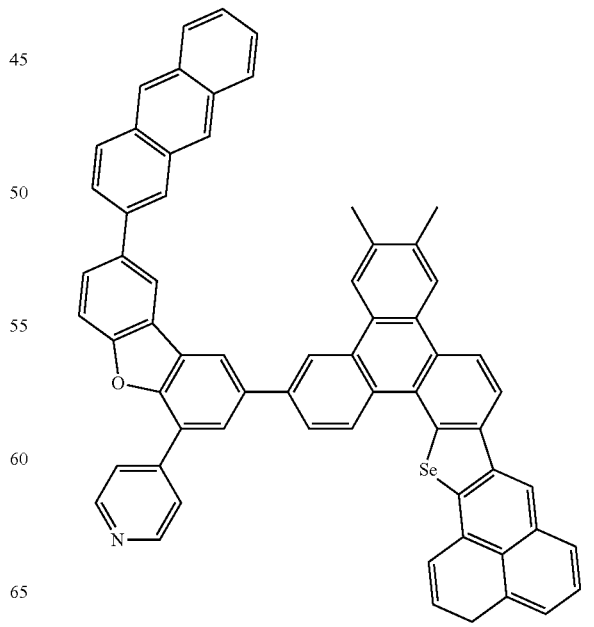

Compound 189
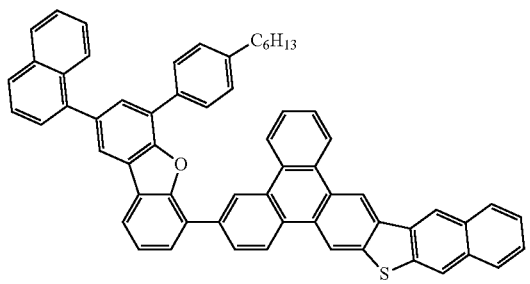
Compound 192
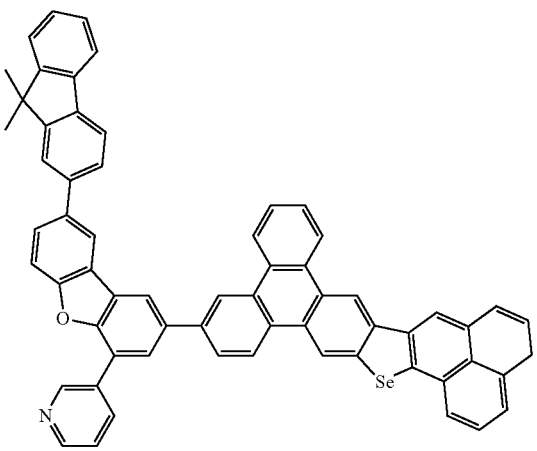
Compound 190
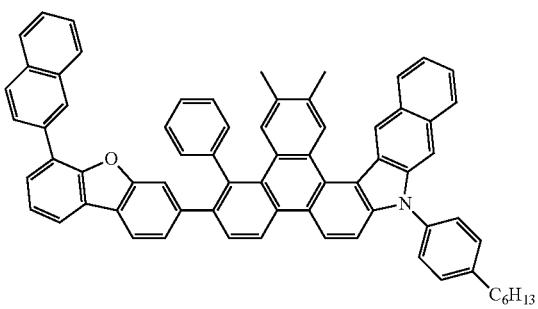
Compound 193
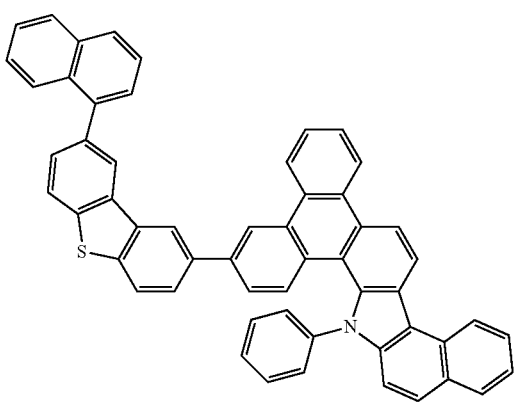
Compound 191
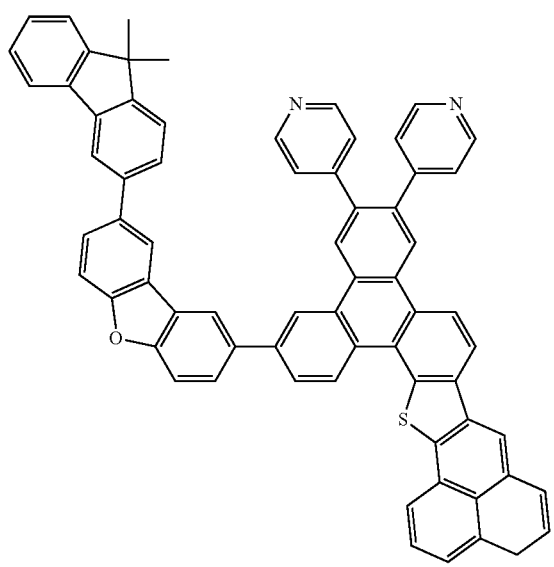
Compound 194
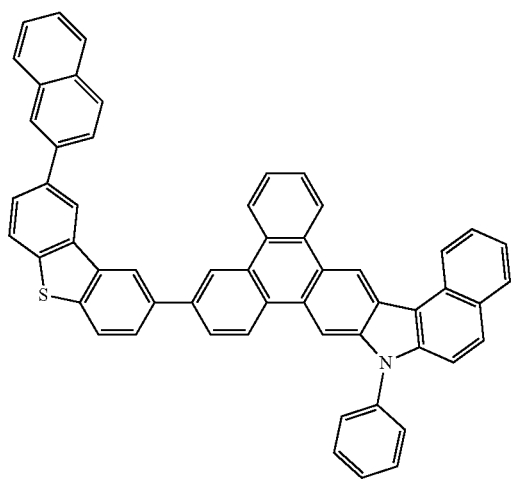

-continued
Compound 195
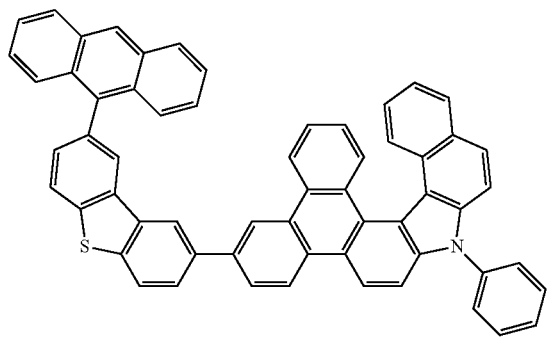
Compound 196
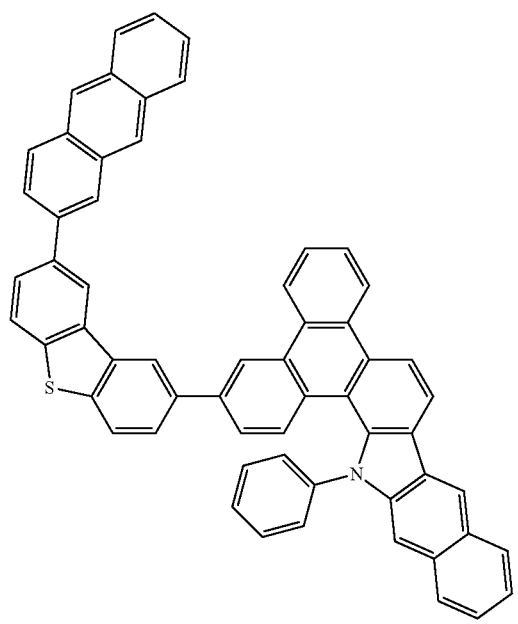
Compound 197
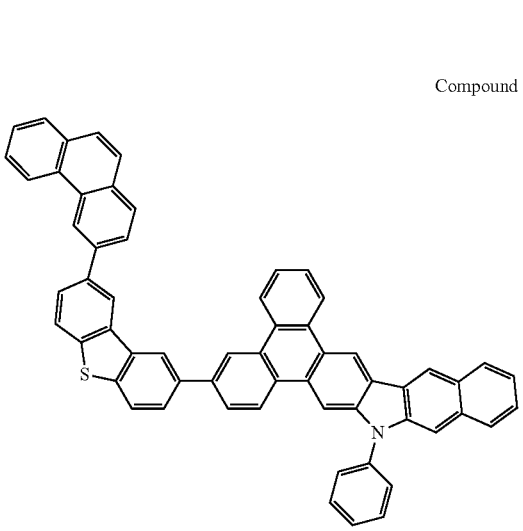
-continued
Compound 198
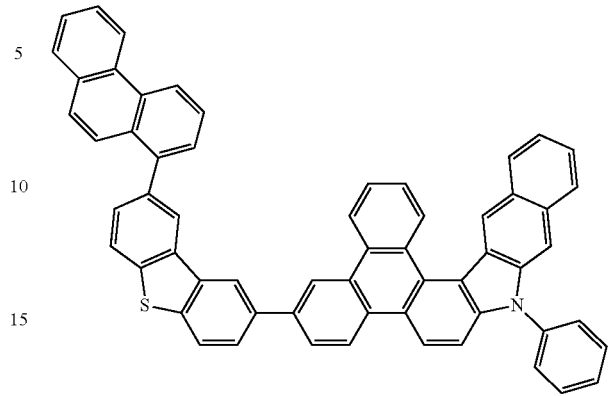
Compound 199
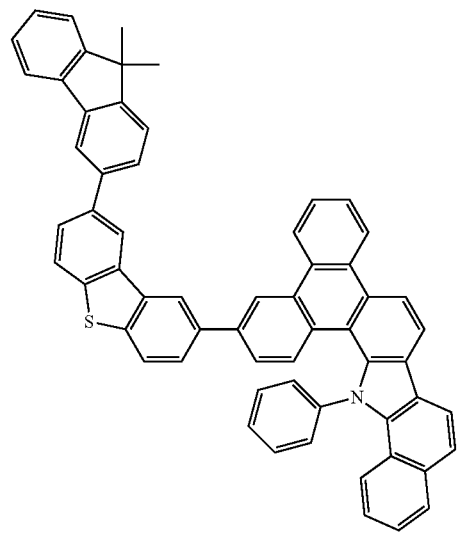
Compound 200
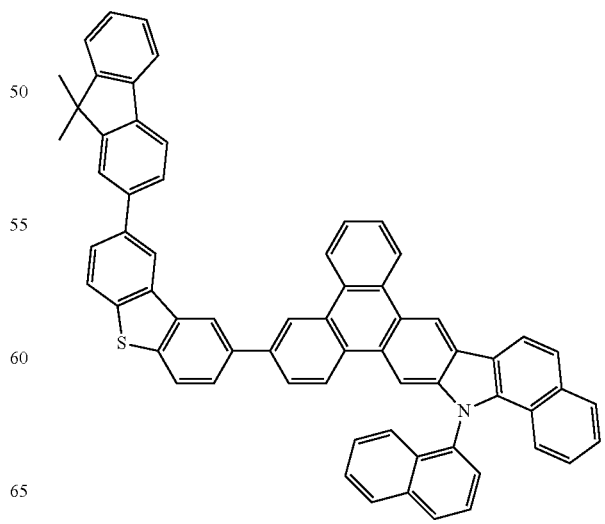

Compound 201
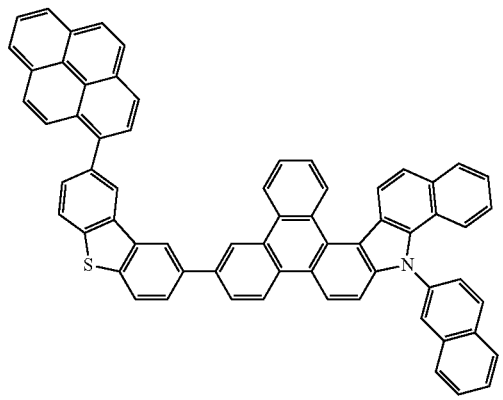
Compound 202
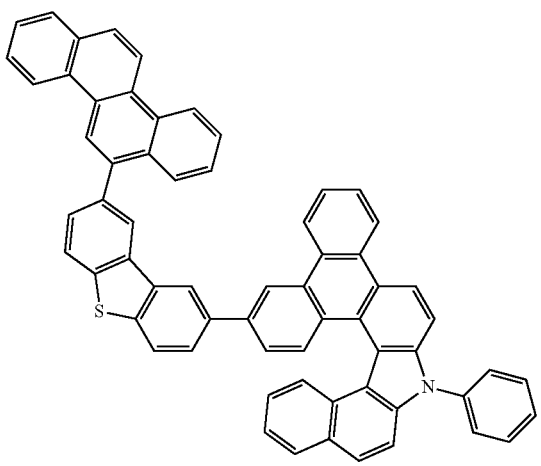
Compound 203
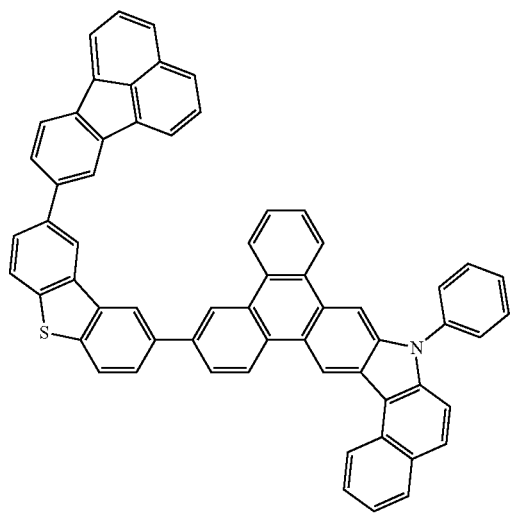
Compound 204
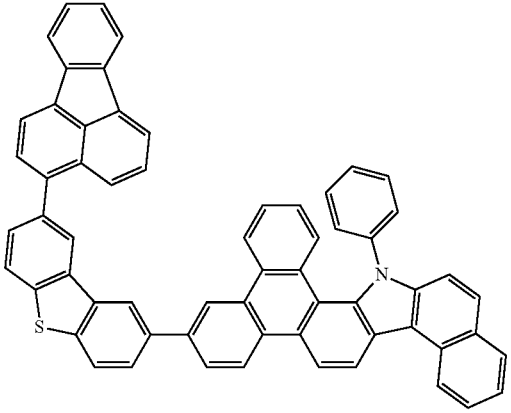
Compound 205
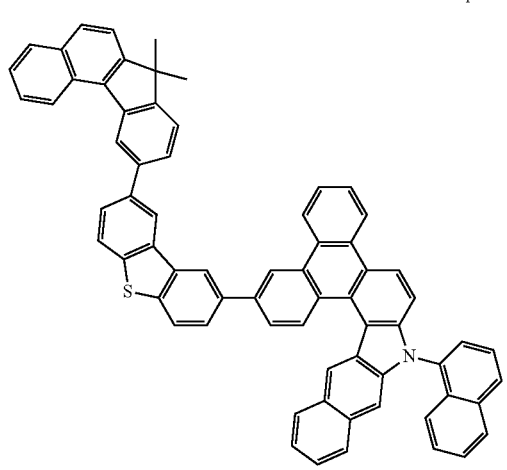
Compound 206
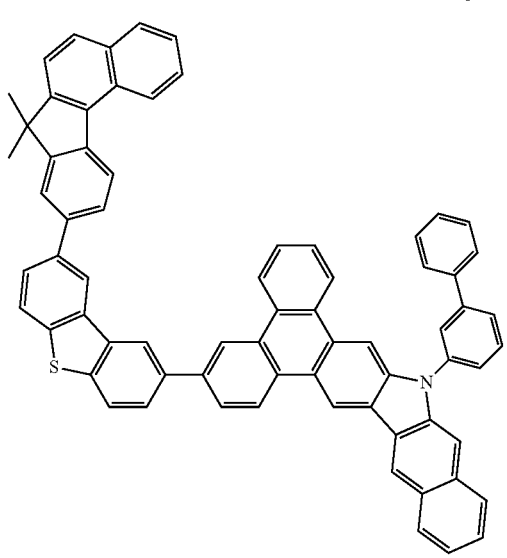

Compound 207
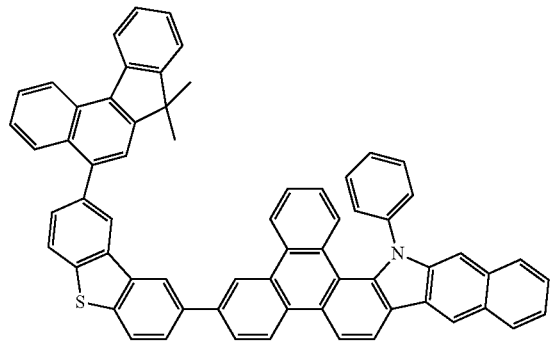
Compound 208
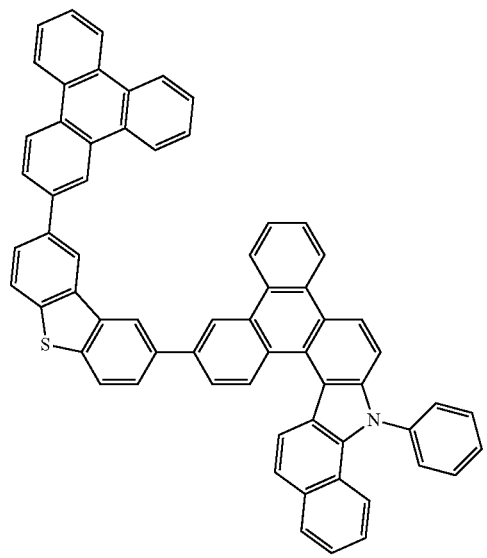
Compound 209
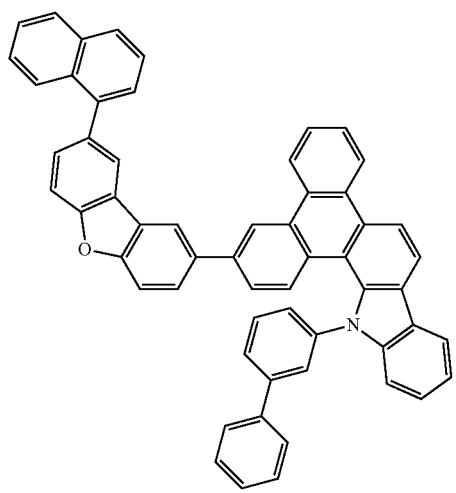
Compound 210
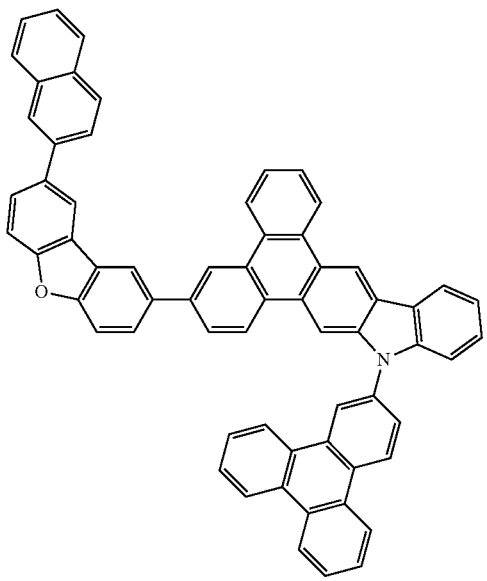
Compound 211
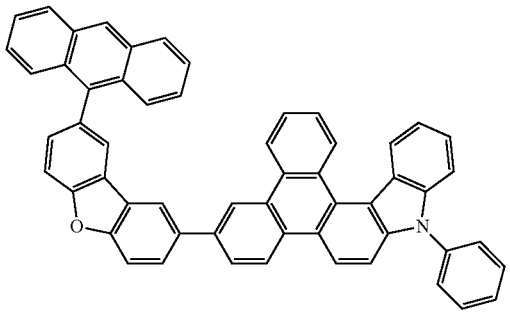
Compound 212
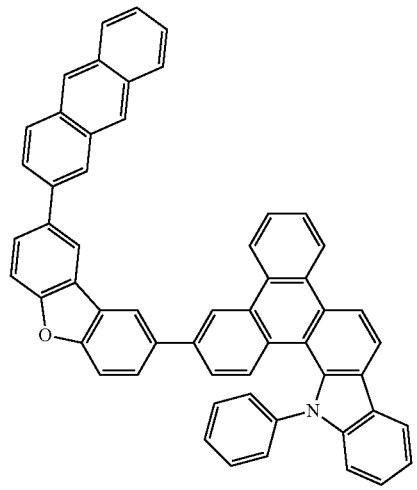

Compound 213
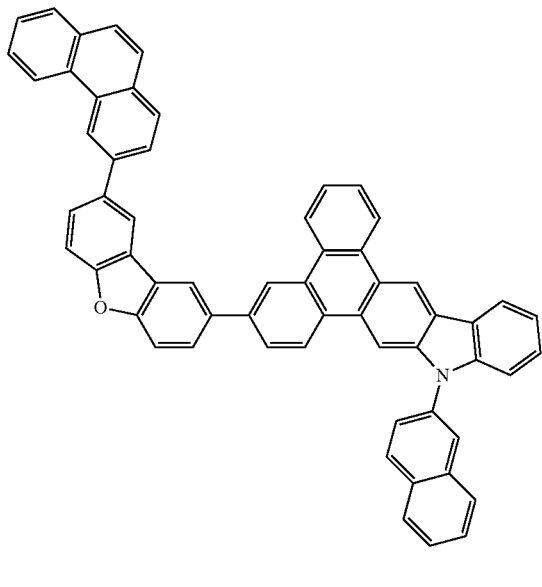
Compound 216
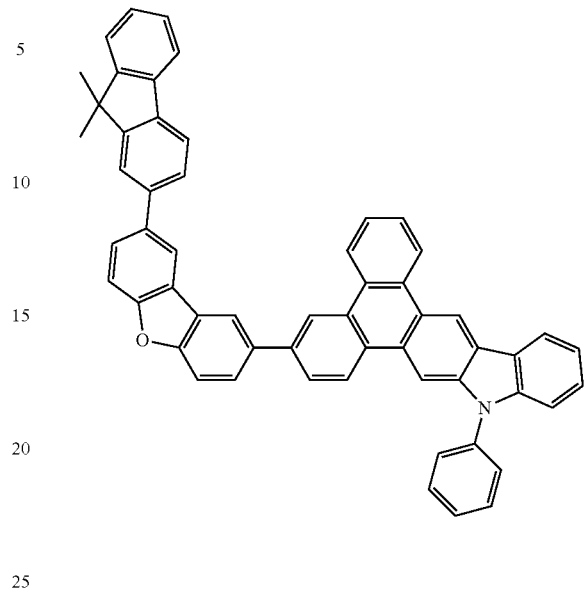
Compound 214
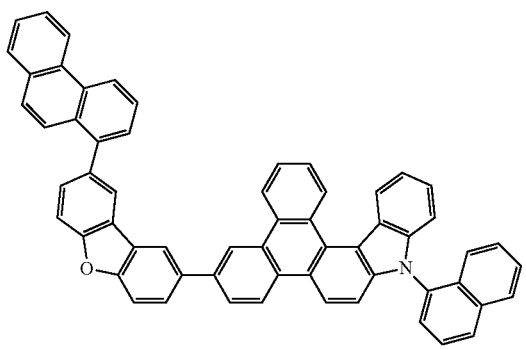
Compound 217
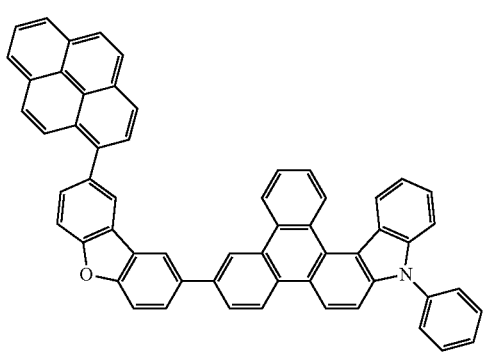
Compound 215
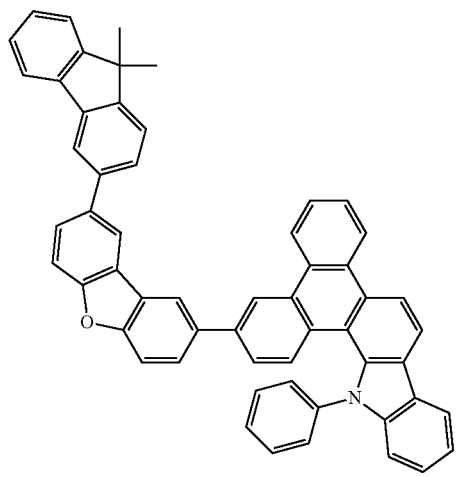
Compound 218
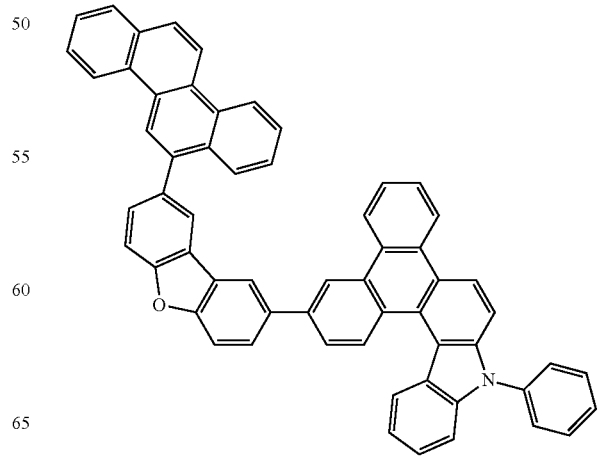

-continued
Compound 219
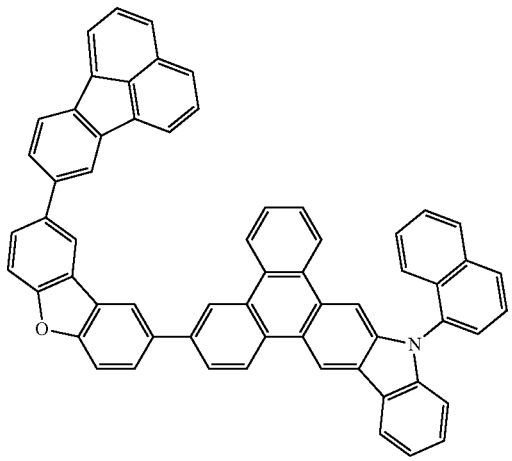
Compound 220
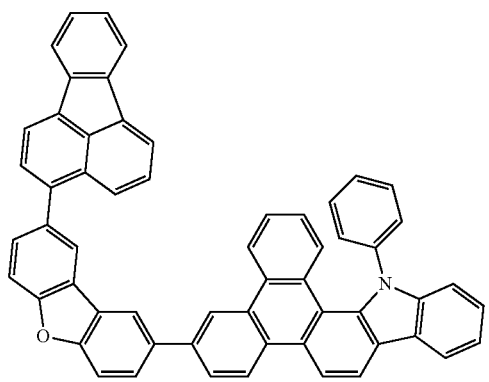
Compound 221
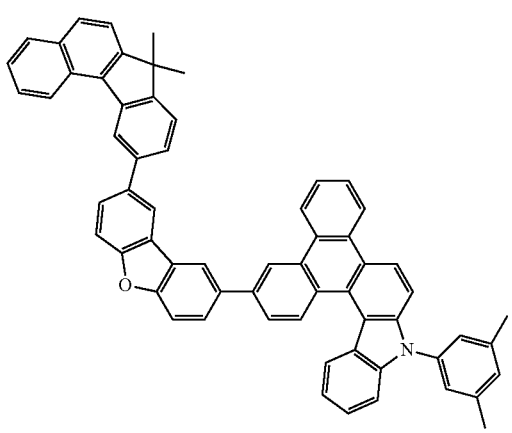
-continued
Compound 222
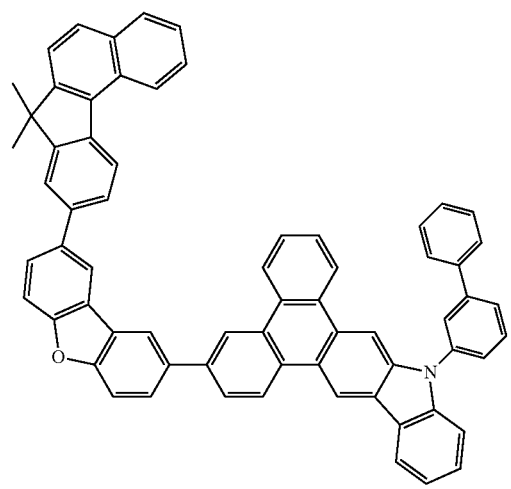
Compound 223
Compound 224
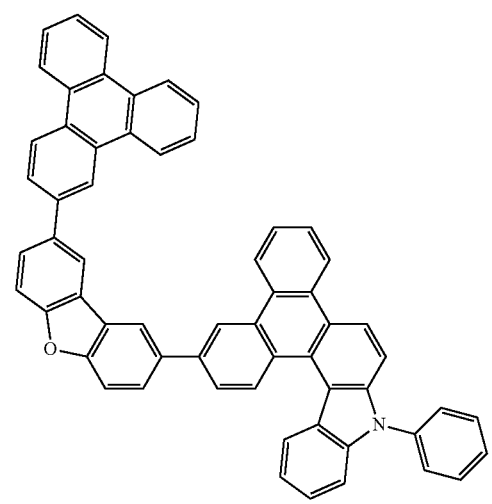

-continued
Compound 225
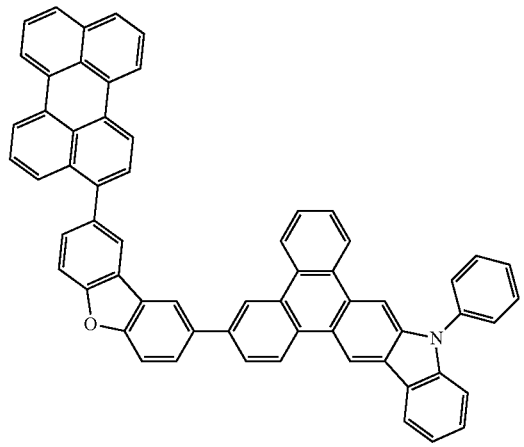
Compound 226
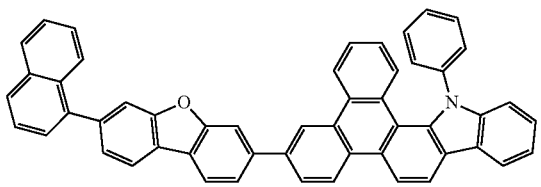
Compound 227
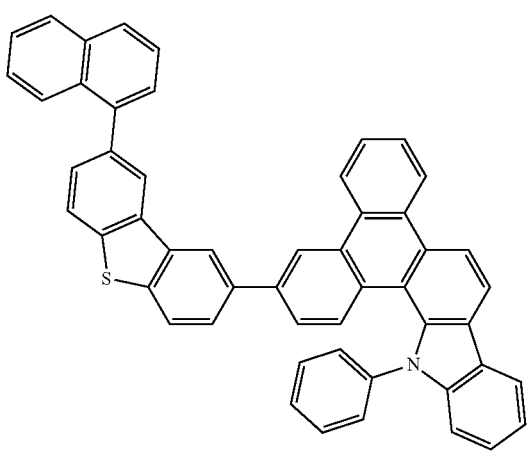
-continued
Compound 228
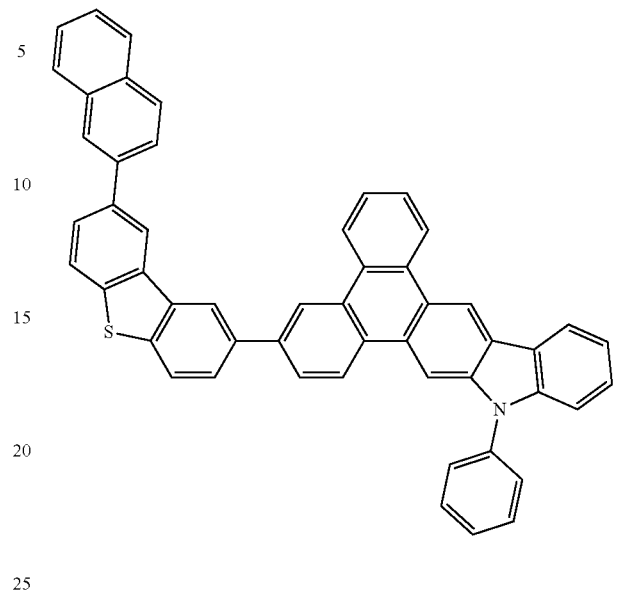
Compound 229
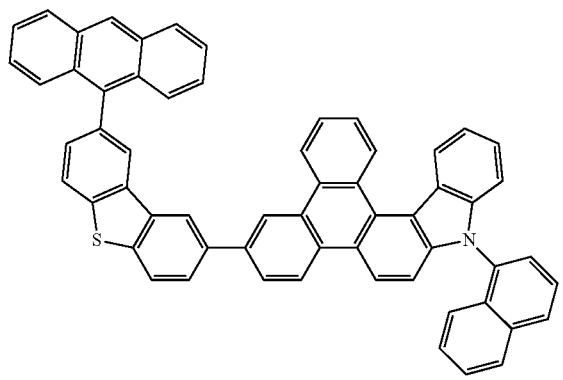
Compound 230
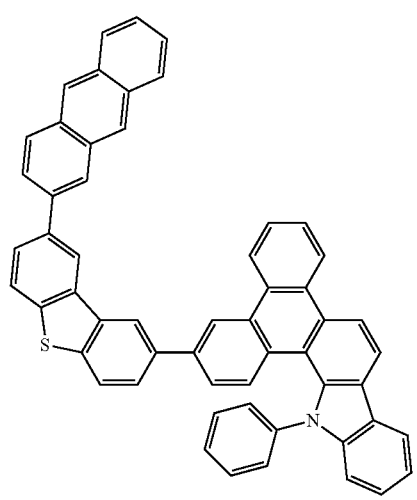

US 11,575,090 B2
Compound 231
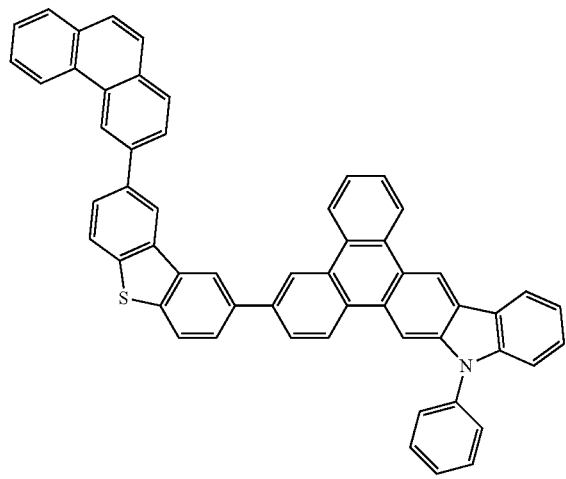
Compound 232
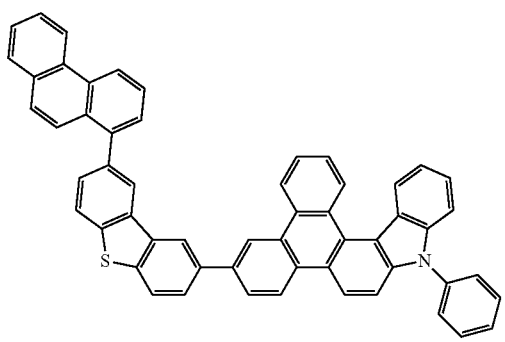
Compound 233
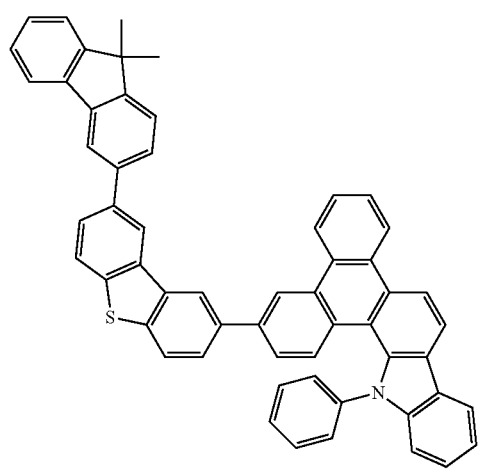
Compound 234
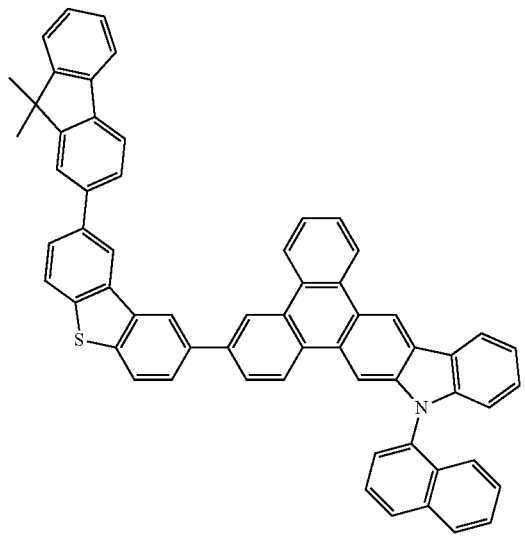
Compound 235
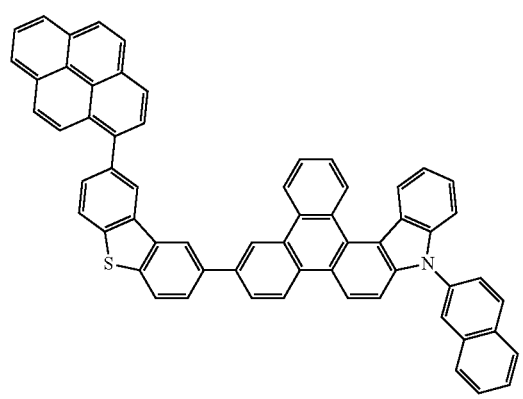
Compound 236
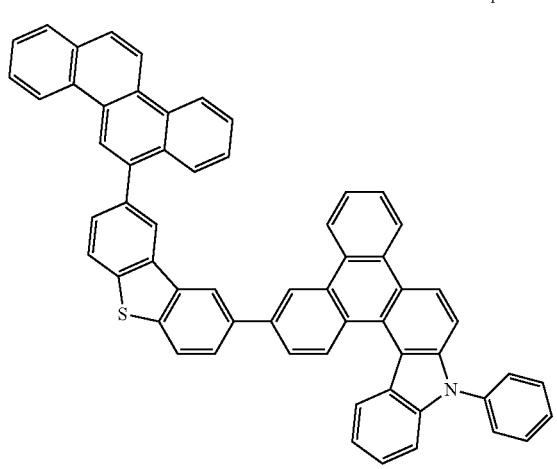

Compound 237
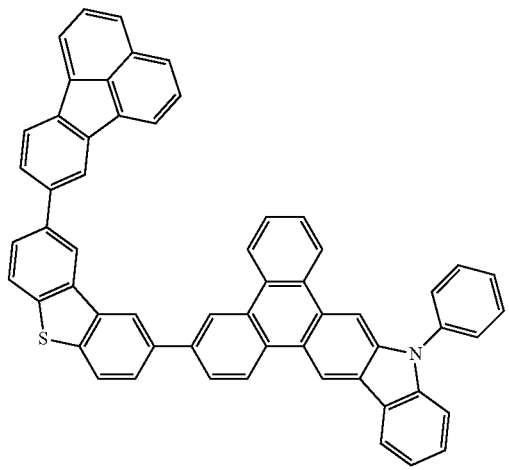
Compound 238
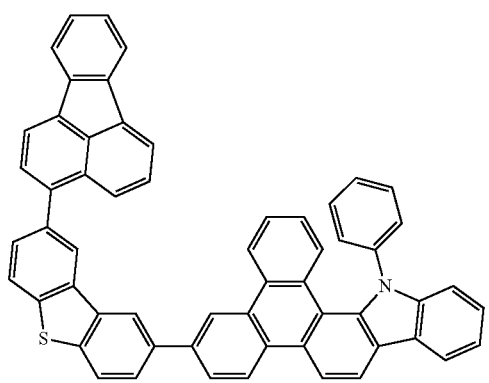
Compound 239
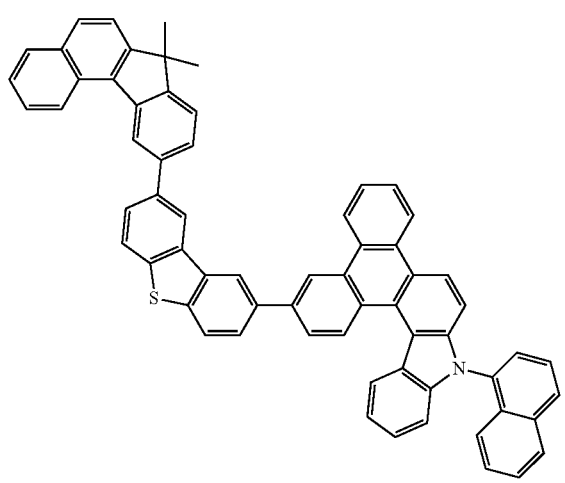
Compound 240
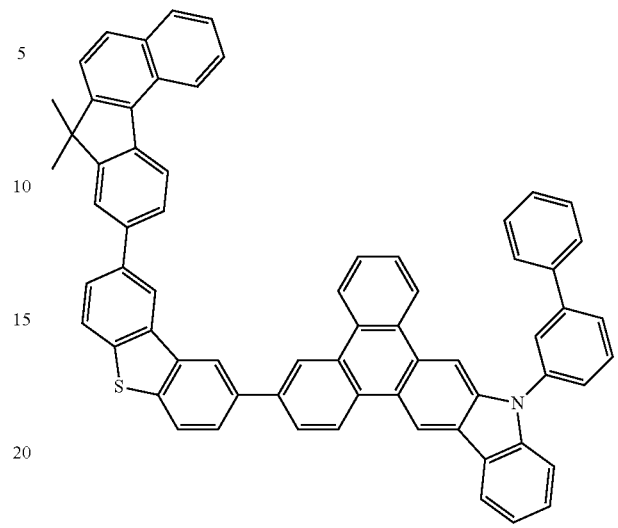
Compound 241
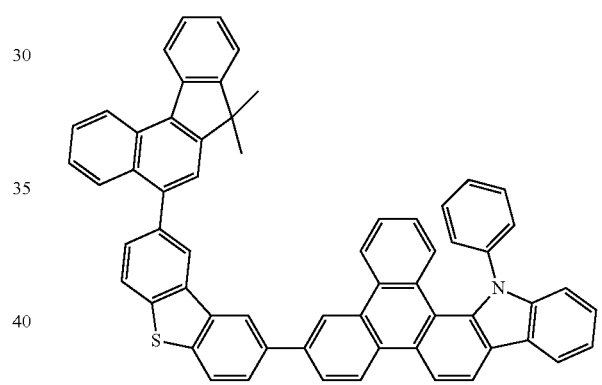
Compound 242
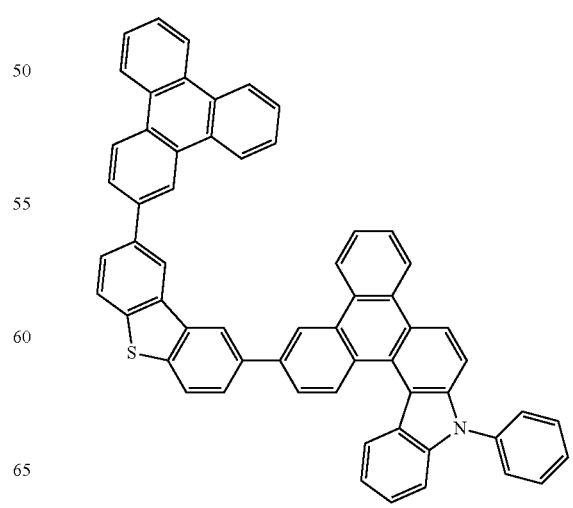

Compound 243
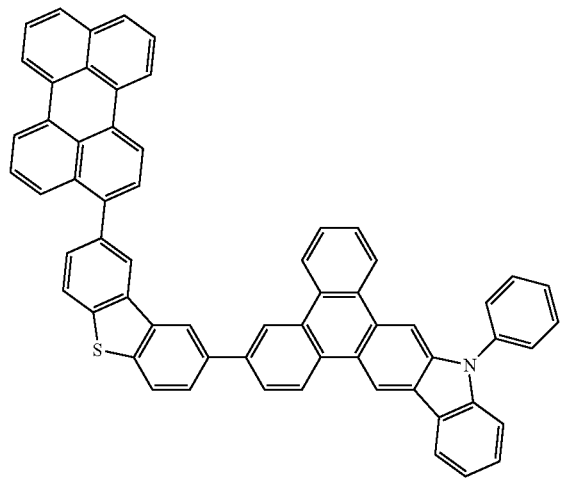
Compound 244
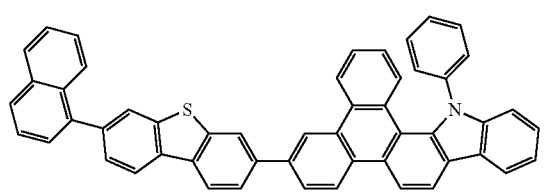
Compound 245
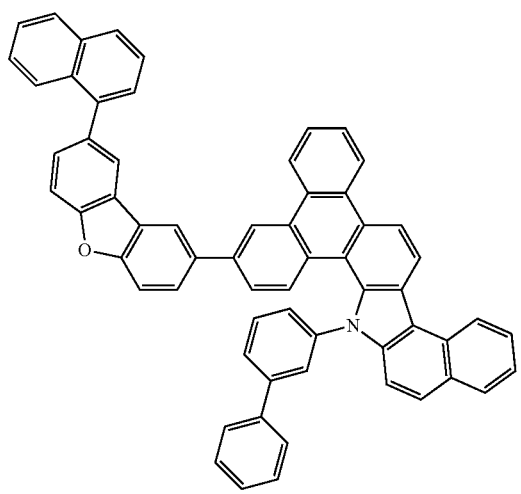
Compound 246
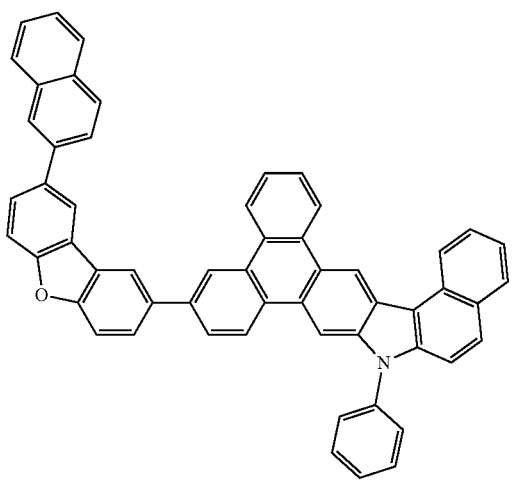
Compound 247
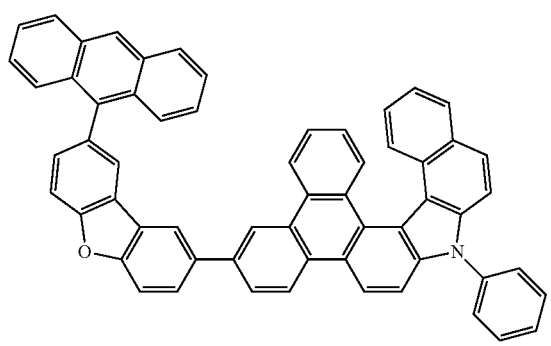
Compound 248
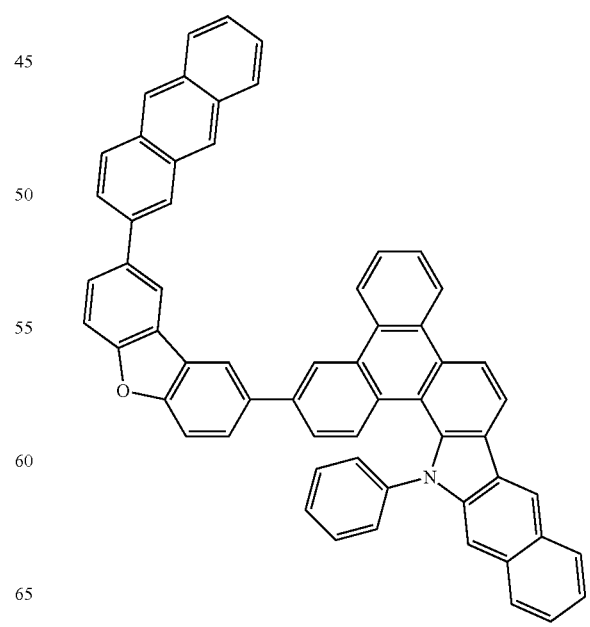

Compound 249
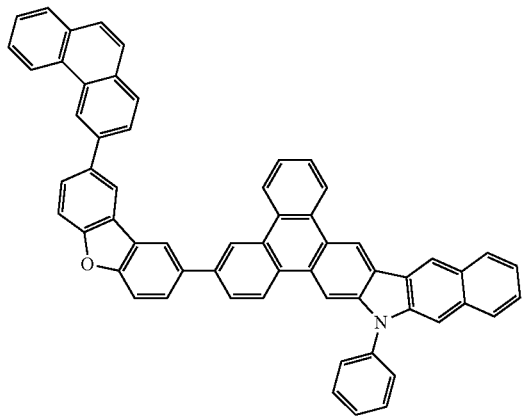
Compound 250
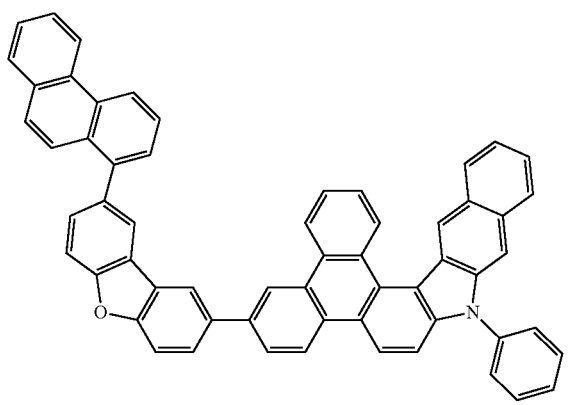
Compound 251
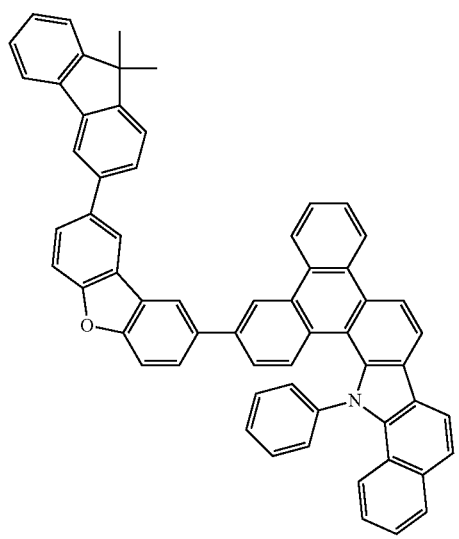
Compound 252
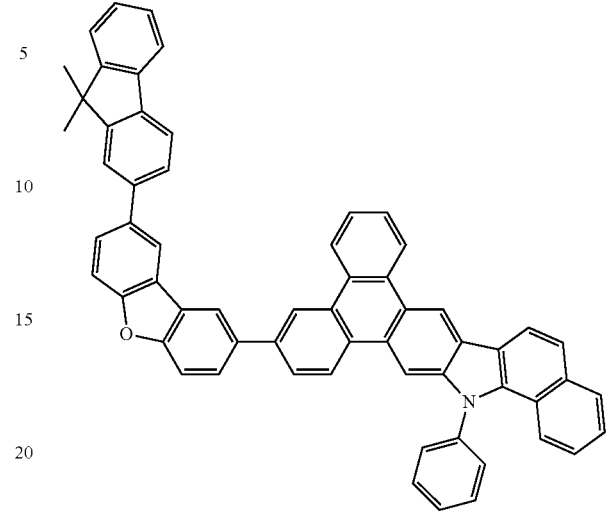
Compound 253
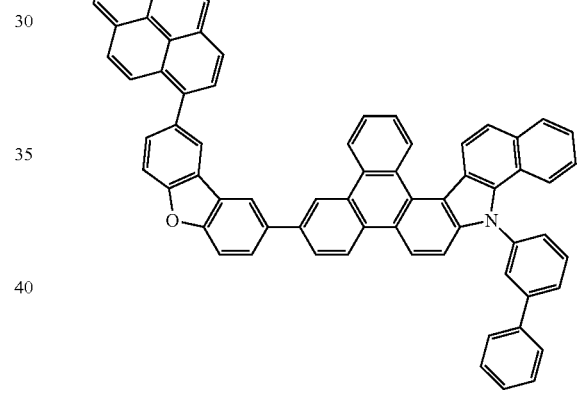
Compound 254
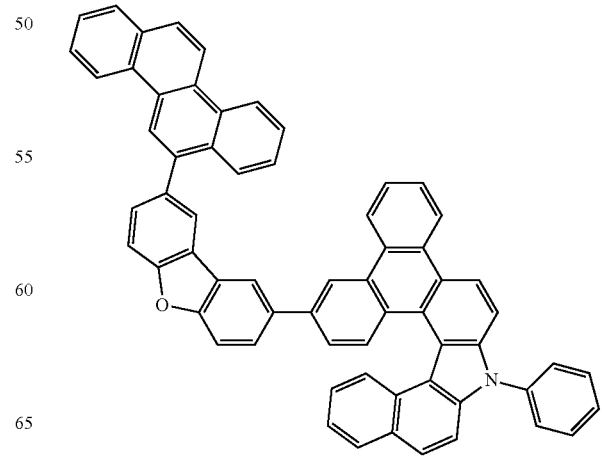

Compound 255
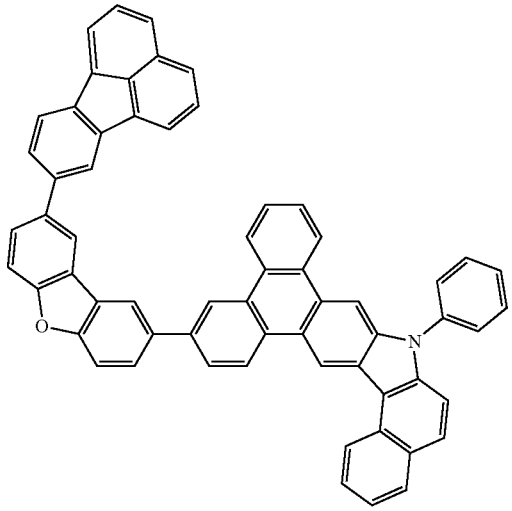
Compound 258
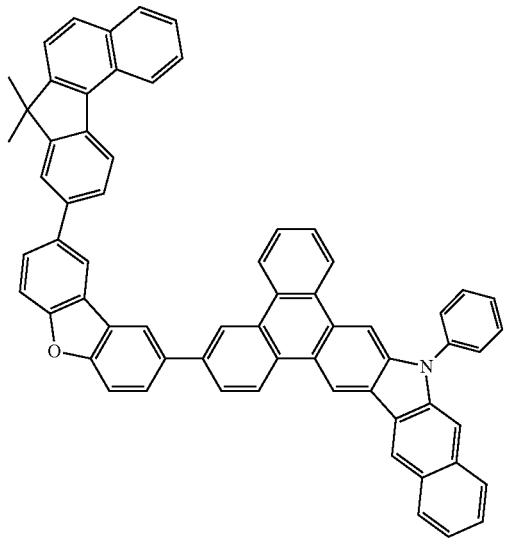
Compound 256
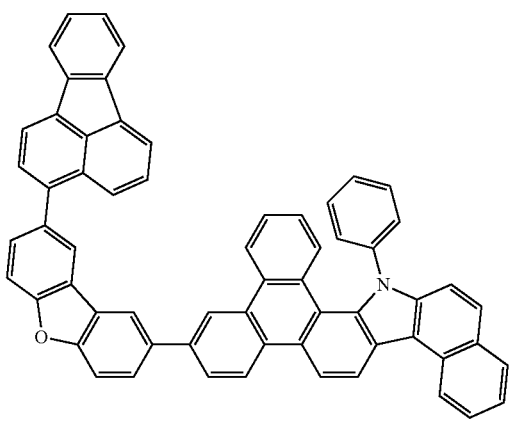
Compound 259
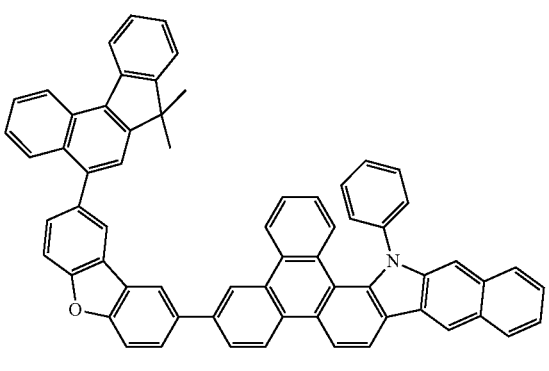
Compound 257
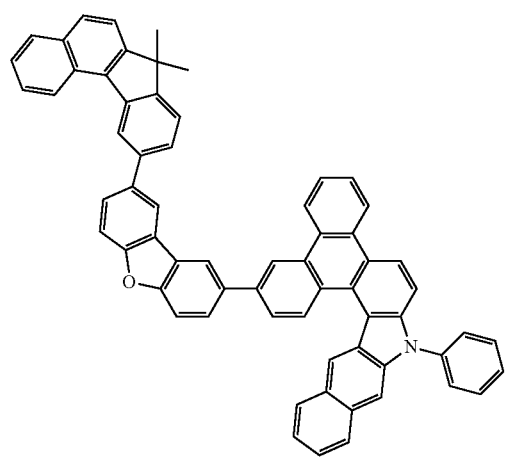
Compound 260
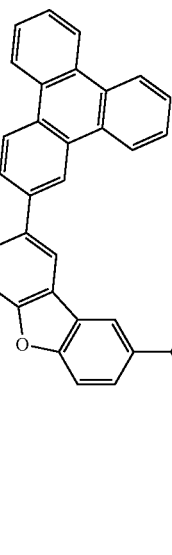

-continued

Compound 261
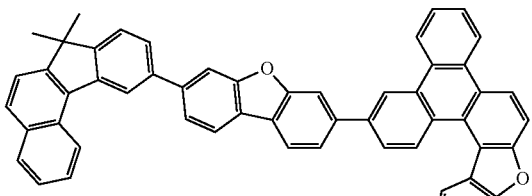

Compound 262
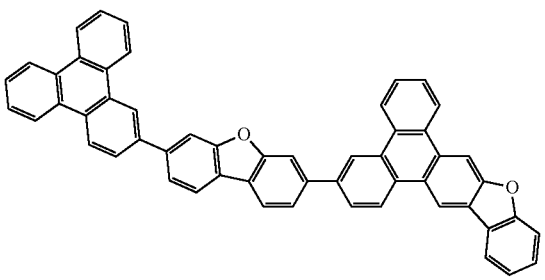

Compound 263
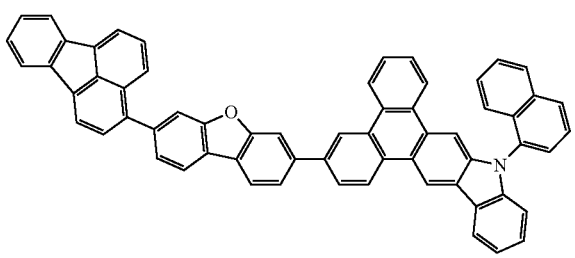

Compound 264
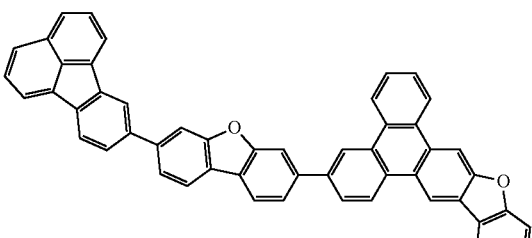

Compound 265
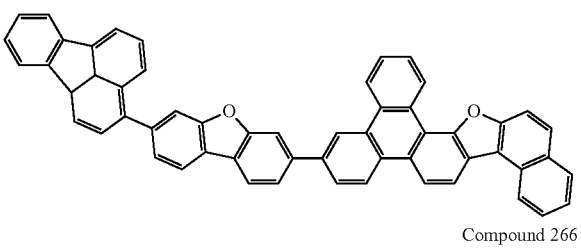

Compound 266
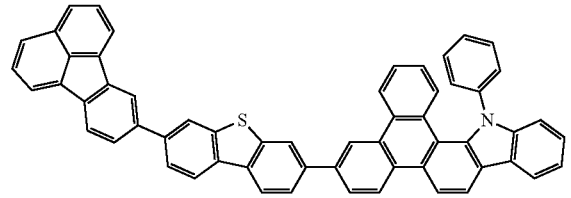

-continued

Compound 267
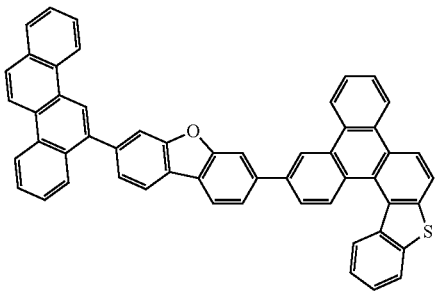

Compound 268
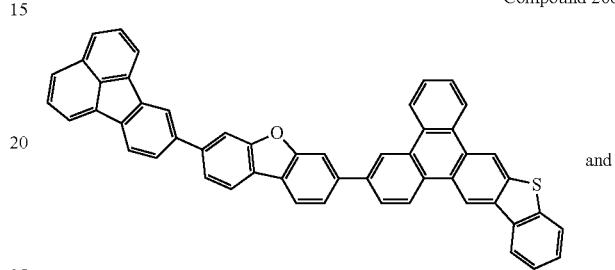

and

Compound 269
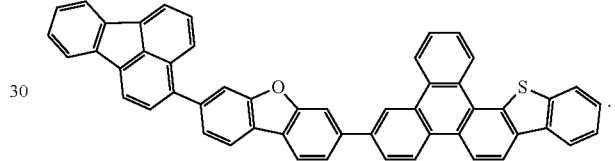

An organic electroluminescence device is described to comprise an anode, a cathode and one or more organic layers formed between the anode and the cathode, wherein at least one of the organic layers comprises the organic compound of formula (1). The organic layers may comprise an emissive layer having a host, wherein the organic compound of formula (1) is comprised as the host.

The organic layers may further comprise an electron transport layer (ETL) having an electron transport material (ETM), and wherein the organic compound of formula (1) is comprised as the electron transport material.

The organic layers may further comprise a hole blocking layer, wherein the organic compound of formula (1) is comprised as the hole blocking layer.

The organic electroluminescence device may be a lighting panel.

Alternatively, the organic electroluminescence device may be a backlight panel.

Device Examples

Referring to the FIGURE, an organic EL device 510 may comprise an anode 310, a cathode 380 and one or more organic layers 320, 330, 340E, 350, 360, 370 formed between the anode 310 and the cathode 380. Between the bottom anode 310 and the top cathode 380, the one or more organic layers may comprise a hole injection layer (HIL) 320, a hole transport layer (HTL) 330, an emissive layer (EML) 340E, a hole blocking layer (HBL) 350, an electron transport layer (ETL) 360 and an electron injection layer (EIL) 370. The one or more organic layers may be fabricated by depositing the layers described, in order.

The emissive layer 340E may comprise a 15% dopant D1. The dopant D1 may be a green guest material for tuning the wavelength at which the emissive layer 340E emits light, so that the color of emitted light may be green.

A method of producing the organic EL device 510 of the FIGURE is described. The anode 310 is about 120-160 nm of indium tin oxide substrate (ITO substrate). The ITO substrate with 9~12 ohm/square in resistance is formed and cleaned in a number of cleaning steps in an ultrasonic bath (e.g., detergent, deionized water). The cathode 380 may be consisted of a low work function metal, such as Al, Mg, Ca, Li or K, by thermal evaporation. Preferably, the cathode 380 may be preferably consisted of 160 nm of Al.

Before vapor deposition of the one or more organic layers, the cleaned ITO substrates may be further treated by UV and ozone. All pre-treatment processes for ITO substrate are under clean room (class 100), so that the anode 310 may be completed.

The organic layers 320, 330, 340E, 350, 360, 370 are applied onto the anode 310 in order by vapor deposition in a high-vacuum unit ($10^{-7}$ torr), such as resistively heated quartz boats. The thickness of the respective organic layer and the vapor deposition rate (0.1~0.3 nm/sec) are precisely monitored or set with the aid of a quartz-crystal monitor.

The stack of the device examples is consisted of sequentially, from the ITO substrate, 20 nm of dipyrazino[2,3-f:2,3-]quinoxaline-2,3,6,7,10,11-hexacarbonitrile (HAT-CN) as the hole injection layer (HIL), 110 nm of N,N-Bis(naphthalene-1-yl)-N,N-bis(phenyl)-benzidine(NPB) as the hole transporting layer (HTL), a green dopant D1 of bis(2-phenylpyridinato)(2,4-diphenylpyridinato)-iridium(III) doped in with the organic compound of formula (1) as host as the emissive layer (EML).

On the emissive layer (EML) 340E having a thickness of about 30 nm, a compound HB1 may be a hole blocking material (HBM) to form a hole blocking layer (HBL) 350 having a thickness of about 10 nm. 2-(naphthalen-1-yl)-9-(4-(1-(4-(10-(naphthalene-2-yl)anthracen-9-yl)-phenyl)-1H-benzo[d]imidazol-2-yl)phenyl)-1,10-phenanthroline (ET1) may be applied as an electron transporting material to co-deposit with 8-hydroxyquinolato-lithium(LiQ) at a ratio of 1:1, thereby forming an electron transporting layer 360 of the organic EL device 510. The electron transporting layer 360 may have a thickness of about 35 nm.

The cathode 380 having a thickness of about 160 nm may help electrons injecting the electron transporting layer 360 from cathode 380. Between the cathode 380 (e.g., Al in Table 2) and the electron transporting layer (ETL) 360, a thin electron injecting layer 370 of LiQ is introduced. The electron injecting layer (EIL) 370 has a thickness of about 1 nm may be to reduce the electron injection barrier and to improve the performance of the organic EL device 510. The material of the electron injecting layer 370 may alternatively be metal halide or metal oxide with low work function, such as LiF, MgO, or $Li_2O$.

COMPARATIVE EXAMPLE

A comparative example with compound H1 is fabricated similarly to the device example except that the compound H1 is used as the host in the EML.

The device results and data are summarized in Tables 1 and 2 from those devices. As used herein, the compounds HAT-CN, NPB, D1, H1, HB1 and ET1 for producing organic EL devices in this invention may have the formulas as follows:

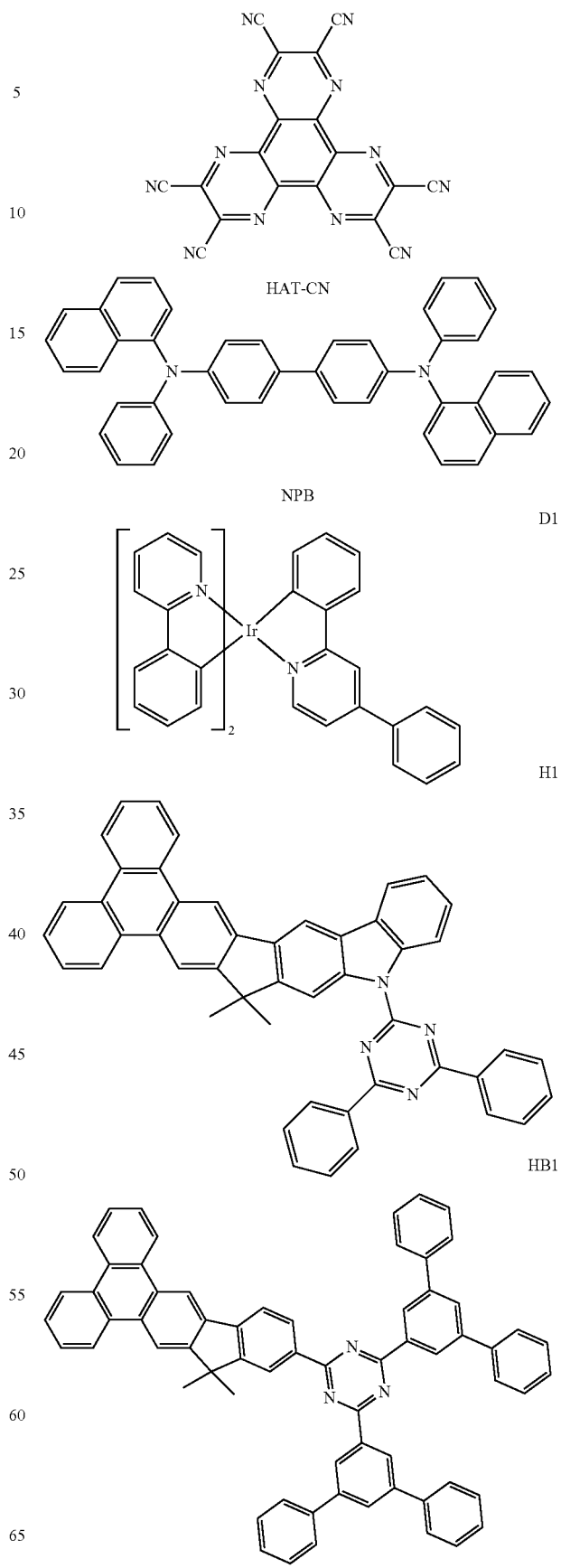

ET1

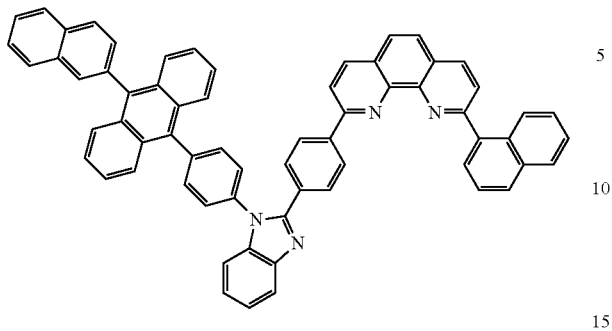

TABLE 1

Device structures of invention compounds and comparative compounds
(The "comp." is short for "compound".)

| Device | HIL 20 nm | HTL 110 nm | EML (30 nm, doping 15%) 85% (Host Comp.) | 15% | HBL 10 nm | ETL (35 nm) 50% | 50% | EIL 1 nm |
|---|---|---|---|---|---|---|---|---|
| Example 1 | HAT-CN | NPB | Comp. 2 | D1 | HB1 | ET1 | LiQ | LiQ |
| Example 2 | HAT-CN | NPB | Comp. 12 | D1 | HB1 | ET1 | LiQ | LiQ |
| Example 3 | HAT-CN | NPB | Comp. 16 | D1 | HB1 | ET1 | LiQ | LiQ |
| Example 4 | HAT-CN | NPB | Comp. 27 | D1 | HB1 | ET1 | LiQ | LiQ |
| Example 5 | HAT-CN | NPB | Comp. 53 | D1 | HB1 | ET1 | LiQ | LiQ |
| Example 6 | HAT-CN | NPB | Comp. 66 | D1 | HB1 | ET1 | LiQ | LiQ |
| Example 7 | HAT-CN | NPB | Comp. 82 | D1 | HB1 | ET1 | LiQ | LiQ |
| Example 8 | HAT-CN | NPB | Comp. 98 | D1 | HB1 | ET1 | LiQ | LiQ |
| Example 9 | HAT-CN | NPB | Comp. 110 | D1 | HB1 | ET1 | LiQ | LiQ |
| Example 10 | HAT-CN | NPB | Comp. 132 | D1 | HB1 | ET1 | LiQ | LiQ |
| Example 11 | HAT-CN | NPB | Comp. 150 | D1 | HB1 | ET1 | LiQ | LiQ |
| Example 12 | HAT-CN | NPB | Comp. 159 | D1 | HB1 | ET1 | LiQ | LiQ |
| Example 13 | HAT-CN | NPB | Comp. 161 | D1 | HB1 | ET1 | LiQ | LiQ |
| Example 14 | HAT-CN | NPB | Comp. 182 | D1 | HB1 | ET1 | LiQ | LiQ |
| Example 15 | HAT-CN | NPB | Comp. 189 | D1 | HB1 | ET1 | LiQ | LiQ |
| Example 16 | HAT-CN | NPB | Comp. 208 | D1 | HB1 | ET1 | LiQ | LiQ |
| Example 17 | HAT-CN | NPB | Comp. 218 | D1 | HB1 | ET1 | LiQ | LiQ |
| Example 18 | HAT-CN | NPB | Comp. 227 | D1 | HB1 | ET1 | LiQ | LiQ |
| Example 19 | HAT-CN | NPB | Comp. 260 | D1 | HB1 | ET1 | LiQ | LiQ |
| Example 20 | HAT-CN | NPB | Comp. 268 | D1 | HB1 | ET1 | LiQ | LiQ |
| Comparative Example | HAT-CN | NPB | H1 | D1 | HB1 | ET1 | LiQ | LiQ |

To those organic EL devices of Table 1, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

The I-V-B (at 1000 nits) test reports of those organic EL devices of Table 1 may be summarized in Table 2 below. The half-life is defined as the time that the initial luminance of 1000 cd/m² has dropped to half. The device data are normalized to Comparative Example and is summarized in the right three columns of Table 2.

As known to the person skilled in the art, the driving voltage, current efficiency or half-life is a parameter important to produce a commercially useful OLED device, and is also one of the most difficult parameters to improve. In general, a few percent improvement is consider a significant improvement to those skilled in the OLED arts.

TABLE 2

Device results (The "comp." is short for "compound".)

| Device | CIE(y) | Driving Voltage (V) | Current Efficiency (Yield; cd/A) | Half-life (hours) | Driving Voltage (a.u.)* | Current Efficiency (a.u.)* | Half-life (a.u.)* |
|---|---|---|---|---|---|---|---|
| Example 1 Comp. 2 | 0.54 | 4.0 | 29 | 500 | 0.784 | 1.61 | 1.43 |

TABLE 2-continued

Device results (The "comp." is short for "compound".)

| Device | CIE(y) | Driving Voltage (V) | Current Efficiency (Yield; cd/A) | Half-life (hours) | Driving Voltage (a.u.)* | Current Efficiency (a.u.)* | Half-life (a.u.)* |
|---|---|---|---|---|---|---|---|
| Example 2 Comp. 12 | 0.54 | 3.5 | 34 | 690 | 0.686 | 1.89 | 1.97 |
| Example 3 Comp. 16 | 0.56 | 3.4 | 35 | 750 | 0.667 | 1.94 | 2.14 |
| Example 4 Comp. 27 | 0.53 | 4.4 | 24 | 440 | 0.863 | 1.33 | 1.26 |
| Example 5 Comp. 53 | 0.54 | 4.2 | 27 | 480 | 0.824 | 1.50 | 1.37 |
| Example 6 Comp. 66 | 0.56 | 4.3 | 25 | 460 | 0.843 | 1.39 | 1.31 |
| Example 7 Comp. 82 | 0.55 | 4.1 | 28 | 510 | 0.804 | 1.56 | 1.46 |
| Example 8 Comp. 98 | 0.54 | 4.2 | 27 | 500 | 0.824 | 1.50 | 1.43 |
| Example 9 Comp. 110 | 0.53 | 3.6 | 34 | 710 | 0.706 | 1.89 | 2.03 |
| Example 10 Comp. 132 | 0.56 | 3.9 | 30 | 490 | 0.765 | 1.67 | 1.40 |
| Example 11 Comp. 150 | 0.55 | 3.8 | 32 | 570 | 0.745 | 1.78 | 1.63 |
| Example 12 Comp. 159 | 0.54 | 4.8 | 21 | 380 | 0.941 | 1.17 | 1.09 |
| Example 13 Comp. 161 | 0.55 | 4.6 | 22 | 400 | 0.902 | 1.22 | 1.14 |
| Example 14 Comp. 182 | 0.53 | 4.7 | 22 | 390 | 0.922 | 1.22 | 1.11 |
| Example 15 Comp. 189 | 0.53 | 4.9 | 20 | 360 | 0.961 | 1.11 | 1.03 |
| Example 16 Comp. 208 | 0.54 | 3.7 | 33 | 660 | 0.725 | 1.83 | 1.89 |
| Example 17 Comp. 218 | 0.55 | 4.1 | 29 | 530 | 0.804 | 1.61 | 1.51 |
| Example 18 Comp. 227 | 0.54 | 3.8 | 31 | 550 | 0.745 | 1.72 | 1.57 |
| Example 19 Comp. 260 | 0.55 | 3.1 | 38 | 800 | 0.608 | 2.11 | 2.29 |
| Example 20 Comp. 268 | 0.54 | 3.3 | 37 | 820 | 0.647 | 2.06 | 2.34 |
| Comparative Example Comp. H1 | 0.53 | 5.1 | 18 | 350 | 1 | 1 | 1 |

*Value is normalized to comparative example compound H1

Comparing Device Examples 1-20 and Comparative Example in Table 2 and Table 1, it is observed that replacing a host compound H1 of a comparative device with an invention compound of formula (1) substantially increases the half-life or current efficiency, and/or substantially reduces the driving voltage of the device. Referring to the right three columns of Table 2, each of the half-life increase, current increase, and voltage reduction is more than a few percent improvement. Therefore, the invention compound of formula (1) is considered a significant improvement to those skilled in the OLED arts.

TABLE 3

Device structures of invention compounds and comparative compounds (The "comp." is short for "compound".)

| Device | HIL 20 nm | HTL 110 nm | EML (30 nm) 85% Host | EML (30 nm) 15% dopant | HBL 10 nm | ETL (35 nm) 50% | ETL (35 nm) 50% | EIL 1 nm |
|---|---|---|---|---|---|---|---|---|
| Example 21 | HAT-CN | NPB | H1 | D1 | HB1 | Comp. 8 | LiQ | LiQ |
| Example 22 | HAT-CN | NPB | H1 | D1 | HB1 | Comp. 44 | LiQ | LiQ |
| Example 23 | HAT-CN | NPB | H1 | D1 | HB1 | Comp. 51 | LiQ | LiQ |
| Example 24 | HAT-CN | NPB | H1 | D1 | HB1 | Comp. 140 | LiQ | LiQ |
| Example 25 | HAT-CN | NPB | H1 | D1 | HB1 | Comp. 156 | LiQ | LiQ |
| Example 26 | HAT-CN | NPB | H1 | D1 | HB1 | Comp. 164 | LiQ | LiQ |
| Example 27 | HAT-CN | NPB | H1 | D1 | HB1 | Comp. 192 | LiQ | LiQ |
| Example 28 | HAT-CN | NPB | H1 | D1 | HB1 | Comp. 239 | LiQ | LiQ |

TABLE 3-continued

Device structures of invention compounds and comparative compounds
(The "comp." is short for "compound".)

| Device | HIL | HTL | EML (30 nm) 85% Host | EML (30 nm) 15% dopant | HBL | ETL (35 nm) 50% | ETL (35 nm) 50% | EIL |
|---|---|---|---|---|---|---|---|---|
|  | 20 nm | 110 nm |  |  | 10 nm |  |  | 1 nm |
| Comparative Example | HAT-CN | NPB | H1 | D1 | HB1 | ET1 | LiQ | LiQ |

To those organic EL devices of Table 3, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

The I-V-B (at 1000 nits) test reports of those organic EL devices of Table 3 may be summarized in Table 4 below. The half-life is defined as the time that the initial luminance of 1000 cd/m² has dropped to half. The device data are normalized to Comparative Example and is summarized in the right three columns of Table 4.

As known to the person skilled in the art, the driving voltage, current efficiency or half-life is a parameter important to produce a commercially useful OLED device, and is also one of the most difficult parameters to improve. In general, a few percent improvement is consider a significant improvement to those skilled in the OLED arts.

TABLE 4

Device results (The "comp." is short for "compound".)

| Device | CIE(y) | Driving Voltage (V) | Current Efficiency (Yield; cd/A) | Half-life (hours) | Driving Voltage (a.u.)* | Current Efficiency (a.u.)* | Half-life (a.u.)* |
|---|---|---|---|---|---|---|---|
| Example 21 Comp. 8 | 0.55 | 4.3 | 29 | 510 | 0.843 | 1.61 | 1.46 |
| Example 22 Comp. 44 | 0.53 | 4.1 | 31 | 540 | 0.804 | 1.72 | 1.54 |
| Example 23 Comp. 51 | 0.54 | 4.4 | 29 | 500 | 0.863 | 1.61 | 1.43 |
| Example 24 Comp. 140 | 0.54 | 4.2 | 30 | 510 | 0.824 | 1.67 | 1.46 |
| Example 25 Comp. 156 | 0.53 | 4.5 | 28 | 480 | 0.882 | 1.56 | 1.37 |
| Example 26 Comp. 164 | 0.55 | 4.6 | 25 | 460 | 0.902 | 1.39 | 1.31 |
| Example 27 Comp. 192 | 0.54 | 4.7 | 24 | 450 | 0.922 | 1.33 | 1.29 |
| Example 28 Comp. 239 | 0.53 | 4.5 | 26 | 460 | 0.882 | 1.44 | 1.31 |
| Comparative Example Comp. ET1 | 0.53 | 5.1 | 18 | 350 | 1 | 1 | 1 |

*Value is normalized to comparative example compound H1

Comparing Device Examples 21-28 and Comparative Example in Table 4 and Table 3, it is observed that replacing a compound ET1 of an ETL with an invention compound of formula (1) substantially increases the half-life or current efficiency, and/or substantially reduces the driving voltage of the device. Referring to the right three columns of Table 4, each of the half-life increase, current increase, and voltage reduction is more than a few percent improvement. Therefore, the invention compound of formula (1) is considered a significant improvement to those skilled in the OLED arts.

TABLE 5

Device structures of invention compounds and comparative compounds (The "comp." is short for "compound".)

| Device | HIL 20 nm | HTL 110 nm | EML (30 nm) 85% Host | EML (30 nm) 15% dopant | HBL 10 nm | ETL (35 nm) 50% | ETL (35 nm) 50% | EIL 1 nm |
|---|---|---|---|---|---|---|---|---|
| Example 29 | HAT-CN | NPB | H1 | D1 | Comp. 152 | ET1 | LiQ | LiQ |
| Example 30 | HAT-CN | NPB | H1 | D1 | Comp. 157 | ET1 | LiQ | LiQ |
| Example 31 | HAT-CN | NPB | H1 | D1 | Comp. 160 | ET1 | LiQ | LiQ |
| Example 32 | HAT-CN | NPB | H1 | D1 | Comp. 163 | ET1 | LiQ | LiQ |
| Example 33 | HAT-CN | NPB | H1 | D1 | Comp. 173 | ET1 | LiQ | LiQ |
| Comparative Example | HAT-CN | NPB | H1 | D1 | HB1 | ET1 | LiQ | LiQ |

To those organic EL devices of Table 5, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

The I-V-B (at 1000 nits) test reports of those organic EL devices of Table 5 may be summarized in Table 6 below. The half-life is defined as the time that the initial luminance of 1000 cd/m$^2$ has dropped to half. The device data are normalized to Comparative Example and is summarized in the right three columns of Table 6.

As known to the person skilled in the art, the driving voltage, current efficiency or half-life is a parameter important to produce a commercially useful OLED device, and is also one of the most difficult parameters to improve. In general, a few percent improvement is consider a significant improvement to those skilled in the OLED arts.

Comparing Device Examples 29-33 and Comparative Example in Table 6 and Table 5, it is observed that replacing a compound HB1 of a Comparative Device with an invention compound of formula (1) substantially increases the half-life or current efficiency, and/or substantially reduces the driving voltage of the device. Referring to the right three columns of Table 6, each of the half-life increase, current increase, and voltage reduction is more than a few percent improvement. Therefore, the invention compound of formula (1) is considered a significant improvement to those skilled in the OLED arts.

Experimental Examples

Detailed preparation of the organic compounds of the present invention will be clarified by exemplary embodiments below, but the present invention is not limited thereto. EXPERIMENTAL EXAMPLES 1 to 30 show the preparation of the organic compounds of the present invention.

TABLE 6

Device results (The "comp." is short for "compound".)

| Device | CIE(y) | Driving Voltage (V) | Current Efficiency (Yield; cd/A) | Half-life (hours) | Driving Voltage (a.u.)* | Current Efficiency (a.u.)* | Half-life (a.u.)* |
|---|---|---|---|---|---|---|---|
| Example 29 Comp. 152 | 0.55 | 5 | 19 | 370 | 0.980 | 1.06 | 1.057 |
| Example 30 Comp. 157 | 0.54 | 4.6 | 24 | 430 | 0.902 | 1.33 | 1.229 |
| Example 31 Comp. 160 | 0.55 | 4.7 | 23 | 410 | 0.922 | 1.28 | 1.171 |
| Example 32 Comp. 163 | 0.54 | 4.9 | 23 | 400 | 0.961 | 1.28 | 1.143 |
| Example 33 Comp. 173 | 0.53 | 4.9 | 21 | 380 | 0.961 | 1.17 | 1.086 |
| Comparative Example Comp. HB1 | 0.53 | 5.1 | 18 | 350 | 1 | 1 | 1 |

*Value is normalized to comparative example compound H1

Experimental Example 1

Synthesis of 1-bromo-2-iodo-4-methoxybenzene

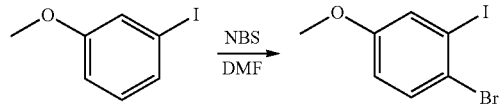

A mixture of 40 g (171 mmol) of 1-iodo-3-methoxybenzene, 32 g (179 mmol) of N-bromosuccinimide, and 600 ml of DMF was degassed and placed under nitrogen, and then heated at 80° C. for 12 hrs. After the reaction finished, the mixture was allowed to cool to room temperature. Subsequently, the solvent was removed under reduced pressure, and the crude product was purified by column chromatography, yielding 45 g of 1-bromo-2-iodo-4-methoxybenzene as yellow oil (84.1%). $^1$H NMR (CDCl$_3$, 400 MHz): chemical shift (ppm) 7.43 (dd, 1H), 7.35 (dd, 1H), 6.73 (dd, 1H), 3.74 (s, 3H).

Synthesis of 2-bromo-5-methoxy-1,1'-biphenyl

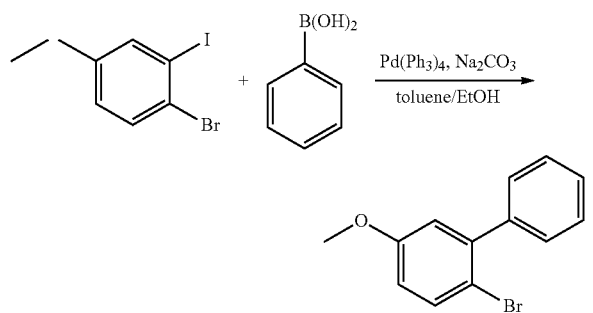

A mixture of 40 g (127.8 mmol) of 1-bromo-2-iodo-4-methoxybenzene, 15.6 g (127.8 mmol) of phenylboronic acid, 2.95 g (2.56 mmol) of Pd(Ph$_3$)$_4$, 155 ml of 2M Na$_2$CO$_3$, 100 ml of EtOH and 300 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 30 g of 2-bromo-5-methoxy-1,1'-biphenyl as colorless liquid (89.2%). $^1$H NMR (CDCl$_3$, 400 MHz): chemical shift (ppm) 7.55 (d, 1H), 7.46-7.38 (m, 5H), 6.89 (d, 1H), 6.79 (dd, 1H), 3.81 (s, 3H).

Synthesis of (5-methoxy-[1,1'-biphenyl]-2-yl)boronic Acid

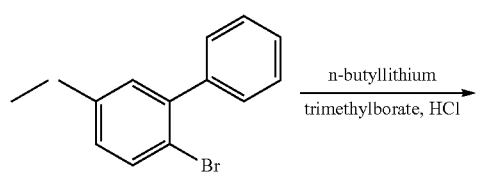

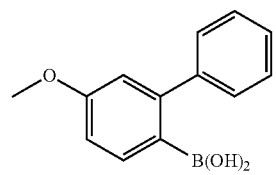

The compound 2-bromo-5-methoxy-1,1'-biphenyl (30 g, 114 mmol) was mixed with 600 ml of dry THF. To the mixture, 54.7 ml of N-butyllithium (137 mmol) was added at −60° C. and the mixture was stirred for 1 hrs. After the reaction finished, 17.8 g (171 mmol) of trimethyl borate was added and the mixture was stirred overnight. 228 ml (228 mmol) of 1M HCl was added and the mixture was stirred for 1 hrs. The mixture was extracted with ethyl acetate/H$_2$O, and the organic layer was removed under reduced pressure. The crude product was washed by hexane, yielding 19.5 g of (5-methoxy-[1,1'-biphenyl]-2-yl)boronic acid as white solid (75%).

Synthesis of 3-(5-methoxy-[1,1'-biphenyl]-2-yl)dibenzo[b,d]-thiophene

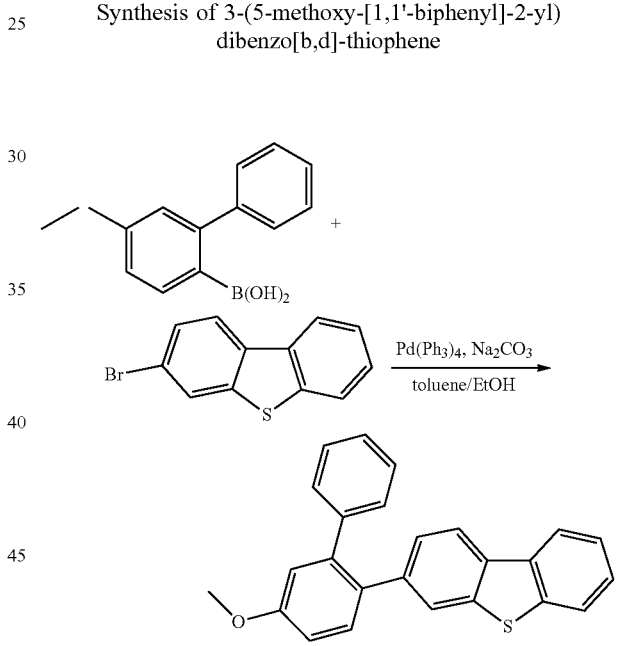

A mixture of 20 g (87.7 mmol) of (5-methoxy-[1,1'-biphenyl]-2-yl)-boronic acid, 25.4 g (96.5 mmol) of 3-bromodibenzo[b,d]thiophene, 2.03 g (1.75 mmol) of Pd(Ph$_3$)$_4$, 87.7 ml of 2M Na$_2$CO$_3$, 200 ml of EtOH and 400 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 23.1 g of 3-(5-methoxy-[1,1'-biphenyl]-2-yl)-dibenzo[b,d]thiophene as white solid (71.9%). $^1$H NMR (CDCl$_3$, 400 MHz): chemical shift (ppm) 8.47 (d, 1H), 8.12-8.06 (m, 3H), 8.01 (d, 1H), 7.77-7.74 (m, 3H), 7.49-7.45 (m, 4H), 7.41-7.38 (m, 2H), 7.02 (d, 1H), 3.81 (s, 3H).

Synthesis of 6-methoxybenzo[b]triphenyleno[2,3-d]thiophene

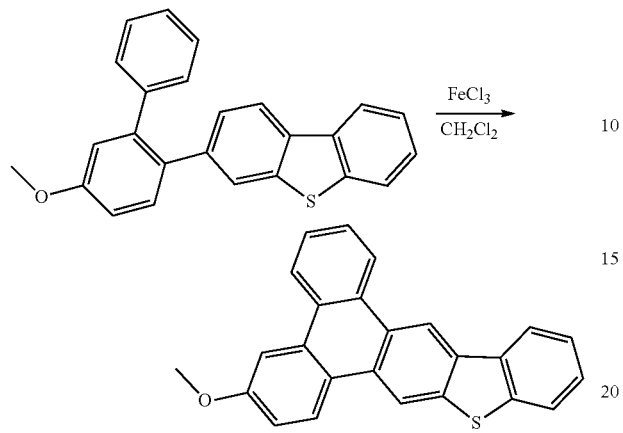

The compound 3-(5-methoxy-[1,1'-biphenyl]-2-yl)dibenzo[b,d]-thiophene (20 g, 54.6 mmol) was mixed with 700 ml of CH$_2$Cl$_2$. To the mixture, 88.5 g of FeCl$_3$(546 mmol) was added and the mixture was stirred for 1 hrs. After the reaction finished, the solvent was removed under reduced pressure, and the crude product was purified by column chromatography, yielding 8.5 g of 6-methoxybenzo[b]triphenyleno[2,3-d]-thiophene as white solid (42.7%). $^1$H NMR (CDCl$_3$, 400 MHz): chemical shift (ppm) 8.91-8.89 (m, 2H), 8.81 (d, 1H), 8.49 (d, 1H), 8.14 (m, 2H), 7.99 (d, H), 7.89-7.85 (m, 2H), 7.62 (s, 1H), 7.54-7.51 (m, 2H), 7.36 (d, 1H), 3.82 (s, 3H).

Synthesis of benzo[b]triphenyleno[2,3-d]thiophen-6-ol

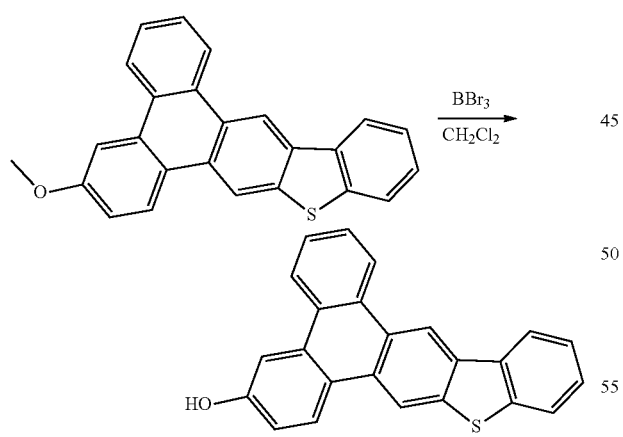

The compound 6-methoxybenzo[b]triphenyleno[2,3-d]-thiophene (10 g, 27.4 mmol) was mixed with 400 ml of CH$_2$Cl$_2$. To the mixture, 8.25 g of BBr$_3$(32.9 mmol) was added and the mixture was stirred overnight. After the reaction finished, the solvent was removed under reduced pressure, and the crude product was purified by column chromatography, yielding 8.8 g of benzo[b]triphenyleno[2,3-d]thiophen-6-ol as white solid (91.5%). $^1$H NMR (CDCl$_3$, 400 MHz): chemical shift (ppm) 8.89-8.87 (m, 2H), 8.78 (d, 1H), 8.45 (d, 1H), 8.09 (m, 2H), 7.94 (d, H), 7.86-7.83 (m, 2H), 7.58 (s, 1H), 7.51-7.48 (m, 2H), 7.31 (d, 1H), 5.41 (s, 1H).

Synthesis of benzo[b]triphenyleno[2,3-d]thiophen-6-yl trifluoro-methanesulfonate

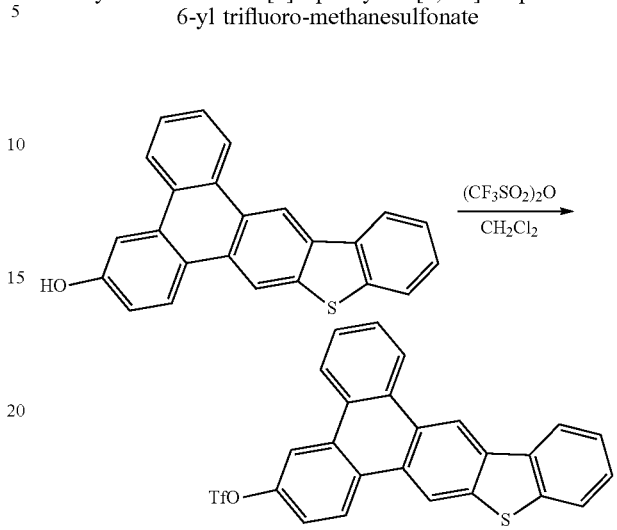

The compound benzo[b]triphenyleno[2,3-d]thiophen-6-ol (10 g, 28.5 mmol) was mixed with 450 ml of CH$_2$Cl$_2$. To the mixture, 3.4 g of pyridine(42.8 mmol) was added and the mixture was stirred for 1 hrs. To the mixture, 13.7 g of (CF$_3$SO$_2$)$_2$O (48.5 mmol) was added and the mixture was stirred for 1 hrs. After the reaction finished, the solvent was removed under reduced pressure, and the crude product was purified by column chromatography, yielding 10.5 g of benzo[b]triphenyleno[2,3-d]thiophen-6-yltrifluoro-methanesulfonate as yellow solid (55.9%). $^1$H NMR (CDCl$_3$, 400 MHz): chemical shift (ppm) 8.99-8.95 (m, 3H), 8.47 (d, 1H), 8.14-8.11 (m, 3H), 7.97 (d, H), 7.88-7.85 (m, 2H), 7.58 (s, 1H), 7.53-7.51 (m, 2H).

Synthesis of 2-(benzo[b]triphenyleno[2,3-d]thiophen-6-yl)-4,4,5,5-tetramethyl-1,3,2-dioxaborolane

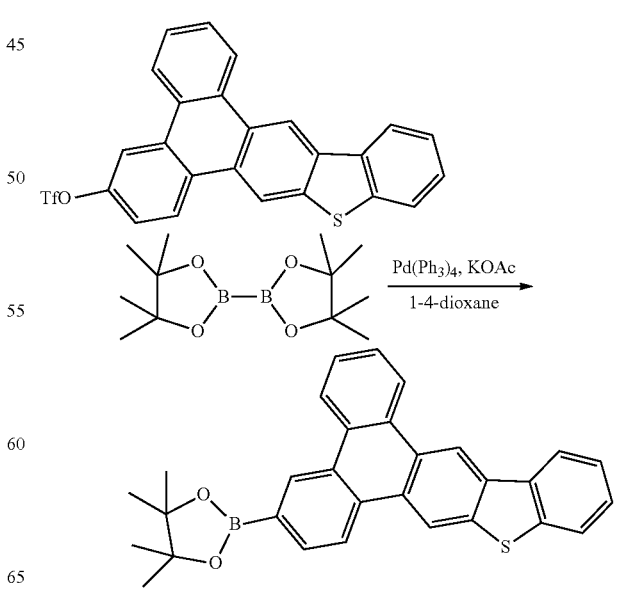

A mixture of 5 g (10.4 mmol) of benzo[b]triphenyleno[2,3-d]thiophen-6-yl trifluoromethanesulfonate, 3.16 g (12.4 mmol) of bis(pinacolato)diboron, 0.48 g (0.4 mmol) of Pd(Ph₃)₄, 2.04 g (20.8 mmol) of potassium acetate, and 60 ml of 1,4-dioxane was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 3.1 g of 2-(benzo[b]triphenyleno[2,3-d]thiophen-6-yl)-4,4,5,5-tetramethyl-1,3,2-dioxaborolane as white solid (65%). $^1$H NMR (CDCl₃, 400 MHz): chemical shift (ppm) 8.94-8.88 (m, 3H), 8.47 (d, 1H), 8.15-8.12 (m, 3H), 7.99 (d, 1H), 7.87-7.84 (m, 3H), 7.54-7.52 (m, 2H), 1.27 (s, 12H).

Synthesis of 2-(benzo[b]triphenyleno[2,3-d]thiophen-6-yl)-8-(naphthalen-2-yl)dibenzo[b,d]furan (Compound 78)

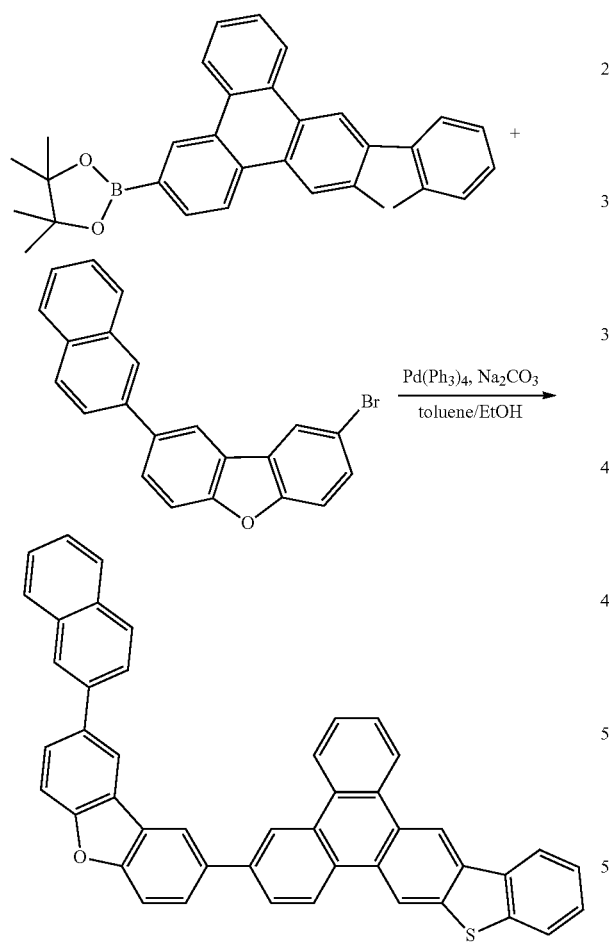

A mixture of 3 g (6.51 mmol) of 2-(benzo[b]triphenyleno[2,3-d]-thiophen-6-yl)-4,4,5,5-tetramethyl-1,3,2-dioxaborolane, 2.68 g (7.17 mmol) of 2-bromo-8-(naphthalen-2-yl)dibenzo[b,d]furan, 0.15 g (0.13 mmol) of Pd(Ph₃)₄, 6.5 ml of 2M Na₂CO₃, 20 ml of EtOH and 40 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 2.7 g of 2-(benzo[b]triphenyleno[2,3-d]thiophen-6-yl)-8-(naphthalen-2-yl)dibenzo[b,d]furan as yellow solid (66%). $^1$H NMR (CDCl₃, 400 MHz): chemical shift (ppm) 8.99-8.93 (m, 3H), 8.46 (d, 1H), 8.33 (s, 1H), 8.13-8.09 (m, 3H), 8.01-7.97 (m, 3H), 7.91-7.83 (m, 5H), 7.74-7.69 (m, 5H), 7.59-7.56 (m, 3H), 7.51-7.48 (m, 2H).

Experimental Example 2

Synthesis of 9-(5-methoxy-[1,1'-biphenyl]-2-yl)naphtho[2,1-b]-benzofuran

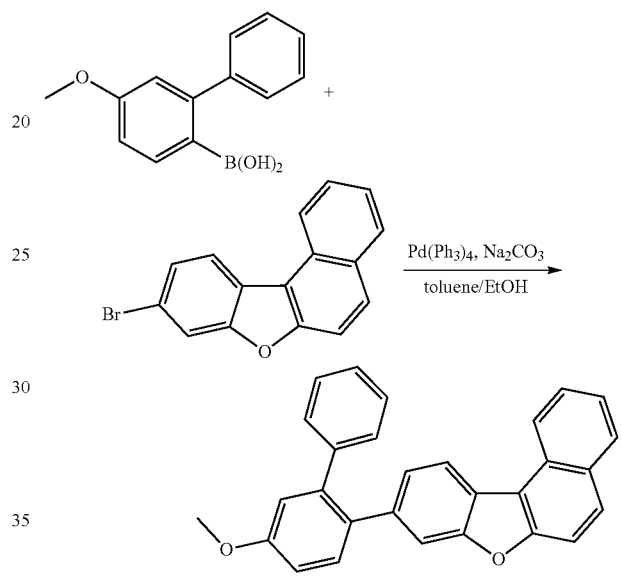

A mixture of 20 g (87.7 mmol) of (5-methoxy-[1,1'-biphenyl]-2-yl)-boronic acid, 28.7 g (96.5 mmol) of 9-bromonaphtho[2,1-b]benzofuran, 2.03 g (1.75 mmol) of Pd(Ph₃)₄, 87.7 ml of 2M Na₂CO₃, 200 ml of EtOH and 400 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 24.1 g of 9-(5-methoxy-[1,1'-biphenyl]-2-yl)naphtho[2,1-b]benzofuran as white solid (68.7%). $^1$H NMR (CDCl₃, 400 MHz): chemical shift (ppm) 8.55 (d, 1H), 8.18 (d, 1H), 7.96 (d, 1H), 7.81-7.76 (m, 3H), 7.64-7.59 (m, 6H), 7.50-7.44 (m, 4H), 7.02 (d, 1H), 3.82 (s, 3H).

Synthesis of 11-methoxynaphtho[2,1-b]triphenyleno[2,3-d]furan

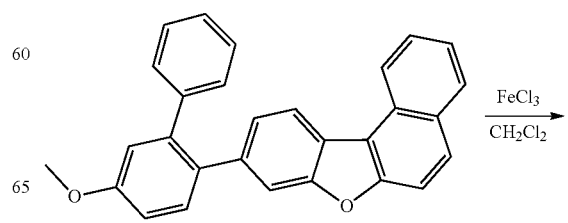

-continued

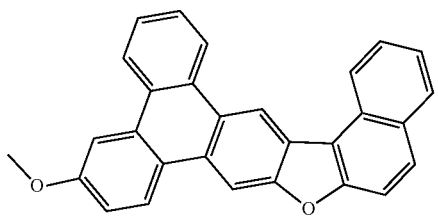

The compound 9-(5-methoxy-[1,1'-biphenyl]-2-yl)naphtho[2,1-b]-benzofuran (20 g, 50 mmol) was mixed with 700 ml of $CH_2Cl_2$. To the mixture, 81 g of $FeCl_3$ (500 mmol) was added and the mixture was stirred for 1 hrs. After the reaction finished, the solvent was removed under reduced pressure, and the crude product was purified by column chromatography, yielding 8.7 g of 11-methoxynaphtho[2,1-b]triphenyleno[2,3-d]furan as white solid (43.7%). $^1$H NMR ($CDCl_3$, 400 MHz): chemical shift (ppm) 8.91-8.89 (m, 2H), 8.81 (d, 1H), 8.53 (d, 1H), 8.17-8.13 (m, 3H), 7.87-7.84 (m, 2H), 7.68-7.61 (m, 5H), 7.37 (d, 1H), 3.82 (s, 3H).

Synthesis of naphtho[2,1-b]triphenyleno[2,3-d]furan-11-ol

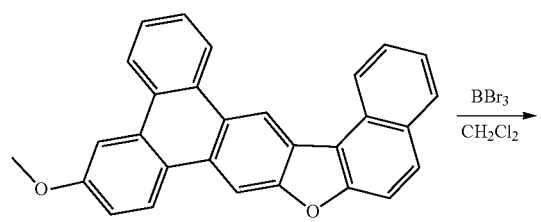

The compound 11-methoxynaphtho[2,1-b]triphenyleno[2,3-d]furan (10 g, 25.1 mmol) was mixed with 400 ml of $CH_2Cl_2$. To the mixture, 7.55 g of $BBr_3$ (30.1 mmol) was added and the mixture was stirred overnight. After the reaction finished, the solvent was removed under reduced pressure, and the crude product was purified by column chromatography, yielding 8.6 g of naphtho[2,1-b]triphenyleno[2,3-d]furan-11-ol as white solid (89.1%). $^1$H NMR ($CDCl_3$, 400 MHz): chemical shift (ppm) 8.92-8.89 (m, 2H), 8.77 (d, 1H), 8.55 (d, 1H), 8.18-8.12 (m, 3H), 7.89-7.84 (m, 2H), 7.69-7.62 (m, 5H), 7.37 (d, 1H), 5.38 (s, 1H).

Synthesis of naphtho[2,1-b]triphenyleno[2,3-d]furan-11-yl trifluoromethanesulfonate

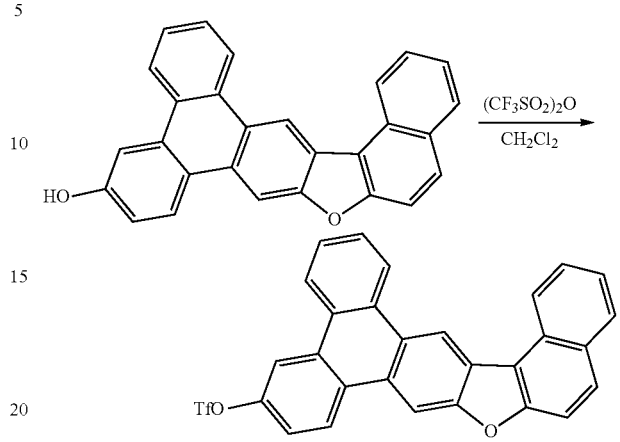

The compound naphtho[2,1-b]triphenyleno[2,3-d]furan-11-ol (10 g, 26 mmol) was mixed with 450 ml of $CH_2Cl_2$. To the mixture, 3.1 g of pyridine (39 mmol) was added and the mixture was stirred for 1 hrs. To the mixture, 12.5 g of $(CF_3SO_2)_2O$ (44.2 mmol) was added and the mixture was stirred for 1 hrs. After the reaction finished, the solvent was removed under reduced pressure, and the crude product was purified by column chromatography, yielding 9.7 g of naphtho[2,1-b]triphenyleno[2,3-d]furan-11-yl trifluoromethanesulfonate as yellow solid (72.4%). $^1$H NMR ($CDCl_3$, 400 MHz): chemical shift (ppm) 8.99 (d, 1H), 8.92 (m, 2H), 8.55 (d, 1H), 8.18-8.12 (m, 3H), 8.08 (s, 1H), 7.87-7.81 (m, 3H), 7.67-7.61 (m, 4H).

Synthesis of 4,4,5,5-tetramethyl-2-(naphtho[2,1-b]triphenyleno[2,3-d]-furan-11-yl)-1,3,2-dioxaborolane

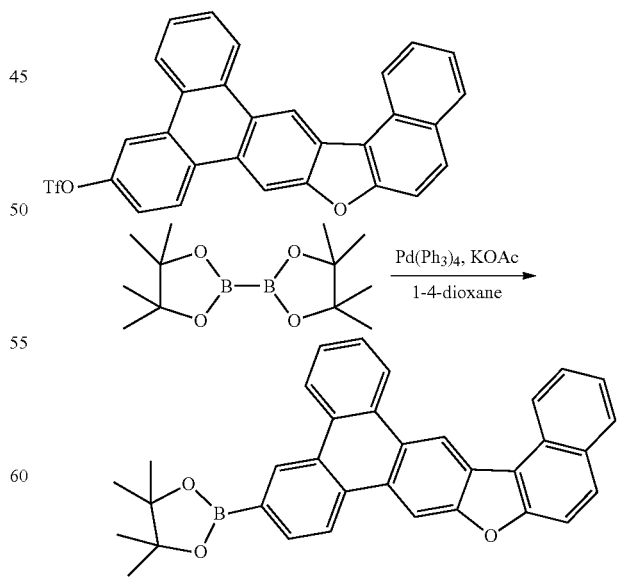

A mixture of 5 g (9.68 mmol) of naphtho[2,1-b]triphenyleno[2,3-d]-furan-11-yltrifluoromethanesulfonate, 2.96 g (11.6 mmol) of bis(pinacolato)diboron, 0.48 g (0.4 mmol) of Pd(Ph$_3$)$_4$, 2.04 g (20.8 mmol) of potassium acetate, and 60 ml of 1,4-dioxane was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 2.9 g of 4,4,5,5-tetramethyl-2-(naphtho[2,1-b]triphenyleno[2,3-d]furan-11-yl)-1,3,2-dioxaborolane as white solid (60.6%). $^1$H NMR (CDCl$_3$, 400 MHz): chemical shift (ppm) 8.94-8.91 (m, 3H), 8.55 (d, 1H), 8.17-8.12 (m, 4H), 7.91-7.84 (m, 3H), 7.69-7.61 (m, 4H), 1.26 (s, 12H).

Synthesis of 11-(8-(naphthalen-2-yl)dibenzo[b,d]furan-2-yl)naphtha-[2,1-b]triphenyleno[2,3-d]furan (Compound 38)

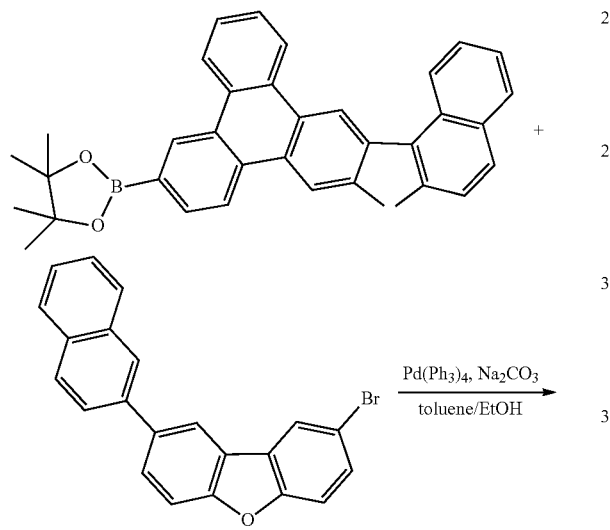

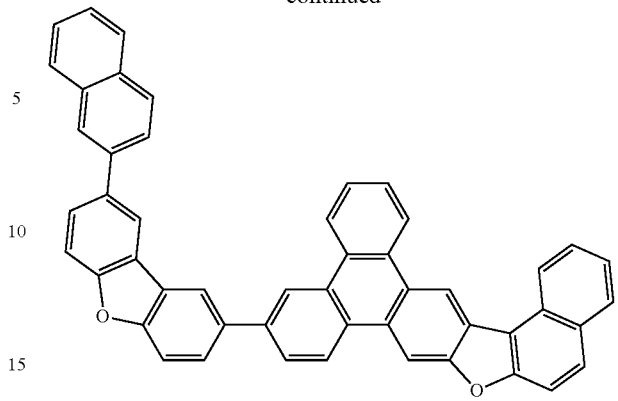

A mixture of 3 g (6.07 mmol) of 2-(benzo[b]triphenyleno[2,3-d]-thiophen-6-yl)-4,4,5,5-tetramethyl-1,3,2-dioxaborolane, 2.5 g (6.68 mmol) of 2-bromo-8-(naphthalen-2-yl)dibenzo[b,d]furan, 0.15 g (0.13 mmol) of Pd(Ph$_3$)$_4$, 6.5 ml of 2M Na$_2$CO$_3$, 20 ml of EtOH and 40 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 2.5 g of 11-(8-(naphthalen-2-yl)dibenzo[b,d]furan-2-yl)naphtha[2,1-b]triphenyleno-[2,3-d]furan as yellow solid (62.5%). $^1$H NMR (CDCl$_3$, 400 MHz): chemical shift (ppm) 8.99-8.94 (m, 3H), 8.56 (d, 1H), 8.36 (s, 1H), 8.18-8.12 (m, 4H), 8.01 (d, 2H), 7.93-7.83 (m, 5H), 7.75-7.66 (m, 8H), 7.59-7.54 (m, 4H).

Example 3-30

We have used the same synthesis methods to get a series of intermediates and the following compounds are synthesized analogously.

| Ex. | Intermediate III |
|---|---|
| 3 | 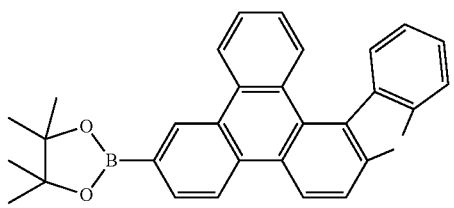 [SMILES: Cc1ccccc1-c1c(C)ccc2c3ccc(B4OC(C)(C)C(C)(C)O4)cc3c3ccccc3c12] |
| 4 | 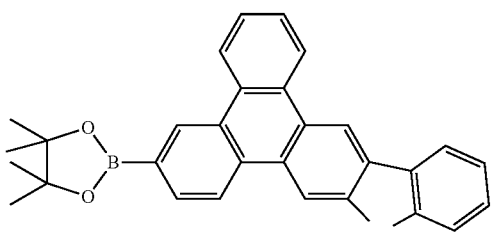 [SMILES: Cc1ccccc1-c1cc2c3ccccc3c3cc(B4OC(C)(C)C(C)(C)O4)ccc3c2cc1C] |

5
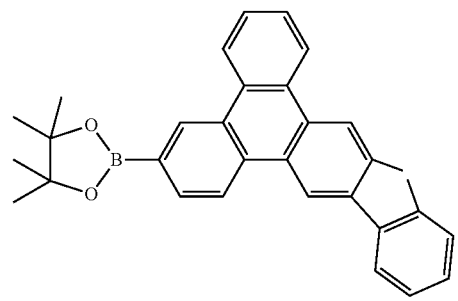 [SMILES: Cc1ccccc1-c1cc2c3ccc(B4OC(C)(C)C(C)(C)O4)cc3c3ccccc3c2cc1C]
6
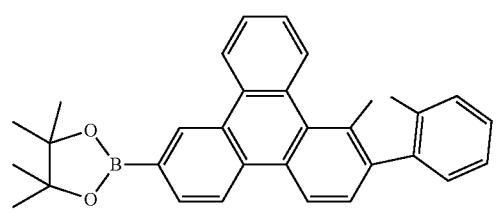 [SMILES: Cc1ccccc1-c1ccc2c3ccc(B4OC(C)(C)C(C)(C)O4)cc3c3ccccc3c2c1C]
7
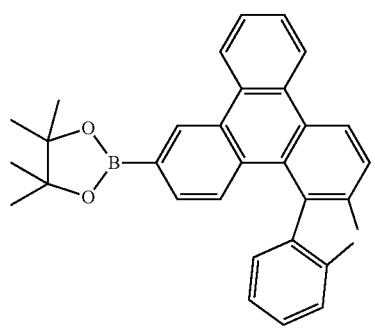 [SMILES: Cc1ccccc1-c1c(C)ccc2c3ccccc3c3cc(B4OC(C)(C)C(C)(C)O4)ccc3c12]
8
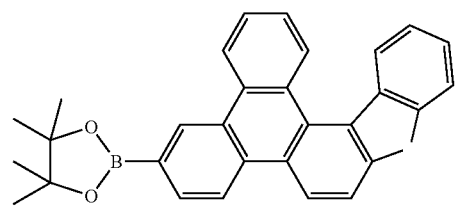 [SMILES: Cc1ccccc1-c1c(C)ccc2c3ccc(B4OC(C)(C)C(C)(C)O4)cc3c3ccccc3c12]
9
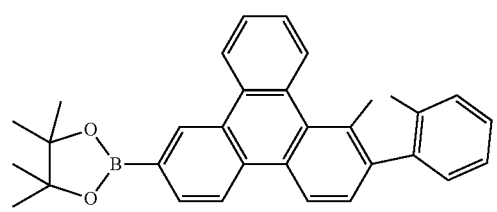 [SMILES: Cc1ccccc1-c1ccc2c3ccc(B4OC(C)(C)C(C)(C)O4)cc3c3ccccc3c2c1C]
10
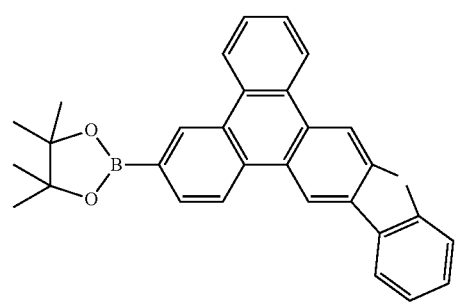 [SMILES: Cc1ccccc1-c1cc2c3ccc(B4OC(C)(C)C(C)(C)O4)cc3c3ccccc3c2cc1C]

-continued
11
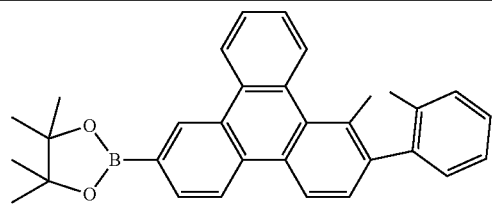
12
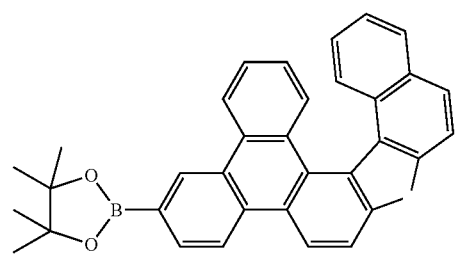 [SMILES: Cc1ccc2ccccc2c1-c1c(C)ccc2c3ccc(B4OC(C)(C)C(C)(C)O4)cc3c3ccccc3c12]
13
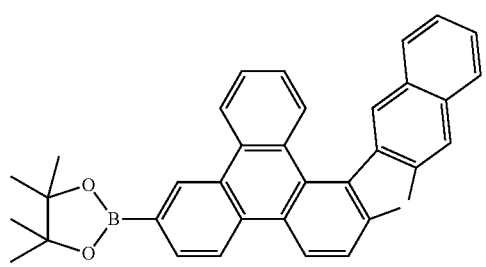 [SMILES: Cc1cc2ccccc2cc1-c1c(C)ccc2c3ccc(B4OC(C)(C)C(C)(C)O4)cc3c3ccccc3c12]
14
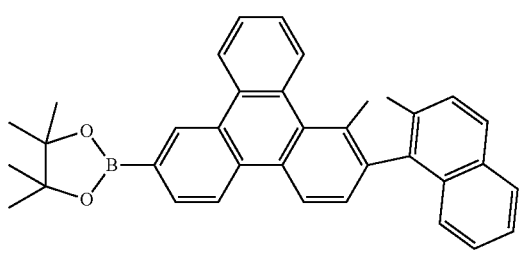 [SMILES: Cc1ccc2ccccc2c1-c1ccc2c3ccc(B4OC(C)(C)C(C)(C)O4)cc3c3ccccc3c2c1C]
15
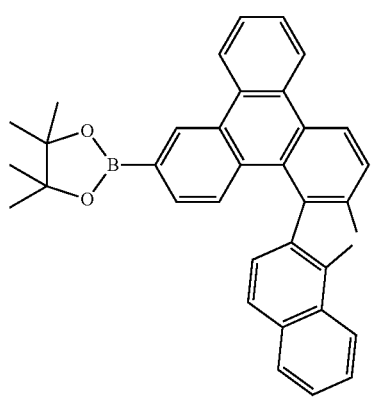 [SMILES: Cc1ccc2c3ccccc3c3cc(B4OC(C)(C)C(C)(C)O4)ccc3c2c1-c1ccc2ccccc2c1C]
16
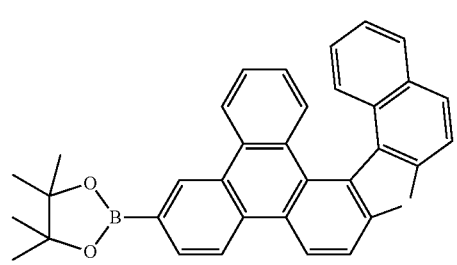 [SMILES: Cc1ccc2ccccc2c1-c1c(C)ccc2c3ccc(B4OC(C)(C)C(C)(C)O4)cc3c3ccccc3c12]

17
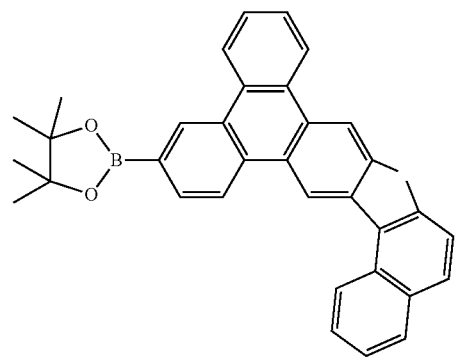 [SMILES: Cc1cc2c3ccccc3c3cc(B4OC(C)(C)C(C)(C)O4)ccc3c2cc1-c1c(C)ccc2ccccc12]
18
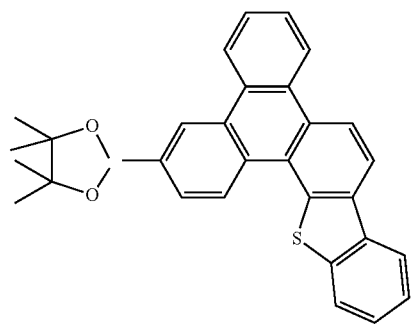
19
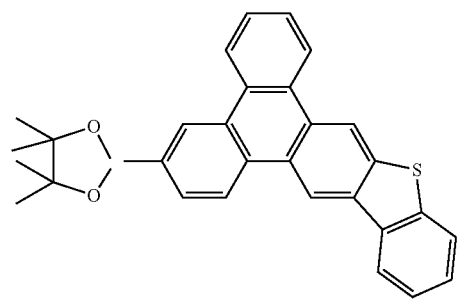
20
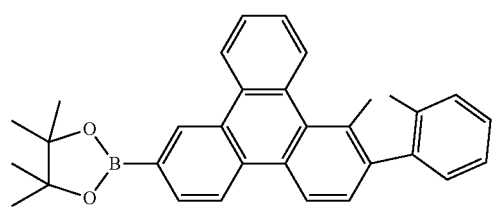 [SMILES: Cc1ccccc1-c1ccc2c3ccc(B4OC(C)(C)C(C)(C)O4)cc3c3ccccc3c2c1C]
21
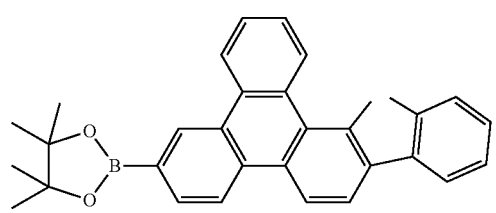 [SMILES: Cc1ccccc1-c1ccc2c3ccc(B4OC(C)(C)C(C)(C)O4)cc3c3ccccc3c2c1C]

-continued
22
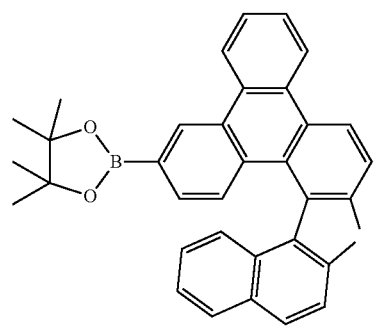 [SMILES: Cc1ccc2ccccc2c1-c1c(C)ccc2c3ccccc3c3cc(B4OC(C)(C)C(C)(C)O4)ccc3c12]
23
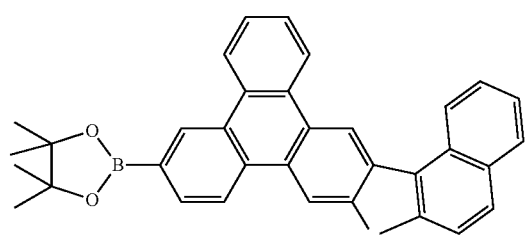 [SMILES: Cc1cc2c3ccc(B4OC(C)(C)C(C)(C)O4)cc3c3ccccc3c2cc1-c1c(C)ccc2ccccc12]
24
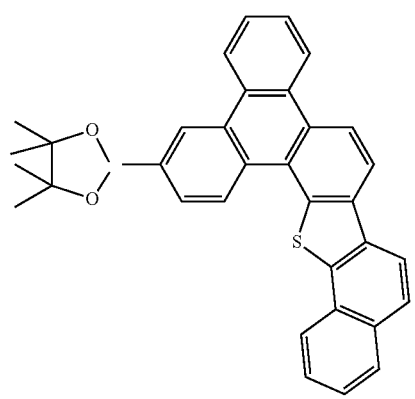
25
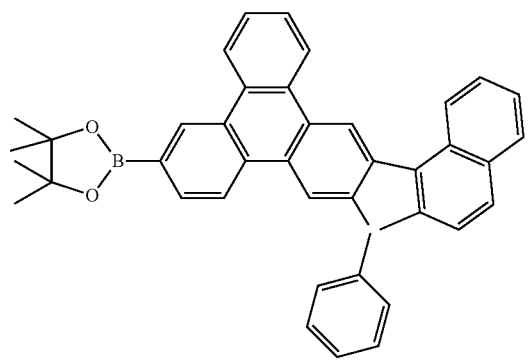

26
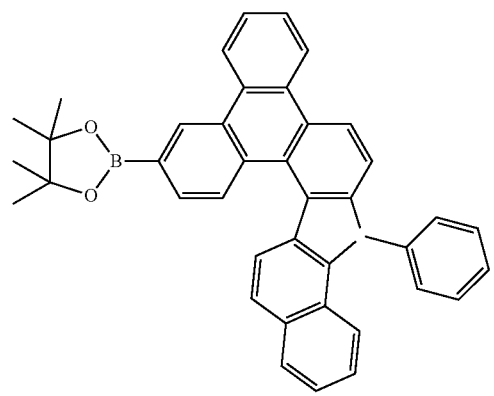
27
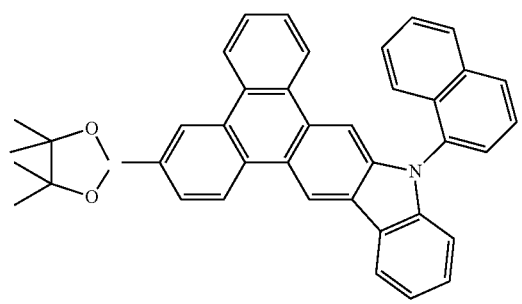
28
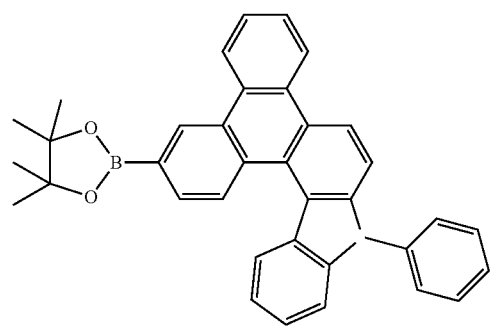
29
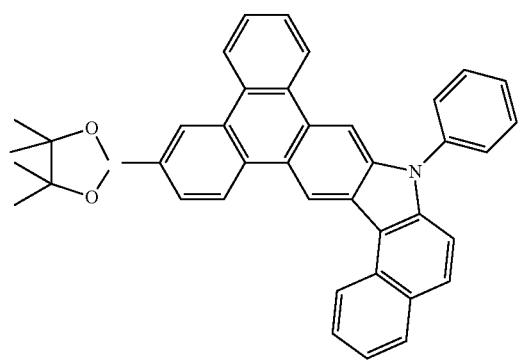
30
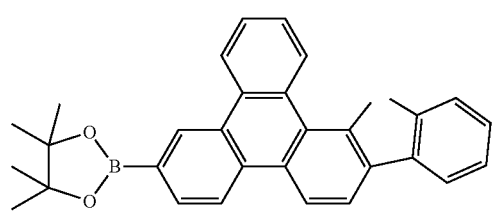 [SMILES: Cc1ccccc1-c1ccc2c3ccc(B4OC(C)(C)C(C)(C)O4)cc3c3ccccc3c2c1C]

-continued
| Ex. | Intermediate IV |
|---|---|
| 3 | 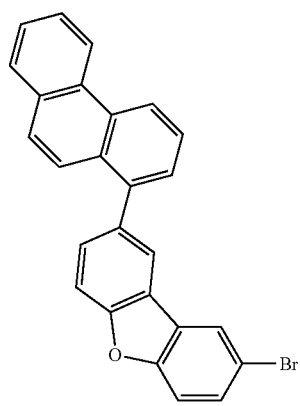 [SMILES: Brc1ccc2oc3ccc(-c4cccc5c4ccc4ccccc45)cc3c2c1] |
| 4 | 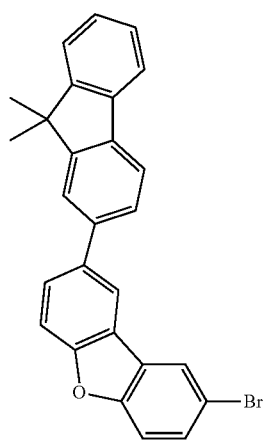 [SMILES: CC1(C)c2ccccc2-c2ccc(-c3ccc4oc5ccc(Br)cc5c4c3)cc21] |
| 5 | 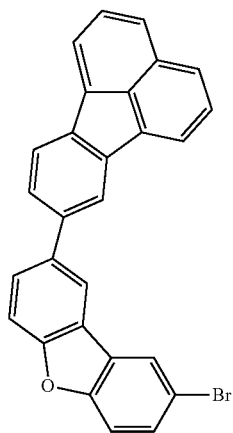 |

6
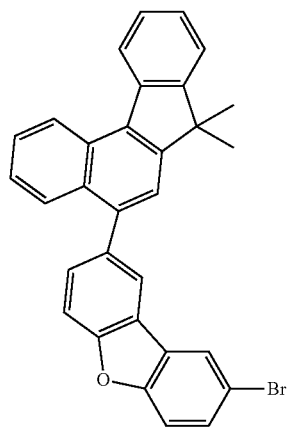 [SMILES: CC1(C)c2ccccc2-c2c1cc(-c1ccc3oc4ccc(Br)cc4c3c1)c1ccccc21]
7
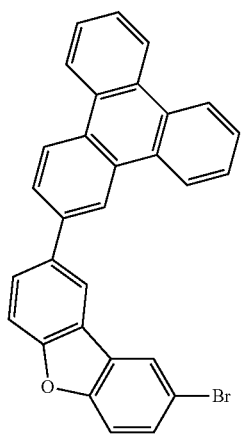 [SMILES: Brc1ccc2oc3ccc(-c4ccc5c6ccccc6c6ccccc6c5c4)cc3c2c1]
8
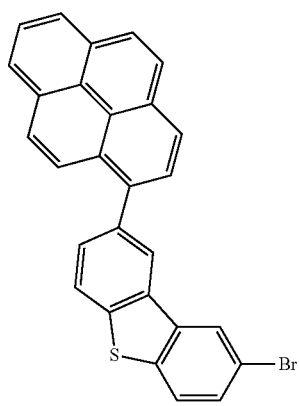 [SMILES: Brc1ccc2sc3ccc(-c4ccc5ccc6cccc7ccc4c5c67)cc3c2c1]

-continued
9
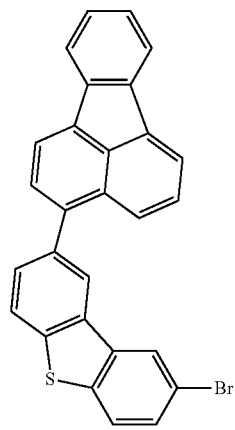
10
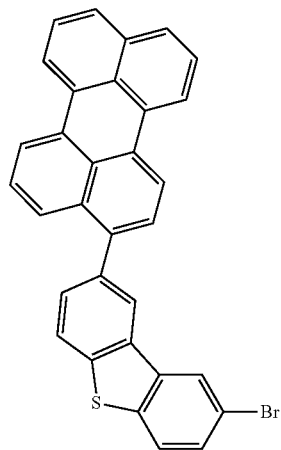 [SMILES: Brc1ccc2sc3ccc(-c4ccc5c6cccc7cccc(c8cccc4c85)c76)cc3c2c1]
11
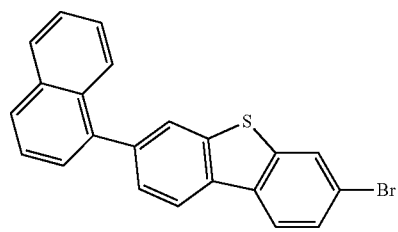 [SMILES: Brc1ccc2c(c1)sc1cc(-c3cccc4ccccc34)ccc12]
12
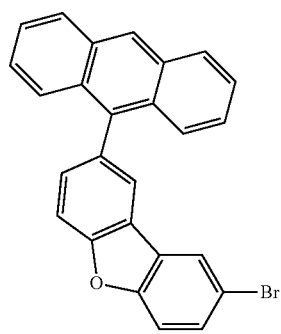 [SMILES: Brc1ccc2oc3ccc(-c4c5ccccc5cc5ccccc45)cc3c2c1]

-continued
13
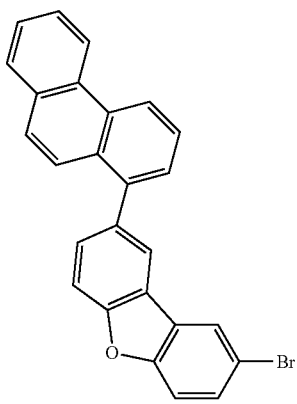 [SMILES: Brc1ccc2oc3ccc(-c4cccc5c4ccc4ccccc45)cc3c2c1]
14
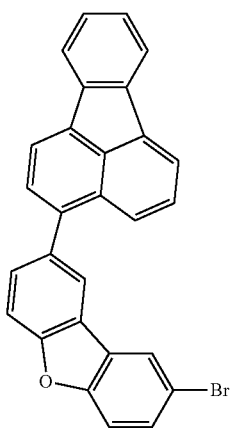 [SMILES: Brc1ccc2oc3ccc(-c4ccc5c6c(cccc46)-c4ccccc4-5)cc3c2c1]
15
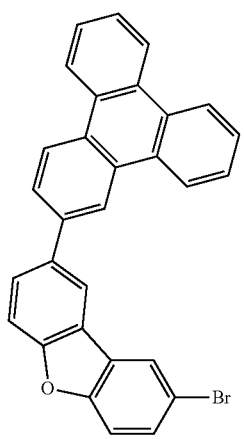
16
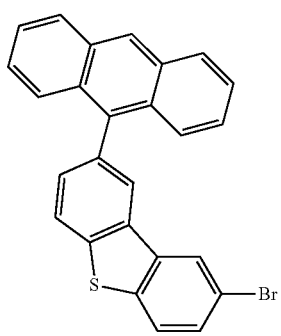 [SMILES: Brc1ccc2sc3ccc(-c4c5ccccc5cc5ccccc45)cc3c2c1]

-continued
17
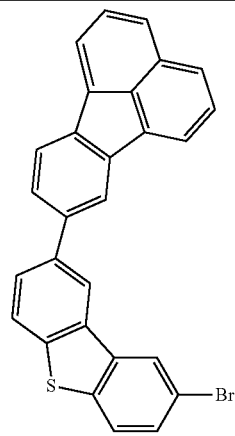
18
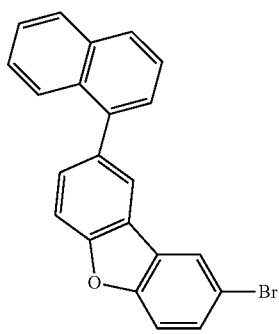
19
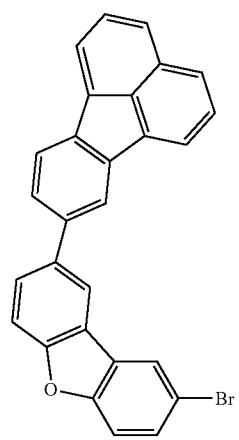 [SMILES: Brc1ccc2sc3ccc(-c4ccc5c(c4)-c4cccc6cccc-5c46)cc3c2c1]
20
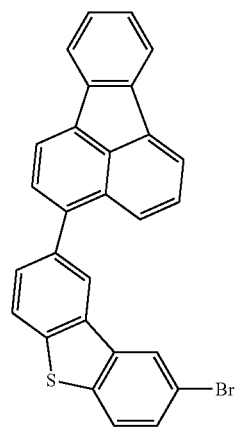 [SMILES: Brc1ccc2sc3ccc(-c4ccc5c6c(cccc46)-c4ccccc4-5)cc3c2c1]

-continued
21 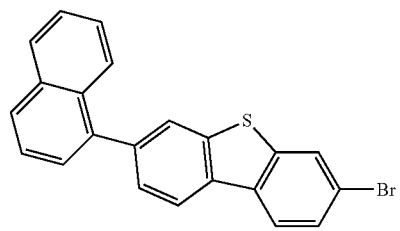 [SMILES: Brc1ccc2c(c1)sc1cc(-c3cccc4ccccc34)ccc12]
22 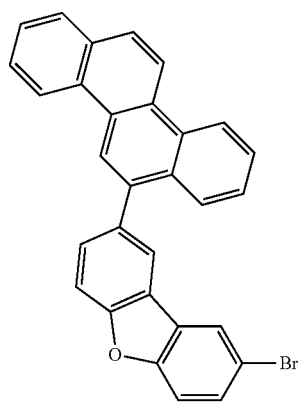 [SMILES: Brc1ccc2oc3ccc(-c4cc5c6ccccc6ccc5c5ccccc45)cc3c2c1]
23 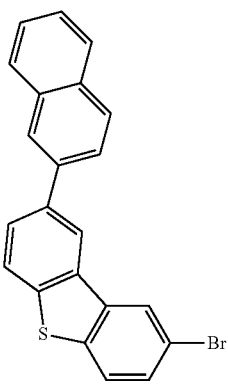 [SMILES: Brc1ccc2sc3ccc(-c4ccc5ccccc5c4)cc3c2c1]
24 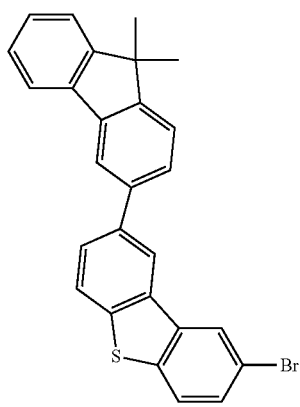 [SMILES: CC1(C)c2ccccc2-c2cc(-c3ccc4sc5ccc(Br)cc5c4c3)ccc21]

25
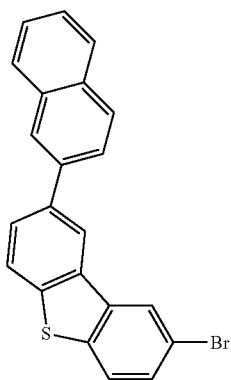 [SMILES: Brc1ccc2sc3ccc(-c4ccc5ccccc5c4)cc3c2c1]
26
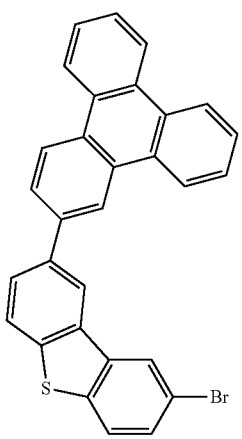
27
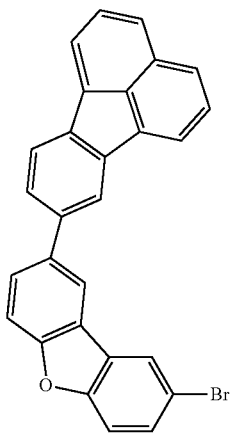 [SMILES: Brc1ccc2oc3ccc(-c4ccc5c(c4)-c4cccc6cccc-5c46)cc3c2c1]

-continued
| | | |
|---|---|---|
| 28 | 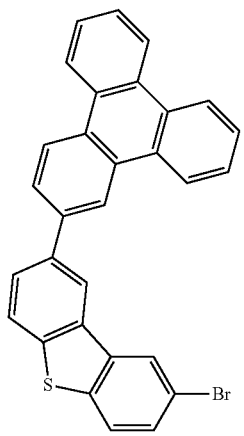 [SMILES: Brc1ccc2sc3ccc(-c4ccc5c6ccccc6c6ccccc6c5c4)cc3c2c1] | |
| 29 | 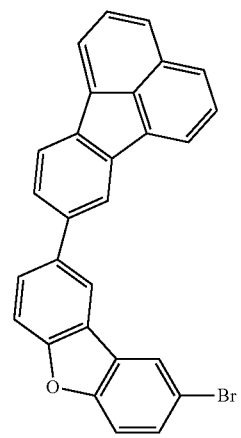 | |
| 30 | 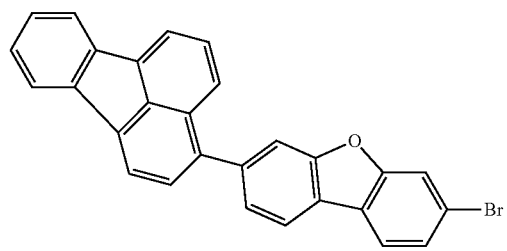 [SMILES: Brc1ccc2c(c1)oc1cc(-c3ccc4c5c(cccc35)-c3ccccc3-4)ccc12] | |
| Ex. | Product | Yield |
|---|---|---|
| 3 | 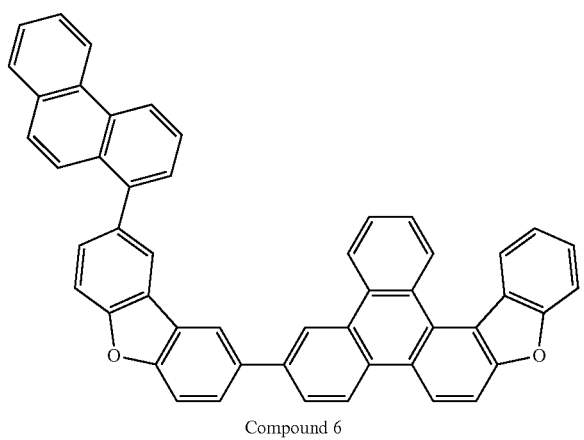 [SMILES: c1ccc2c(c1)ccc1c(-c3ccc4oc5ccc(-c6ccc7c(c6)c6ccccc6c6c7ccc7oc8ccccc8c76)cc5c4c3)cccc12]
Compound 6 | 61% |

| | | |
|---|---|---|
| 4 | 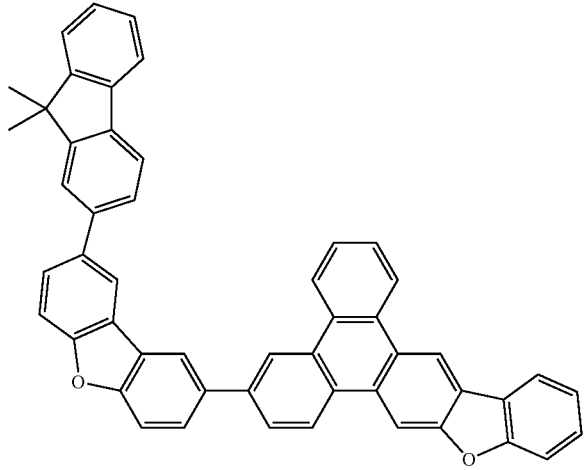
Compound 8 | 67% |
| 5 | 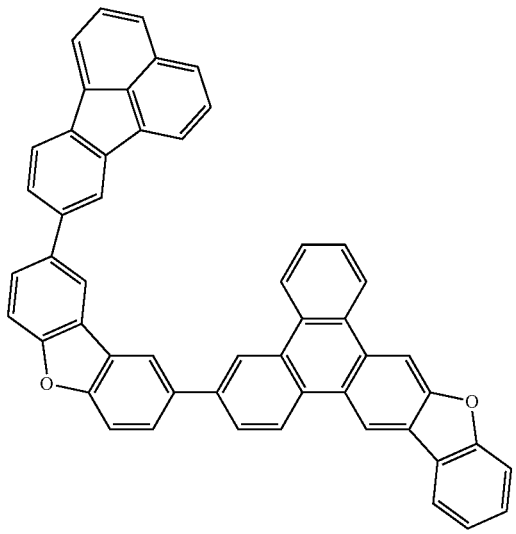
Compound 11 | 57% |
| 6 | 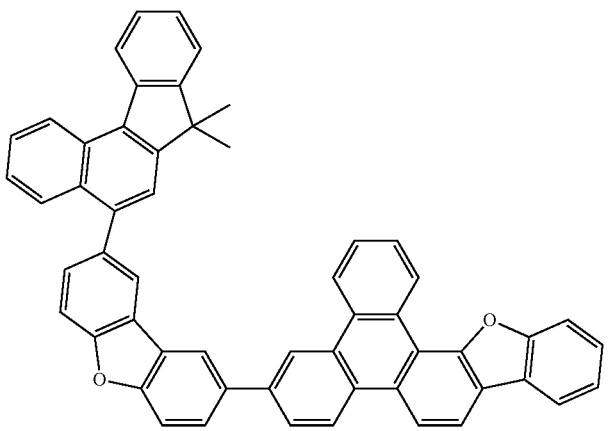
Compound 15 | 54% |

| | | -continued | |
|---|---|---|---|
| 7 | | 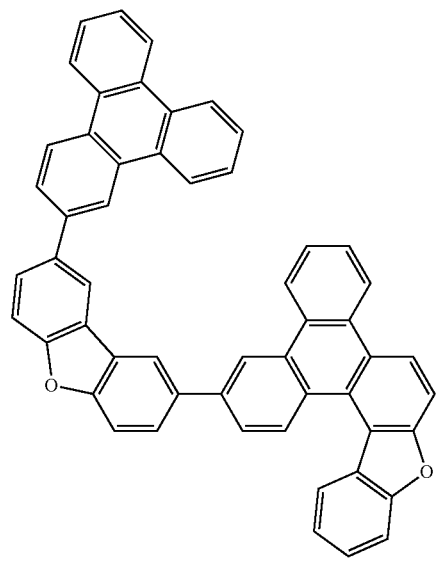<br>Compound 16 | 61% |
| 8 | | 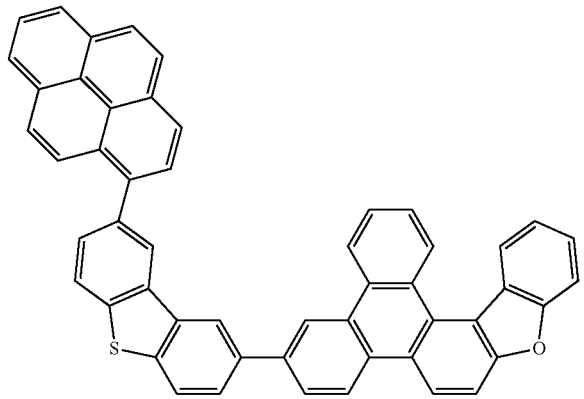<br>Compound 27 | 58% |
| 9 | | 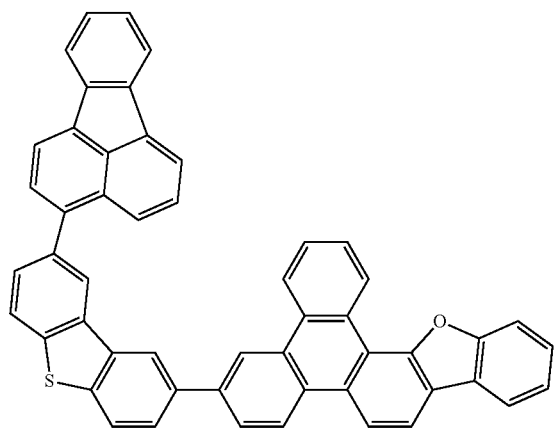<br>Compound 30 | 66% |

-continued
10 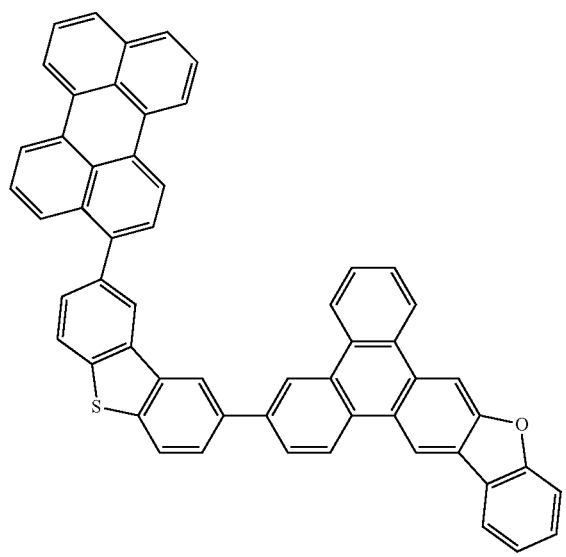 61%
Compound 35
11 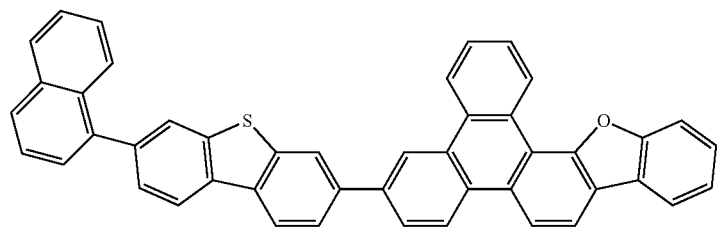 56%
Compound 36
12 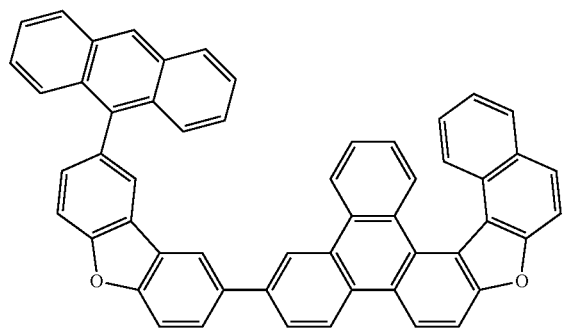 49%
Compound 39

-continued
| 13 | 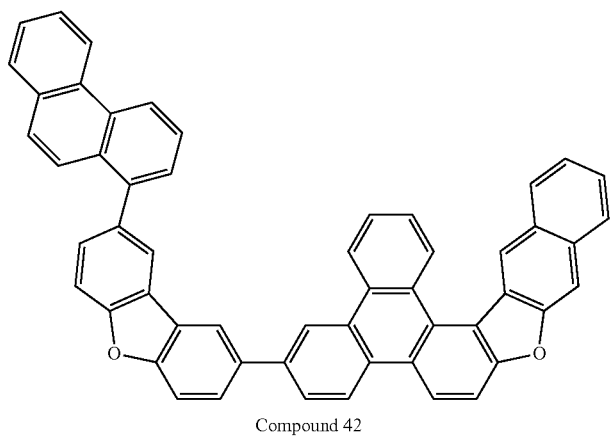 [SMILES: c1ccc2cc3c(cc2c1)oc1ccc2c4ccc(-c5ccc6oc7ccc(-c8cccc9c8ccc8ccccc89)cc7c6c5)cc4c4ccccc4c2c13] Compound 42 | 52% |
| 14 | 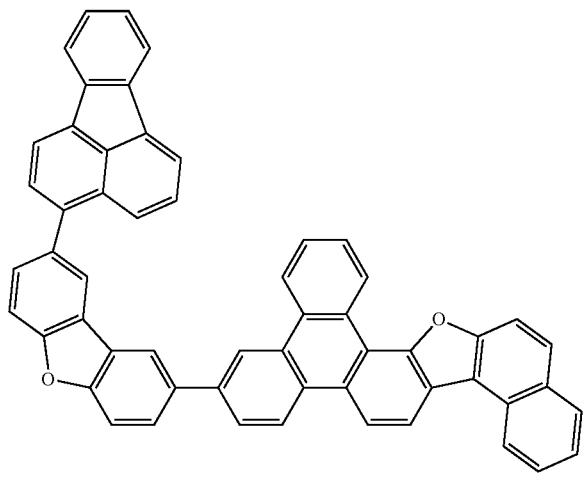 Compound 48 | 57% |
| 15 | 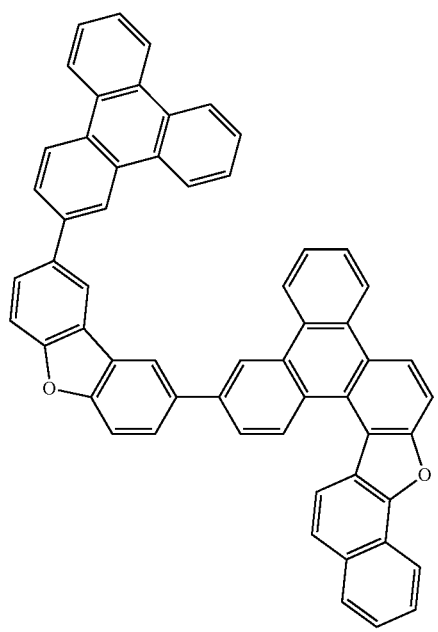 Compound 52 | 56% |

| 16 | 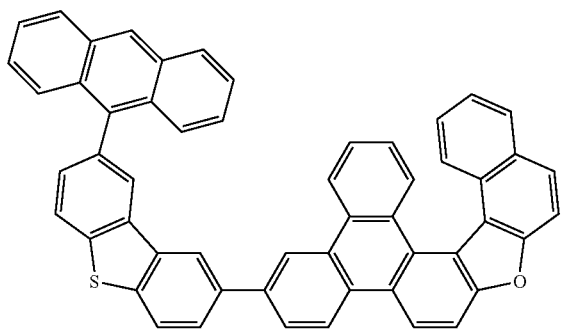
Compound 59 | 51% |
| 17 | 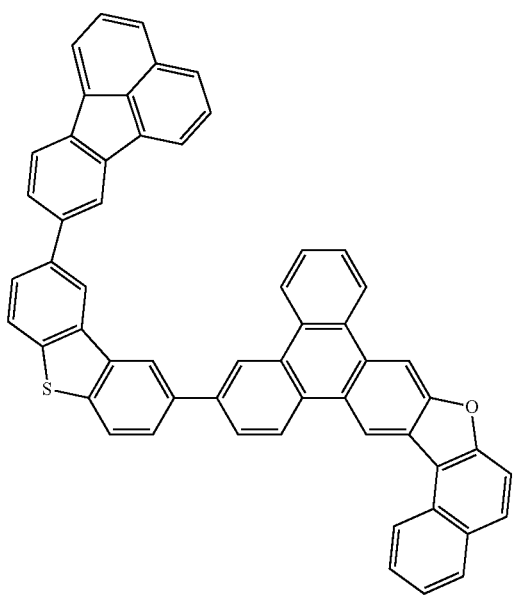
Compound 67 | 52% |
| 18 | 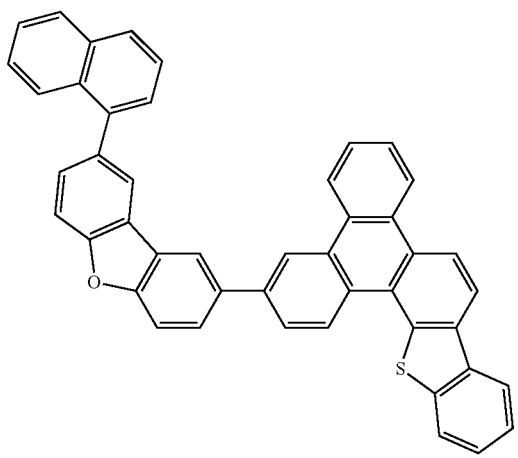
Compound 77 | 68% |

-continued
| | | |
|---|---|---|
| 19 | 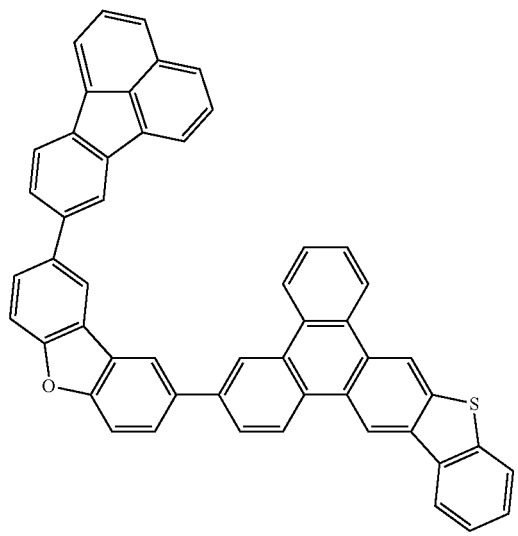
Compound 87 | 59% |
| 20 | 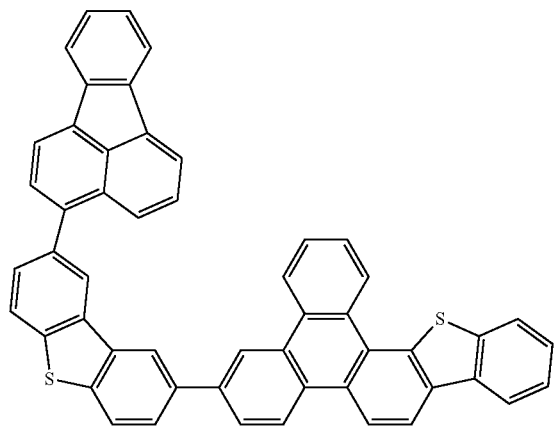
Compound 106 | 57% |
| 21 | 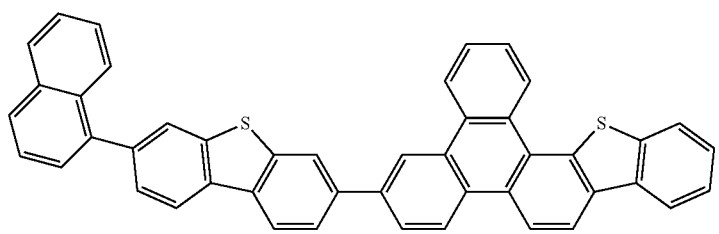
Compound 112 | 63% |

-continued
| | | |
|---|---|---|
| 22 | 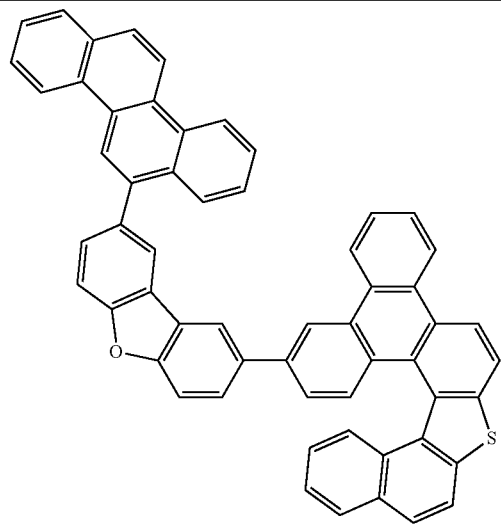
Compound 122 | 52% |
| 23 | 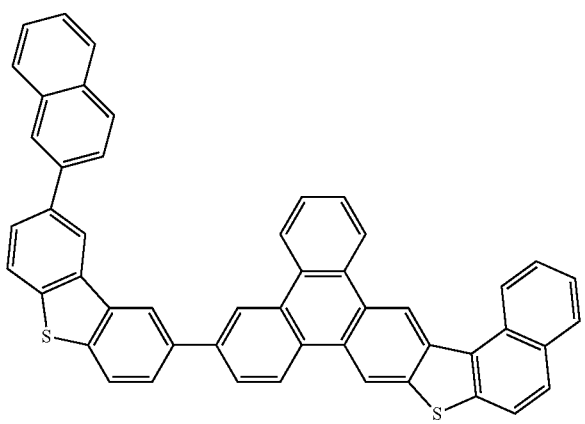
Compound 134 | 65% |
| 24 | 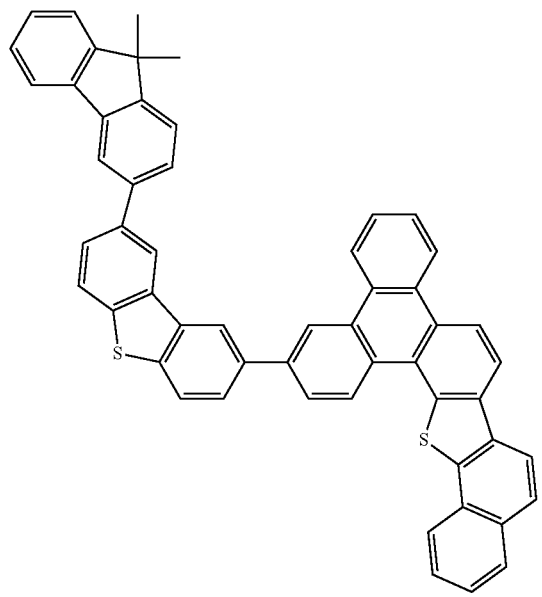
Compound 139 | 62% |

-continued
25 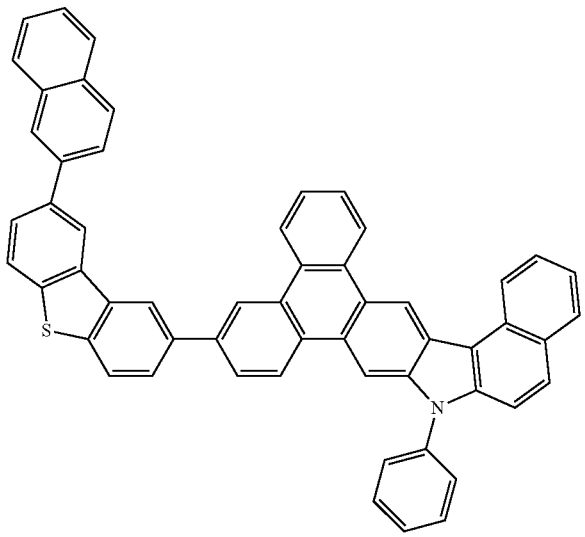 63%
Compound 194
26 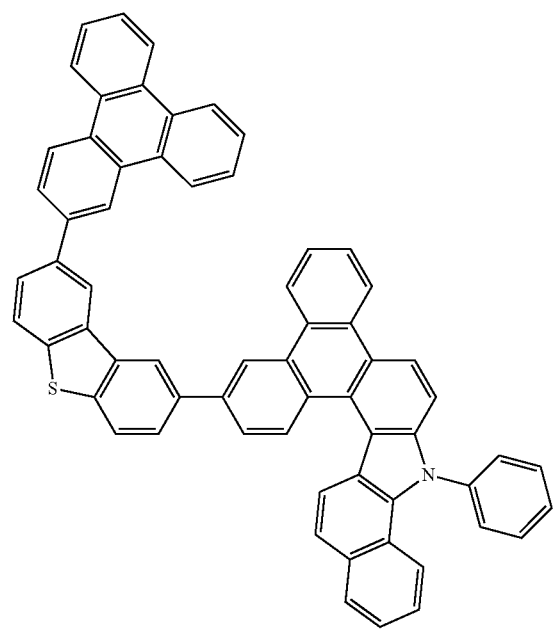 55%
Compound 208

| 27 | 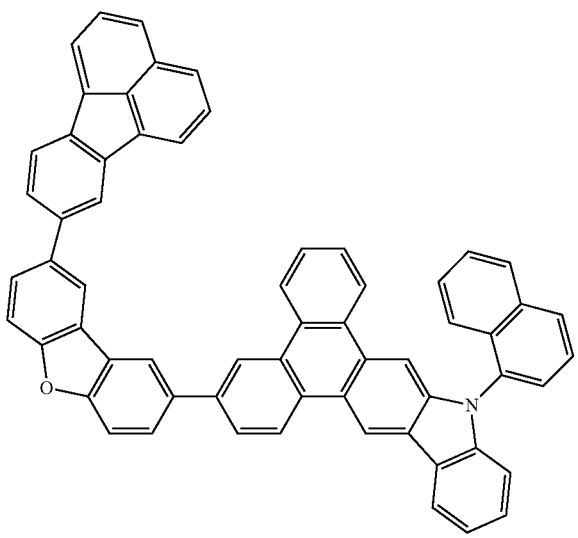<br>Compound 219 | 49% |
| 28 | 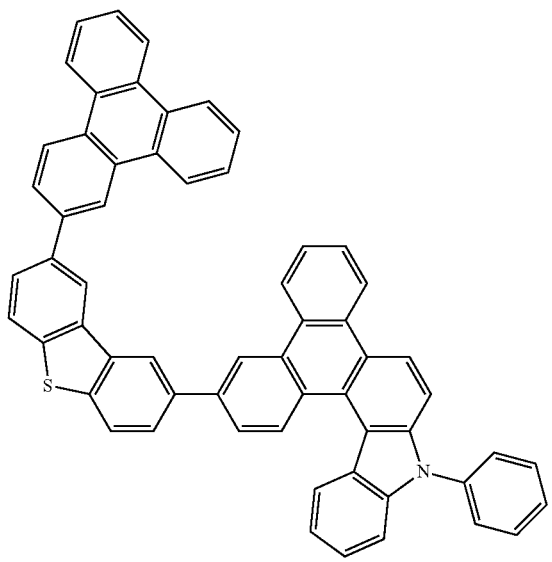<br>Compound 242 | 51% |

-continued 29      52%

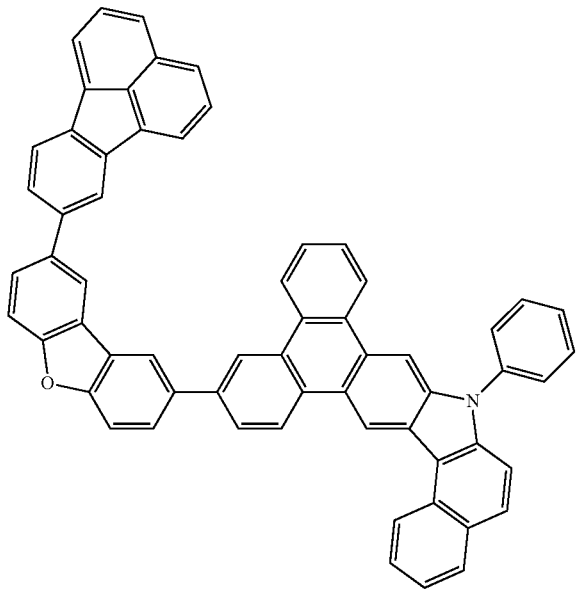

Compound 255

30      57%

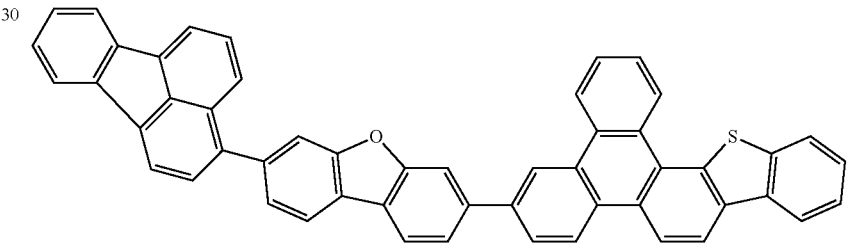

Compound 269

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. An organic compound having the following formula (1):

formula (1)

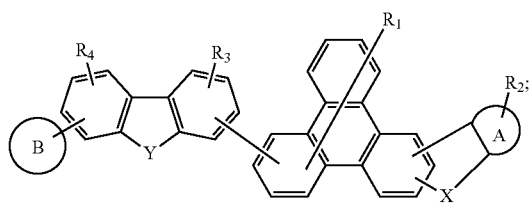

wherein X represents a divalent bridge selected from the group consisting of O, S, Se, $NR_5$ and $SiR_6R_7$;

wherein Y represents a divalent bridge selected from the group consisting of O and S;

wherein ring A represents a monocyclic aromatic group or a polycyclic aromatic group having two or three fused rings;

wherein ring B represents a polycyclic aromatic group or a polycyclic hetero aromatic group having at most five fused rings;

wherein $R_1$, $R_2$, $R_3$, and $R_4$ independently represent mono to a maximum possible number of substitutions, or no substitution;

wherein each of $R_1$ to $R_4$ substituents is selected from the group consisting of alkyl, aryl, aralkyl, heteroaryl, and combinations thereof; and wherein each of $R_5$ to $R_7$ represents no substitution or a substituent selected from the group consisting of alkyl, aryl, aralkyl, heteroaryl, and combinations thereof.

2. An organic compound having the following formula (26):

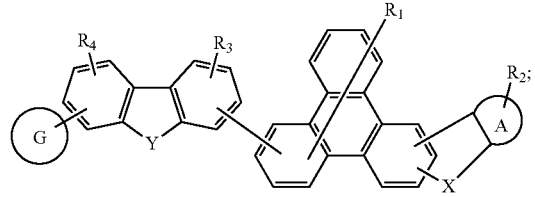

formula (26)

wherein ring G is selected from the group consisting of naphthyl, anthryl, phenanthryl, 9,9-dimethylfluorenyl, pyrenyl, chrysenyl, fluoranthenyl, dimethyl benzofluorenyl, triphenylenyl, perylenyl, and combinations thereof;

wherein ring A is selected from the group consisting of phenyl, naphthyl, anthryl, phenalenyl, and combinations thereof;

wherein X is selected from the group consisting of O, S, Se, $NR_5$ and $SiR_6R_7$;

wherein Y is selected from the group consisting of O and S;

wherein $R_5$ represents no substitution or a substituent selected from the group consisting of pyridinyl, dimethylphenyl, ethyl, hexylphenyl, dibenzothienyl, phenyl, triphenylenyl, anthryl, terphenyl, diphenyltriazinyl, naphthyl, biphenyl, and combinations thereof;

wherein $R_1$, $R_2$, $R_3$, and $R_4$ independently represent mono to a maximum possible number of substitutions, or no substitution;

wherein each of $R_1$ substituents is selected from the group consisting of methyl, hexyl, hexyl, phenyl, pyridinyl, and combinations thereof;

wherein each of $R_2$ substituents is selected from the group consisting of phenyl, pyridinyl, hexylphenyl, triphenylenyl, and combinations thereof;

wherein each of $R_3$ substituents is selected from the group consisting of phenyl, pyridinyl, naphthyl, and combinations thereof;

wherein each of $R_4$ substituents is selected from the group consisting of hexylphenyl, pyridinyl, naphthyl, and combinations thereof; and wherein each of $R_6$ to $R_7$ represents no substitution or a substituent selected from the group consisting of hexyl, hexylphenyl, and combinations thereof.

3. The organic compound according to claim 1, wherein the organic compound has one of the following formula(2) to formula(25):

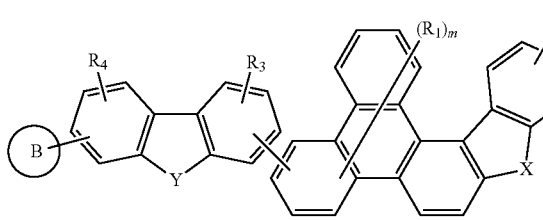

formula(2)

-continued

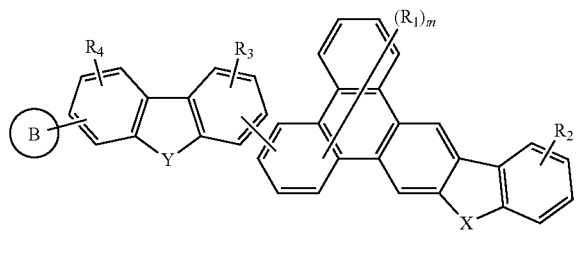

formula(3)

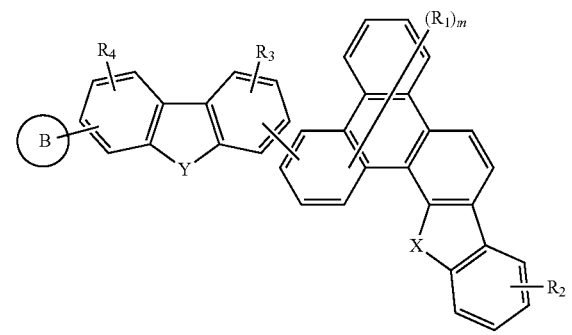

formula(4)

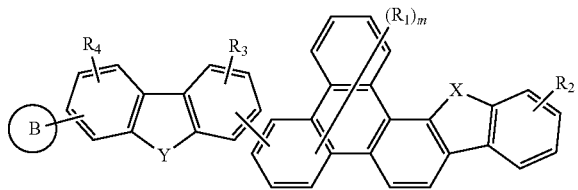

formula(5)

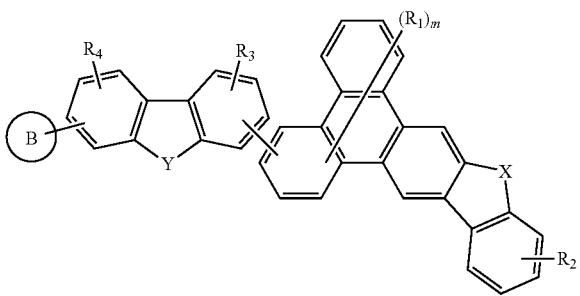

formula(6)

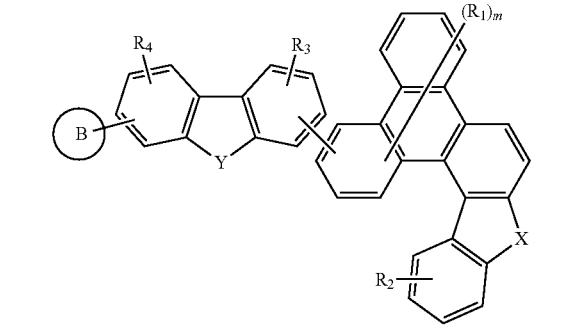

formula(7)

-continued
formula(8)
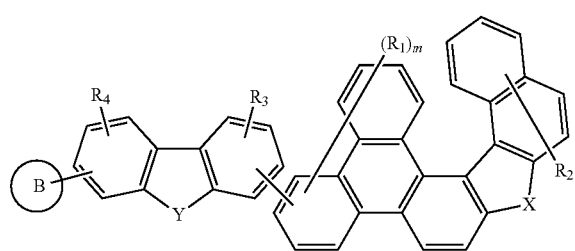
formula(9)
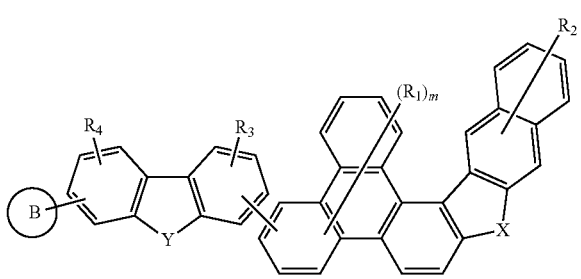
formula(10)
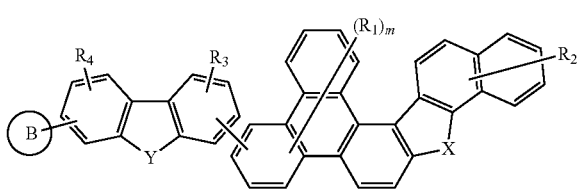
formula(11)
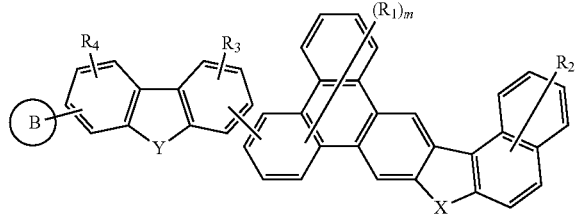
formula(12)
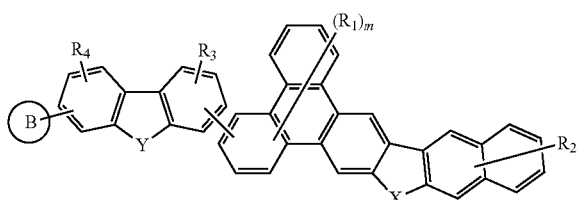
formula(13)
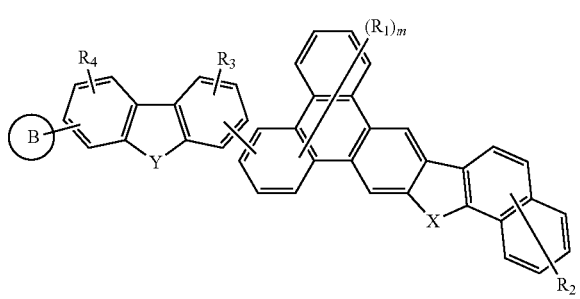
-continued
formula(14)
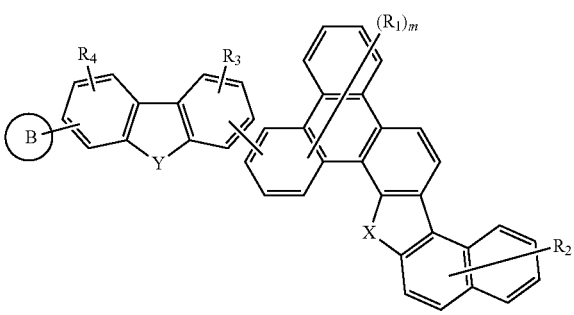
formula(15)
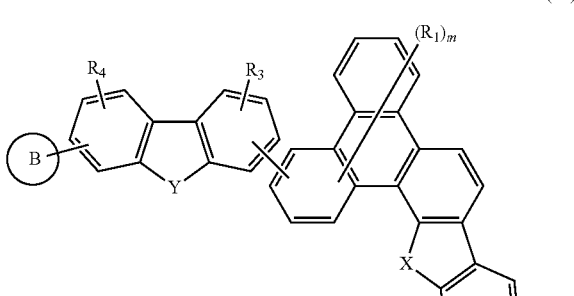
formula(16)
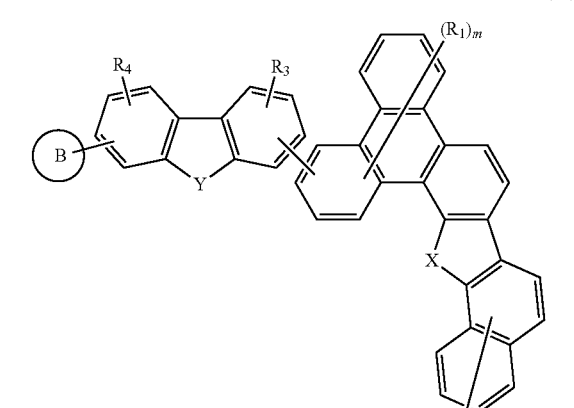
formula(17)
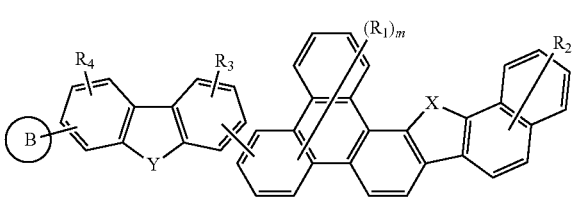
formula(18)
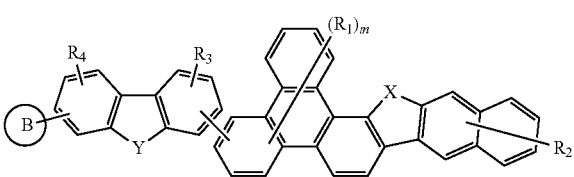

-continued formula(19)
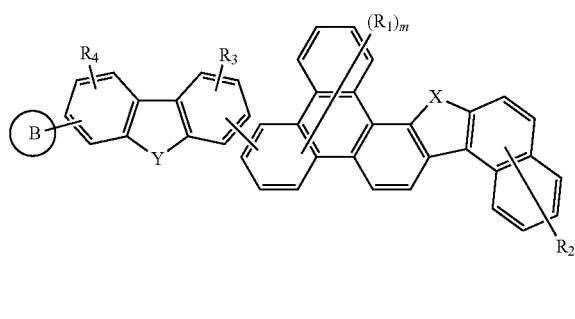

formula(20)
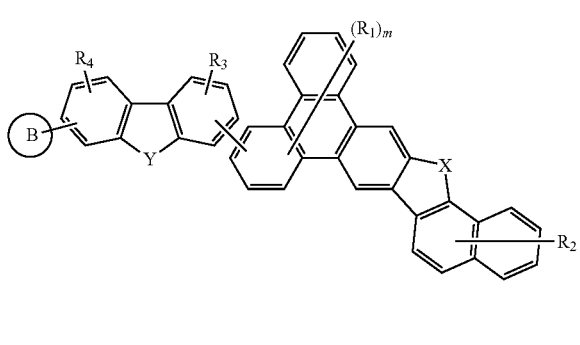

formula(21)
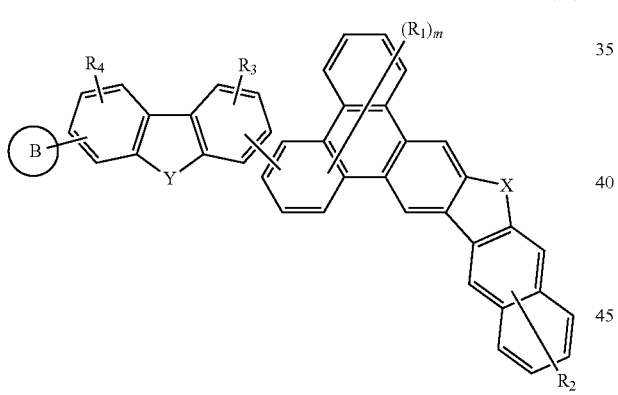

formula(22)
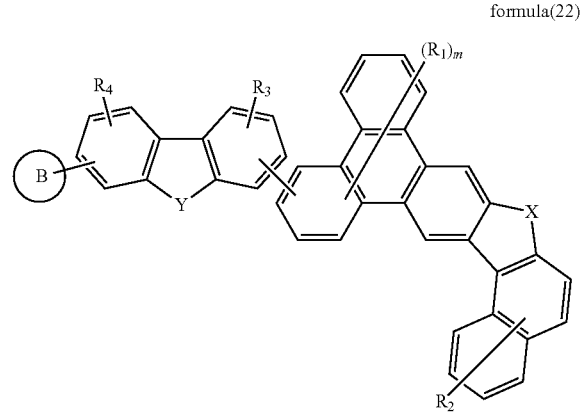

-continued formula(23)
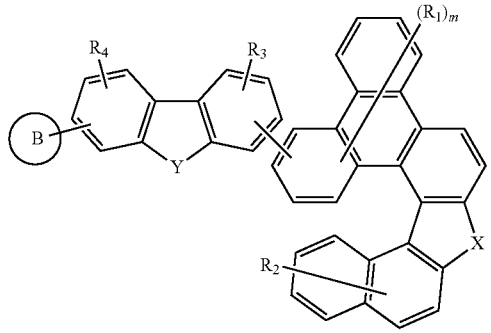

formula(24)
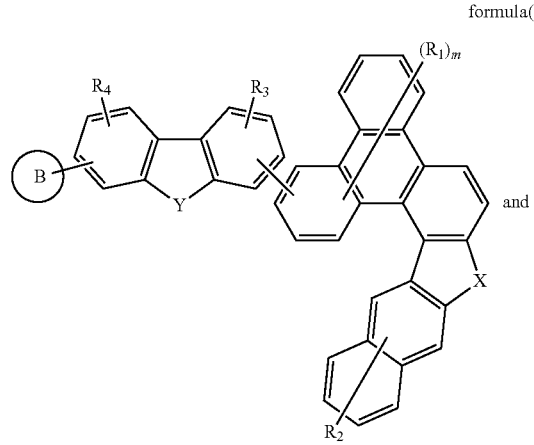

and formula(25)
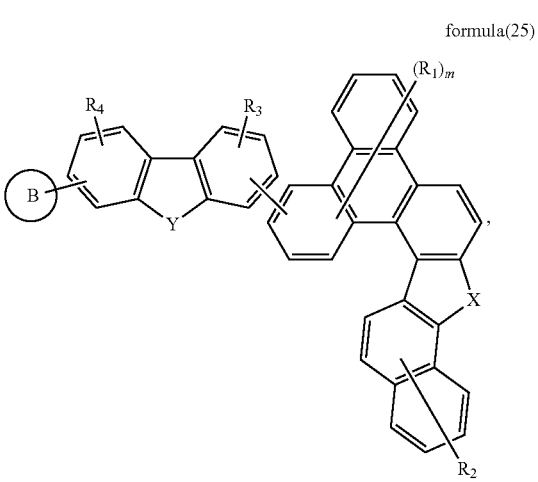

, wherein m represents an integer of 0 to 7.

4. The organic compound according to claim 1, wherein each of $R_1$ to $R_7$ is optionally substituted by a halogen, an alkyl group, an aryl group, or a heteroaryl group.

5. The organic compound according to claim 1, wherein ring B is selected from the group consisting of naphthyl, anthryl, phenanthryl, fluorenyl, pyrenyl, chrysenyl, fluoranthenyl, benzofluorenyl, triphenylenyl, perylenyl, and combinations thereof.

6. The organic compound according to claim 1, wherein ring B represents one of the following substituents:

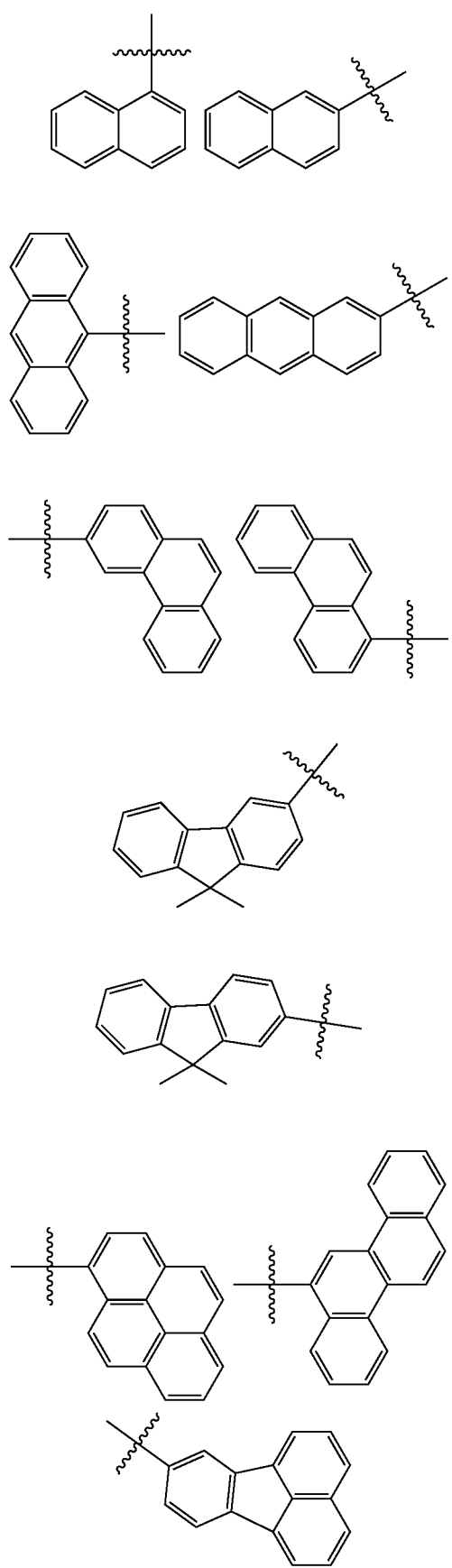
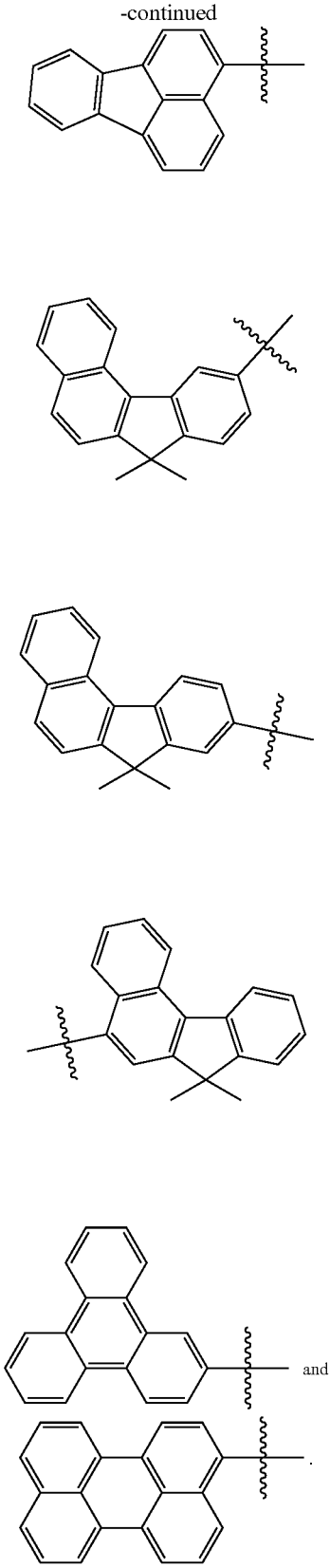
7. The organic compound according to claim 1, wherein the organic compound is represented by one of the following formulas:

Compound 1
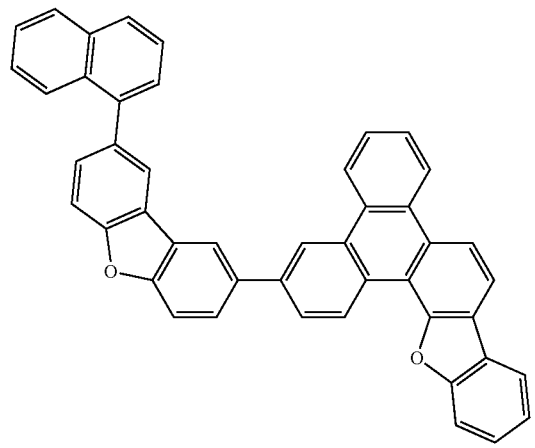
Compound 2
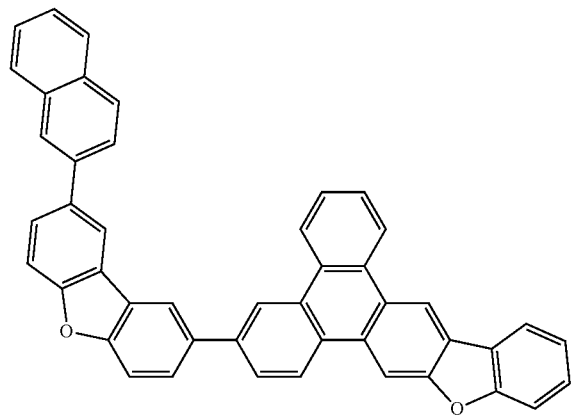
Compound 3
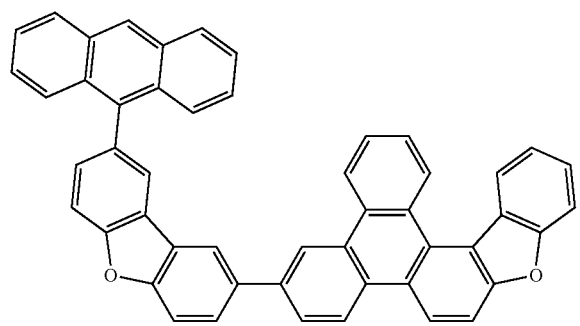
Compound 4
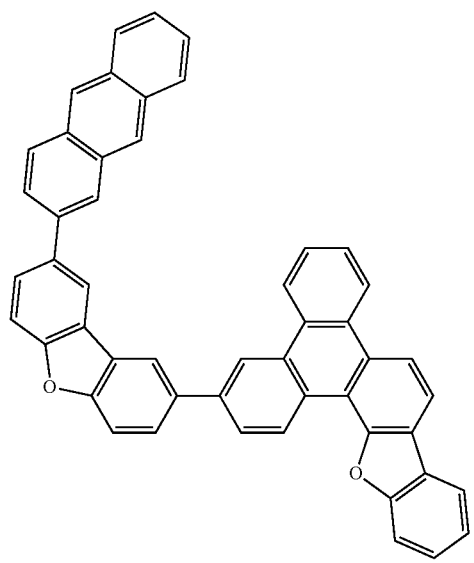
Compound 5
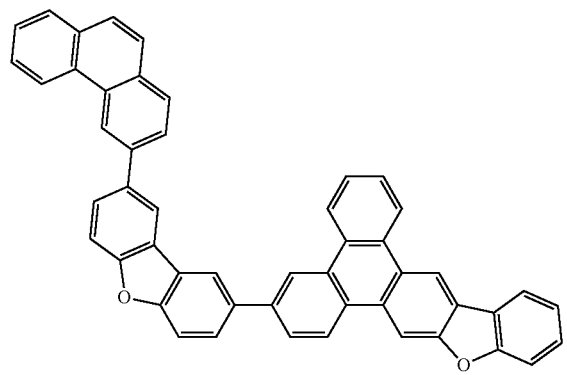
Compound 6
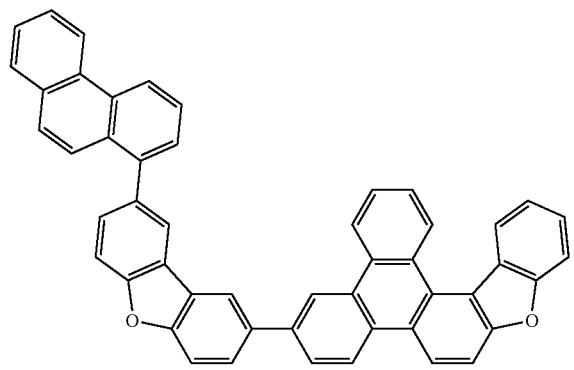

-continued
Compound 7
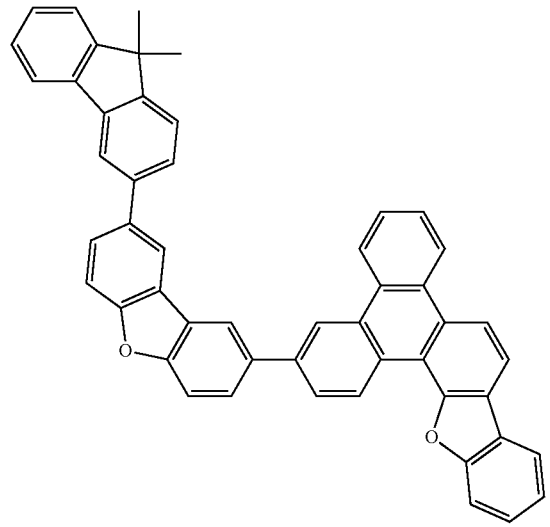
Compound 8
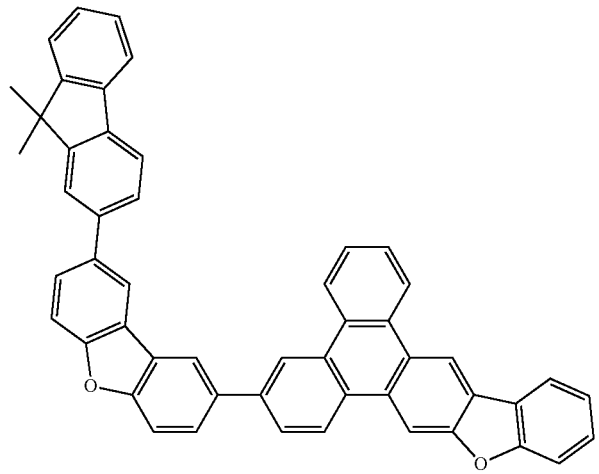
Compound 9
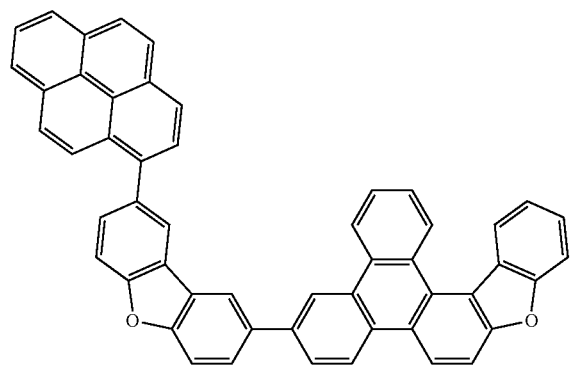
Compound 10
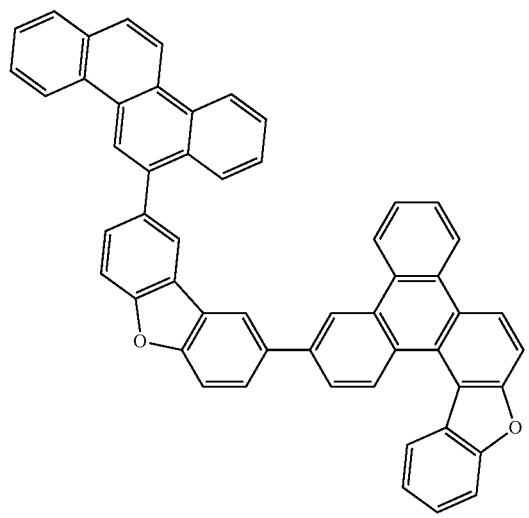
Compound 11
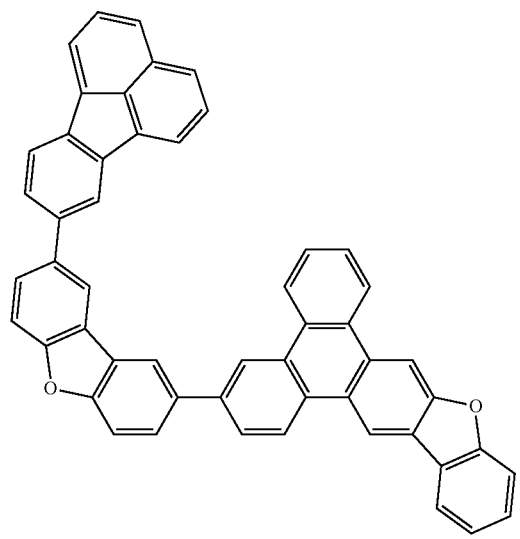
Compound 12
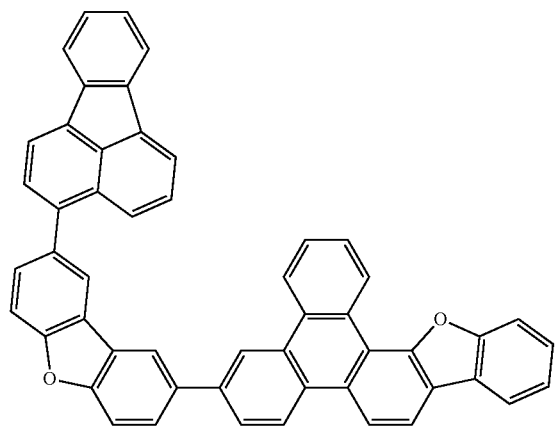

-continued
Compound 13
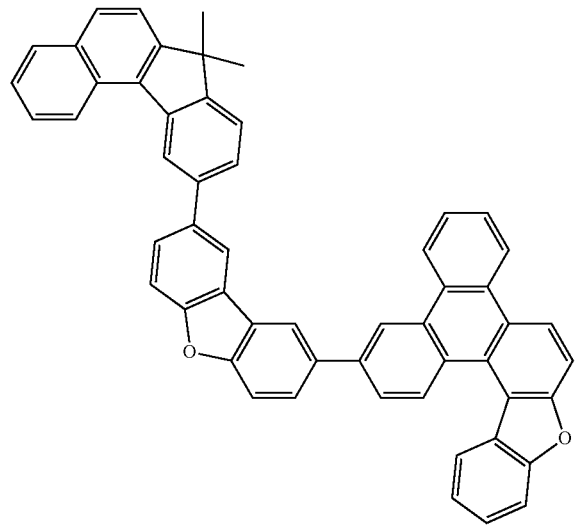
Compound 14
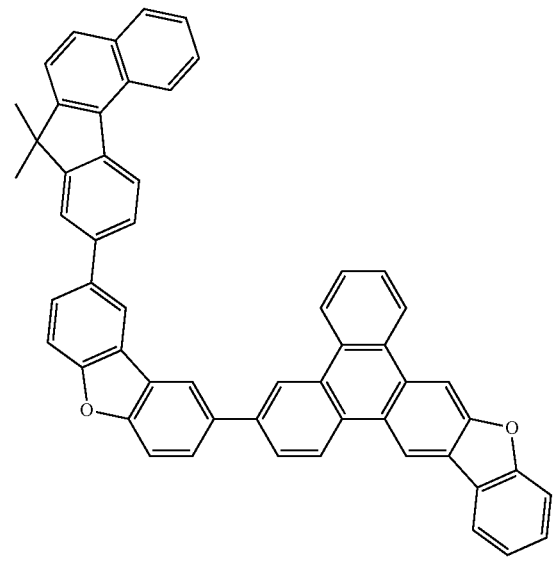
Compound 15
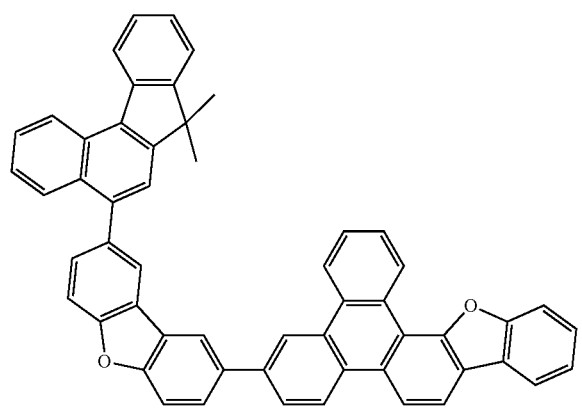
Compound 16
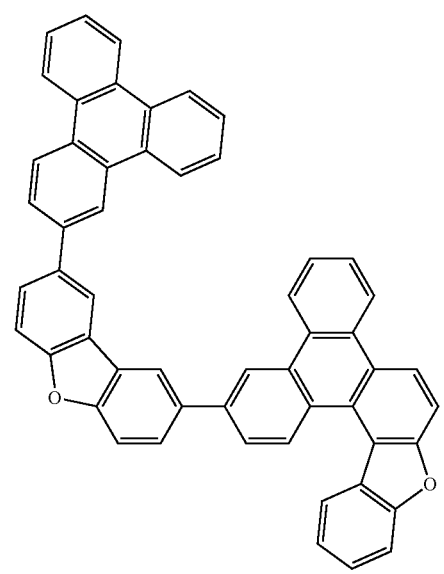

-continued
Compound 17
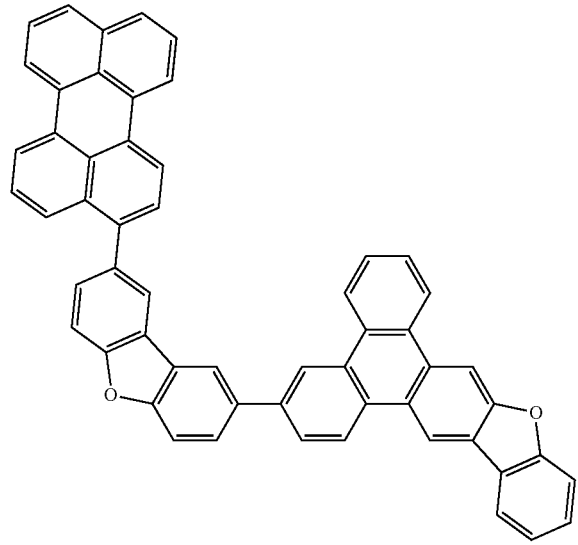
Compound 18
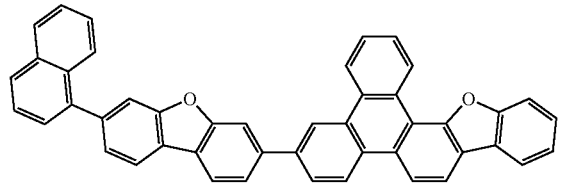
Compound 19
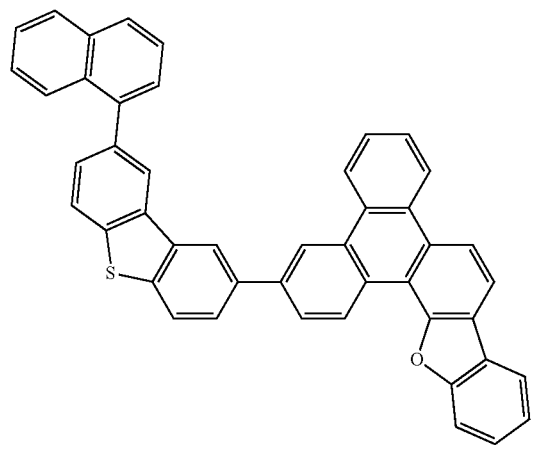
Compound 20
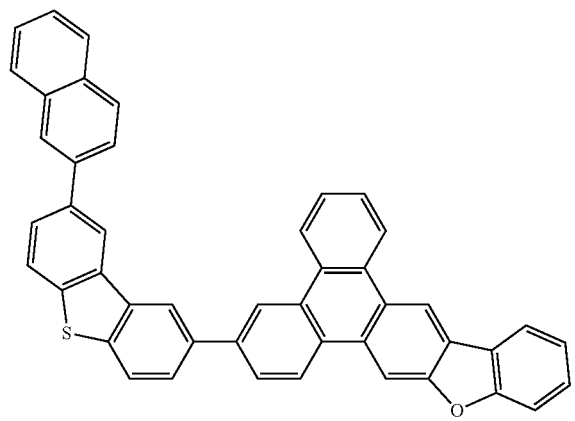
Compound 21
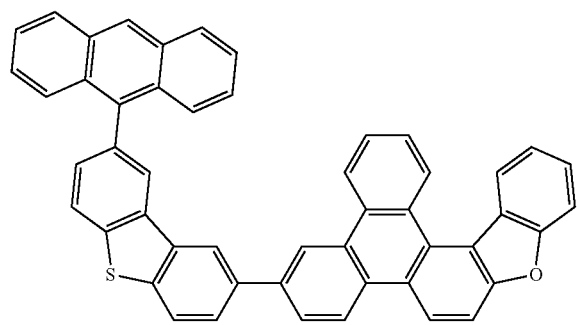
Compound 22
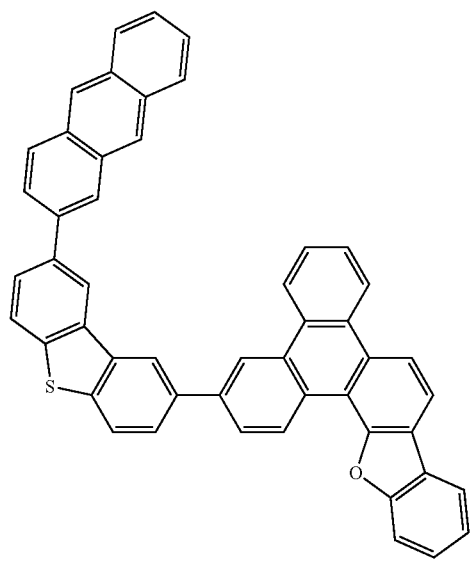

-continued
Compound 23
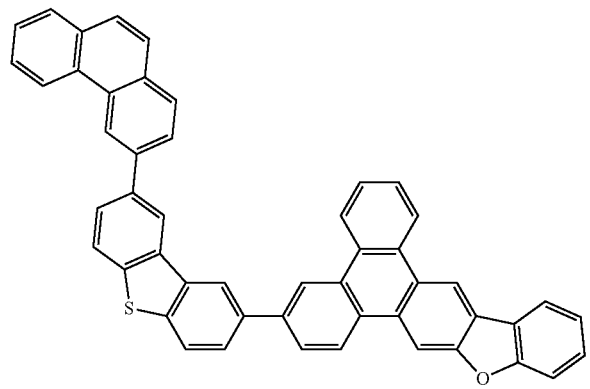
Compound 24
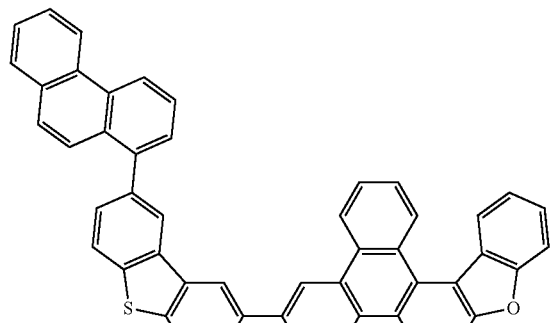
Compound 25
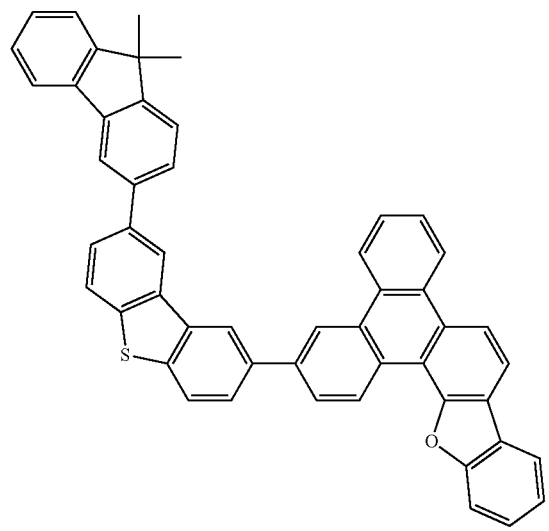
Compound 26
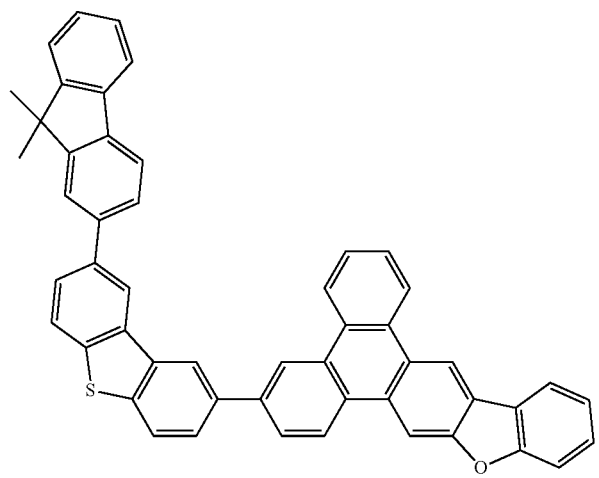
Compound 27
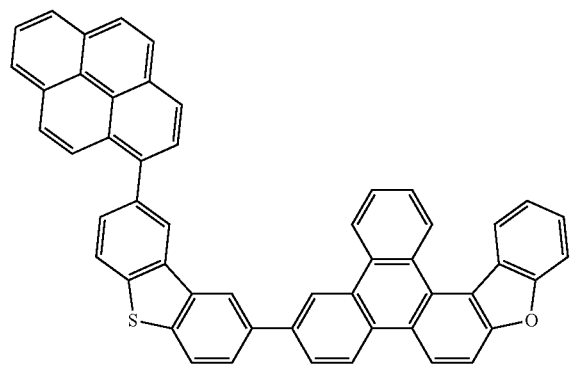
Compound 28
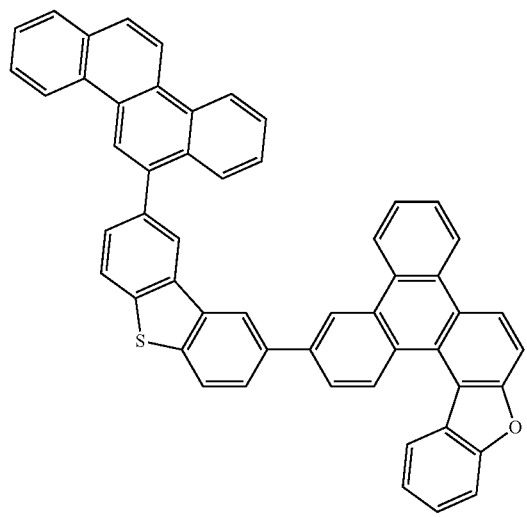

Compound 29
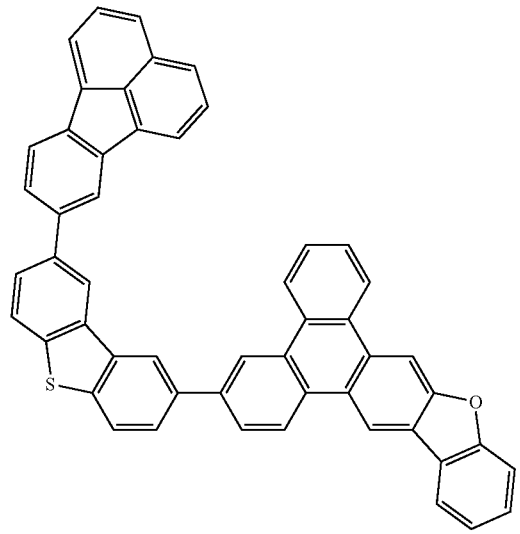
Compound 30
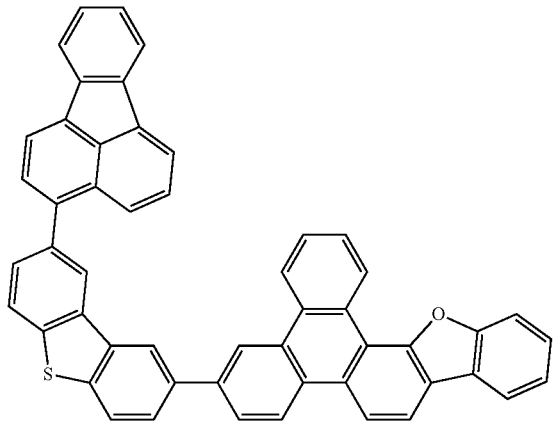
Compound 31
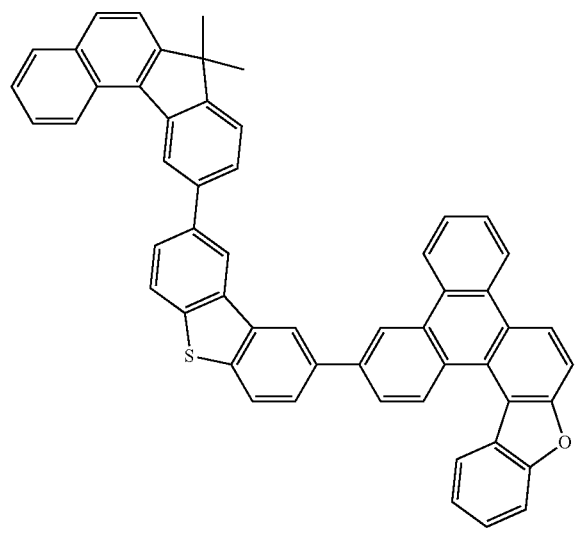
Compound 32
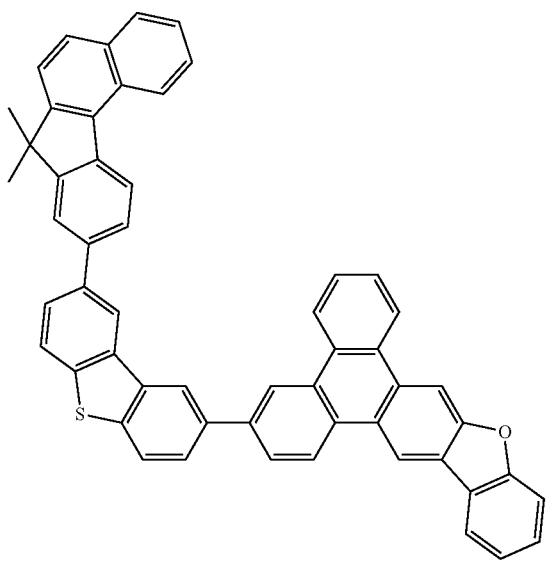

-continued
Compound 33
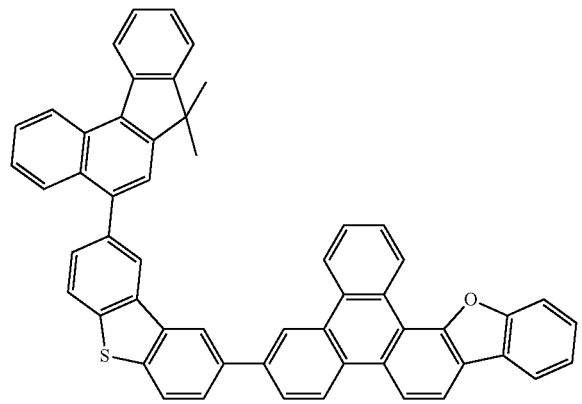
Compound 34
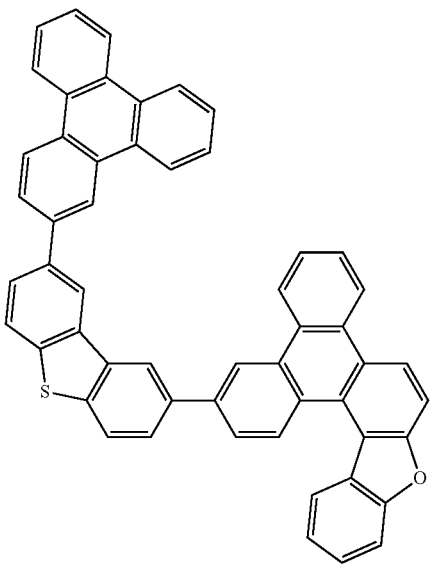
Compound 35
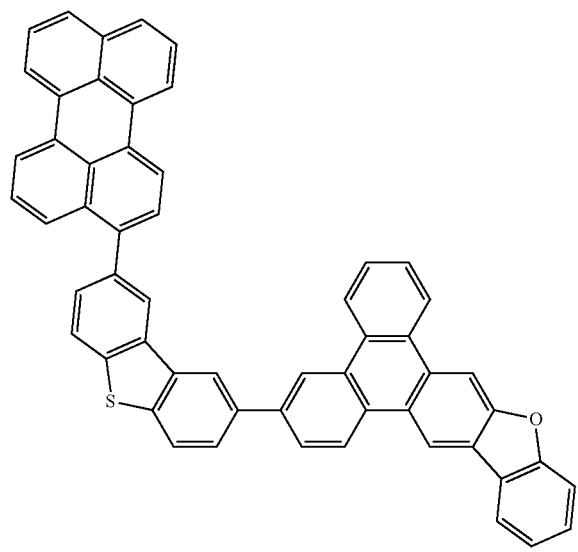
Compound 36
Compound 37
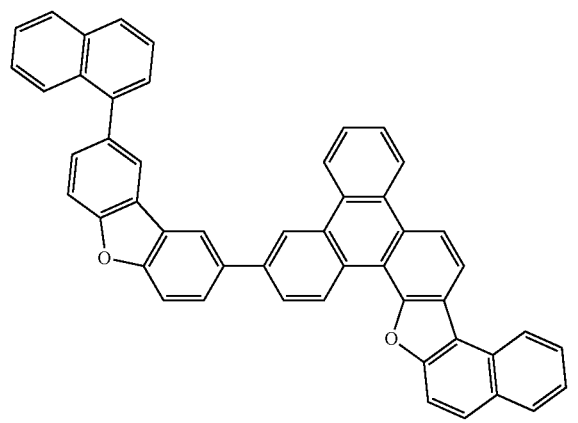
Compound 38
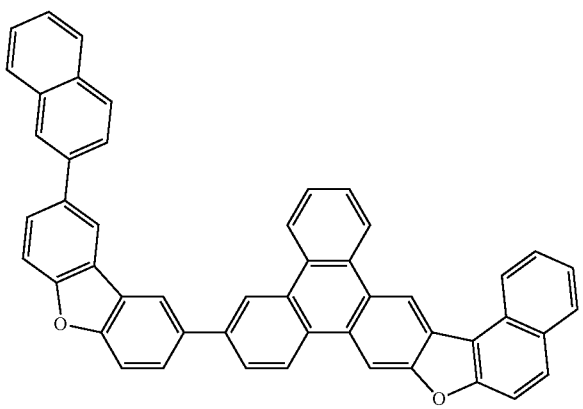

-continued
Compound 39
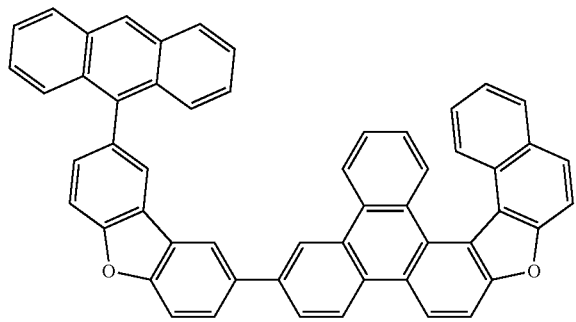
Compound 40
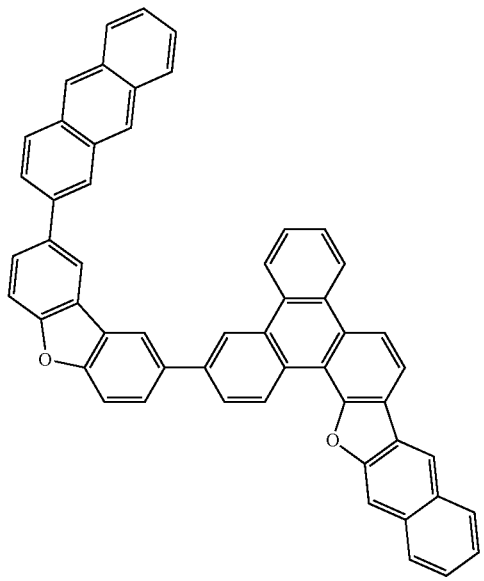
Compound 41
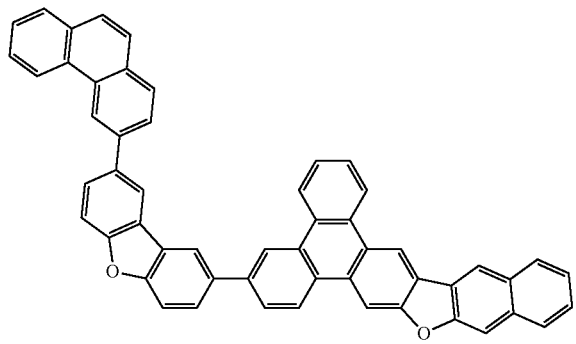
Compound 42
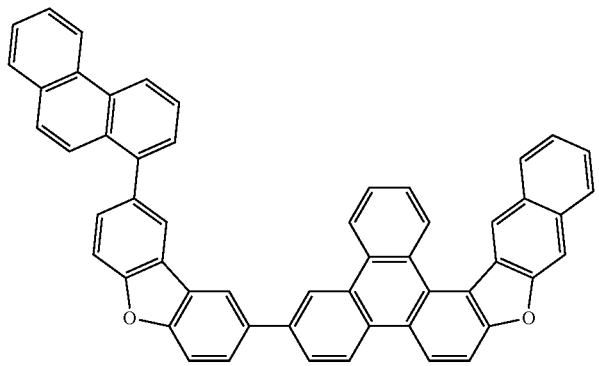
Compound 43
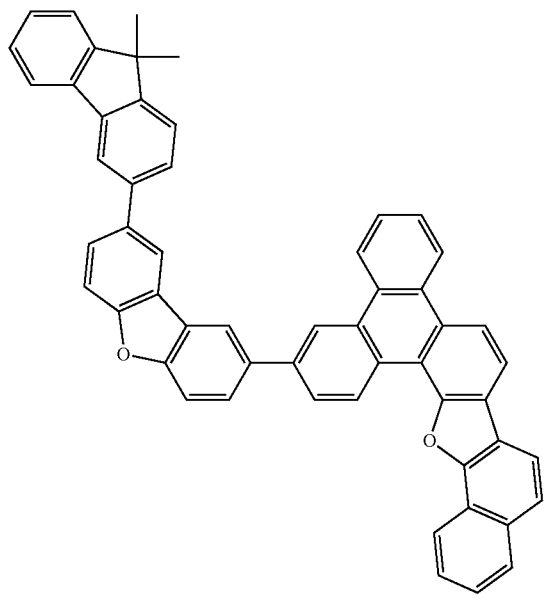
Compound 44
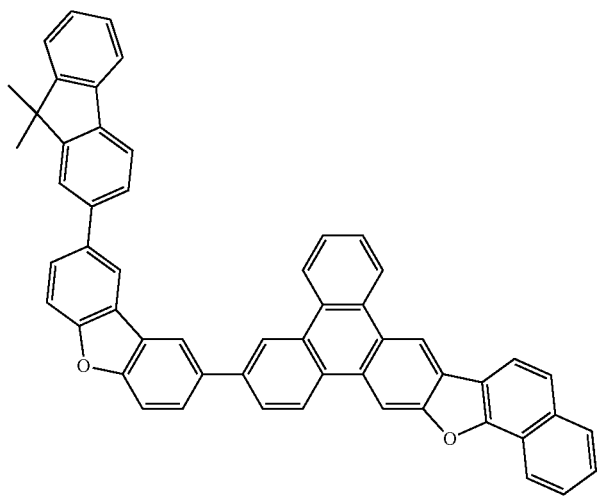

-continued
Compound 45
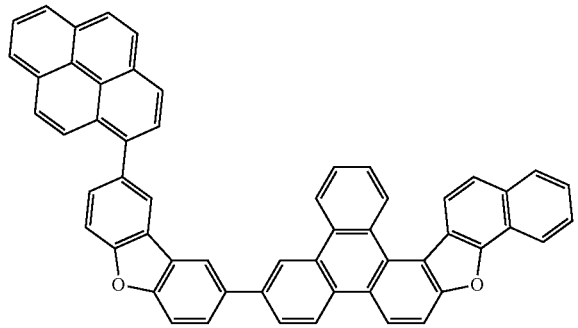
Compound 46
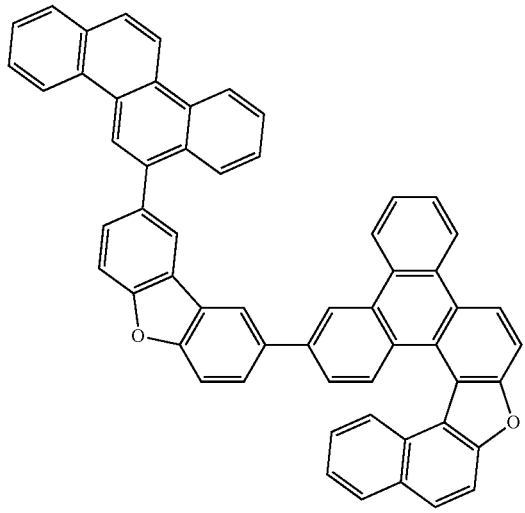
Compound 47
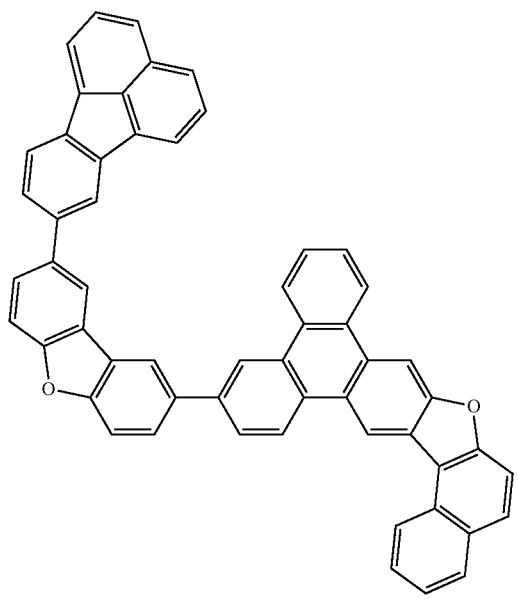
Compound 48
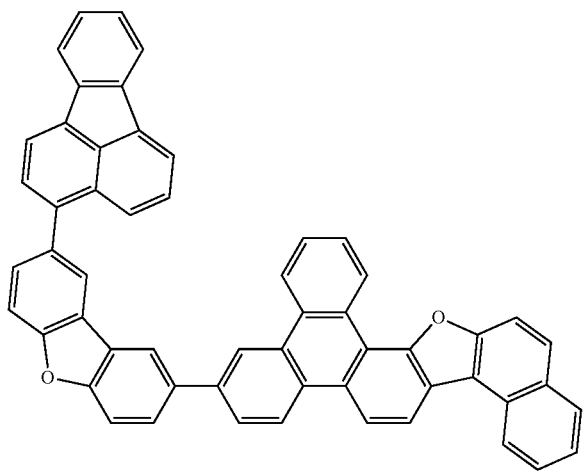

Compound 49
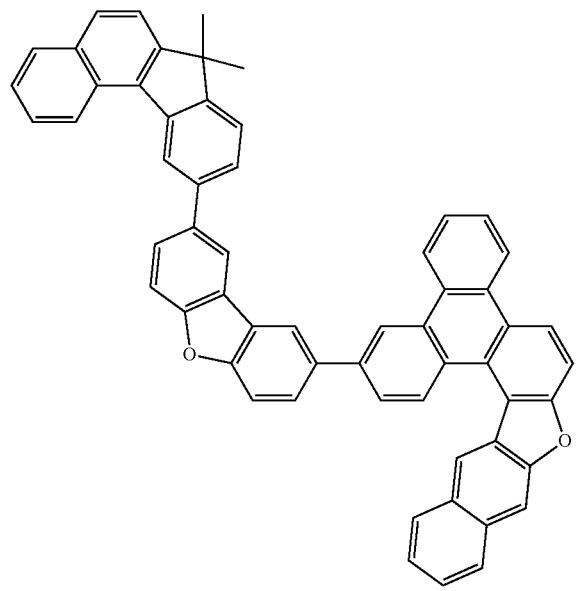
Compound 50
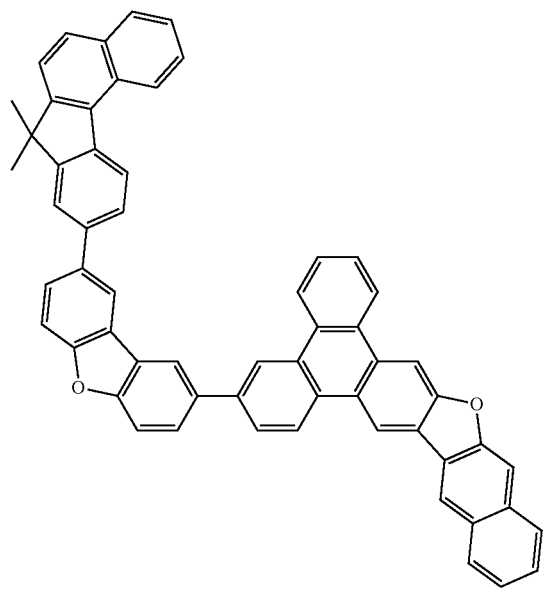
Compound 51
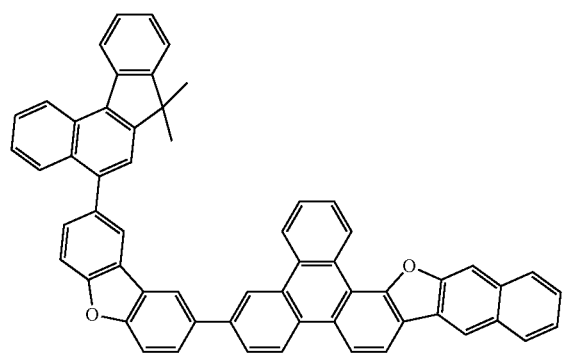
Compound 52
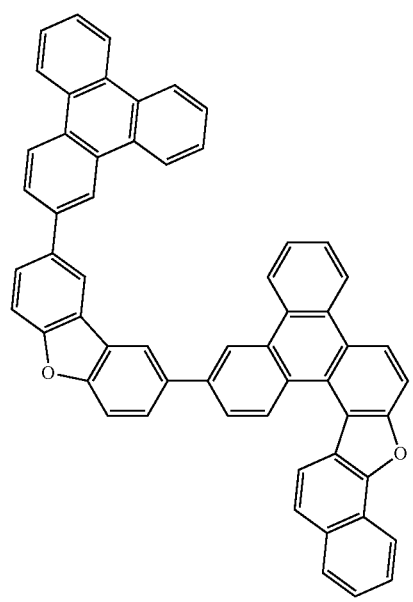

-continued
Compound 53
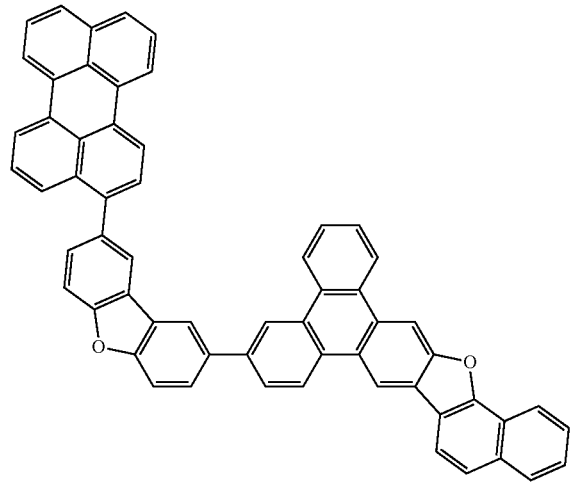
Compound 54
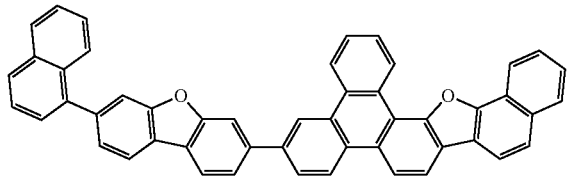
Compound 55
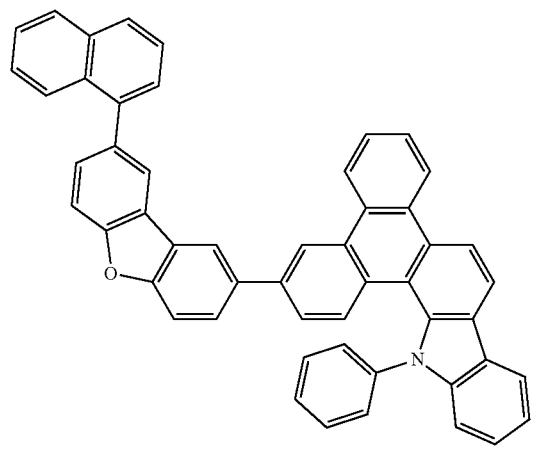
Compound 56
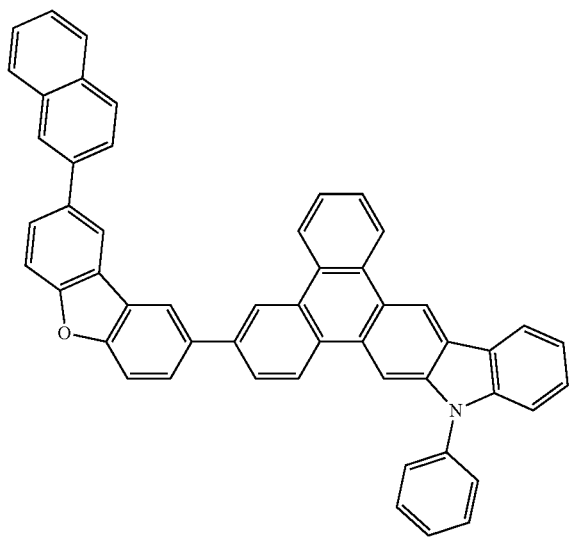
Compound 57
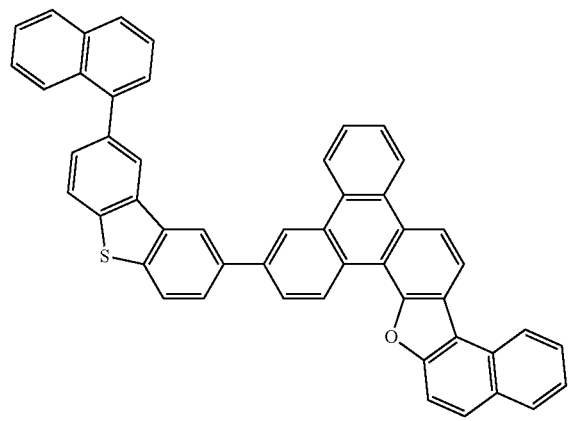
Compound 58
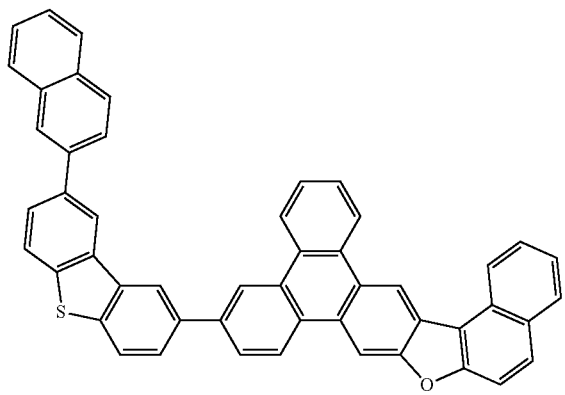

-continued
Compound 59
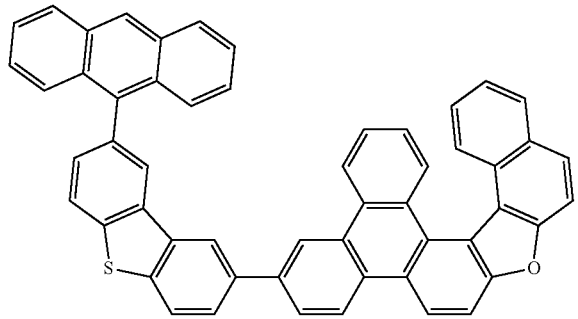
Compound 60
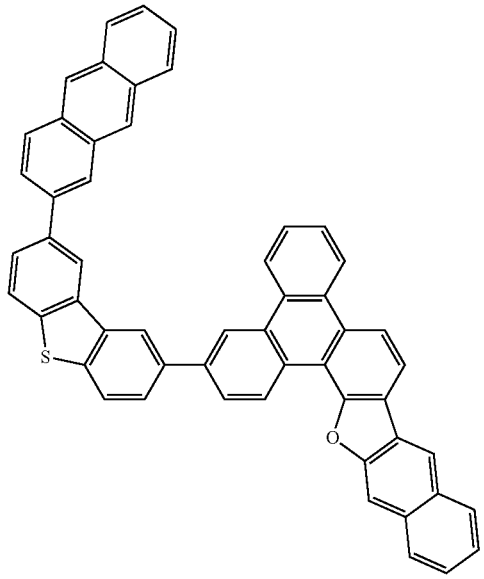
Compound 61
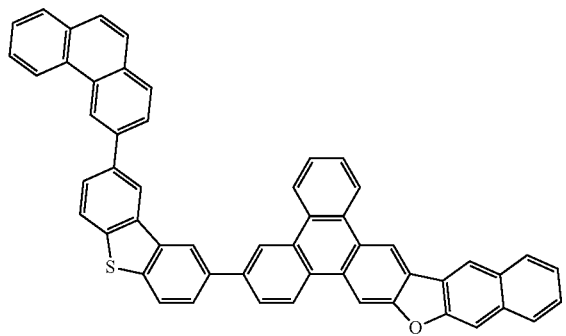
Compound 62
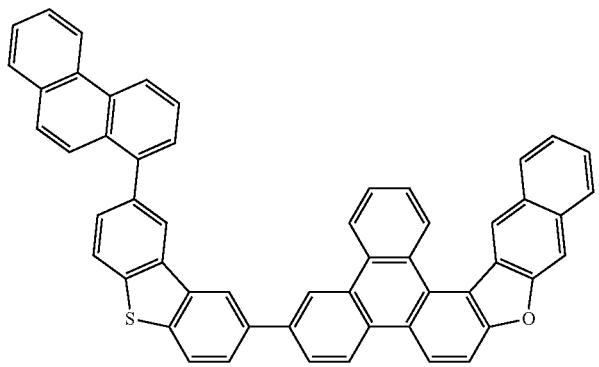
Compound 63
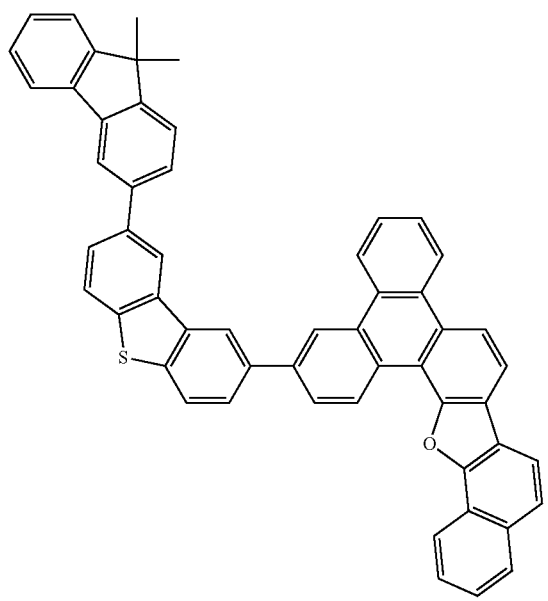
Compound 64
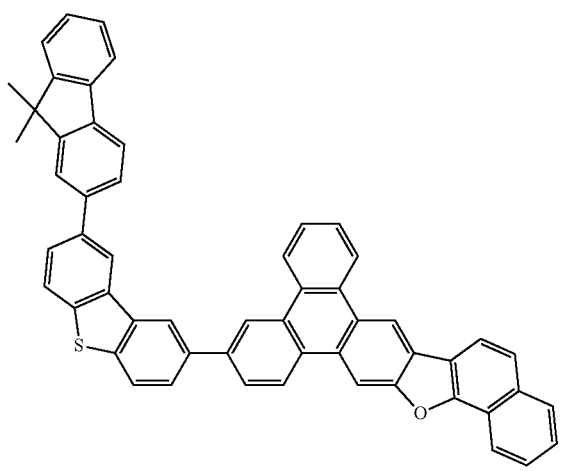

-continued
Compound 65
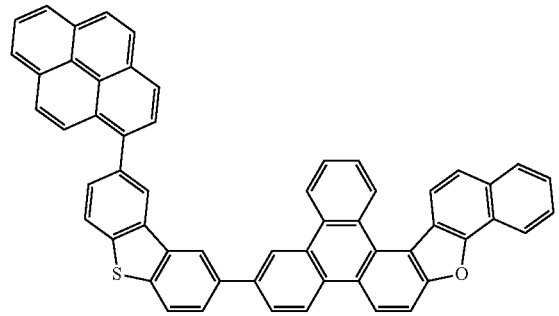
Compound 66
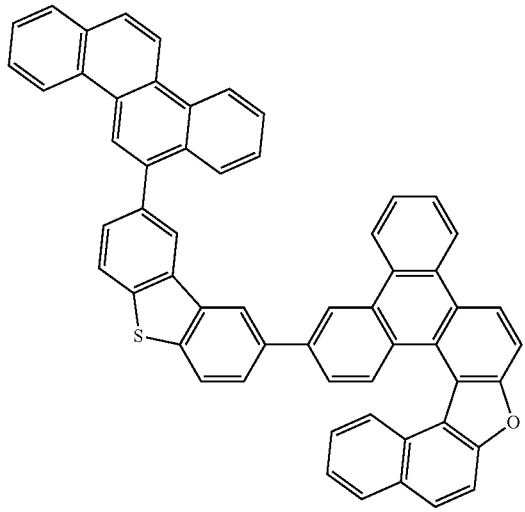
Compound 67
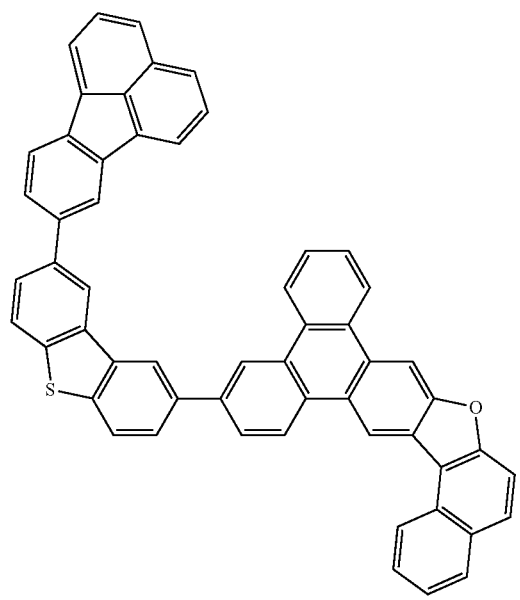
Compound 68
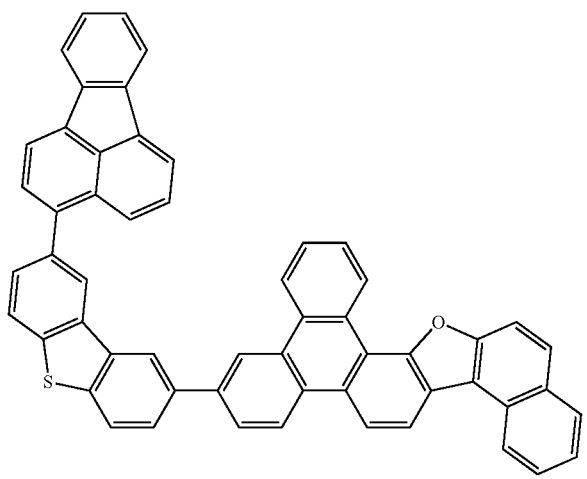

-continued

Compound 69

Compound 70

Compound 71

Compound 72

-continued
Compound 73
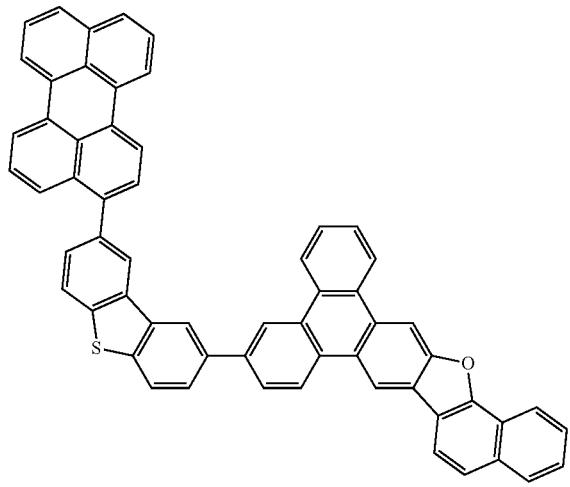
Compound 74
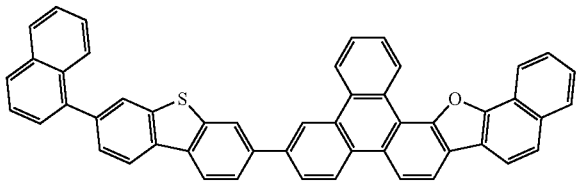
Compound 75
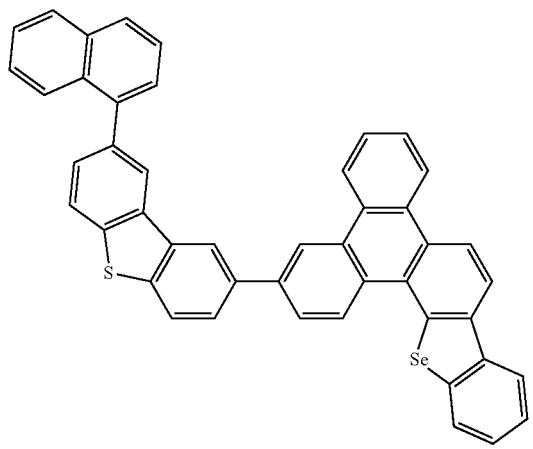
Compound 76
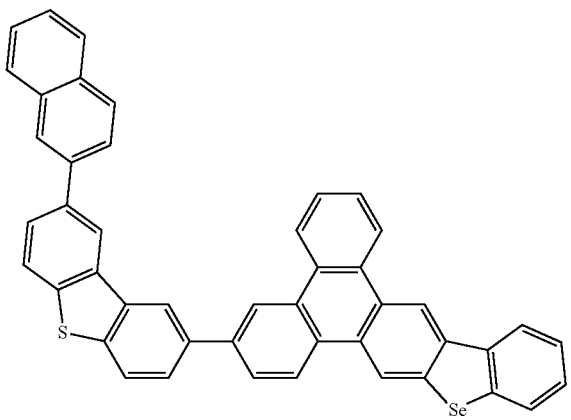
Compound 77
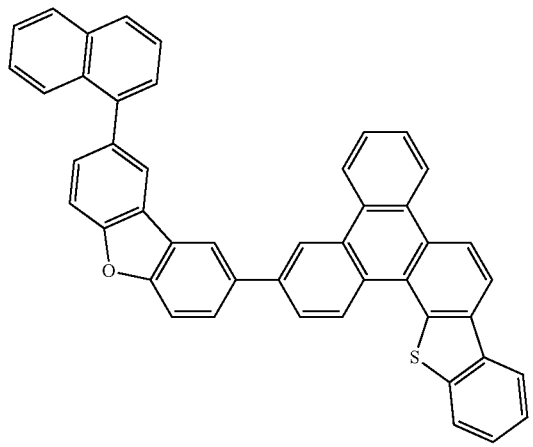
Compound 78
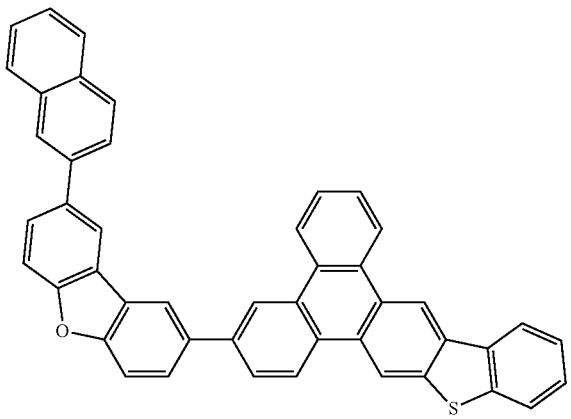

-continued
Compound 79
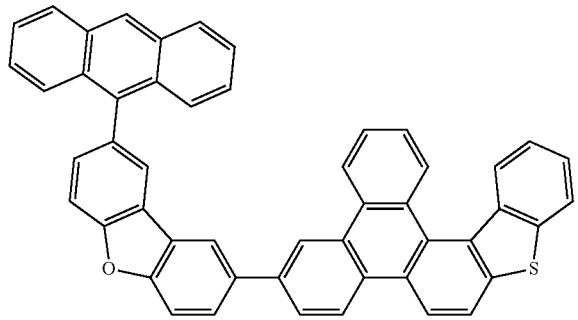
Compound 80
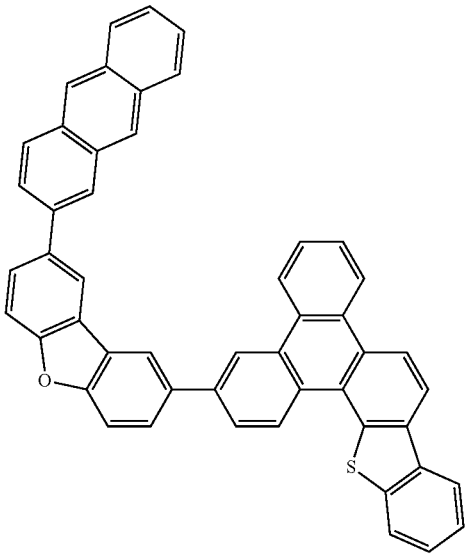
Compound 81
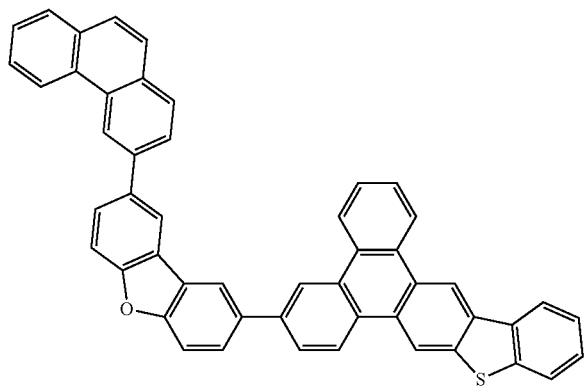
Compound 82
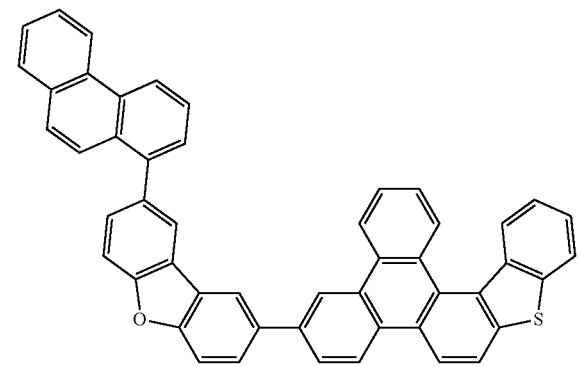
Compound 83
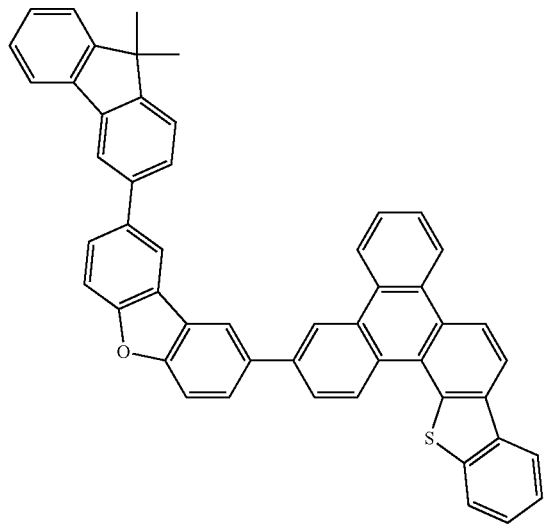
Compound 84
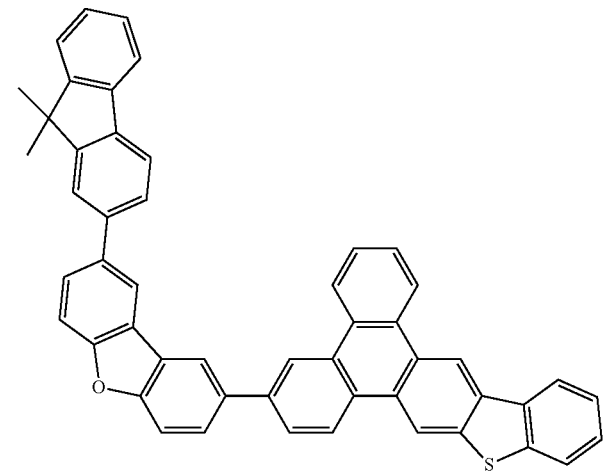

Compound 85
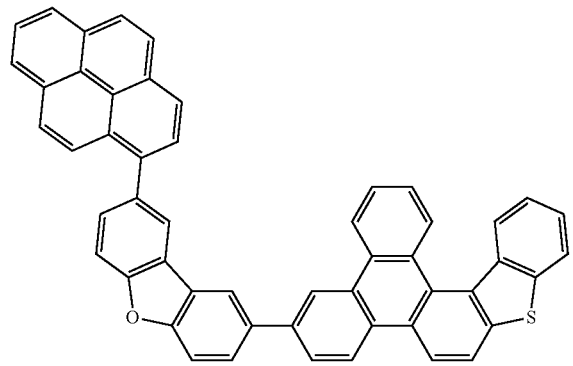
Compound 86
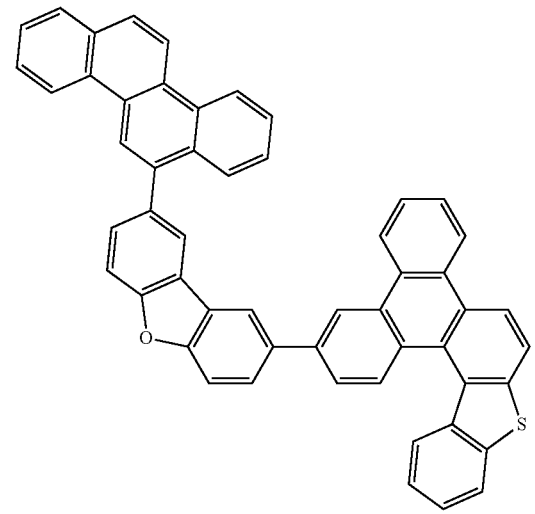
Compound 87
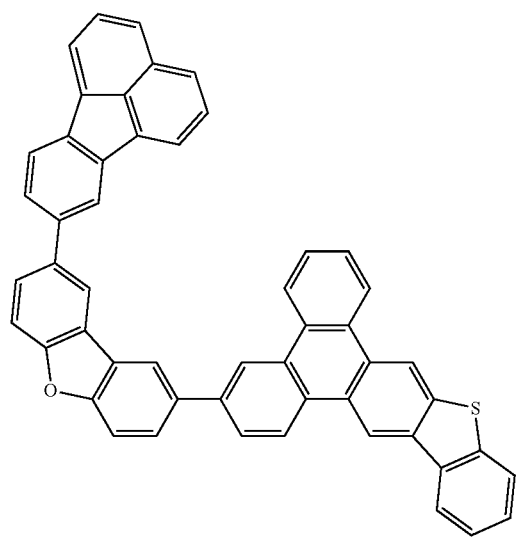
Compound 88
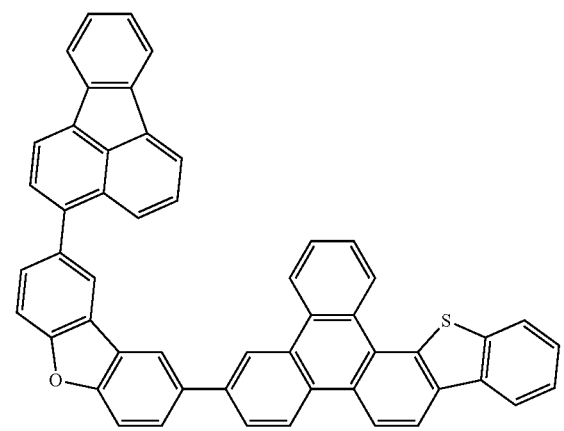
Compound 89
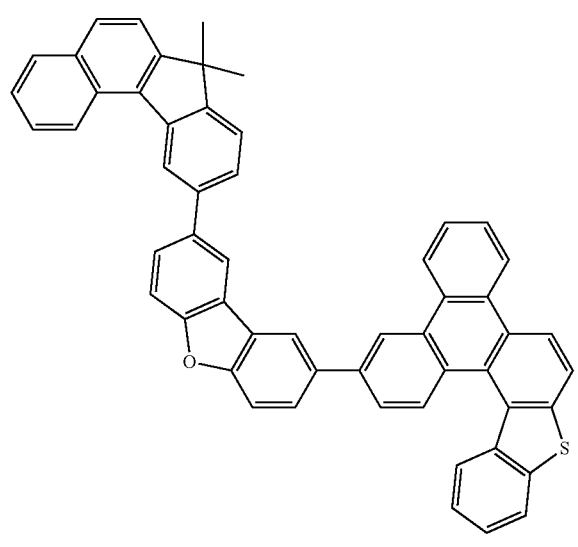
Compound 90
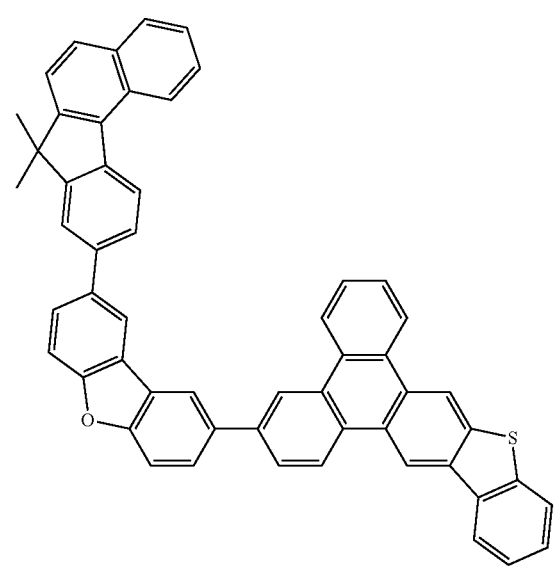

-continued
Compound 91
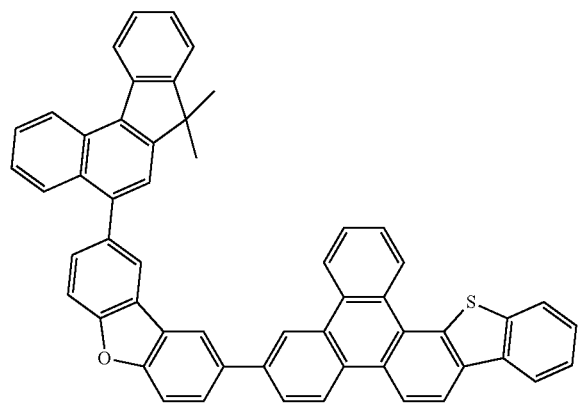
Compound 92
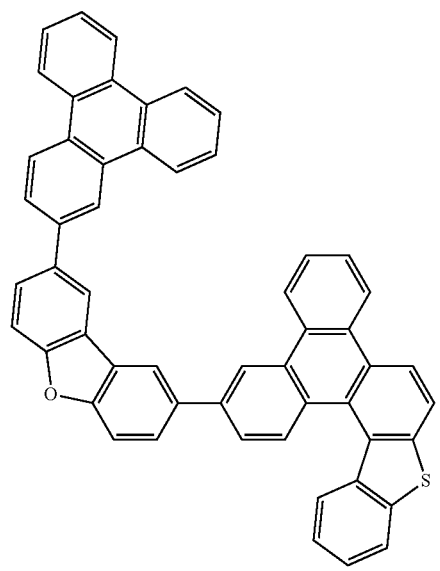
Compound 93
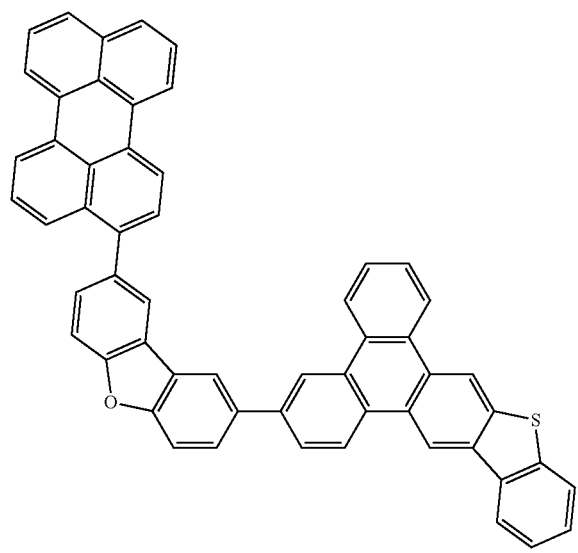
Compound 94
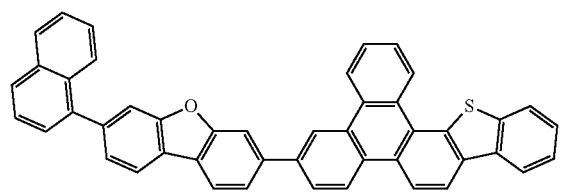
Compound 95
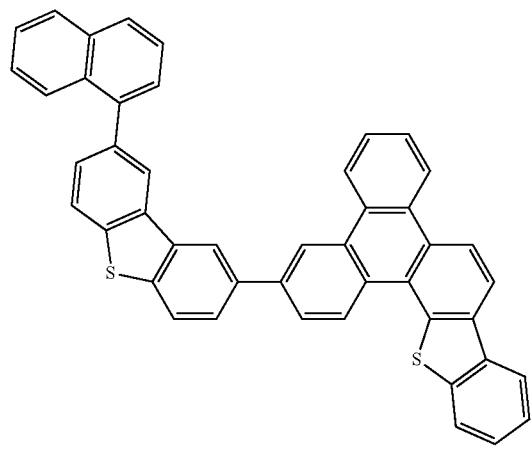
Compound 96
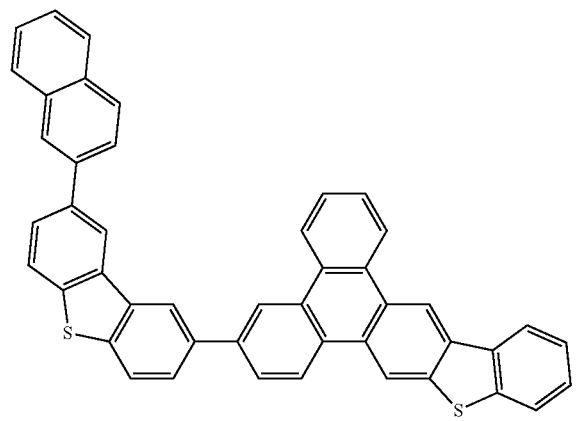

Compound 97
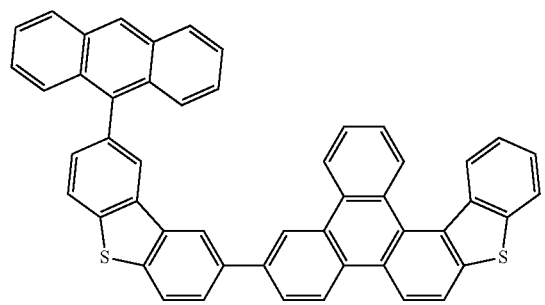
Compound 98
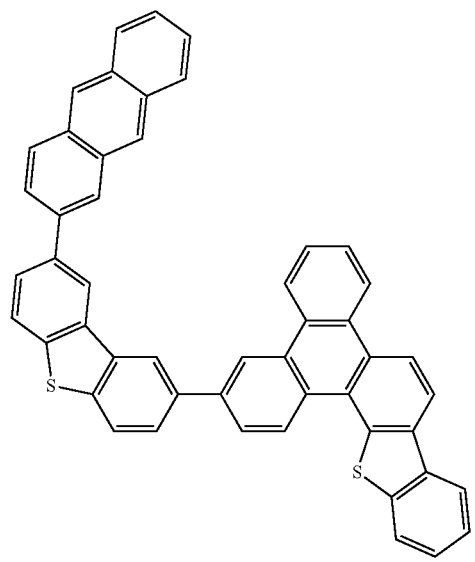
Compound 99
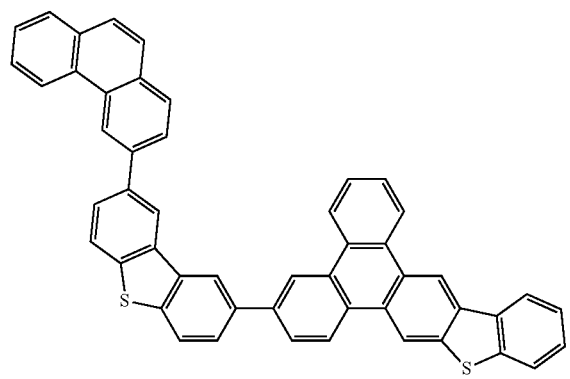
Compound 100
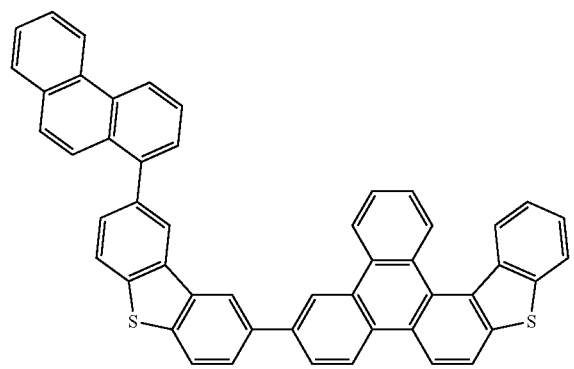
Compound 101
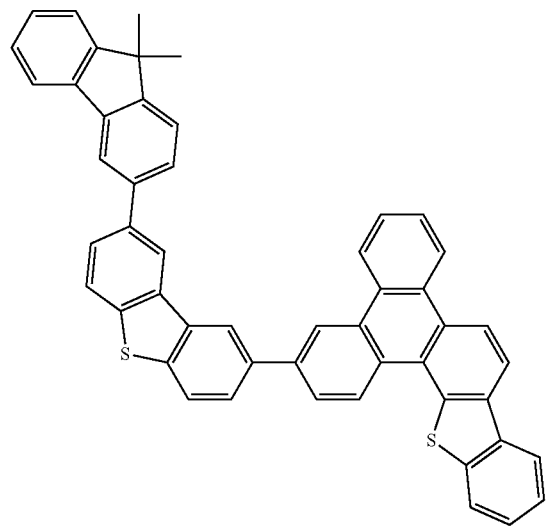
Compound 102
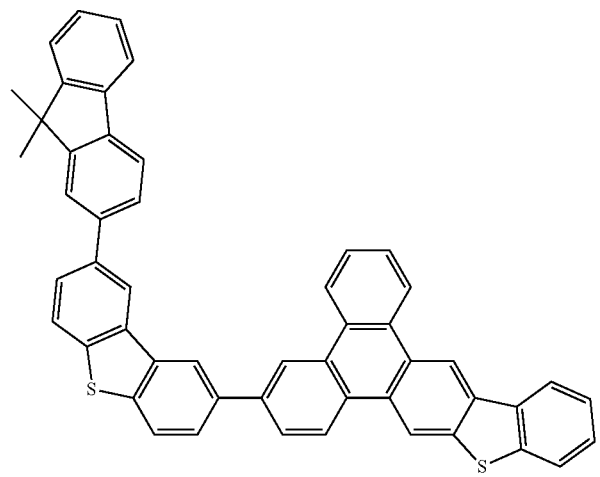

-continued
Compound 103
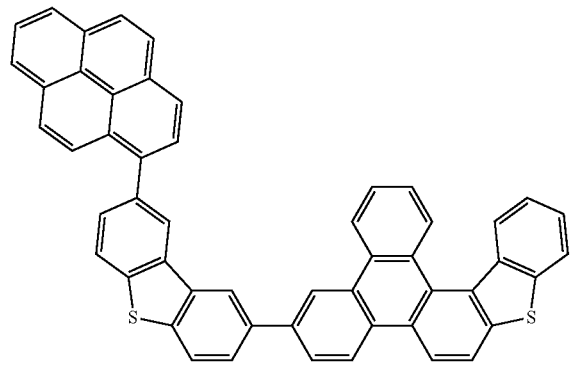
Compound 104
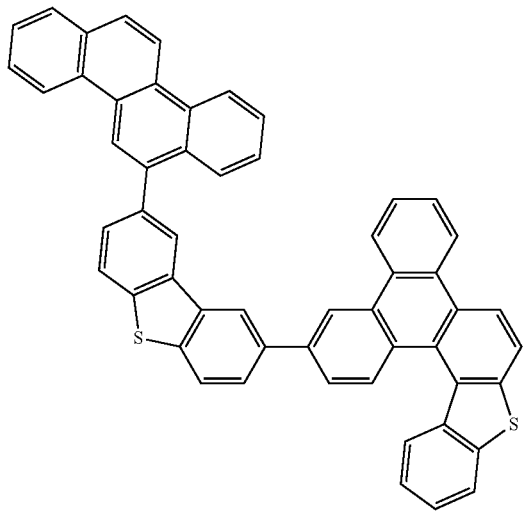
Compound 105
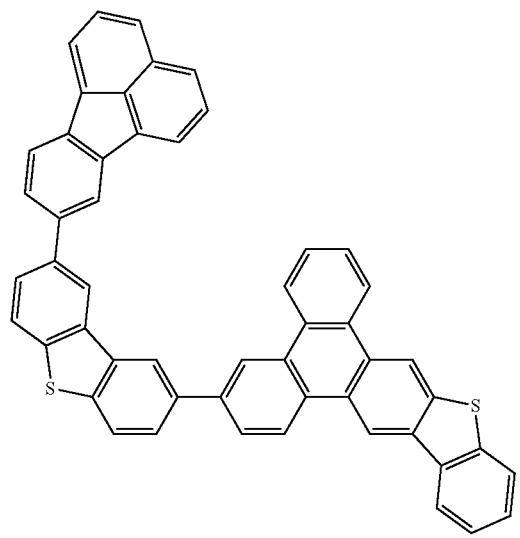
Compound 106
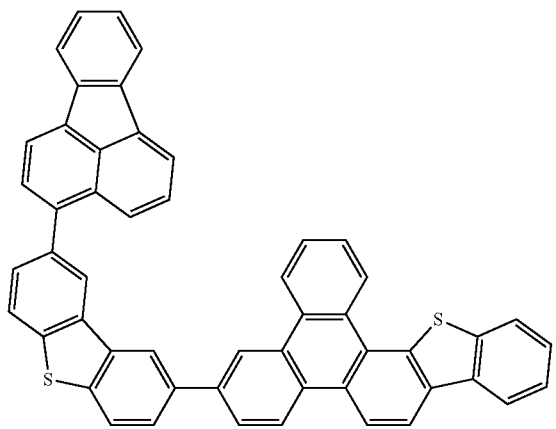
Compound 107
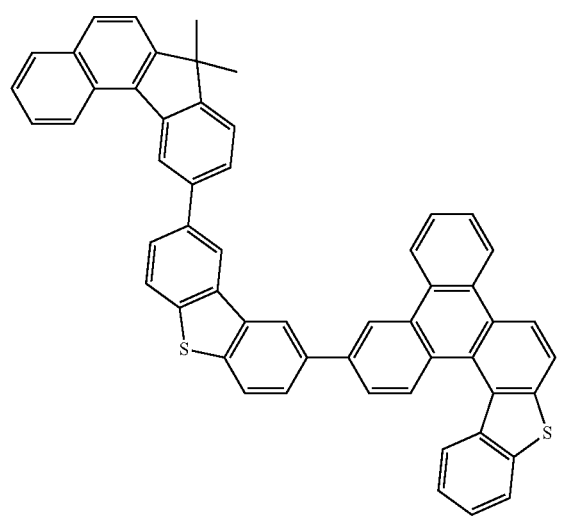
Compound 108
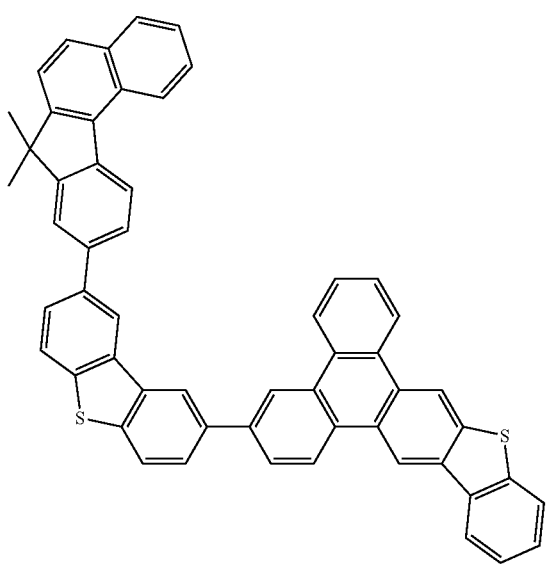

-continued
Compound 109
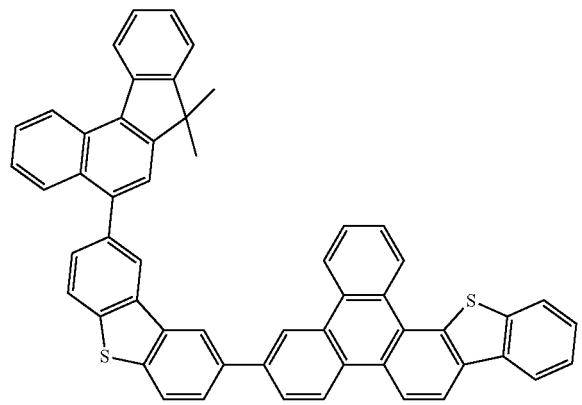
Compound 110
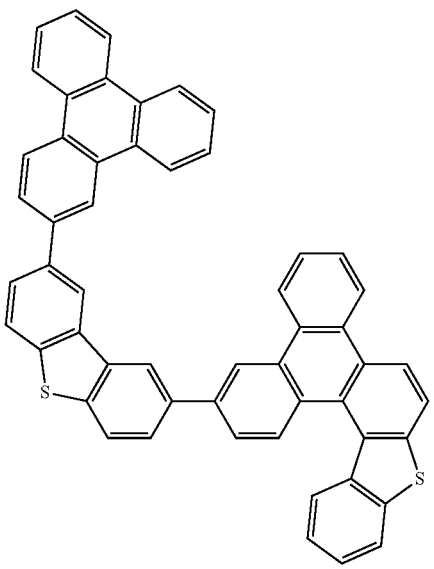
Compound 111
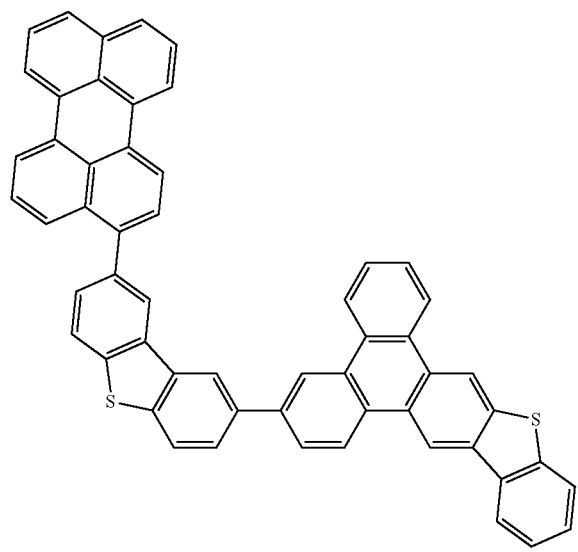
Compound 112
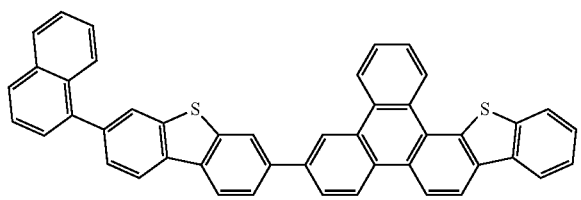
Compound 113
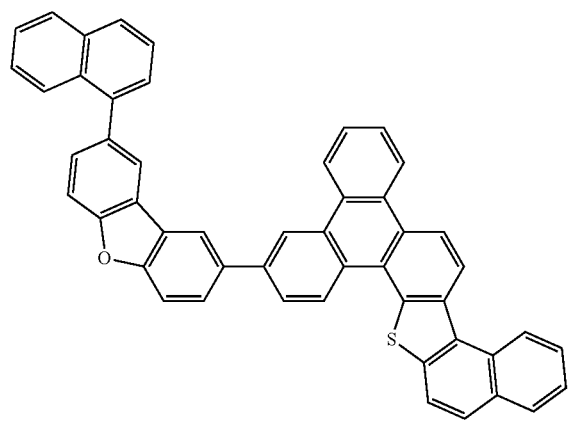
Compound 114
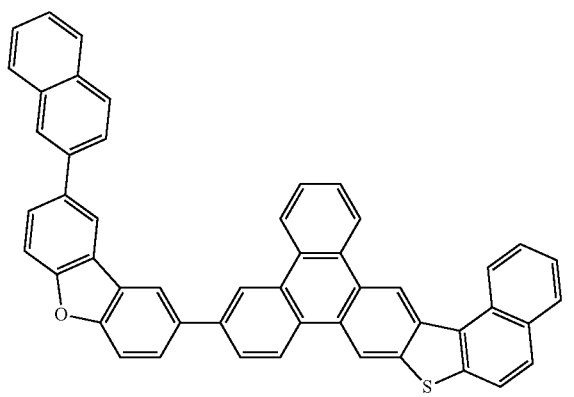

-continued
Compound 115
Compound 116
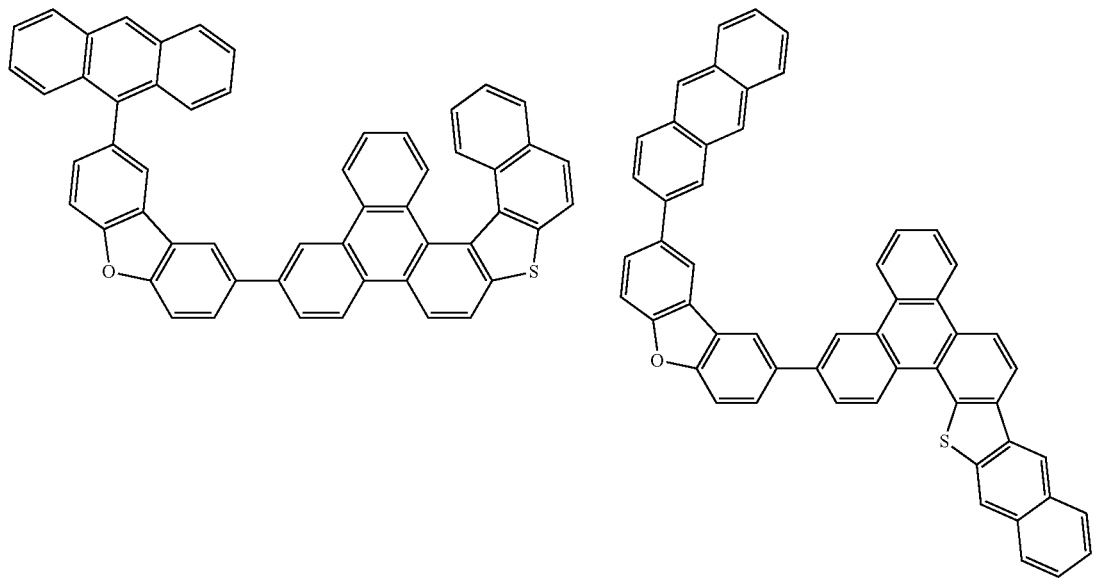
Compound 117
Compound 118
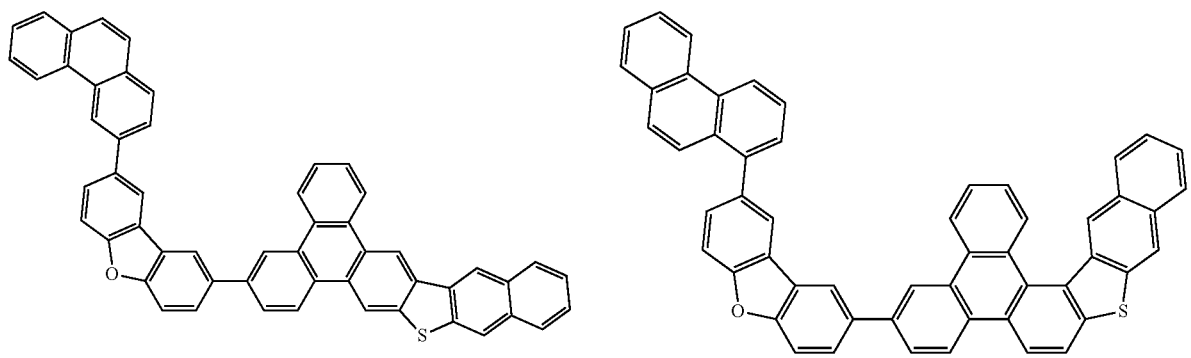
Compound 119
Compound 120
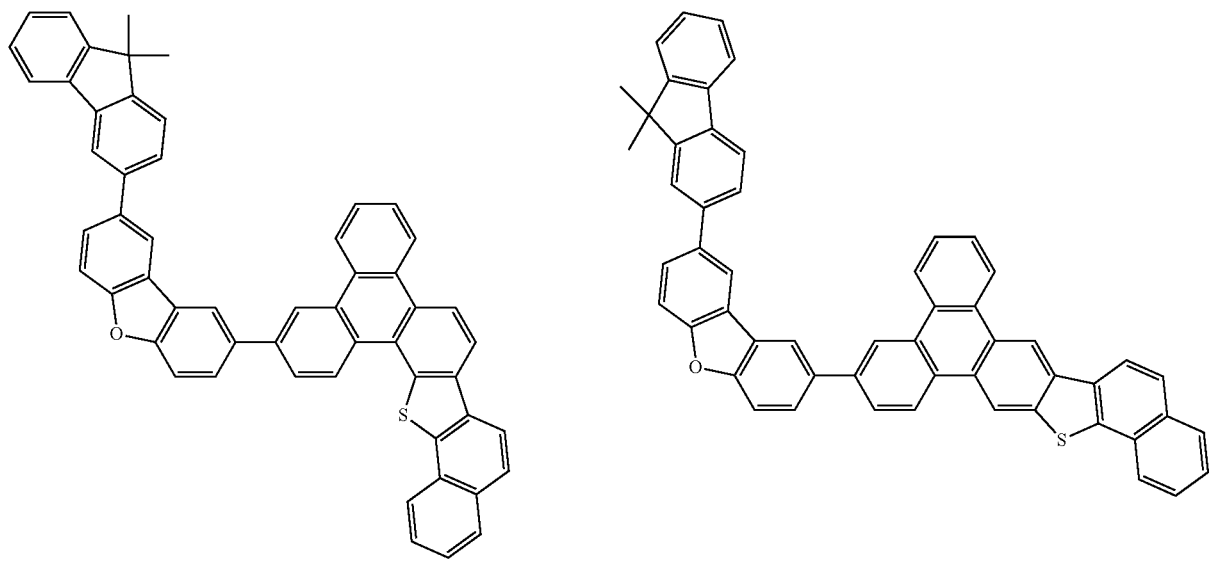

Compound 121
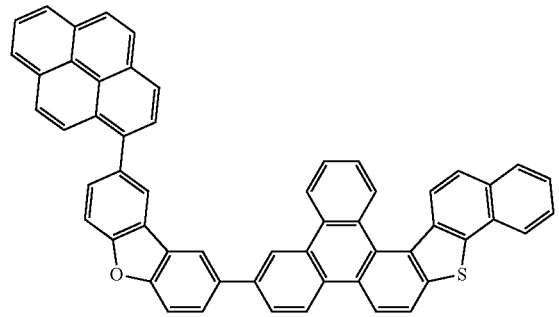
Compound 122
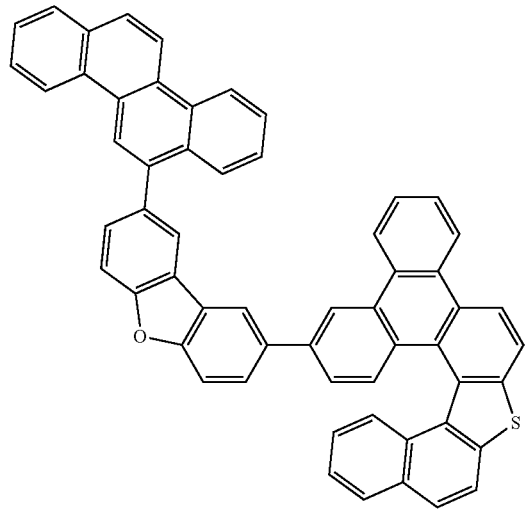
Compound 123
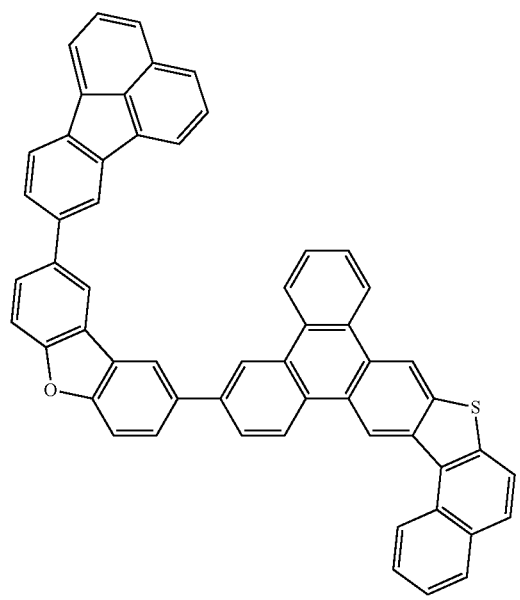
Compound 124
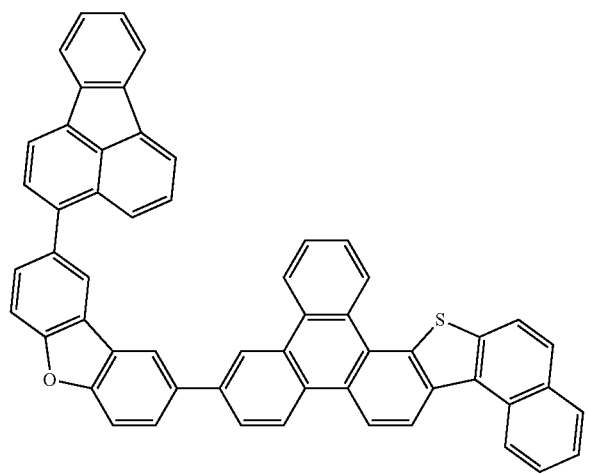

Compound 125
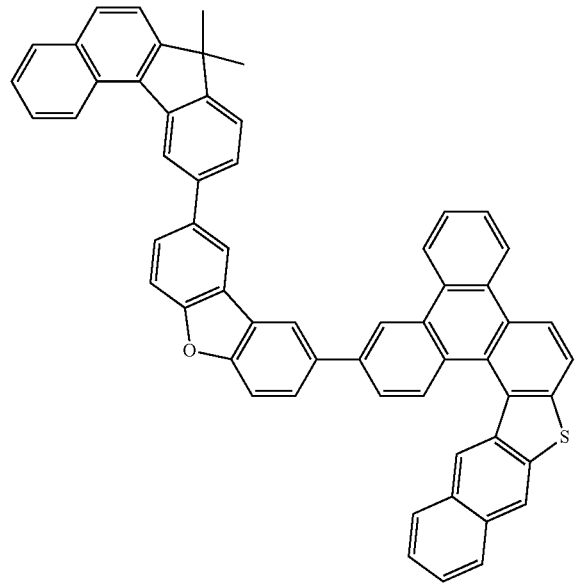
Compound 126
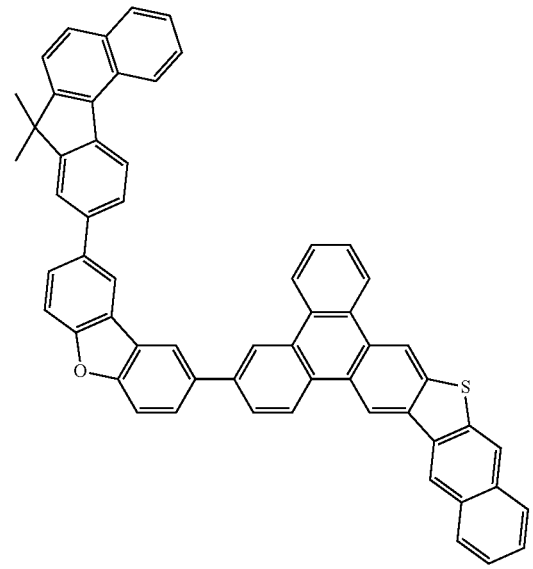
Compound 127
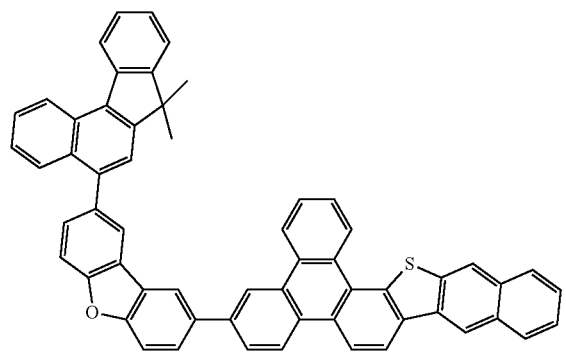
Compound 128
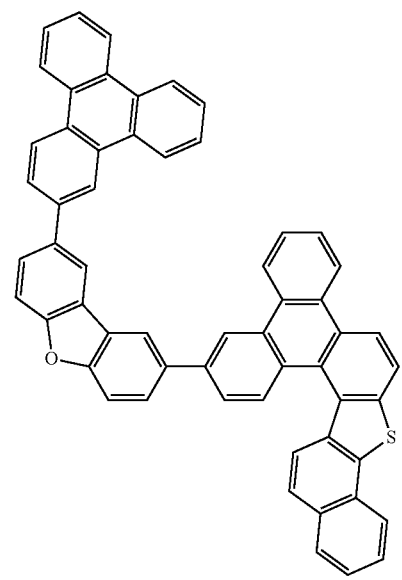

225                                      226
-continued
Compound 129
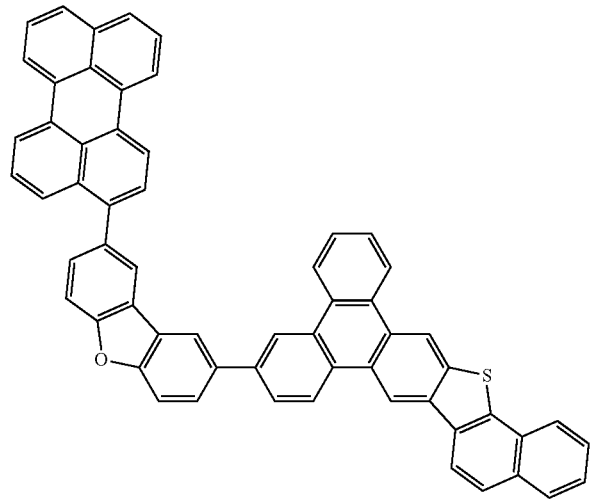
Compound 130
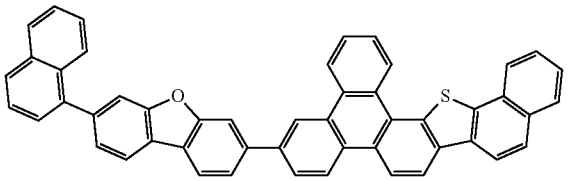
Compound 131
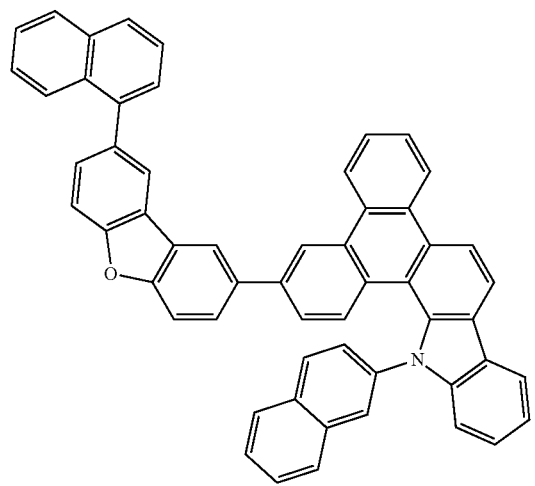
Compound 132
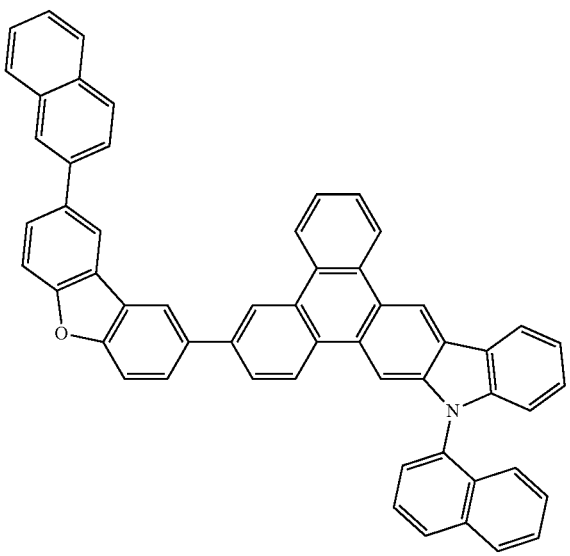
Compound 133
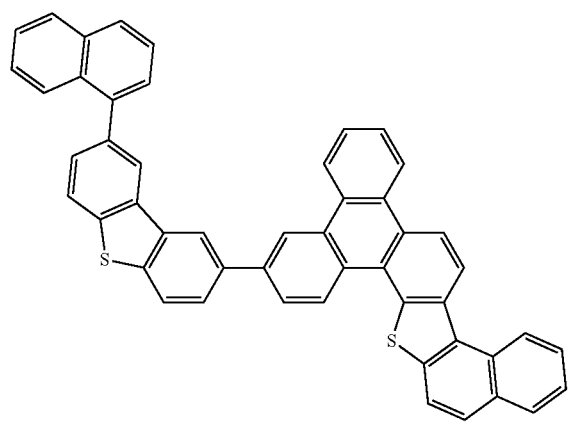
Compound 134
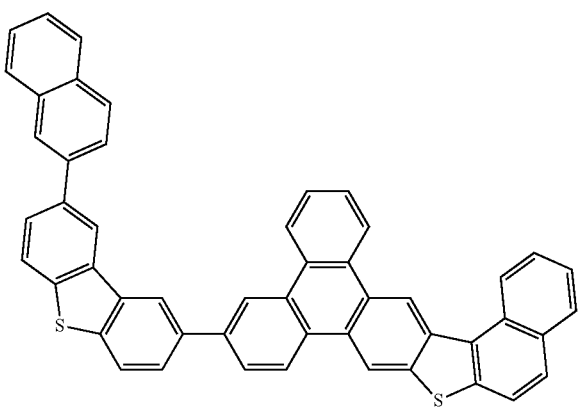

-continued
Compound 135
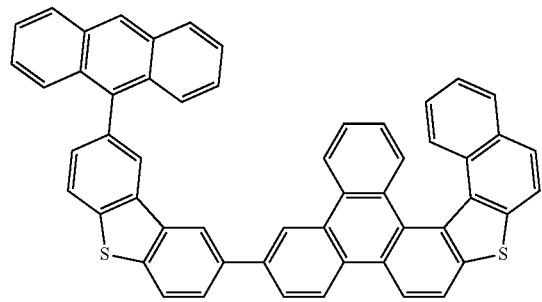
Compound 136
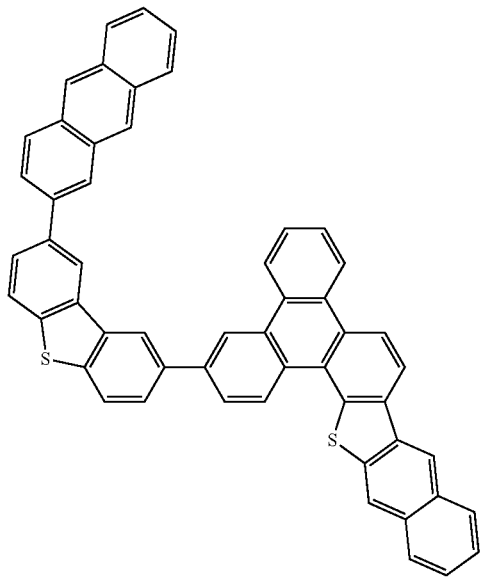
Compound 137
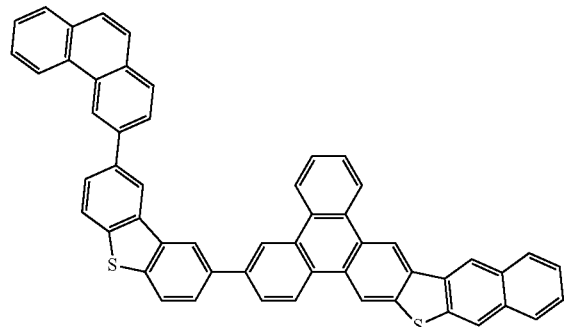
Compound 138
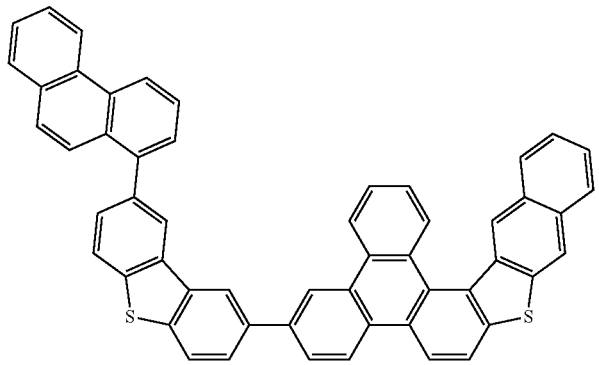
Compound 139
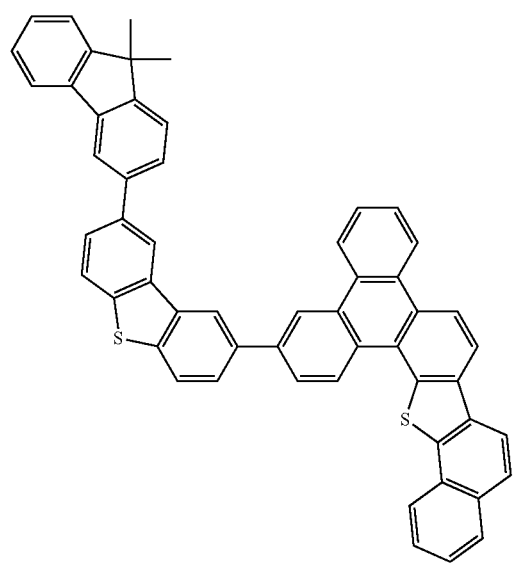
Compound 140
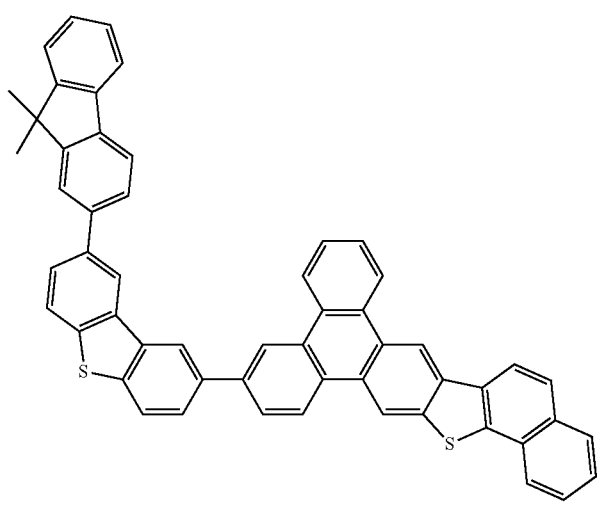

-continued
Compound 141
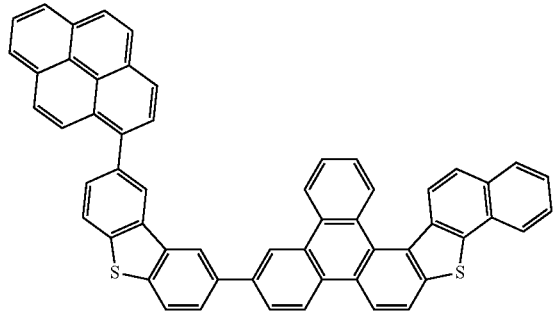
Compound 142
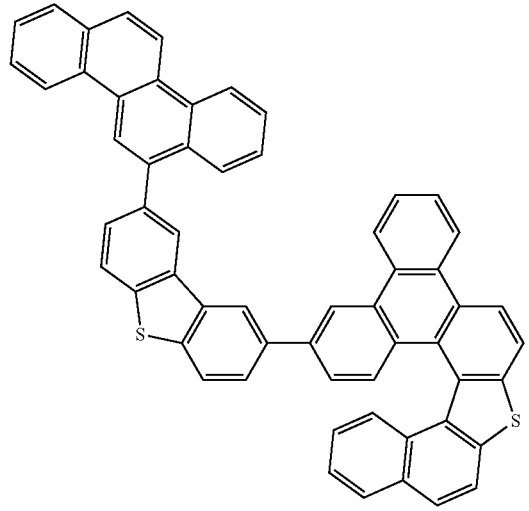
Compound 143
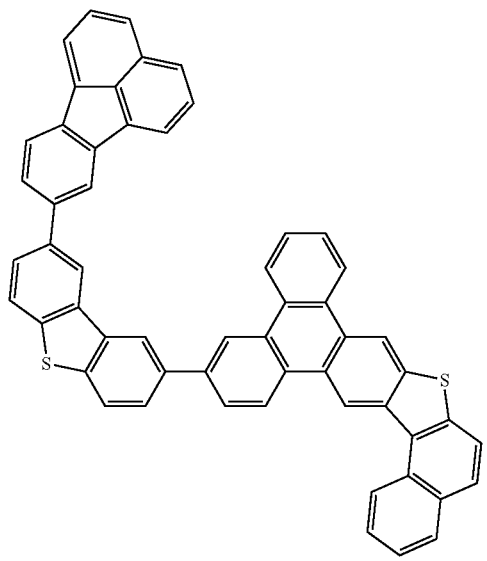
Compound 144
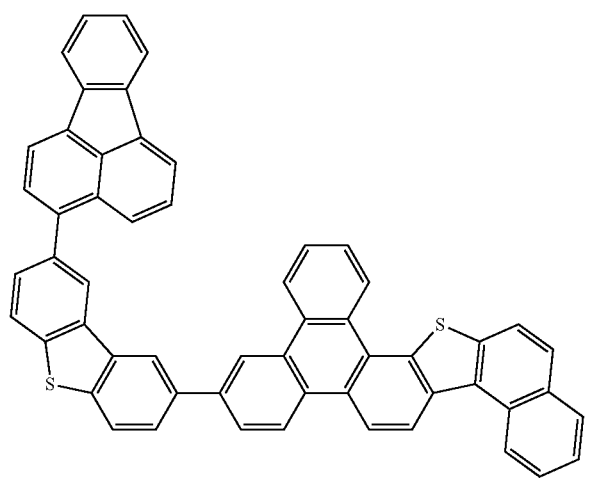

-continued
Compound 145
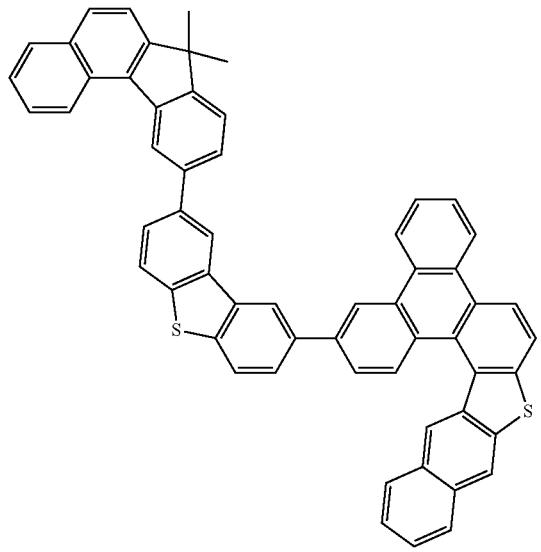
Compound 146
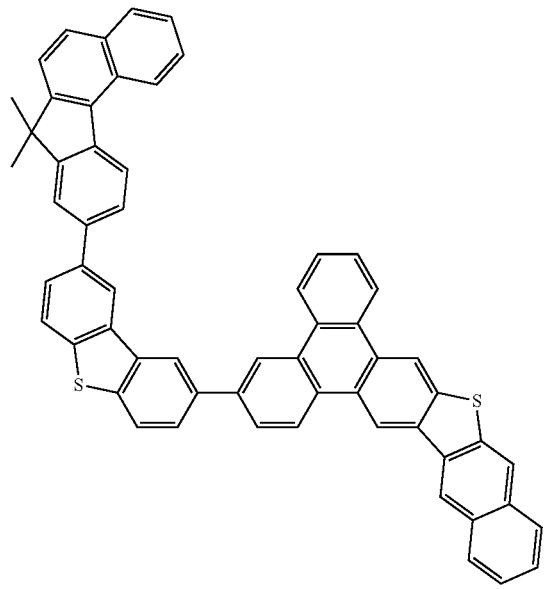
Compound 147
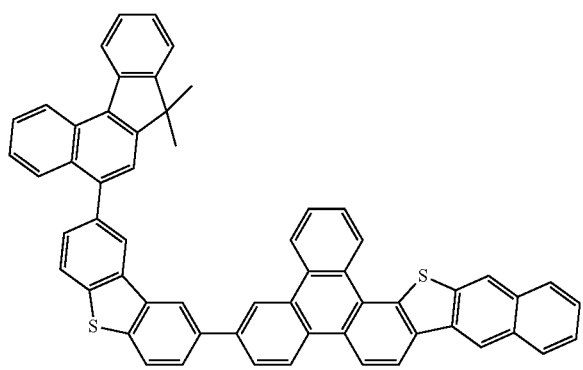
Compound 148
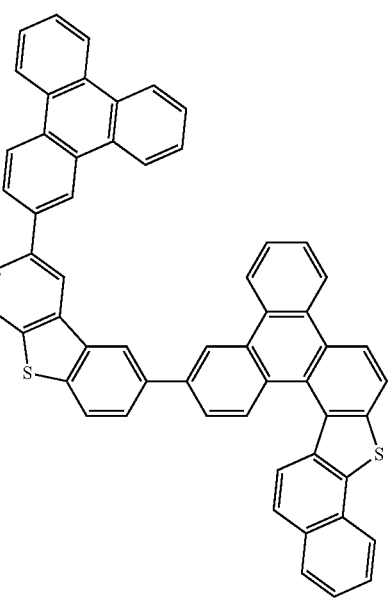

-continued
Compound 149
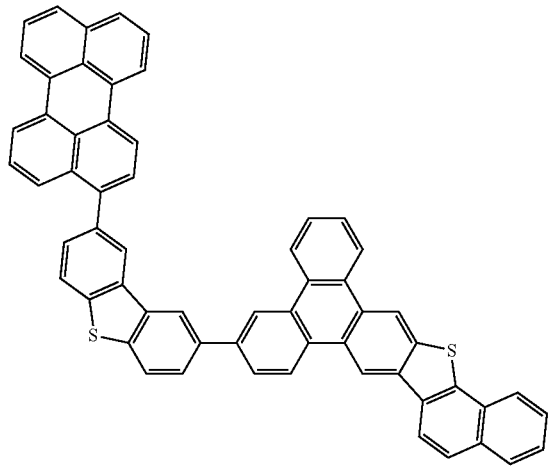
Compound 150
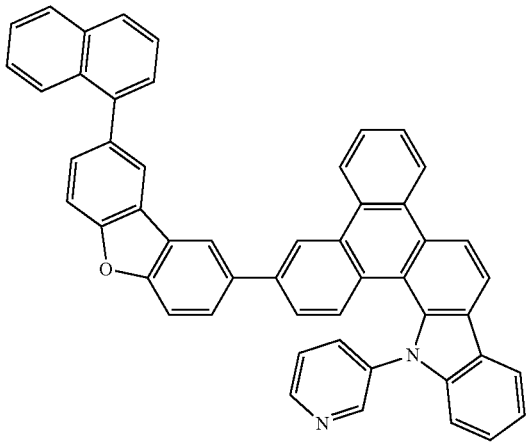
Compound 151
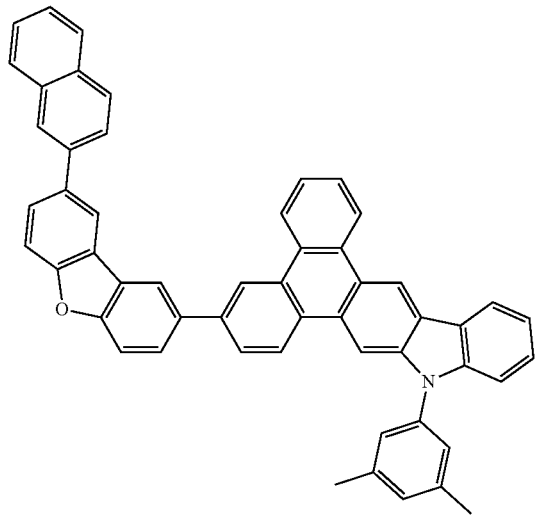
Compound 152
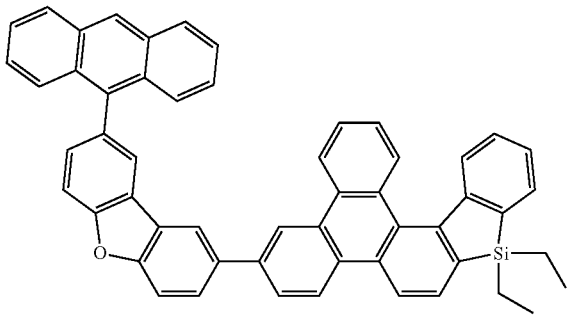
Compound 153
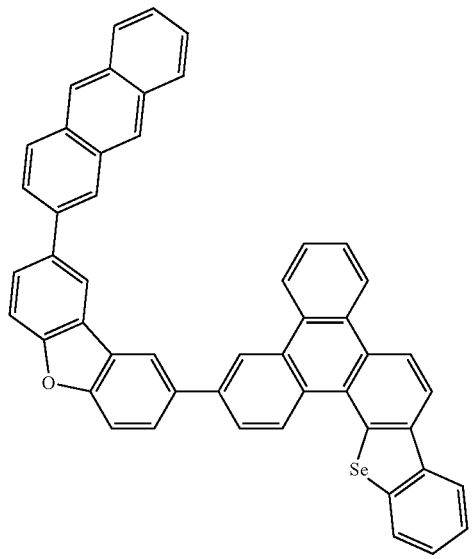
Compound 154
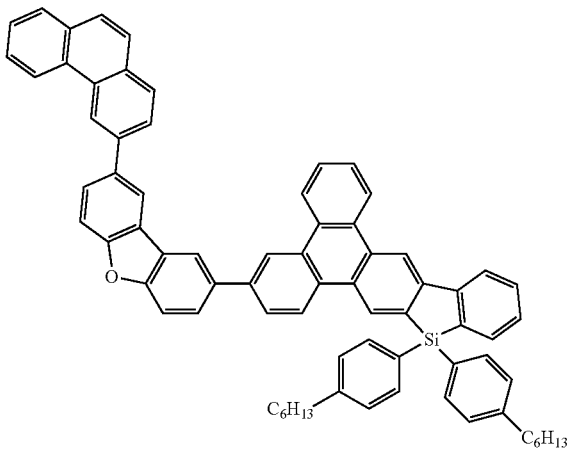

-continued
Compound 155
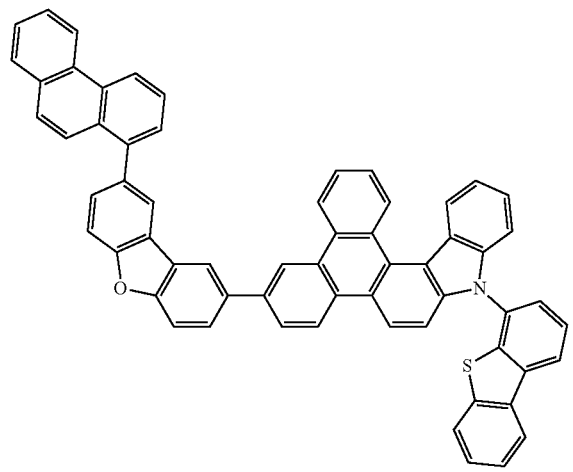
Compound 156
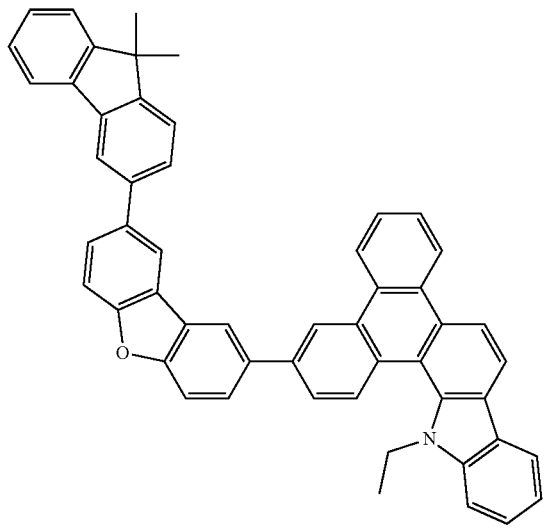
Compound 157
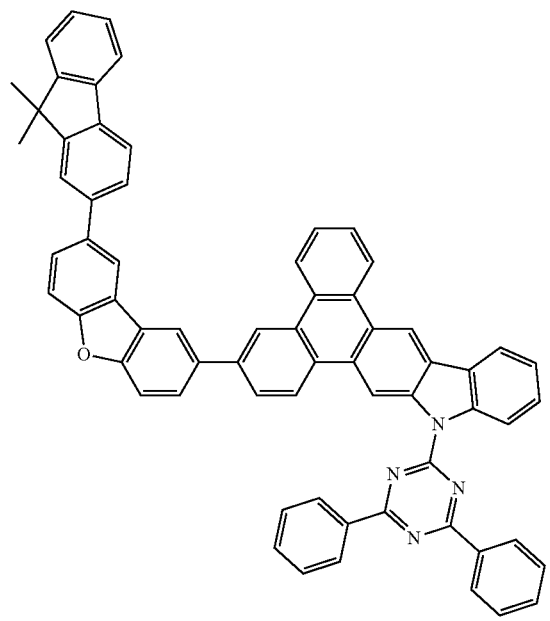
Compound 158
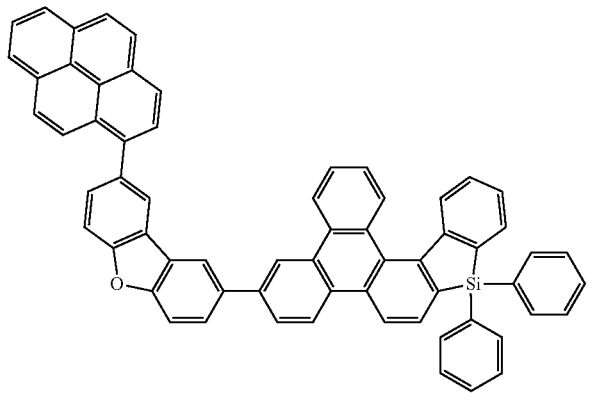

-continued
Compound 159
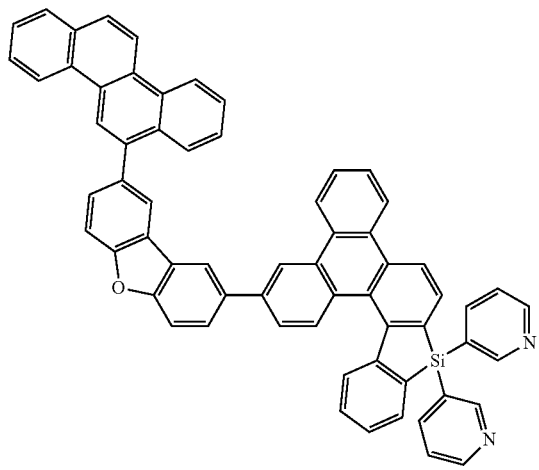
Compound 160
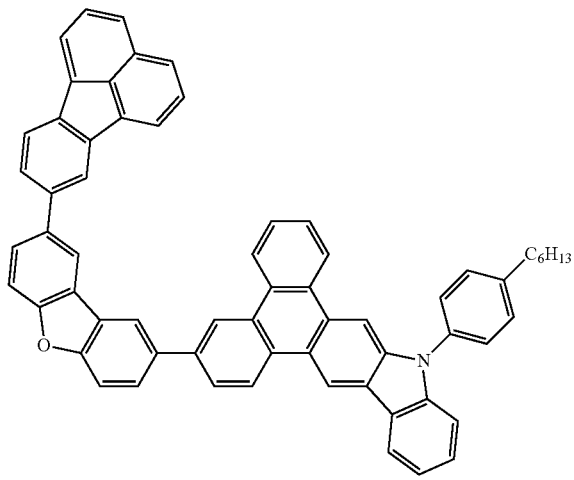
Compound 161
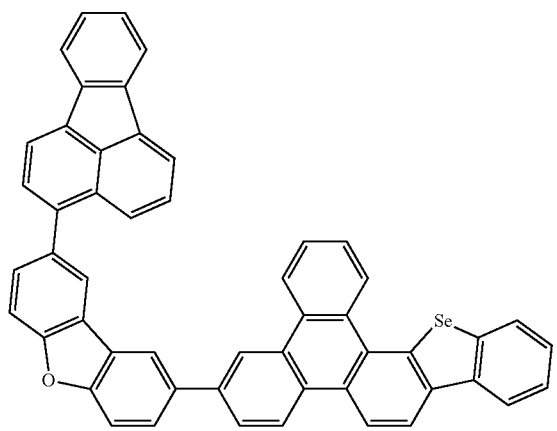
Compound 162
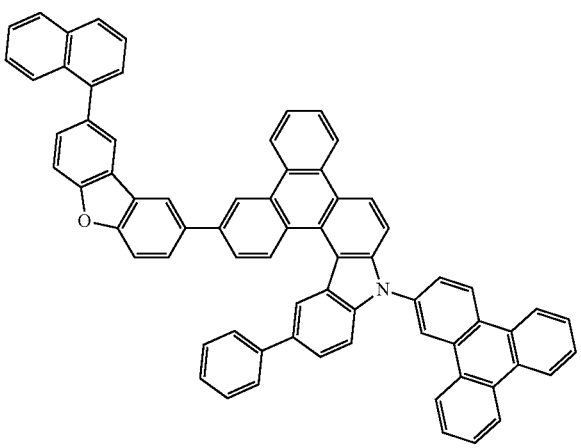
Compound 163
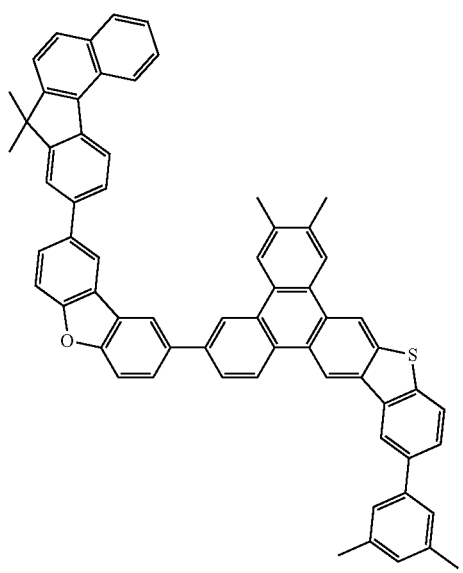
Compound 164
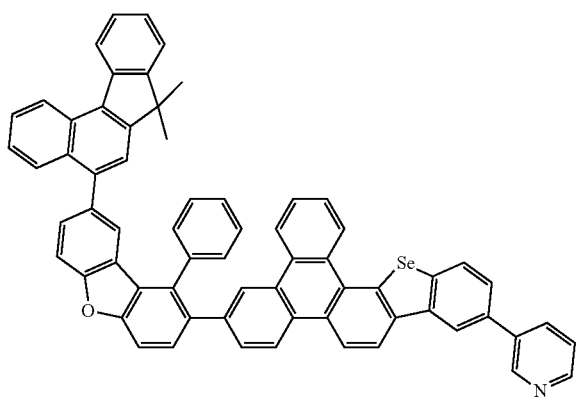

-continued
Compound 165
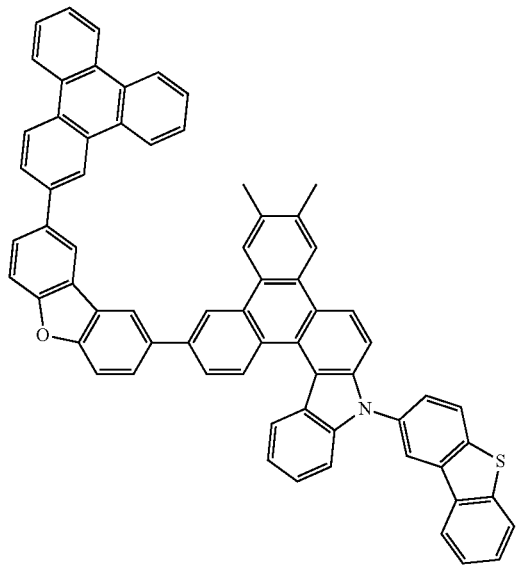
Compound 166
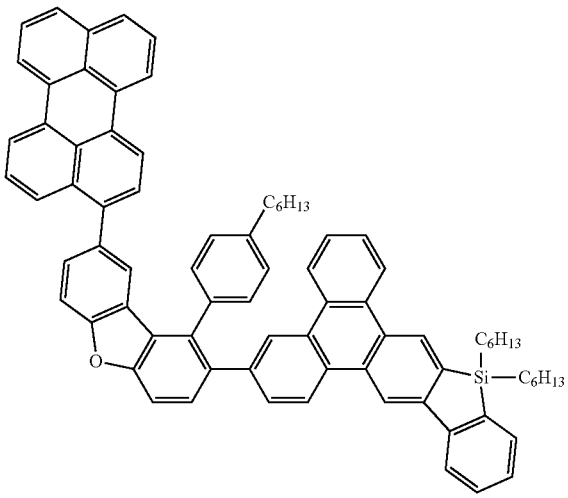
Compound 167
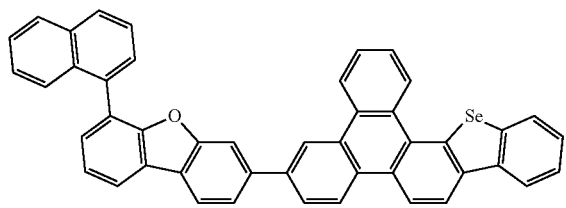
Compound 168
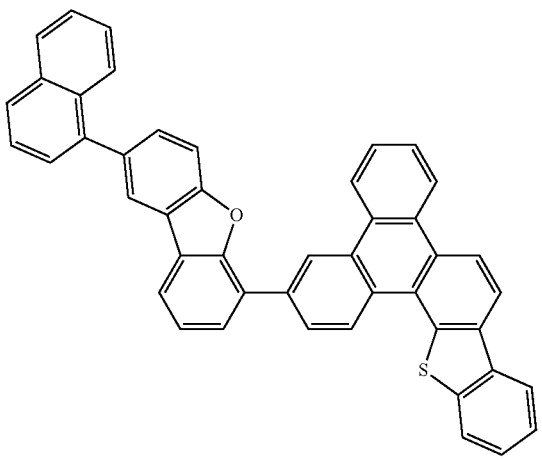
Compound 169
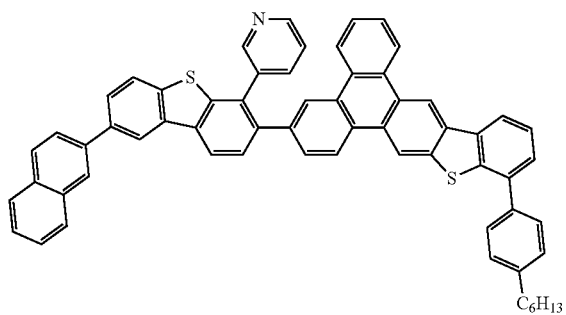
Compound 170
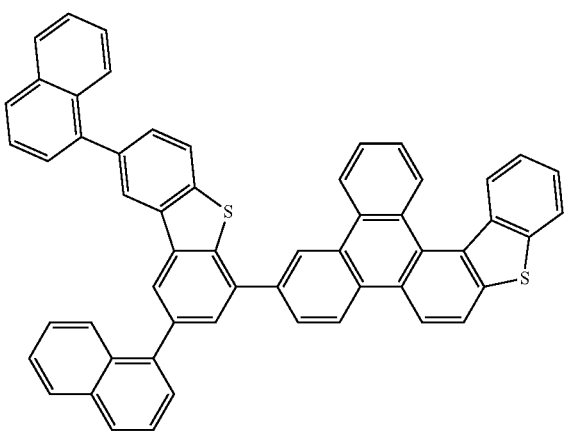

-continued
Compound 171
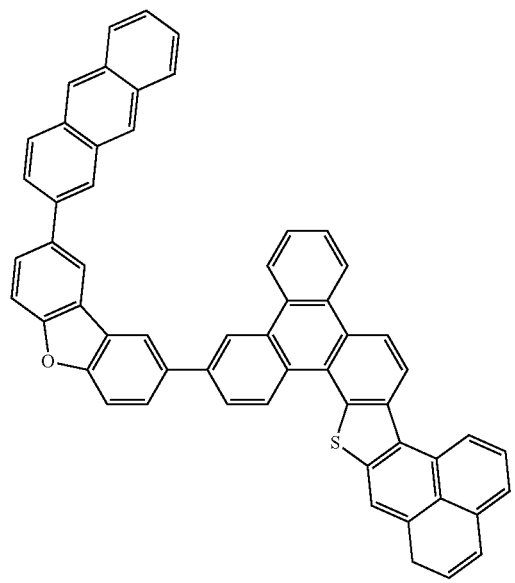
Compound 172
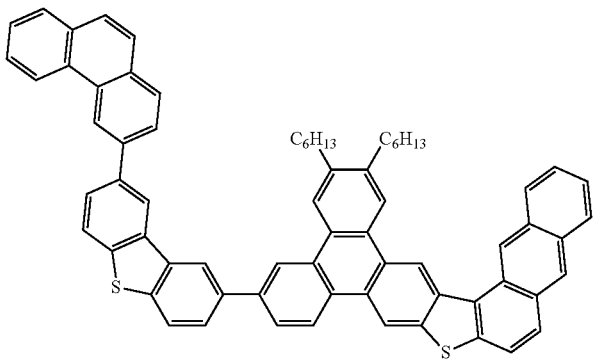
Compound 173
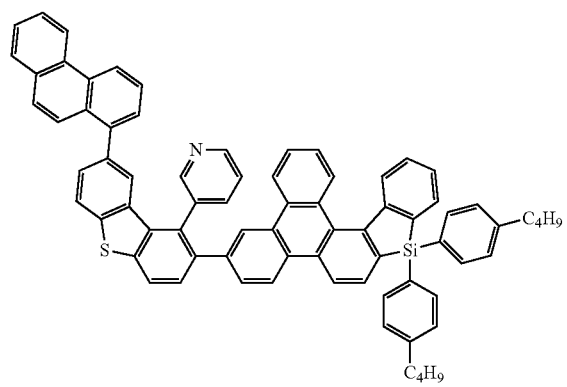
Compound 174
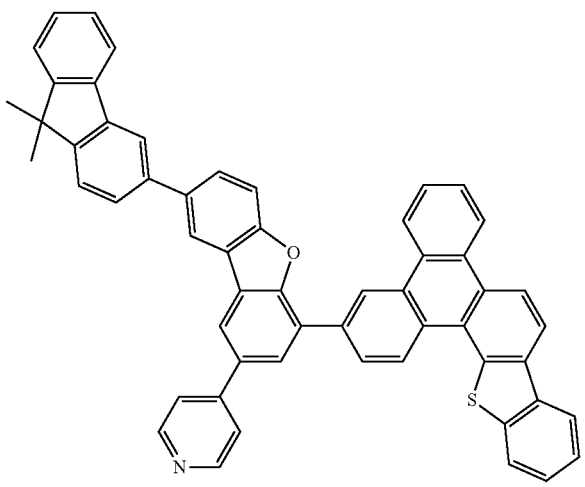
Compound 175
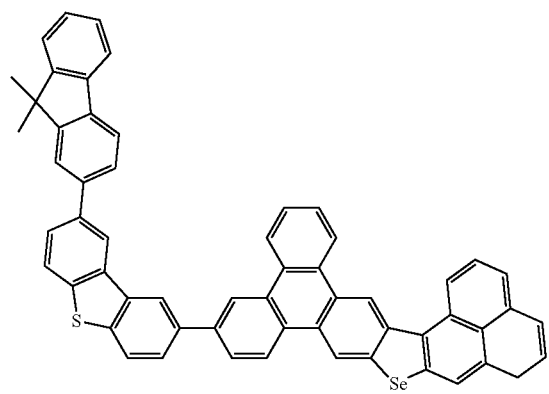
Compound 176
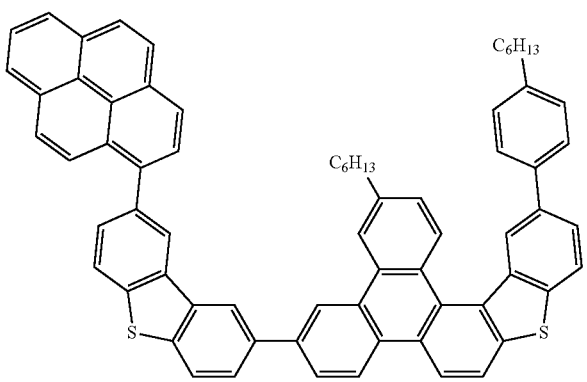

-continued
Compound 177
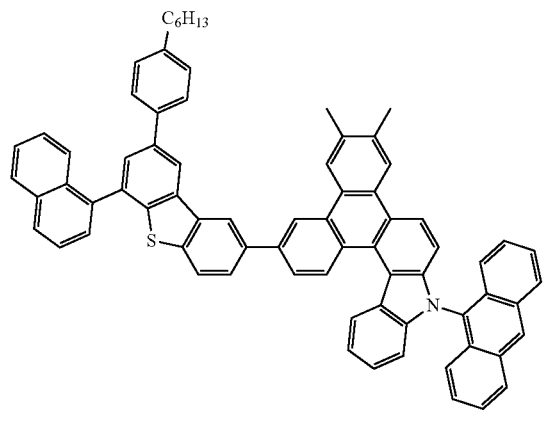
Compound 178
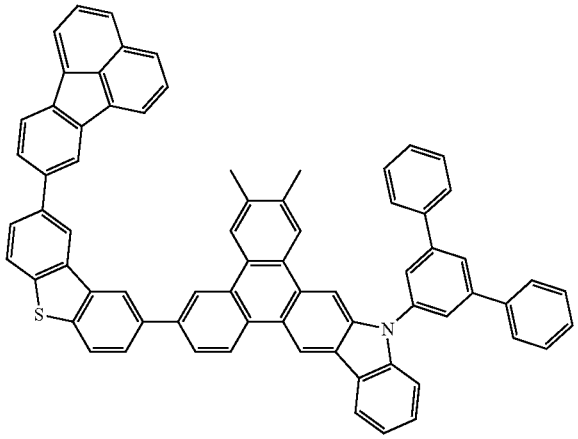
Compound 179
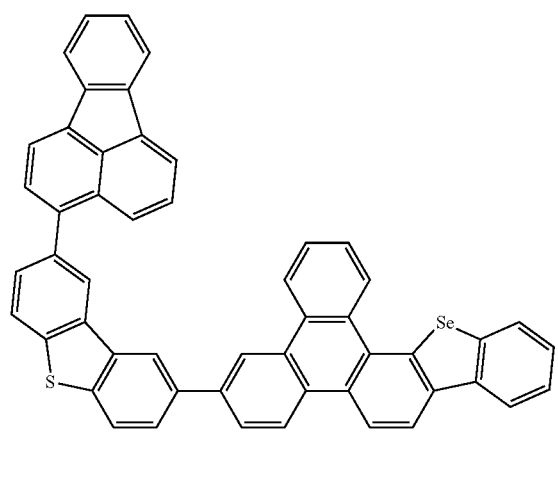
Compound 180
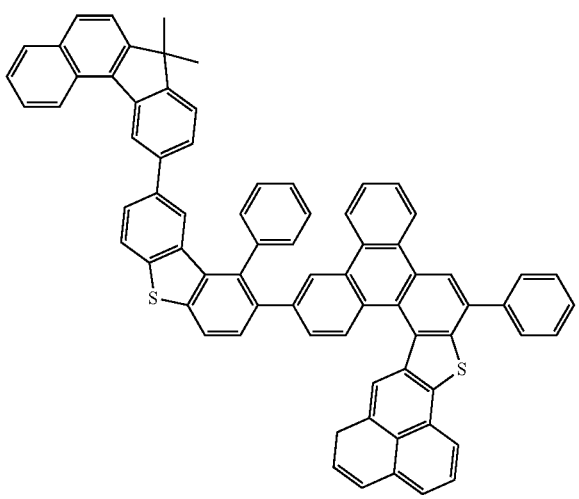
Compound 181
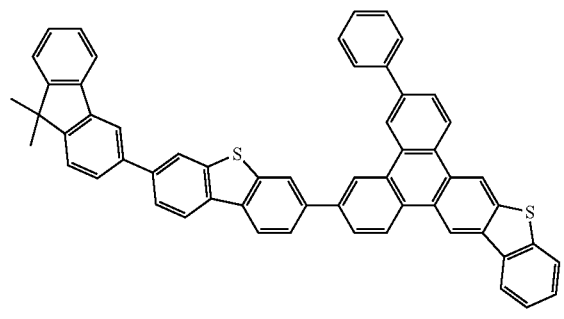
Compound 182
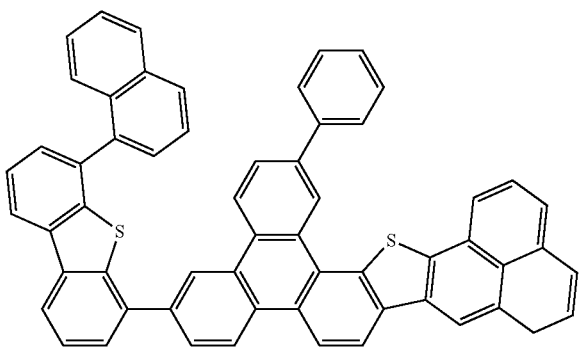

-continued
Compound 183
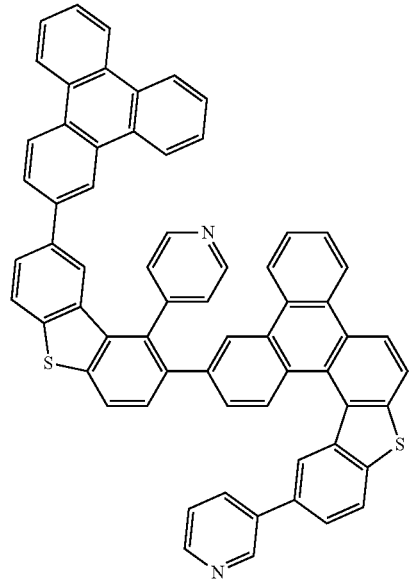
Compound 184
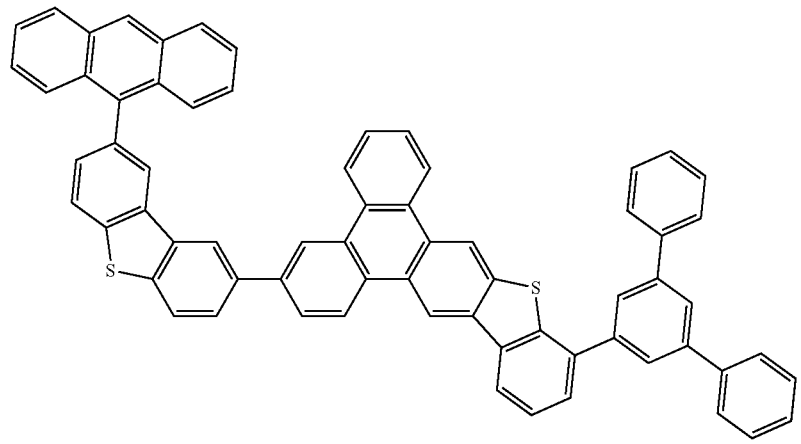
Compound 185
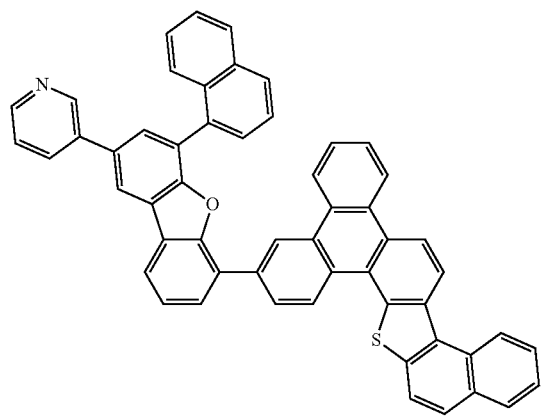
Compound 186
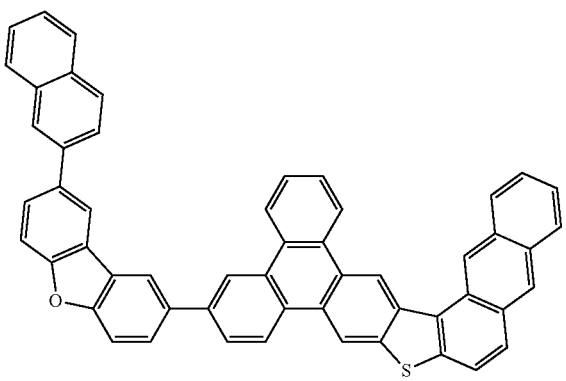

-continued
Compound 187
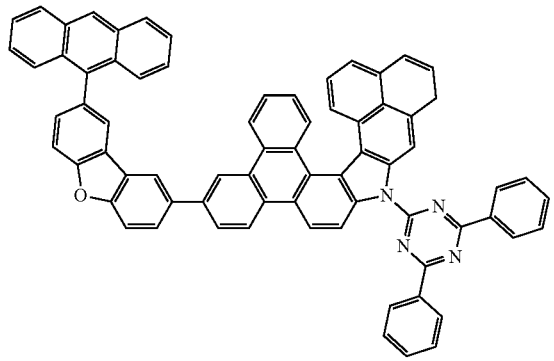
Compound 188
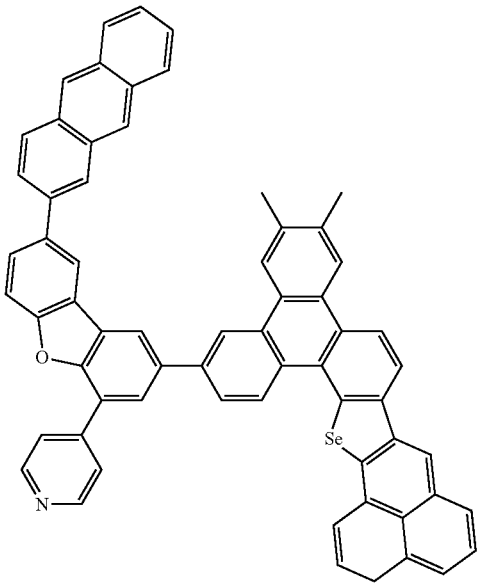
Compound 189
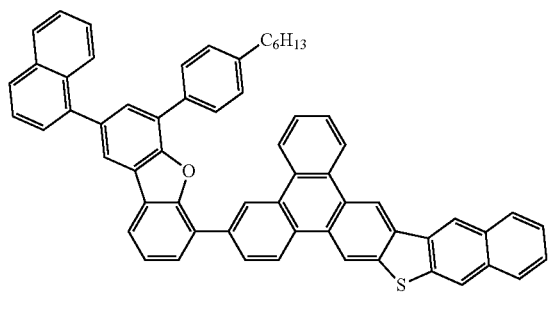
Compound 190
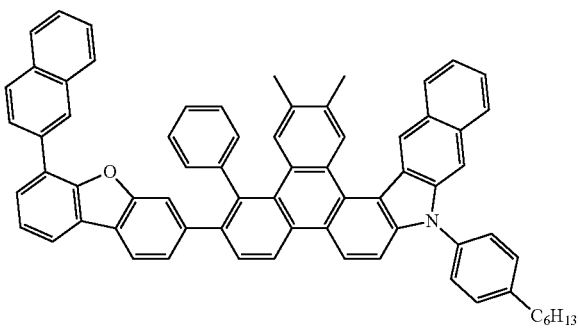
Compound 191
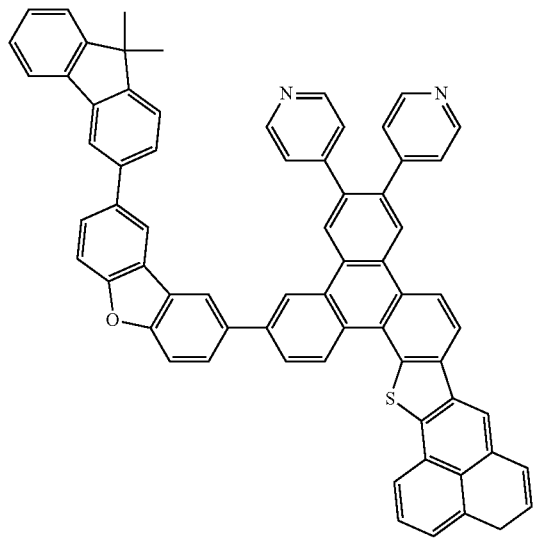
Compound 192
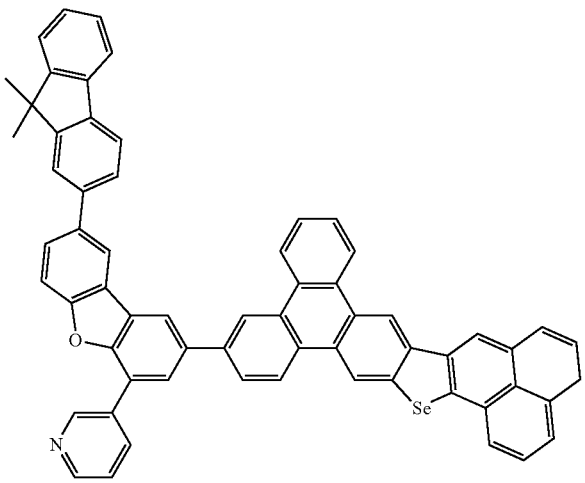

-continued
Compound 193
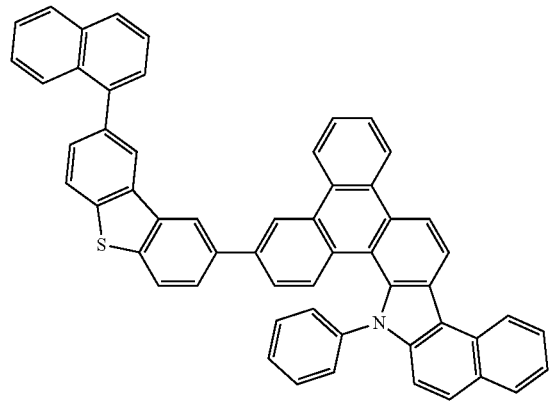
Compound 194
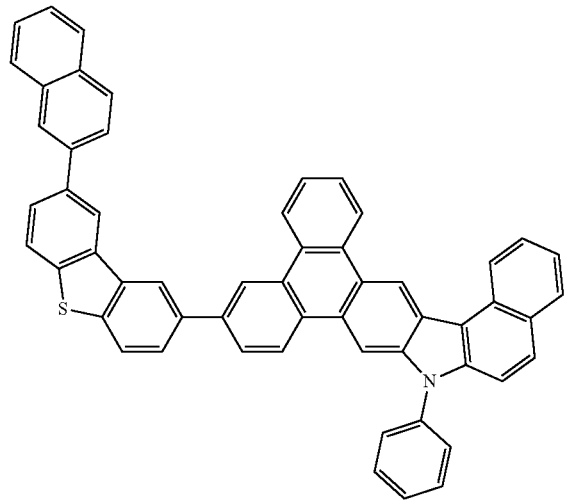
Compound 195
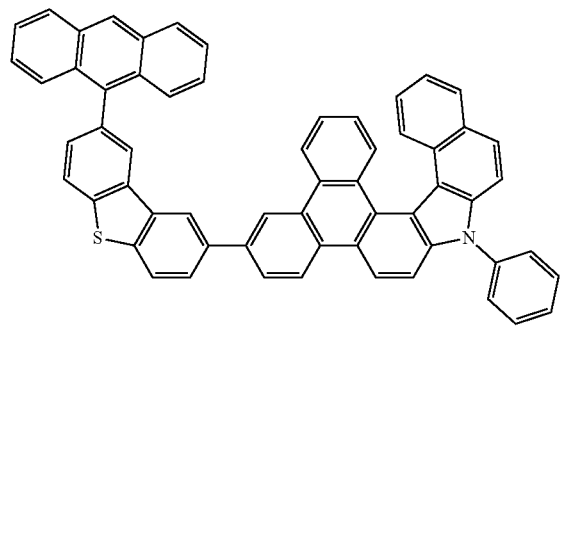
Compound 196
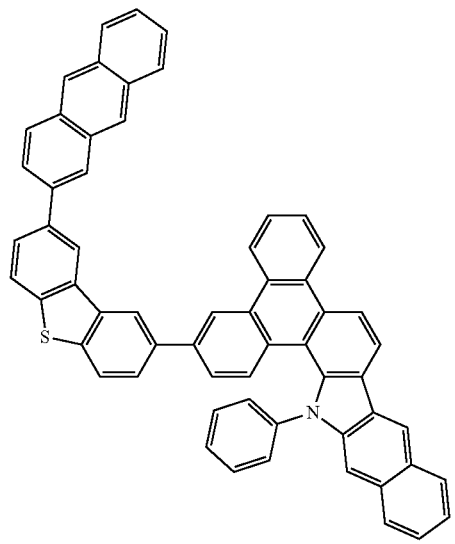
Compound 197
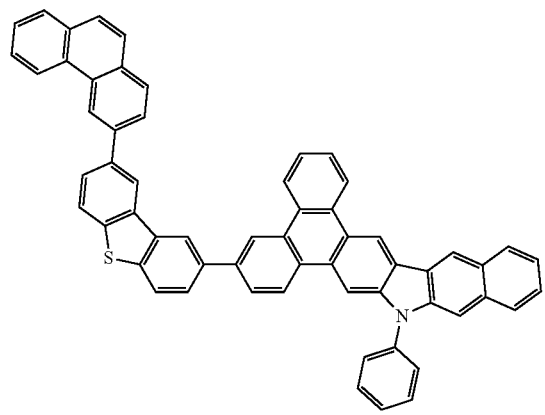
Compound 198
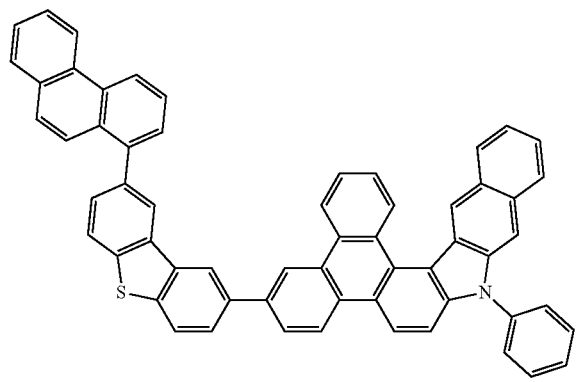

-continued
Compound 199
Compound 200
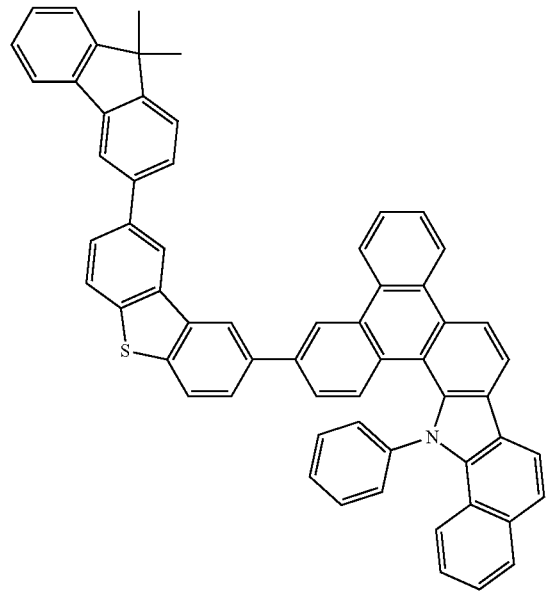
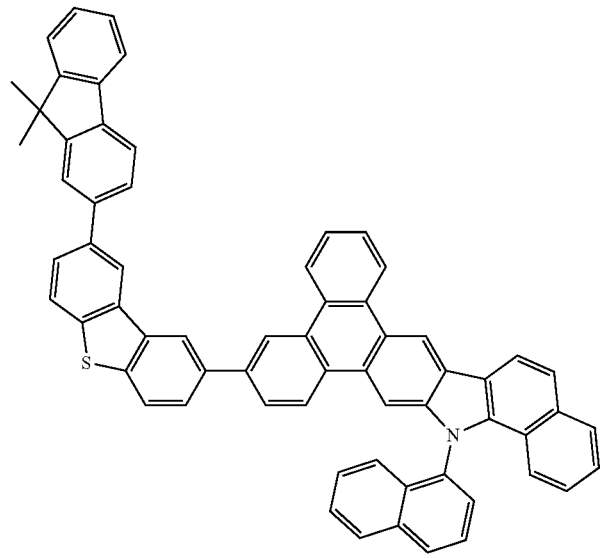
Compound 201
Compound 202
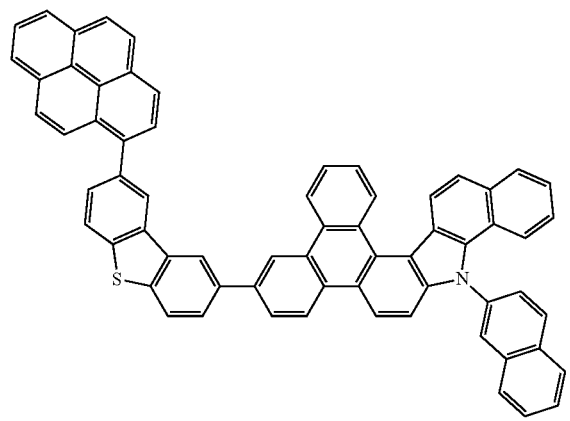
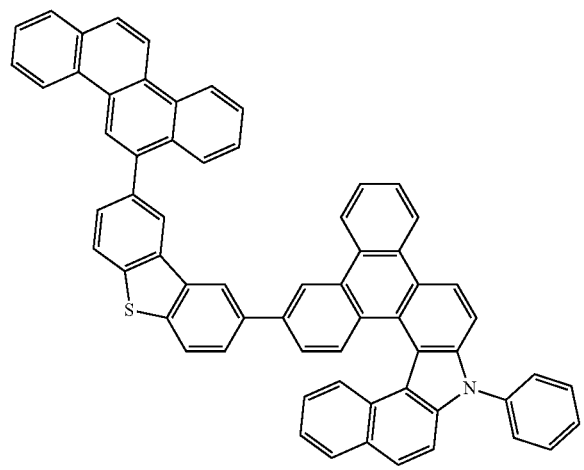
Compound 203
Compound 204
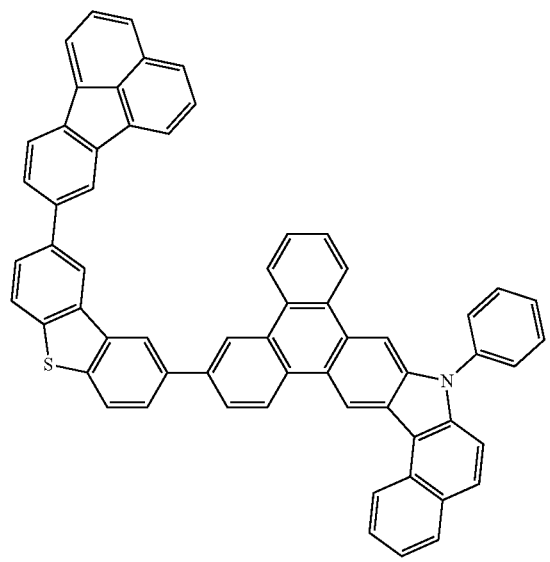

Compound 205
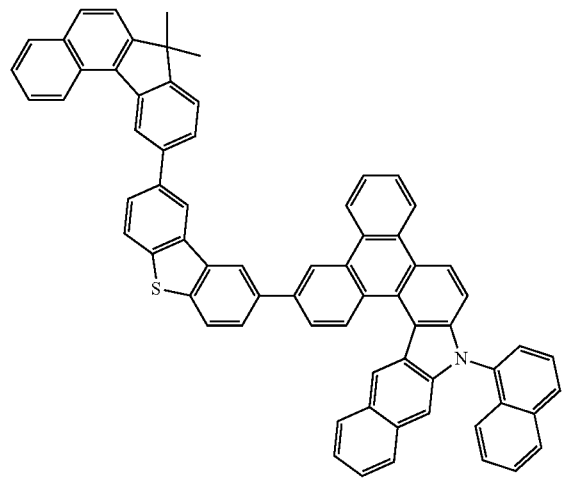
Compound 206
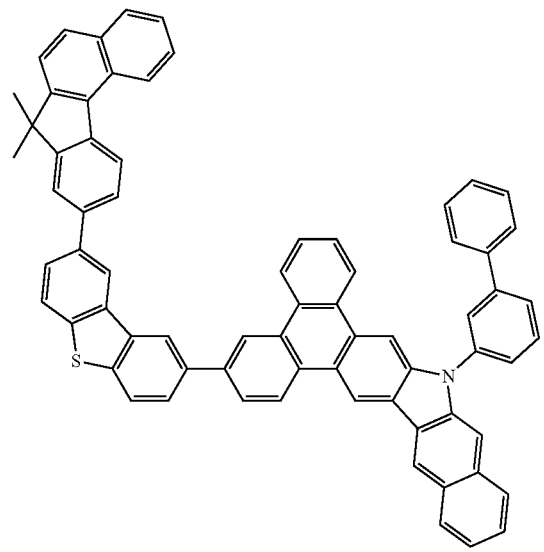
Compound 207
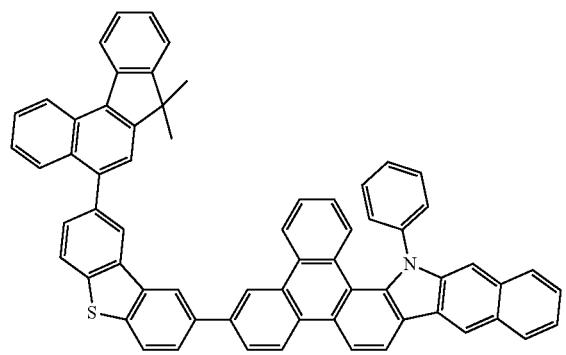
Compound 208
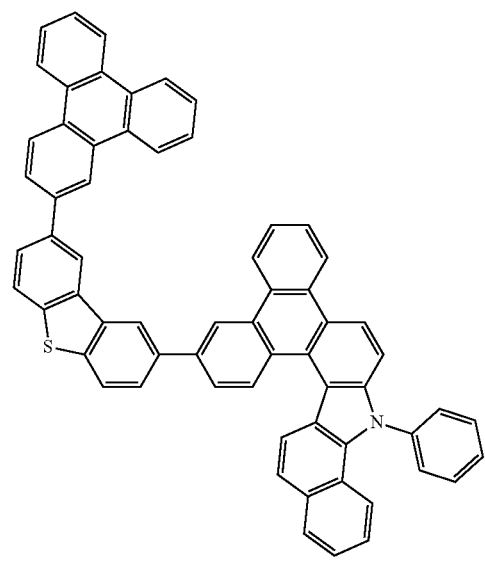

-continued
Compound 209
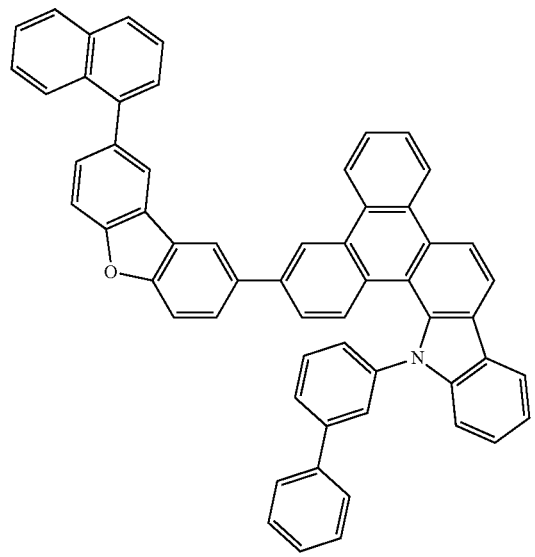
Compound 210
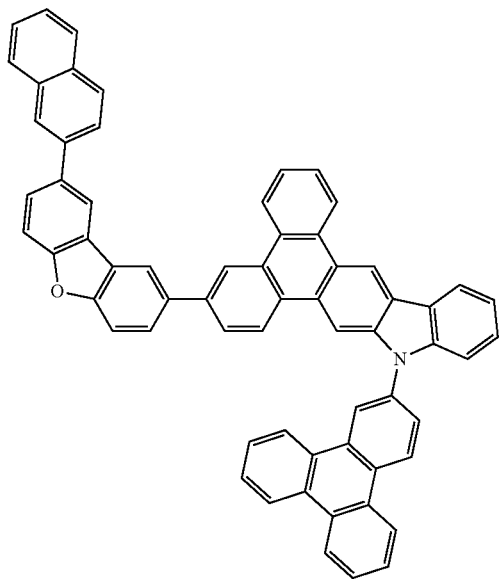
Compound 211
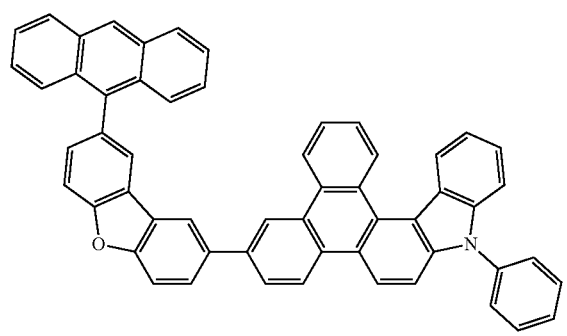
Compound 212
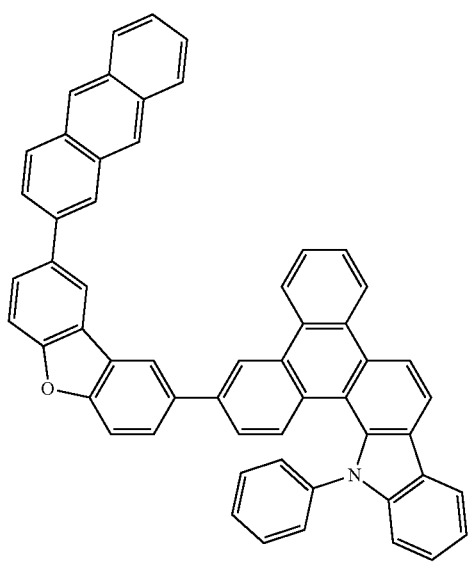

-continued
Compound 213
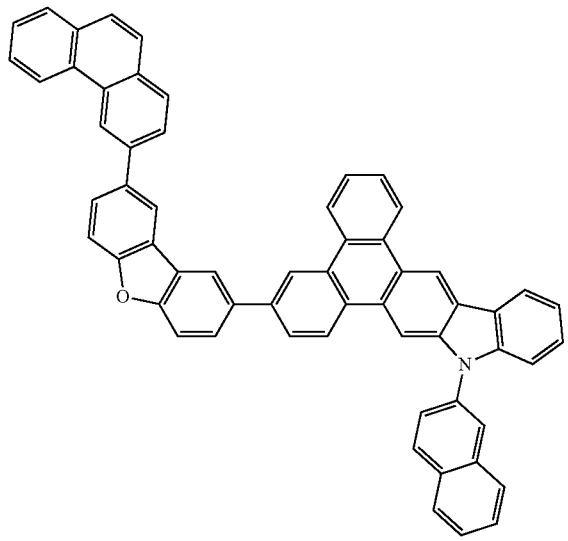
Compound 214
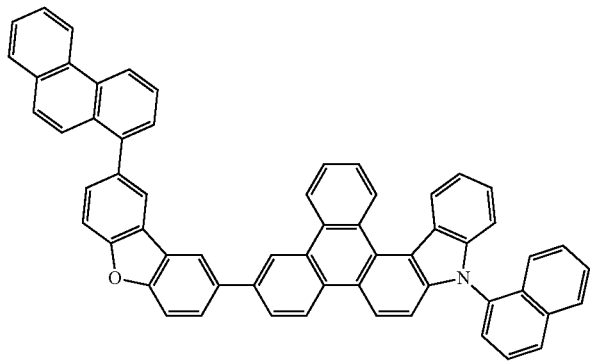
Compound 215
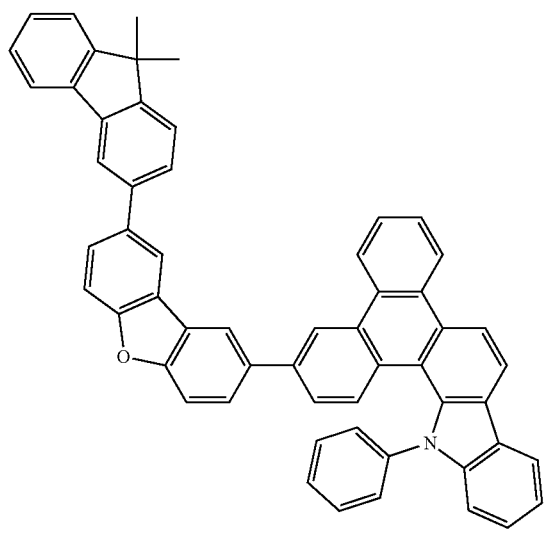
Compound 216
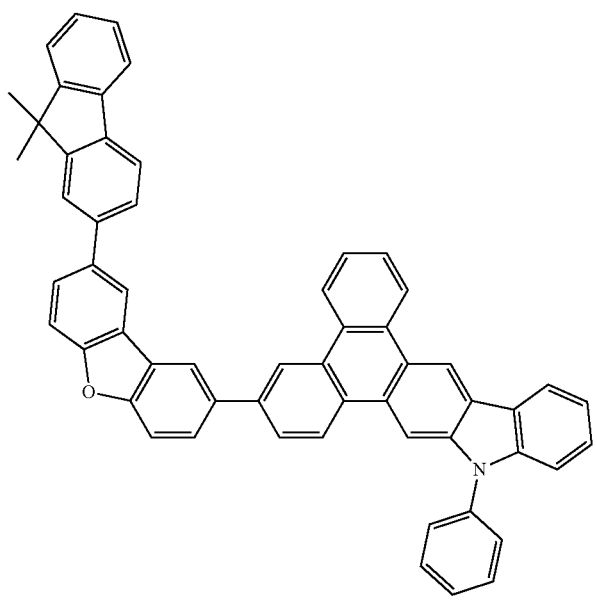
Compound 217
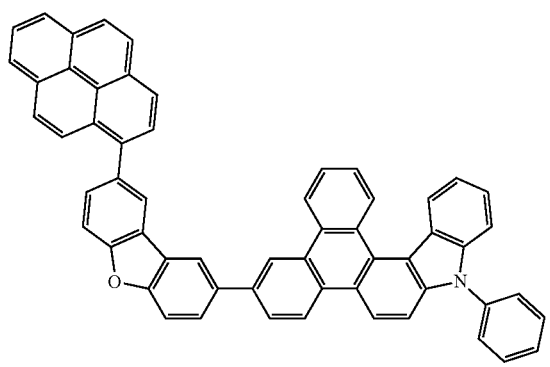
Compound 218
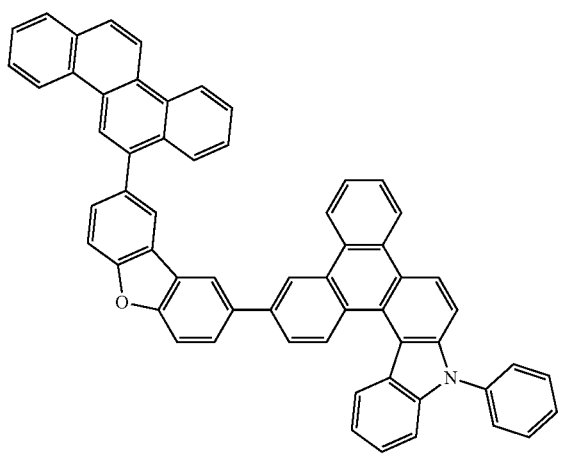

-continued
Compound 219
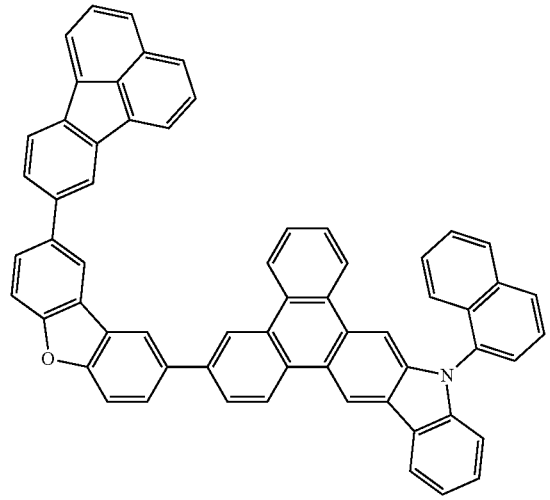
Compound 220
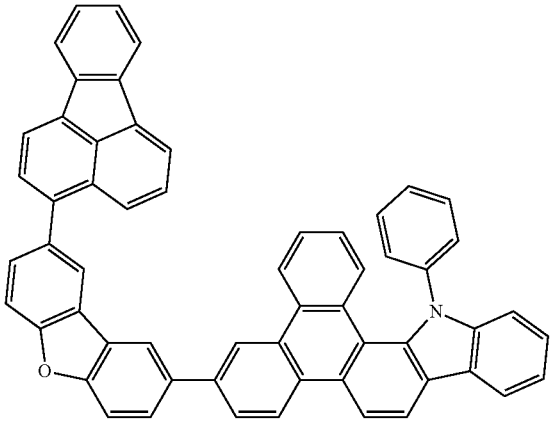
Compound 221
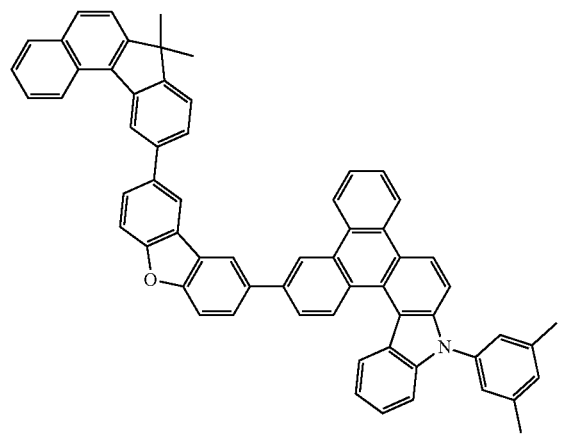
Compound 222
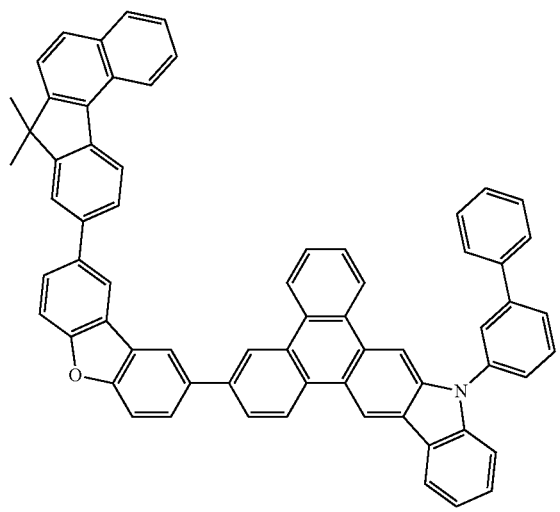
Compound 223
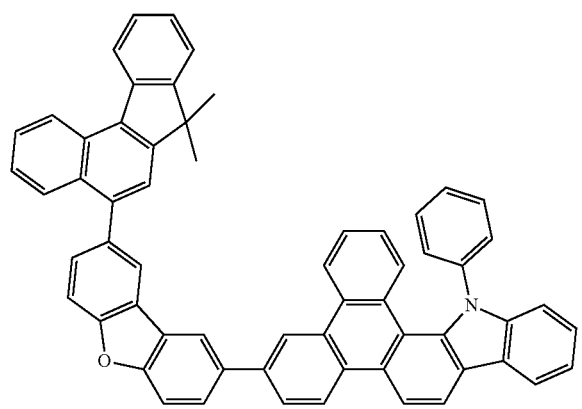
Compound 224
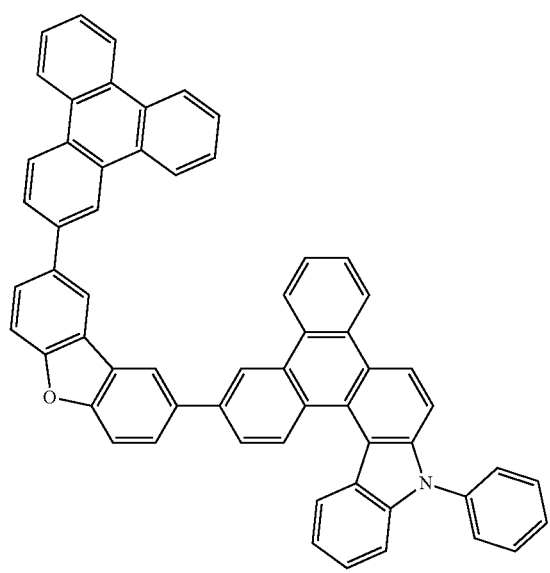

-continued
Compound 225
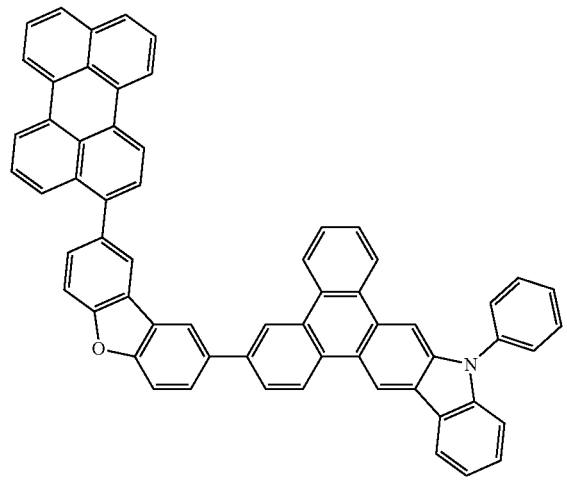
Compound 226
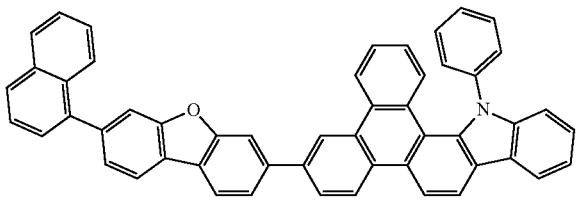
Compound 227
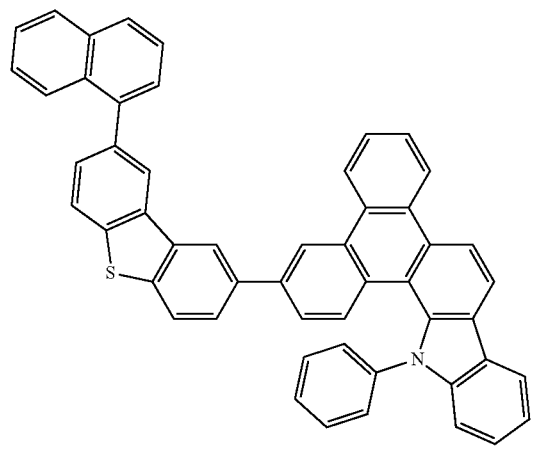
Compound 228
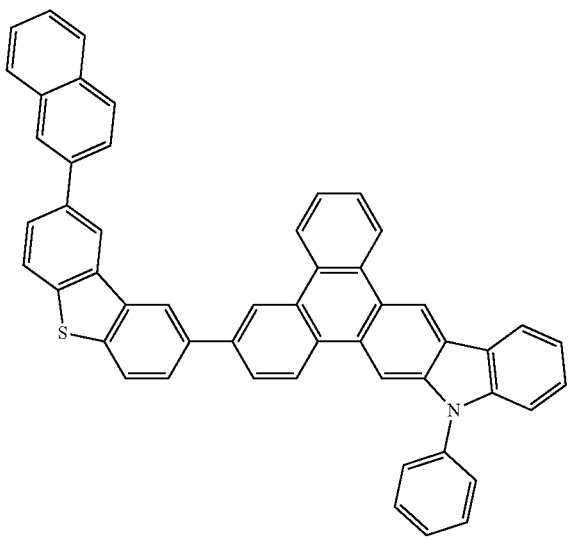
Compound 229
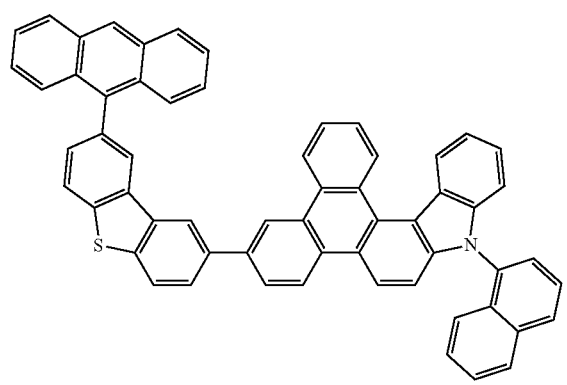
Compound 230
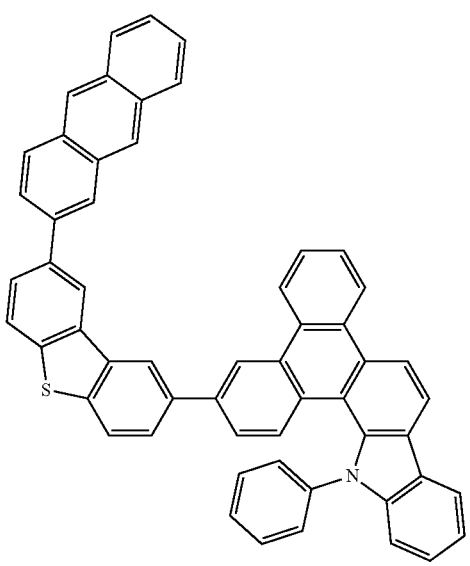

-continued
Compound 231
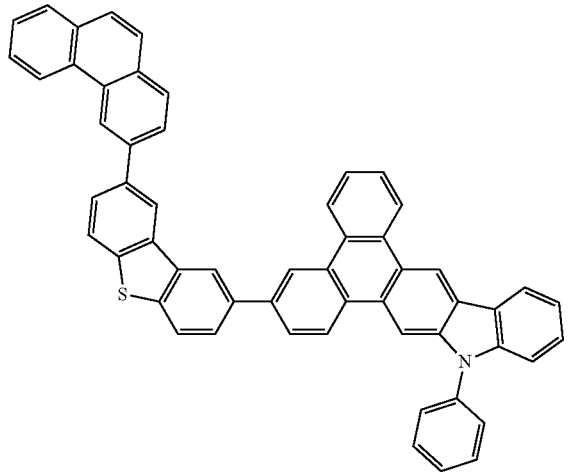
Compound 232
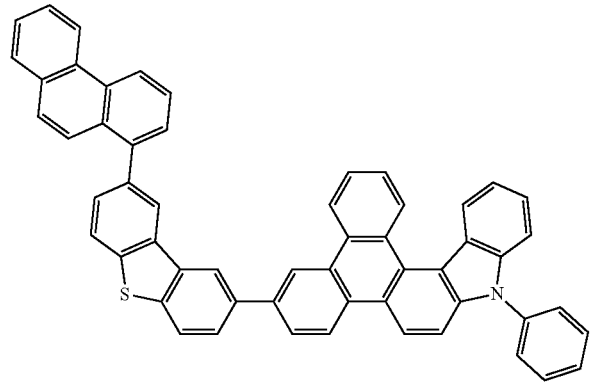
Compound 233
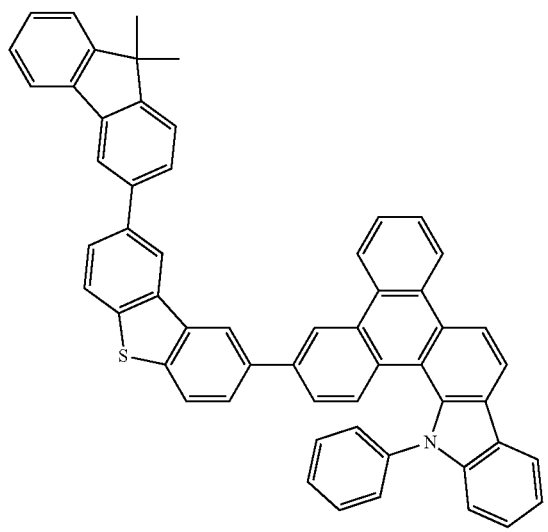
Compound 234
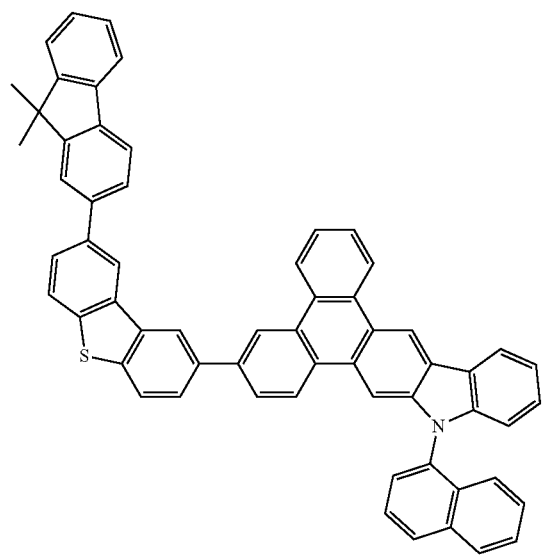
Compound 235
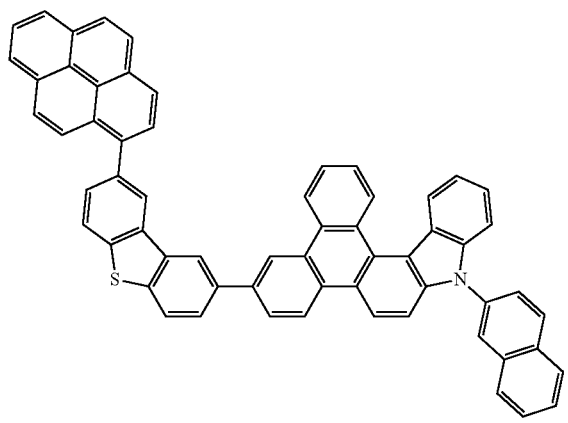
Compound 236
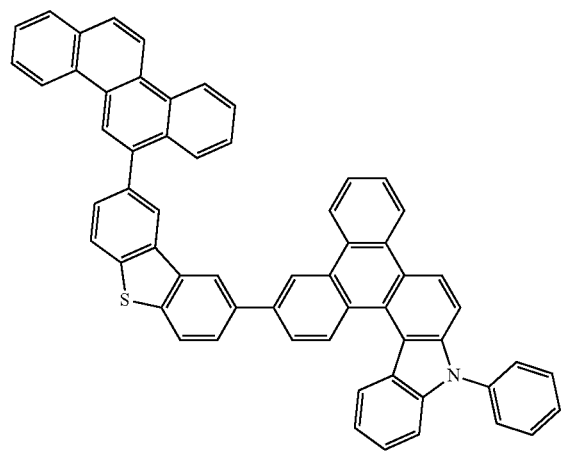

Compound 237
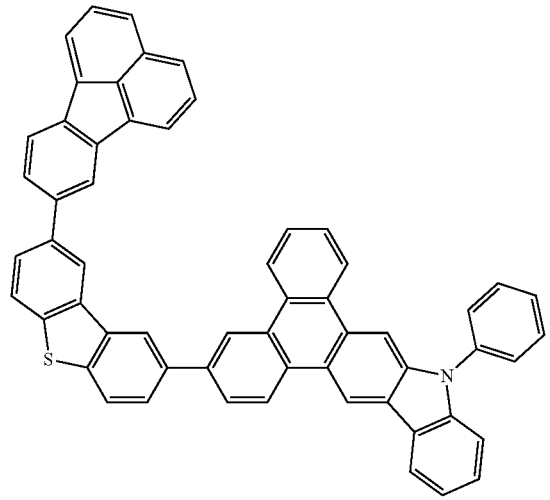
Compound 238
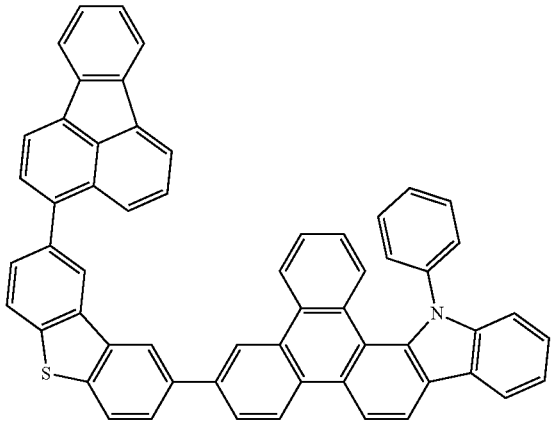
Compound 239
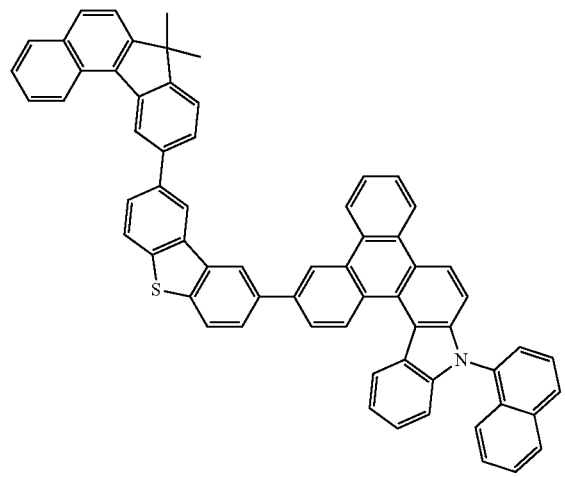
Compound 240
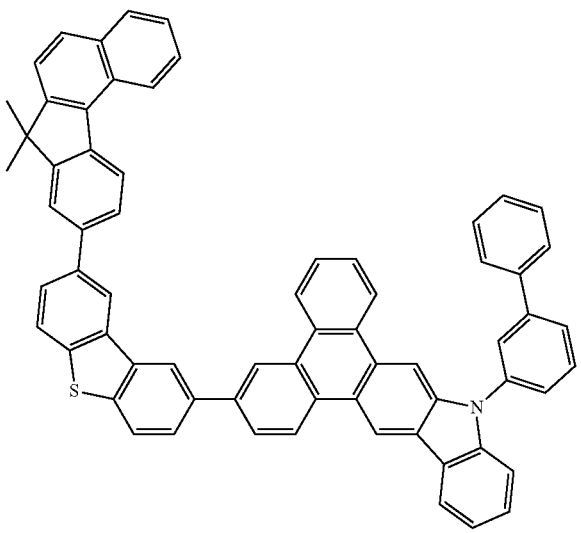
Compound 241
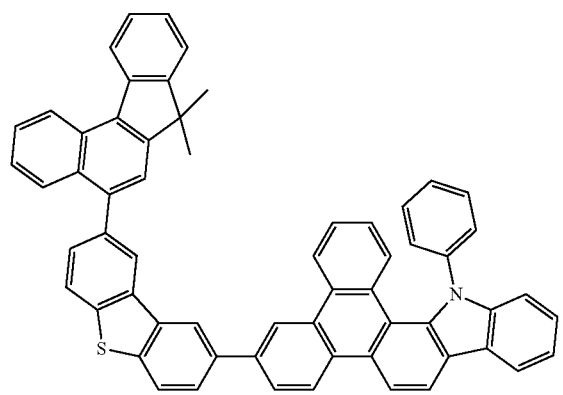
Compound 242
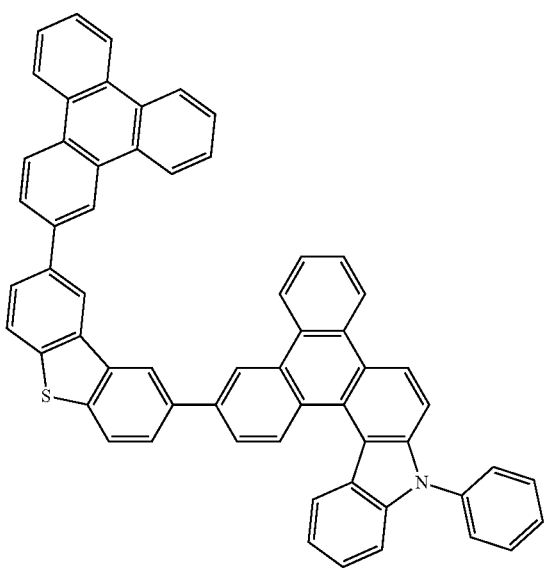

-continued
Compound 243
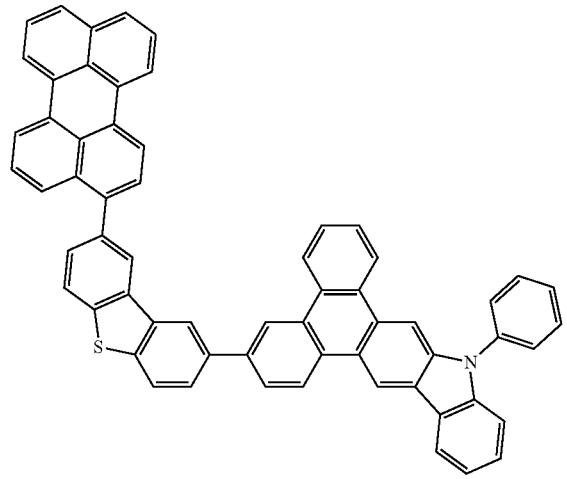
Compound 244
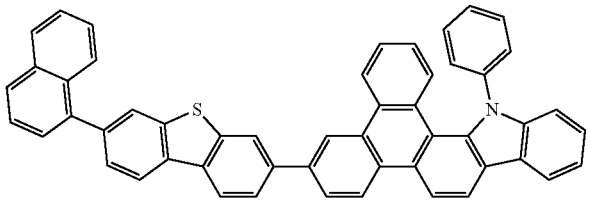
Compound 245
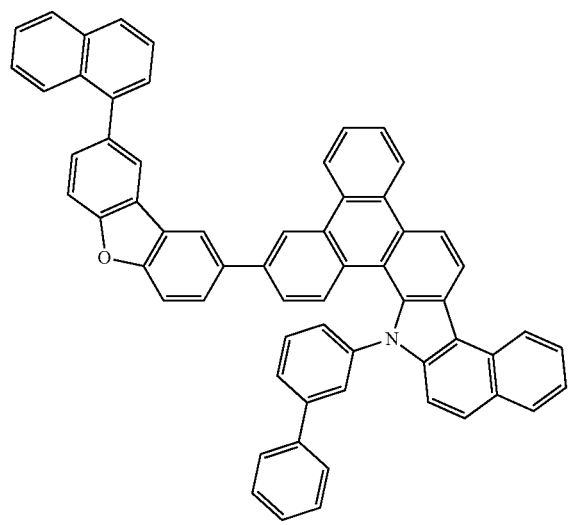
Compound 246
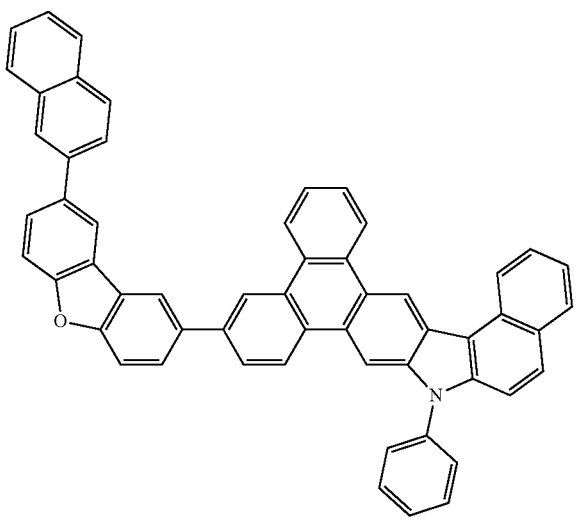
Compound 247
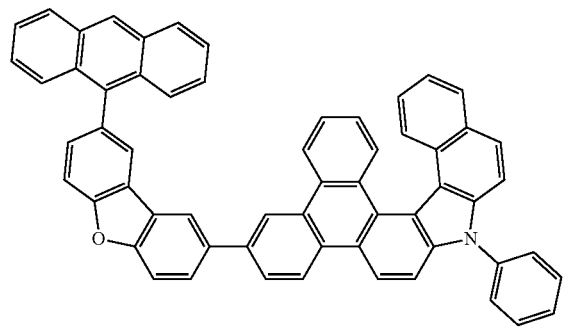
Compound 248
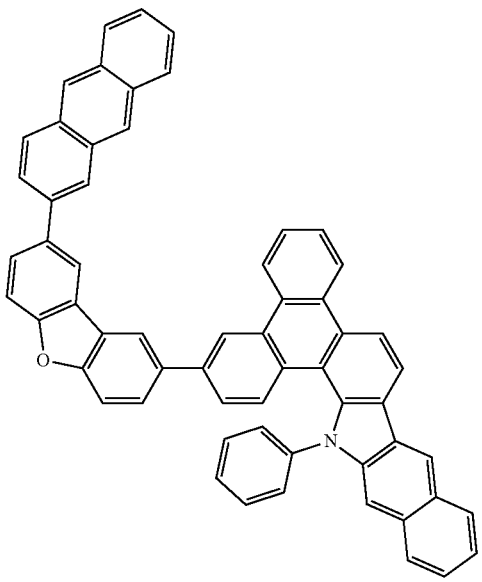

-continued
Compound 249
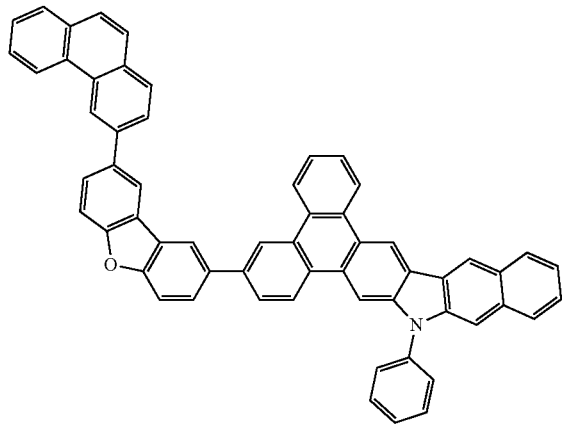
Compound 250
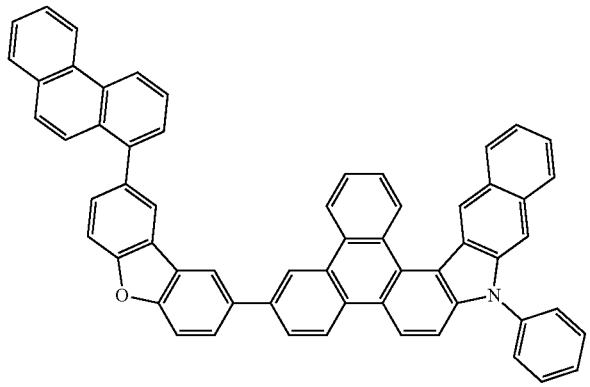
Compound 251
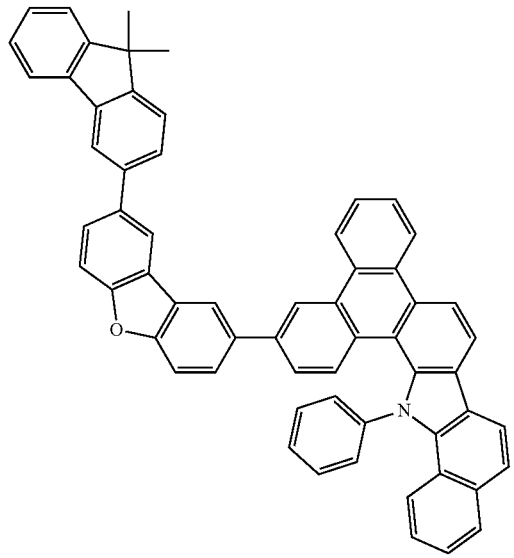
Compound 252
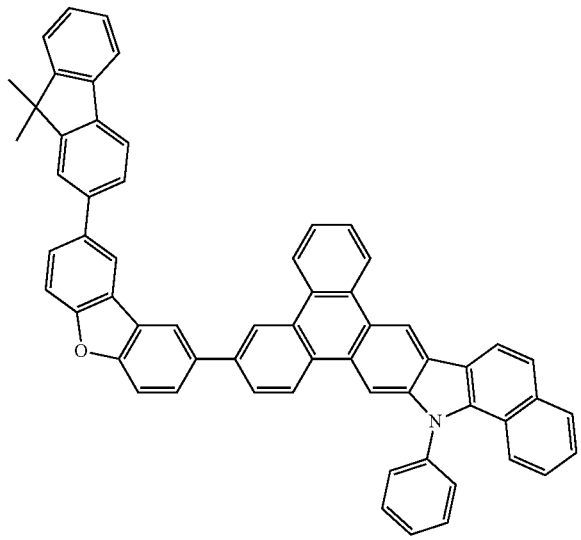
Compound 253
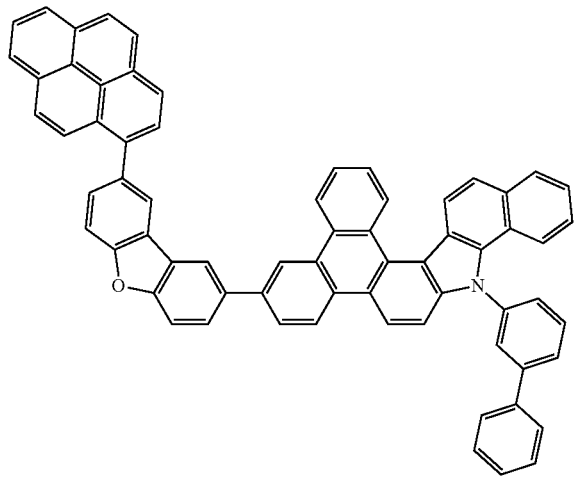
Comopund 254
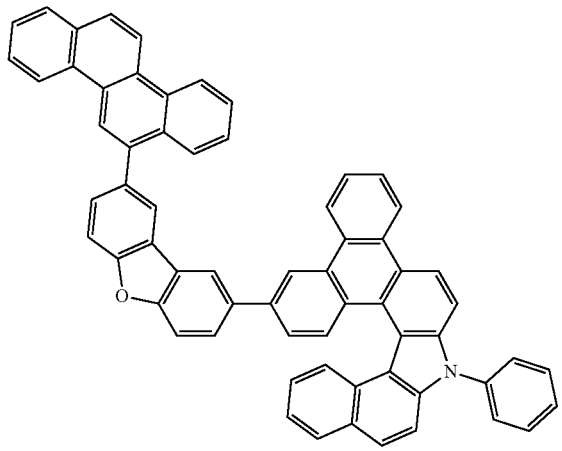

Compound 255
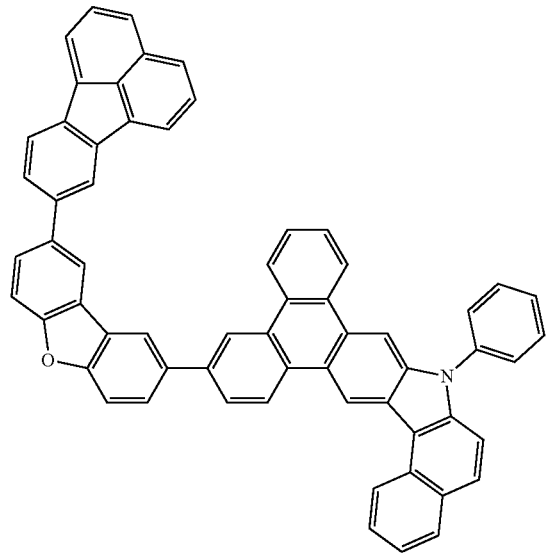
Compound 256
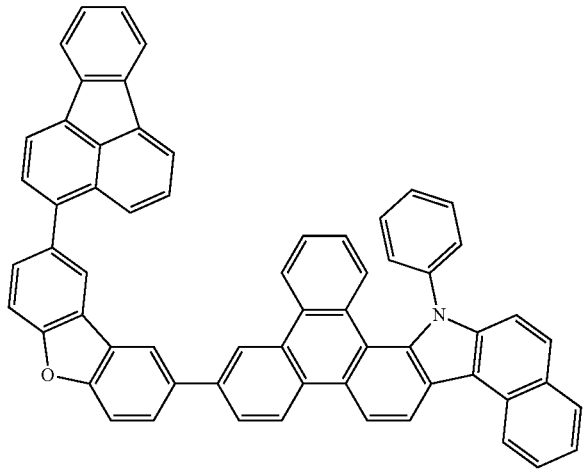
Compound 257
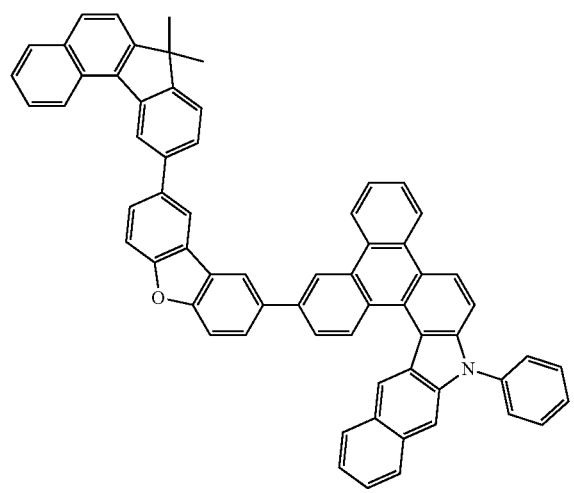
Comound 258
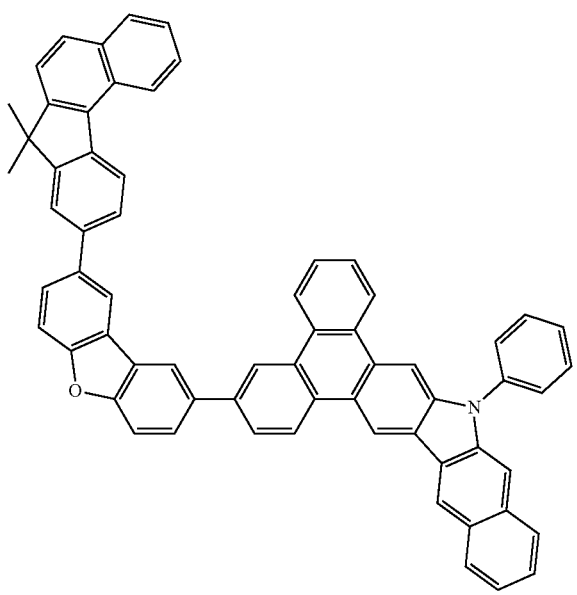

-continued
Compound 259
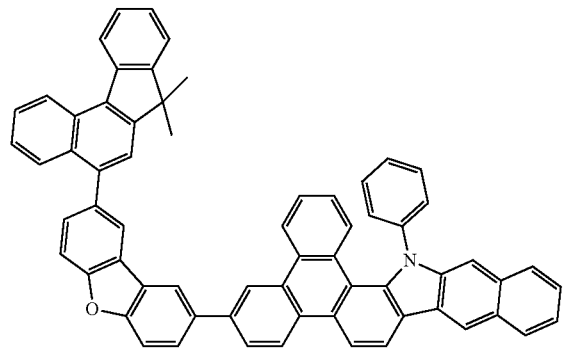
Compound 260
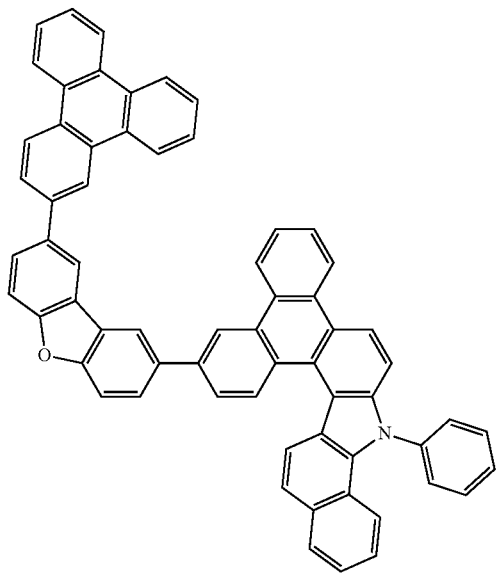
Compound 261
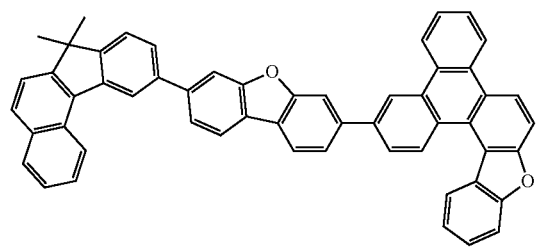
Compound 262
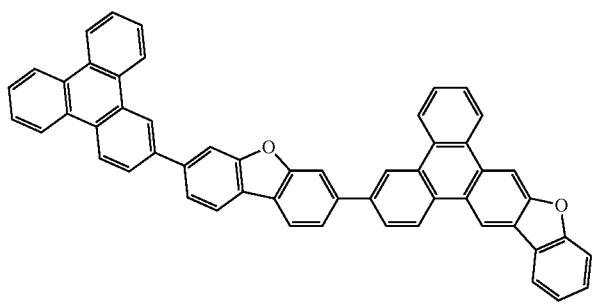
Compound 263
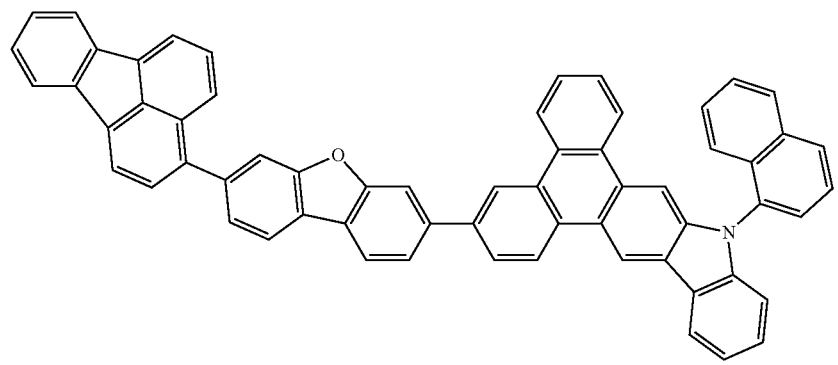

Compound 264
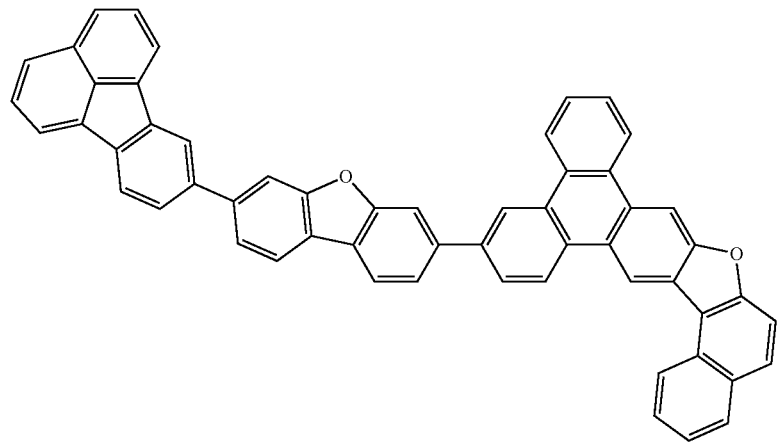
Compound 265
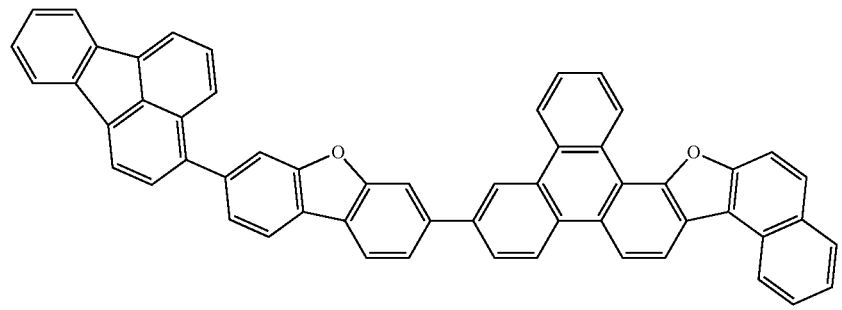
Compound 266
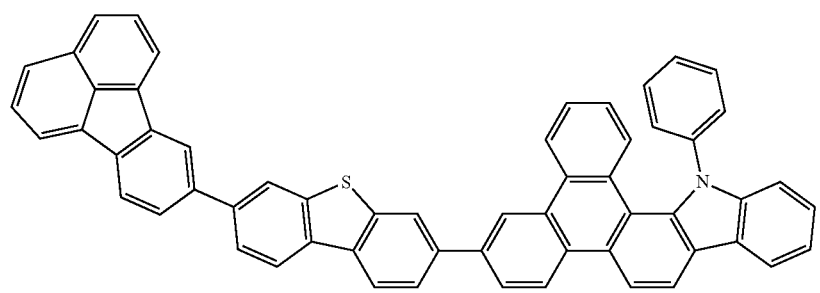
Compound 267
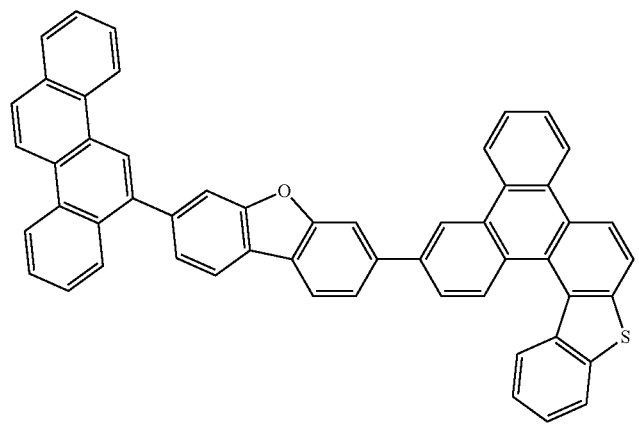

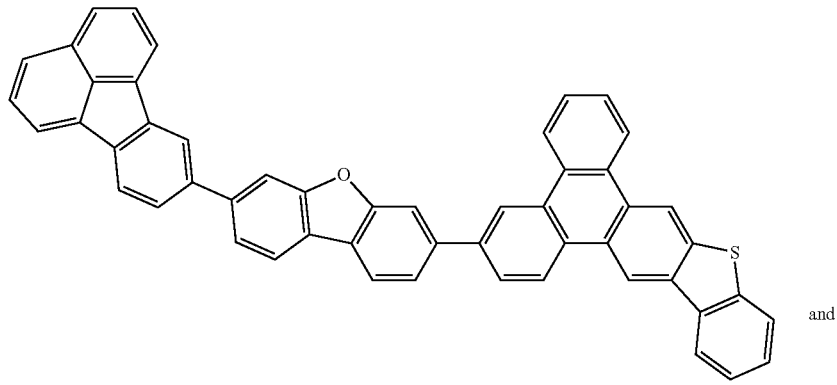

Compound 268 and

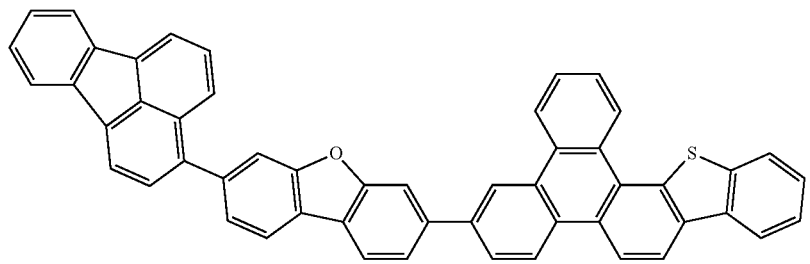

Compound 269

8. An organic electroluminescence device comprising an anode, a cathode and one or more organic layers formed between the anode and the cathode, wherein at least one of the organic layers comprises the organic compound according to claim 1.

9. The organic electroluminescence device according to claim 8, wherein the organic layers comprise an emissive layer having a host, and wherein the organic compound is comprised as the host.

10. The organic electroluminescence device according to claim 8, wherein the organic layers comprise an electron transport material, and wherein the organic compound of claim 1 is comprised as the electron transport material.

11. The organic electroluminescence device according to claim 8, wherein the organic layers comprise a hole blocking layer, and wherein the organic compound of claim 1 is comprised as the hole blocking layer.

12. The organic electroluminescence device according to claim 8, wherein the organic electroluminescence device is a lighting panel.

13. The organic electroluminescence device according to claim 8, wherein the organic electroluminescence device is a backlight panel.

* * * * *